(12) United States Patent
Ryu et al.

(10) Patent No.: US 10,593,894 B2
(45) Date of Patent: Mar. 17, 2020

(54) COMPOSITION FOR ORGANIC OPTOELECTRONIC DEVICE AND ORGANIC OPTOELECTRONIC DEVICE AND DISPLAY DEVICE

(71) Applicant: SAMSUNG SDI CO., LTD., Yongin-si, Gyeonggi-do (KR)

(72) Inventors: Dong Wan Ryu, Suwon-si (KR); Youngkwon Kim, Suwon-si (KR); Changwoo Kim, Suwon-si (KR); Hyung Sun Kim, Suwon-si (KR); Chang Ju Shin, Suwon-si (KR); Eun Sun Yu, Suwon-si (KR); Yuna Jang, Suwon-si (KR); Sung-Hyun Jung, Suwon-si (KR); Ho Kuk Jung, Suwon-si (KR)

(73) Assignee: Samsung SDI Co., Ltd., Yongin-Si, Gyeonggi-do (KR)

( * ) Notice: Subject to any disclaimer, the term of this patent is extended or adjusted under 35 U.S.C. 154(b) by 220 days.

(21) Appl. No.: 15/622,392

(22) Filed: Jun. 14, 2017

(65) Prior Publication Data

US 2018/0019409 A1     Jan. 18, 2018

(30) Foreign Application Priority Data

Jul. 13, 2016   (KR) .................. 10-2016-0088887

(51) Int. Cl.
   *H01L 51/00*   (2006.01)
   *C07D 487/04*   (2006.01)
   (Continued)

(52) U.S. Cl.
   CPC ........ *H01L 51/0072* (2013.01); *C07D 487/04* (2013.01); *C09K 11/025* (2013.01);
   (Continued)

(58) Field of Classification Search
   None
   See application file for complete search history.

(56) References Cited

U.S. PATENT DOCUMENTS 8,637,857 B2   1/2014   Langer et al.
8,795,848 B2   8/2014   Kai et al.
(Continued)

FOREIGN PATENT DOCUMENTS

CN   104271700 A   1/2015
CN   104277824 A   1/2015
(Continued)

OTHER PUBLICATIONS

Chinese Office Action dated Oct. 22, 2018.

*Primary Examiner* — Robert S Loewe
(74) *Attorney, Agent, or Firm* — Lee IP Law, PC

(57) ABSTRACT

Disclosed are a composition for an organic optoelectronic device includes at least one of a first host compound represented by a combination of Chemical Formula 1 and Chemical Formula 2, and at least one of a second host compound represented by a combination of Chemical Formula 3 and Chemical Formula 4, and an organic optoelectronic device including the same, and a display device. Details of Chemical Formulae 1 to 4 are the same as described in the detailed description.

13 Claims, 1 Drawing Sheet

(51) Int. Cl.
*C09K 11/02* (2006.01)
*H01L 51/50* (2006.01)

(52) U.S. Cl.
CPC ...... *H01L 51/0052* (2013.01); *H01L 51/0067* (2013.01); *H01L 51/5016* (2013.01); *H01L 2251/5384* (2013.01)

(56) References Cited

U.S. PATENT DOCUMENTS

| | | | | |
|---|---|---|---|---|
| 2010/0187977 | A1† | 7/2010 | Kai | |
| 2011/0062862 | A1* | 3/2011 | Yamamoto | C07D 487/04 313/504 |
| 2012/0001158 | A1* | 1/2012 | Asari | C07D 487/04 257/40 |
| 2012/0001165 | A1* | 1/2012 | Komori | C07D 403/14 257/40 |
| 2012/0223295 | A1* | 9/2012 | Inoue | C09K 11/06 257/40 |
| 2012/0273764 | A1* | 11/2012 | Yu | C09K 11/06 257/40 |
| 2013/0234119 | A1* | 9/2013 | Mizuki | H01L 51/0072 257/40 |
| 2014/0070204 | A1* | 3/2014 | Nagao | C07D 209/86 257/40 |
| 2014/0151647 | A1* | 6/2014 | Mizuki | H05B 33/20 257/40 |
| 2014/0306207 | A1* | 10/2014 | Nishimura | C07D 401/14 257/40 |
| 2015/0001488 | A1* | 1/2015 | Min | H01L 51/0054 257/40 |
| 2015/0188070 | A1* | 7/2015 | Ogiwara | H01L 51/5012 257/40 |
| 2015/0280158 | A1* | 10/2015 | Ogiwara | H01L 51/5016 257/40 |
| 2015/0325796 | A1* | 11/2015 | Tada | H01L 51/5278 257/40 |
| 2017/0263869 | A1† | 9/2017 | Tada | |

FOREIGN PATENT DOCUMENTS

| | | | | |
|---|---|---|---|---|
| CN | 105378028 | A | | 3/2016 |
| JP | 2007-134677 | A † | | 5/2007 |
| JP | 4388590 | B2 | | 12/2009 |
| JP | 4870245 | B2 | | 2/2012 |
| JP | 2013125653 | A | | 6/2013 |
| JP | 5238025 | B2 | | 7/2013 |
| JP | 5646733 | B2 | | 12/2014 |
| JP | WO 2013/088973 | A1 | | 4/2015 |
| JP | 5723794 | B2 | | 5/2015 |
| KR | 10-2010-0131745 | A | | 12/2010 |
| KR | 10-2012-0052879 | A | | 5/2012 |
| KR | 10-2013-0084093 | A | | 7/2013 |
| KR | 10-2013-0112342 | A | | 10/2013 |
| KR | 10-1324788 | B1 | | 10/2013 |
| KR | 10-2013-0127563 | A | | 11/2013 |
| KR | 10-1423066 | B1 | | 7/2014 |
| KR | 10-1447959 | B1 | | 10/2014 |
| KR | 10-2015-0130928 | | | 11/2015 |
| WO | WO 2010/113761 | A1 | | 10/2010 |
| WO | WO 2011/136755 | A1 | | 11/2011 |
| WO | WO 2012/114928 | A1 | | 8/2012 |
| WO | 2013/088973 | A1 † | | 6/2013 |
| WO | WO 2015/178589 | A1 | | 11/2015 |
| WO | WO-2015174738 | A1 * | 11/2015 | ......... H01L 51/0067 |
| WO | 2016/042997 | A1 † | | 3/2016 |
| WO | WO 2016/042997 | A1 | | 3/2016 |

* cited by examiner
† cited by third party

[FIG. 1]
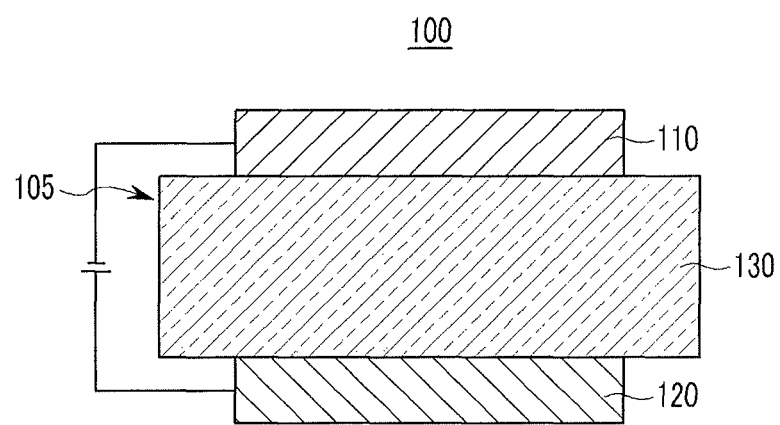
[FIG. 2]
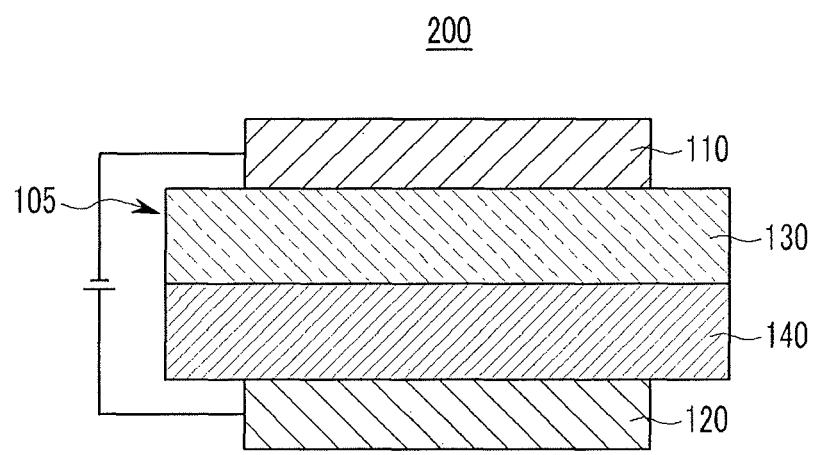

COMPOSITION FOR ORGANIC OPTOELECTRONIC DEVICE AND ORGANIC OPTOELECTRONIC DEVICE AND DISPLAY DEVICE

CROSS-REFERENCE TO RELATED APPLICATION

This application claims priority to and the benefit of Korean Patent Application No. 10-2016-0088887 filed in the Korean Intellectual Property Office on Jul. 13, 2016, the entire contents of which are incorporated herein by reference.

BACKGROUND OF THE INVENTION (a) Field of the Invention

A composition for an organic optoelectronic device, an organic optoelectronic device, and a display device are disclosed.

(b) Description of the Related Art

An organic optoelectronic device (organic optoelectronic diode) is a device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. Herein, the organic layer may include a light emitting layer and optionally an auxiliary layer, and the auxiliary layer may be for example at least one layer selected from a hole injection layer, a hole transport layer, an electron blocking layer, an electron transport layer, an electron injection layer, and a hole blocking layer.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

SUMMARY OF THE INVENTION

An embodiment provides a composition for an organic optoelectronic device capable of realizing an organic optoelectronic device having high efficiency and a long life-span.

Another embodiment provides an organic optoelectronic device including the composition.

Yet another embodiment provides a display device including the organic optoelectronic device.

According to an embodiment, a composition for an organic optoelectronic device includes at least one of a first host compound represented by a combination of Chemical Formula 1 and Chemical Formula 2, and at least one of a second host compound represented by a combination of Chemical Formula 3 and Chemical Formula 4.

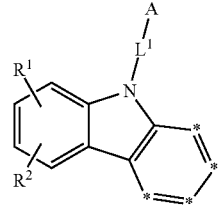

[Chemical Formula 1]

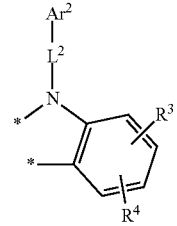

[Chemical Formula 2]

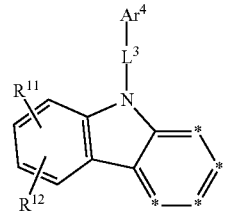

[Chemical Formula 3]

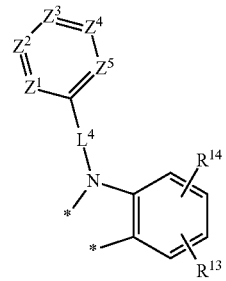

[Chemical Formula 4]

In Chemical Formulae 1 to 4, two adjacent *'s of Chemical Formula 1 are bound to two adjacent *'s of Chemical Formula 2 and the remainder *'s of Chemical Formula 1 not being bound to *'s of Chemical Formula 2 are $CR^a$, two adjacent *'s of Chemical Formula 3 are bound to two adjacent *'s of Chemical Formula 4 and the remainder *'s of Chemical Formula 3 not being bound to *'s of Chemical Formula 4 are $CR^b$, A is a substituted or unsubstituted carbazolyl group, $Ar^2$ and $Ar^3$ are independently a substituted or unsubstituted C6 to C30 aryl group, or a substituted or unsubstituted C2 to C30 heterocyclic group, $L^1$ to $L^4$ are independently a single bond or a substituted or unsubstituted C6 to C30 arylene group, $Z^1$ to $Z^5$ are independently N or $CR^c$, at least two of $Z^1$ to $Z^5$ are N, $R^a$, $R^b$, $R^c$, $R^1$ to $R^4$, and $R^{11}$ to $R^{14}$ are independently hydrogen, deuterium, a substituted or unsubstituted C1 to C10 alkyl group, a substituted or unsubstituted C6 to C20 aryl group, a substituted or unsubstituted C2 to C30 heterocyclic group, or a combination thereof, R$^c$'s are independently present alone or adjacent groups thereof are linked with each other to form a substituted or unsubstituted aliphatic, aromatic, or heteroaromatic monocyclic or polycyclic ring, and the "substituted" refers to replacement of at least one hydrogen by deuterium, a C1 to C4 alkyl group, a C6 to C12 aryl group, or a C2 to C20 heterocyclic group.

According to another embodiment, an organic optoelectronic device includes an anode and a cathode facing each other and at least one organic layer disposed between the anode and the cathode, wherein the organic layer includes the composition for an organic optoelectronic device.

According to another embodiment, a display device includes the organic optoelectronic device.

An organic optoelectronic device having high efficiency and a long life-span may be realized.

BRIEF DESCRIPTION OF THE DRAWINGS

FIGS. 1 and 2 are cross-sectional views showing organic light emitting diodes according embodiments.

DETAILED DESCRIPTION

Hereinafter, embodiments of the present disclosure are described in detail. However, these embodiments are exemplary, the present disclosure is not limited thereto and the present disclosure is defined by the scope of claims.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C6 to C20 arylamine group, a C3 to C30 cycloalkyl group, a C3 to C30 heterocycloalkyl group, a C6 to C30 aryl group, a C2 to C30 heterocyclic group, a C1 to C20 alkoxy group, a C1 to C10 trifluoroalkyl group, a cyano group, or a combination thereof.

In one example, "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heterocyclic group. In a specific example, "substituted" refers to replacement of at least one hydrogen of a substituent or a compound by deuterium, a C1 to C20 alkyl group, a C6 to C20 aryl group, or a C2 to C20 heterocyclic group. In addition, in a specific example, "substituted" refers to replacement of at least one hydrogen of a substituent or a compound by deuterium, a C1 to C4 alkyl group, a C6 to C20 aryl group, or a C2 to C20 heterocyclic group. In addition, in a specific example, "substituted" refers to replacement of at least one hydrogen of a substituent or a compound by deuterium, a methyl group, an ethyl group, a phenyl group, a biphenyl group, a terphenyl group, a naphthyl group, an anthracenyl group, a phenanthrenyl group, a triphenylene group, a fluorenyl group, a pyrimidinyl group, a triazinyl group, a quinazolinyl group, a carbazolyl group, a dibenzofuranyl group, or a dibenzothiophenyl group.

As used herein, when a definition is not otherwise provided, "hetero" refers to one including one to three heteroatoms selected from N, O, S, P, and Si, and remaining carbons in one functional group.

As used herein, when a definition is not otherwise provided, "an alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

As used herein, "an aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quaterphenyl group, and the like, and two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

As used herein, "a heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "a heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heterocyclic group may be a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridinyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted isoquinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but are not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a composition for an organic optoelectronic device according to an embodiment is described.

A composition for an organic optoelectronic device according to an embodiment includes at least two kinds of a host and a dopant, and the host includes a first host compound having relatively strong hole characteristics and a second host compound having relatively strong electron characteristics.

The first host compound is a compound having relatively strong electron transport characteristics and may be represented by a combination of Chemical Formula 1 and Chemical Formula 2.

[Chemical Formula 1]

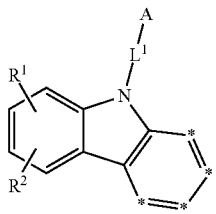

[Chemical Formula 2]

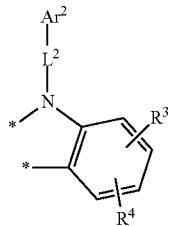

In Chemical Formulae 1 and 2, two adjacent *'s of Chemical Formula 1 are bound to two adjacent *'s of Chemical Formula 2 and the remainder *'s of Chemical Formula 1 not being bound to *'s of Chemical Formula 2 are $CR^a$, A is a substituted or unsubstituted carbazolyl group, $Ar^2$ is a substituted or unsubstituted C6 to C30 aryl group or a substituted or unsubstituted C2 to C30 heterocyclic group, $L^1$ and $L^2$ are independently a single bond or a substituted or unsubstituted C6 to C30 arylene group, and $R^a$ and $R^1$ to $R^4$ are independently hydrogen, deuterium, a substituted or unsubstituted C1 to C10 alkyl group, a substituted or unsubstituted C6 to C20 aryl group, a substituted or unsubstituted C2 to C30 heterocyclic group, or a combination thereof.

In an example embodiment, $R^a$ may independently be hydrogen, deuterium, a substituted or unsubstituted C1 to C4 alkyl group, a substituted or unsubstituted phenyl group, a substituted or unsubstituted biphenyl group, a substituted or unsubstituted naphthyl group, or a combination thereof. In a specific example embodiment, $R^a$ may independently be hydrogen, deuterium, a substituted or unsubstituted phenyl group, or a combination thereof, and for example $R^a$ may be all hydrogen.

The first host compound decreases three-dimensional planarity of a molecular structure due to a carbazolyl group linked with at least one N in an indolocarbazole structure, and increase stability and improve a hole transport property by lowering crystallinity and a deposition temperature.

In addition, hole transport characteristics may be fortified by substituting the indolocarbazole structure with an aryl group or an another carbazolyl group along with the carbazolyl group as a substituent, and thereby a host having fast electron transport characteristics may be supplemented to manufacturing a device having a low driving voltage and high efficiency.

In the present disclosure, "substituted" of Chemical Formulae 1 and 2 refers to replacement of at least one hydrogen by deuterium, a C1 to C4 alkyl group, a C6 to C12 aryl group, or a C2 to C20 heterocyclic group.

In an example embodiment, "substituted" of Chemical Formulae 1 and 2 refers to replacement of at least one hydrogen by a methyl group, an ethyl group, a propyl group, a phenyl group, a biphenyl group, a naphthyl group, a phenanthrenyl group, or a carbazolyl group, and may for example refer to replacement of at least one hydrogen by a methyl group, a phenyl group, or a 9-carbazolyl group. In addition, "substituted" may for example refer to replacement of at least one hydrogen by a methyl group or a phenyl group.

In an example embodiment, Chemical Formula 1 may be for example represented by Chemical Formula 1-I or Chemical Formula 1-II according to a linking point of the substituent A, the carbazolyl group.

[Chemical Formula 1-I]

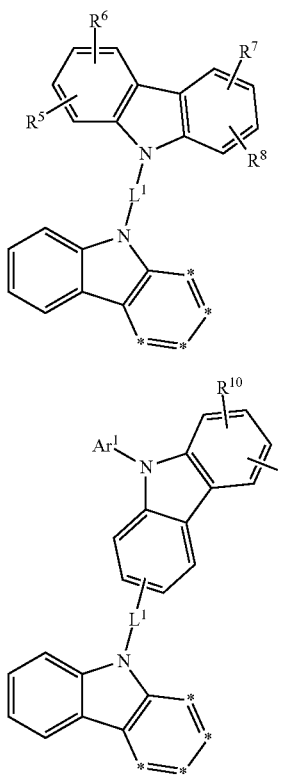

[Chemical Formula 1-II]

[Chemical Formula 1-IIa]

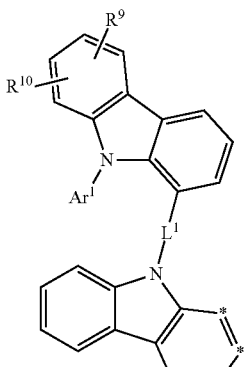

[Chemical Formula 1-IIb]


[Chemical Formula 1-IIc]

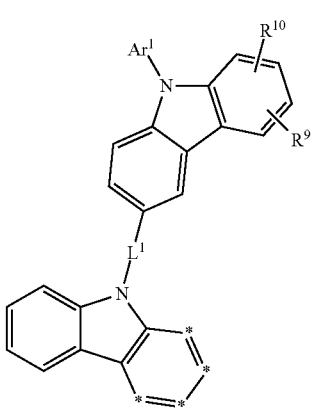

[Chemical Formula 1-IId]

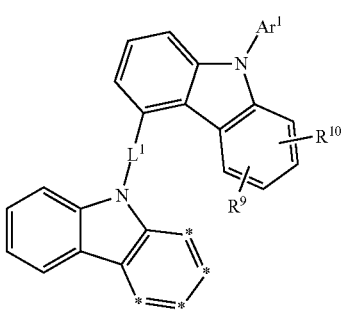

In Chemical Formula 1-I and Chemical Formula 1-II, "*" and L' are the same as above, $R^5$ to $R^{10}$ are the same as definitions of $R^1$ to $R^4$, and $Ar^1$ is a substituted or unsubstituted C6 to C30 aryl group.

In an example embodiment, $Ar^1$ may be a substituted or unsubstituted phenyl group, a substituted or unsubstituted naphthyl group, a substituted or unsubstituted biphenyl group, a substituted or unsubstituted terphenyl group, or a substituted or unsubstituted triphenylene group. In addition, $Ar^1$ may be a substituted or unsubstituted phenyl group, or a substituted or unsubstituted naphthyl group.

In an example embodiment, the $R^1$ to $R^4$ may independently be hydrogen, deuterium, a substituted or unsubstituted C1 to C4 alkyl group, or a substituted or unsubstituted C6 to C12 aryl group, specifically hydrogen, deuterium, or a substituted or unsubstituted C6 to C12 aryl group, and more specifically hydrogen, a phenyl group, or a biphenyl group. In the most specific example embodiment, they may be all hydrogen.

In an example embodiment, $R^5$ to $R^{10}$ are independently hydrogen, deuterium, a substituted or unsubstituted C1 to C4 alkyl group, a substituted or unsubstituted C6 to C12 aryl group, specifically hydrogen, deuterium, or a substituted or unsubstituted C6 to C12 aryl group, and more specifically hydrogen, a phenyl group, or a biphenyl group. In the most specific example embodiment, they may be all hydrogen.

On the other hand, Chemical Formula 1-II may be more specifically represented by one of Chemical Formula 1-IIa, Chemical Formula 1-IIb, Chemical Formula 1-IIc, and Chemical Formula 1-IId.

In Chemical Formula 1-IIa, Chemical Formula 1-IIb, Chemical Formula 1-IIc, and Chemical Formula 1-IId, "*" and $L^1$, $Ar^1$, $R^9$, and $R^{10}$ are the same as described above.

In a more specific example embodiment, Chemical Formula 1-II may be represented by Chemical Formula 1-IIb or Chemical Formula 1-IIc.

In an example embodiment, the first host compound may be for example represented by one of Chemical Formula A, Chemical Formula B, Chemical Formula C, Chemical Formula D, and Chemical Formula E according to a fusion point of Chemical Formula 1 and Chemical Formula 2.

[Chemical Formula A]

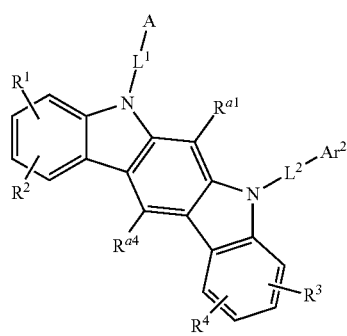

[Chemical Formula B]

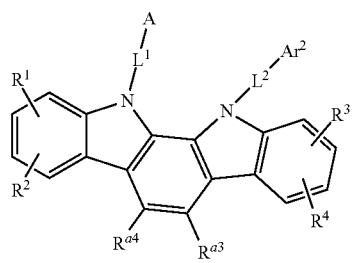

[Chemical Formula C]

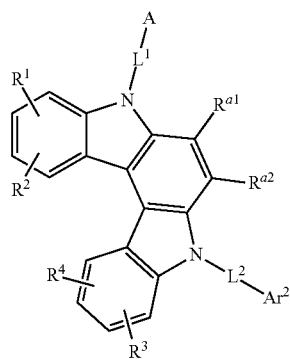

[Chemical Formula D]

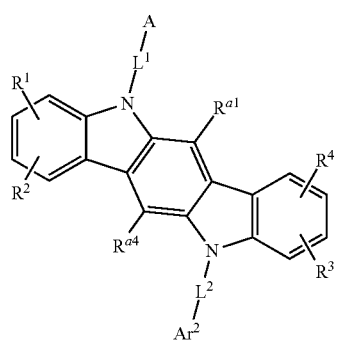

[Chemical Formula E]

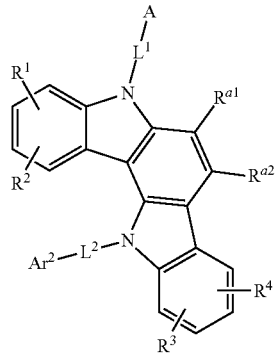

In Chemical Formula A to Chemical Formula E, the substituent A, $Ar^2$, $L^1$ and $L^2$ and $R^1$ to $R^4$ are the same as described above, and $R^{a1}$ to $R^{a4}$ are the same as the definition of $R^a$.

In an example embodiment, $R^{a1}$ to $R^{a4}$ may independently be hydrogen, deuterium, a substituted or unsubstituted C1 to C4 alkyl group, a substituted or unsubstituted phenyl group, a substituted or unsubstituted biphenyl group, a substituted or unsubstituted naphthyl group, or a combination thereof. In addition, in a more specific example embodiment, $R^{a1}$ to $R^{a4}$ may independently be hydrogen, deuterium, a substituted or unsubstituted phenyl group, or a combination thereof, and $R^{a1}$ to $R^{a4}$ may be all hydrogen.

In an example embodiment, the $L^1$ and $L^2$ may independently be a single bond or a substituted or unsubstituted C6 to C20 arylene group, and specifically the $L^1$ may be a single bond, a substituted or unsubstituted phenylene group, a substituted or unsubstituted biphenylene group, or a substituted or unsubstituted terphenylene group and the $L^2$ may be a single bond, or a substituted or unsubstituted phenylene group, and the $L^1$ and $L^2$ may be for example selected from linking groups of Group I.

[Group I]

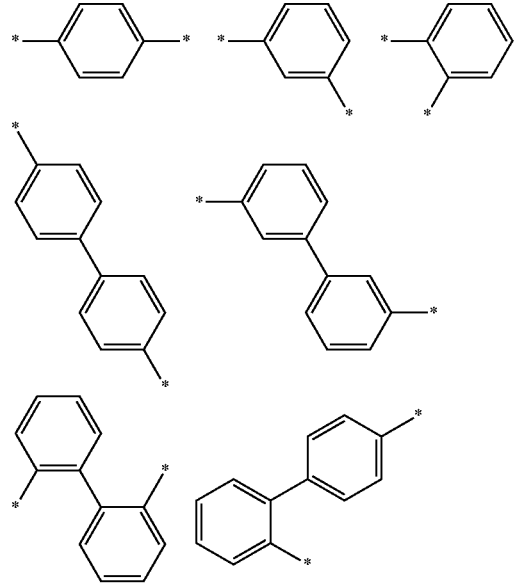

-continued

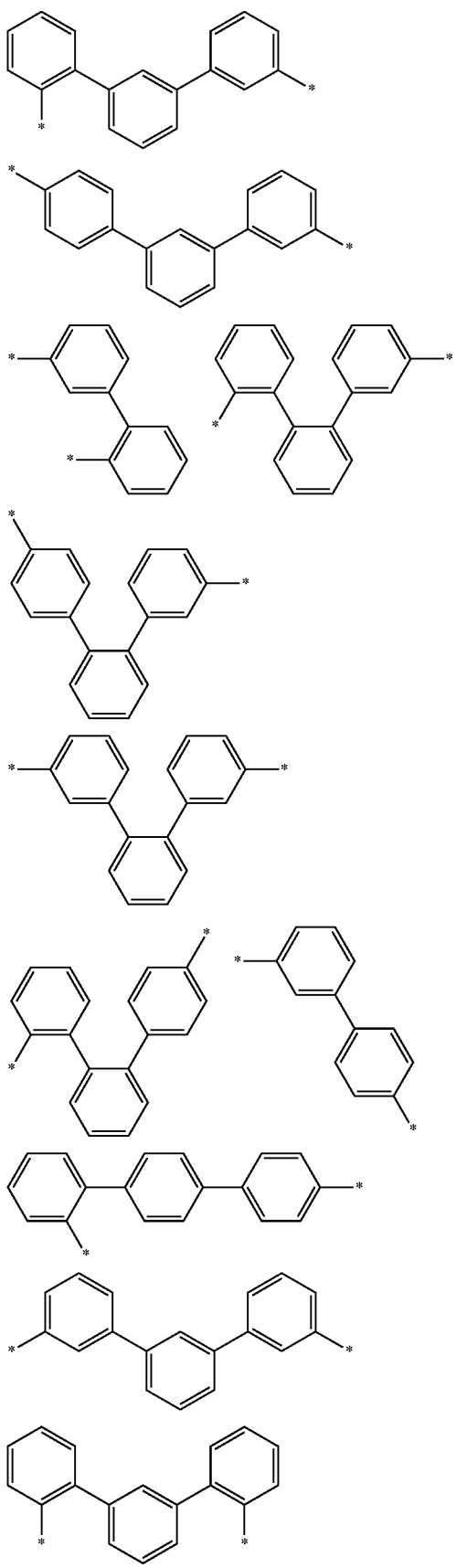

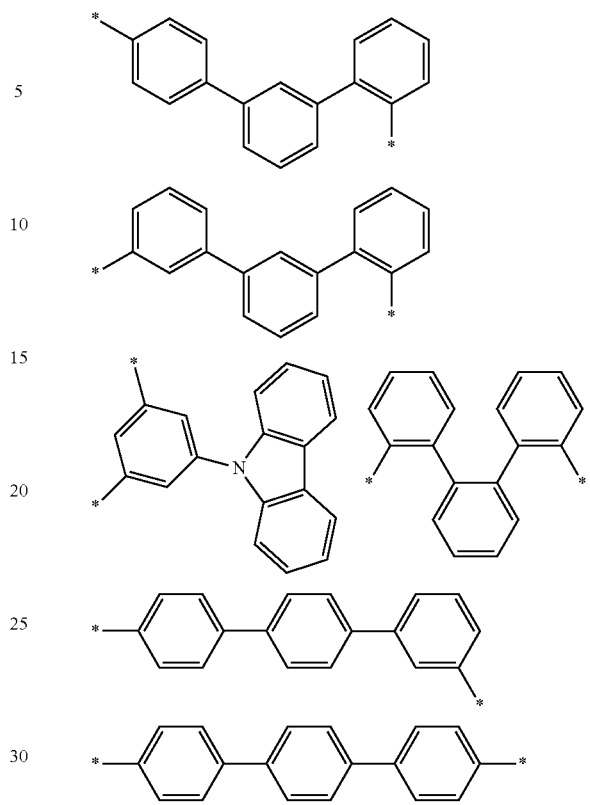

In Group I, * is a linking point with an adjacent atom.

In an example embodiment, the $Ar^1$ may be a substituted or unsubstituted C6 to C20 aryl group, specifically a substituted or unsubstituted phenyl group, a substituted or unsubstituted biphenyl group, a substituted or unsubstituted terphenyl group, a substituted or unsubstituted naphthyl group, a substituted or unsubstituted fluorenyl group, or a substituted or unsubstituted phenanthrenyl group, and may be for example selected from substituents of Group II.

[Group II]

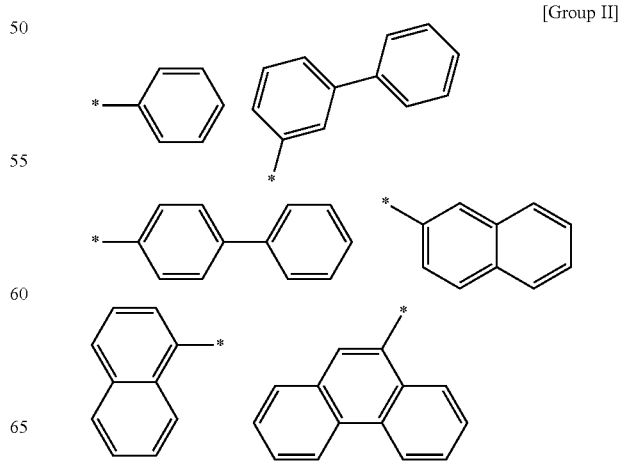

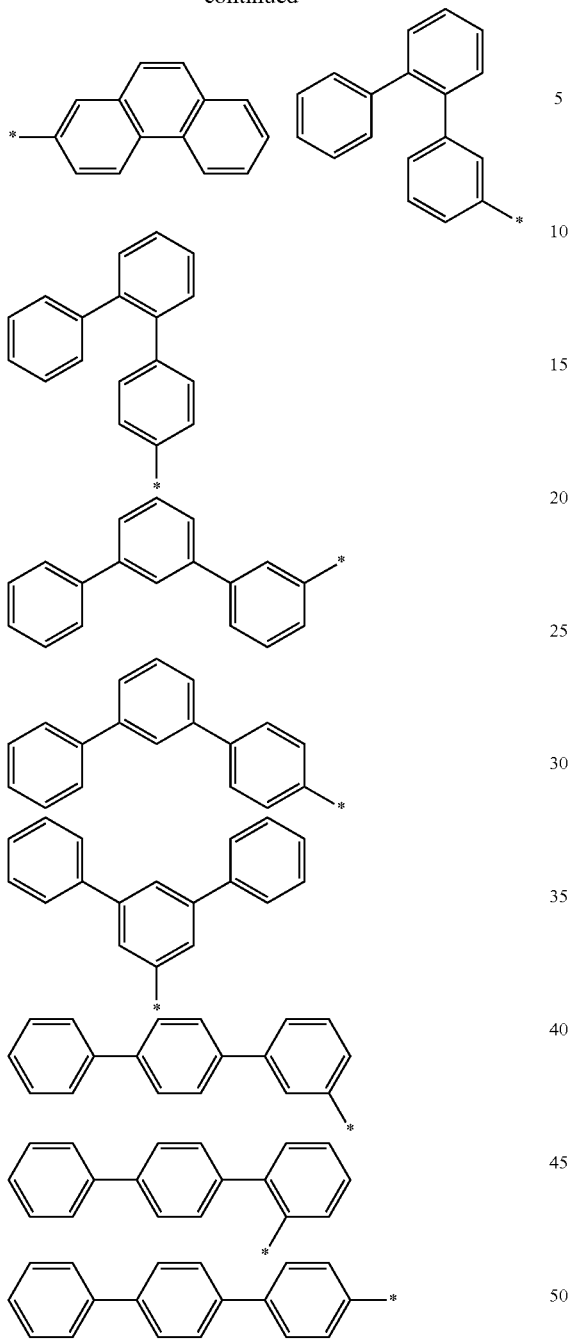

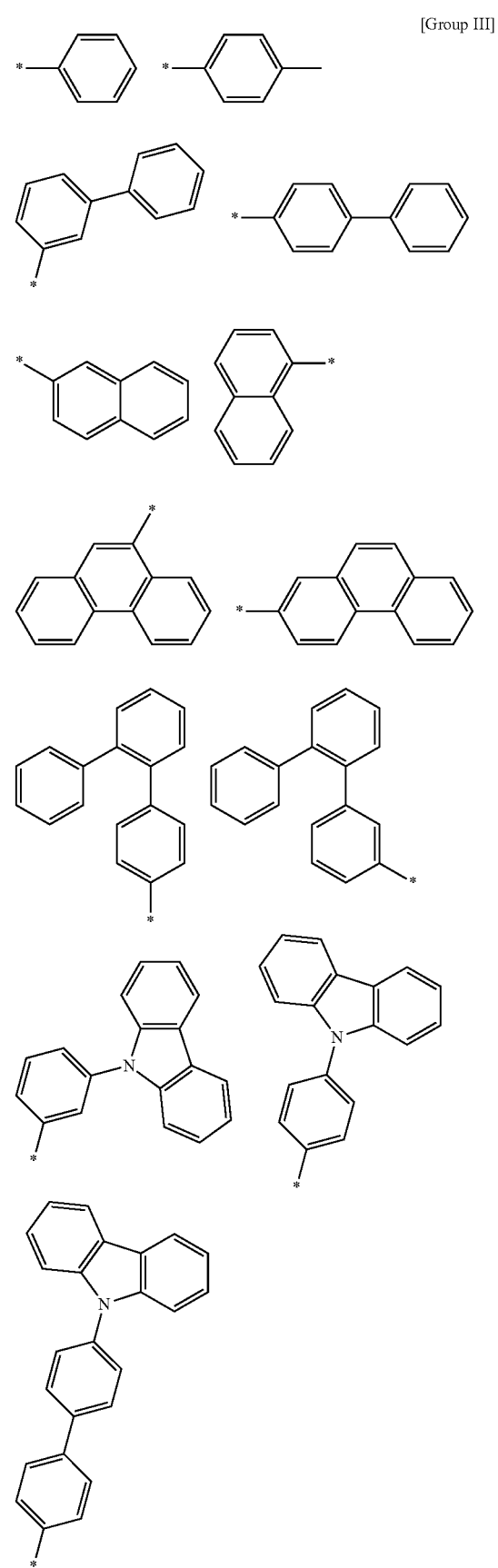

[Group III]

In Group II, * is a linking point with an adjacent atom.

In an example embodiment, the Ar² may be a substituted or unsubstituted C6 to C20 aryl group, or a substituted or unsubstituted C2 to C20 heterocyclic group, and specifically a substituted or unsubstituted phenyl group, a substituted or unsubstituted biphenyl group, a substituted or unsubstituted terphenyl group, a substituted or unsubstituted naphthyl group, a substituted or unsubstituted fluorenyl group, a substituted or unsubstituted phenanthrenyl group, a substituted or unsubstituted carbazolyl group, a substituted or unsubstituted dibenzofuranyl group, or a substituted or unsubstituted dibenzothiophenyl group, and may be for example selected from substituents of Group III.

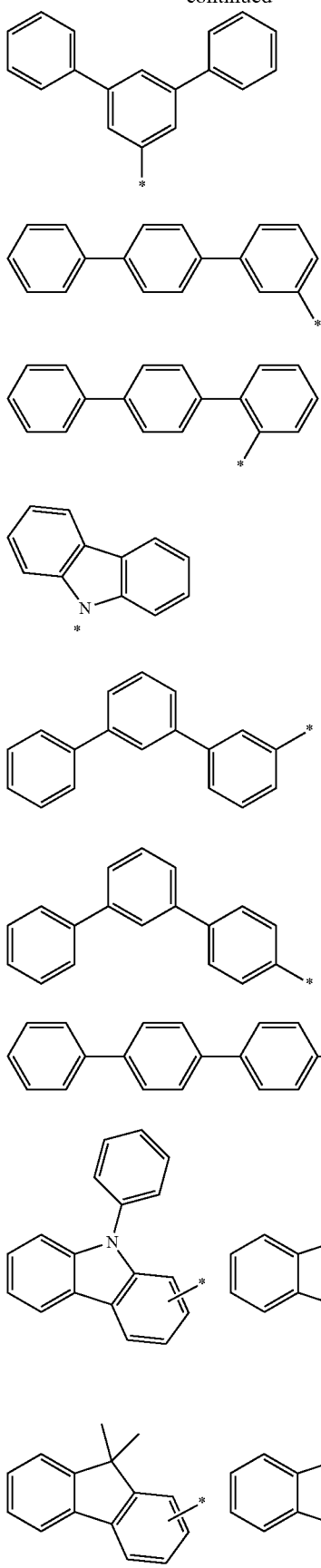

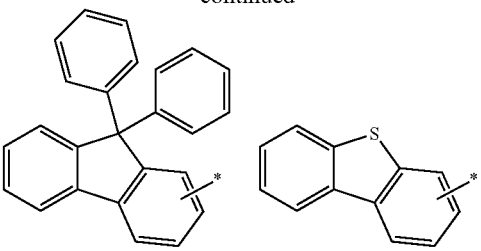

In Group III, * is a linking point with an adjacent atom.

In the most specific example embodiment, the Ar$^1$ may be a substituted or unsubstituted phenyl group, a substituted or unsubstituted para-biphenyl group, a substituted or unsubstituted meta-biphenyl group, a substituted or unsubstituted terphenyl group, a substituted or unsubstituted naphthyl group, or a substituted or unsubstituted phenanthrenyl group, and the Ar$^2$ may be a substituted or unsubstituted phenyl group, a substituted or unsubstituted para-biphenyl group, a substituted or unsubstituted meta-biphenyl group, a substituted or unsubstituted terphenyl group, a substituted or unsubstituted naphthyl group, a substituted or unsubstituted phenanthrenyl group, or a substituted or unsubstituted carbazolyl group.

In a more specific example embodiment, the first host compound may be for example represented by Chemical Formula B, Chemical Formula C, or Chemical Formula E.

In an example embodiment, the R$^{a1}$ to R$^{a4}$ may independently be hydrogen, deuterium, a substituted or unsubstituted C1 to C4 alkyl group, a substituted or unsubstituted C6 to C12 aryl group, specifically hydrogen, deuterium, or a substituted or unsubstituted C6 to C12 aryl group, and more specifically hydrogen, a phenyl group, or a biphenyl group. In the most specific example embodiment, they may be all hydrogen.

In a more specific example embodiment, the first host compound may be represented by one of Chemical Formula A1 to Chemical Formula A4, Chemical Formula B1 to Chemical Formula B4, Chemical Formula C1 to Chemical Formula C4, Chemical Formula D1 to Chemical Formula D4, and Chemical Formula E1 to Chemical Formula E4.

[Chemical Formula A1]

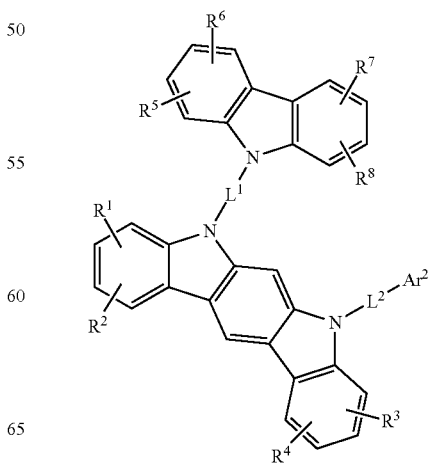

[Chemical Formula A2]
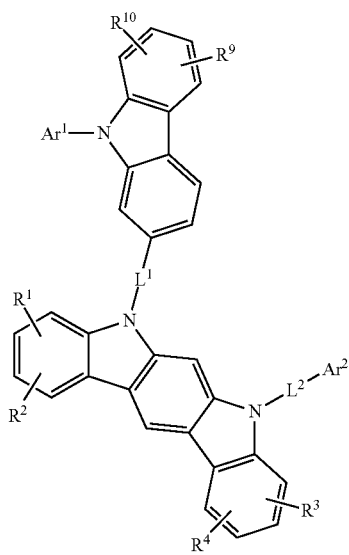
[Chemical Formula A3]
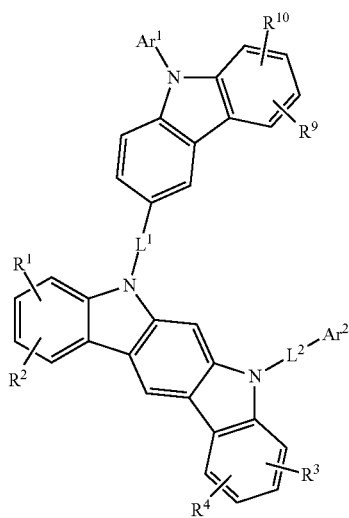
[Chemical Formula A4]
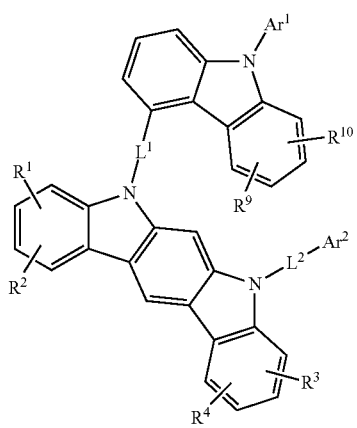
[Chemical Formula B1]
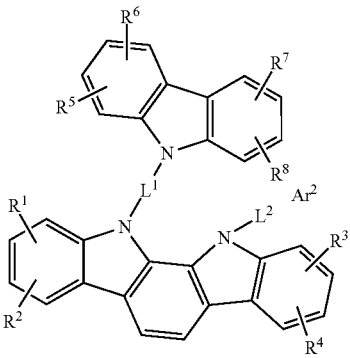
[Chemical Formula B2]
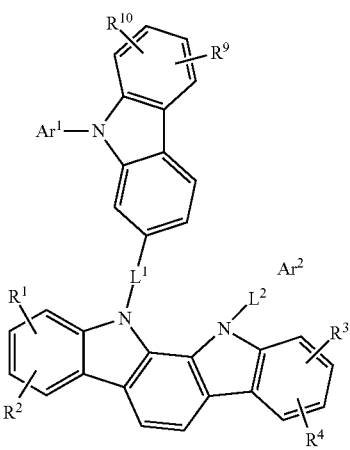
[Chemical Formula B3]
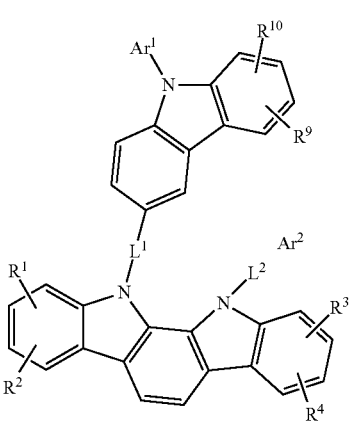

[Chemical Formula B4]
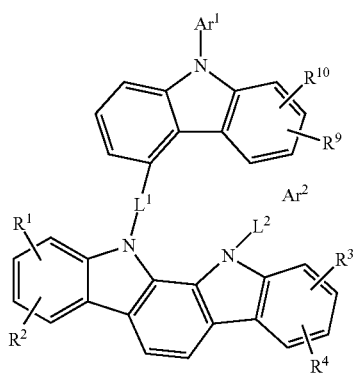
[Chemical Formula C1]
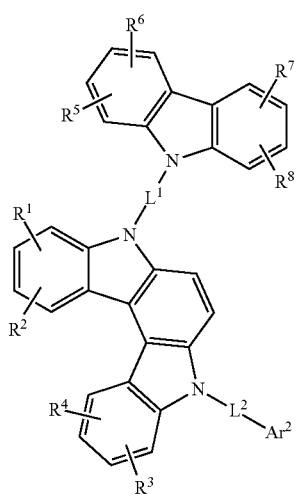
[Chemical Formula C2]
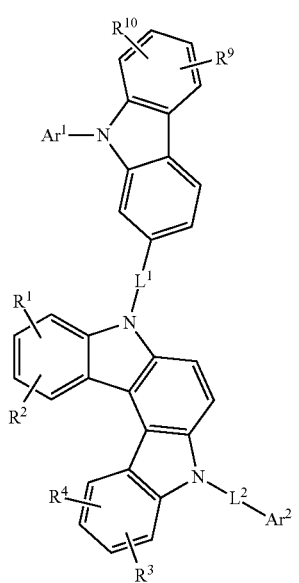
[Chemical Formula C3]
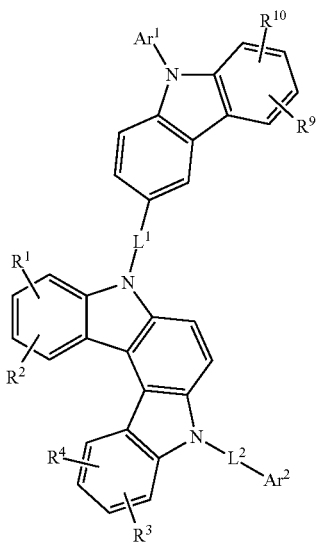
[Chemical Formula C4]
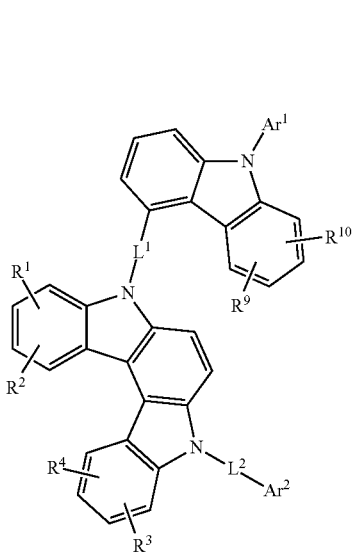
[Chemical Formula D1]
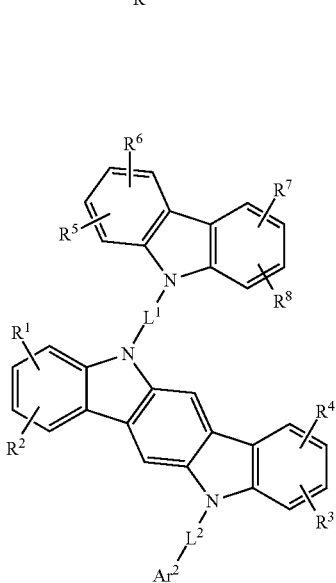

[Chemical Formula D2]
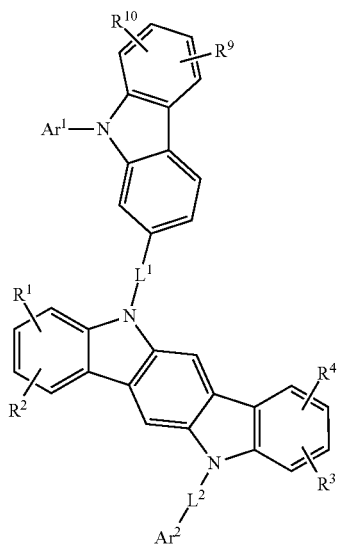
[Chemical Formula D3]
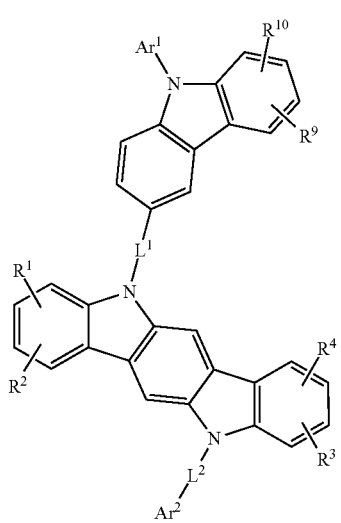
[Chemical Formula D4]
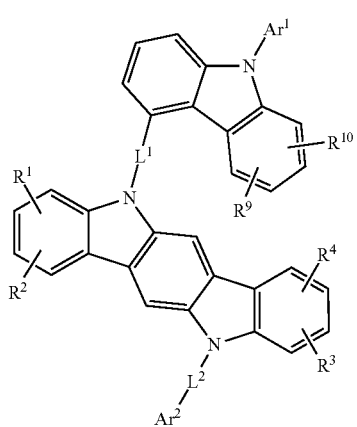
[Chemical Formula E1]
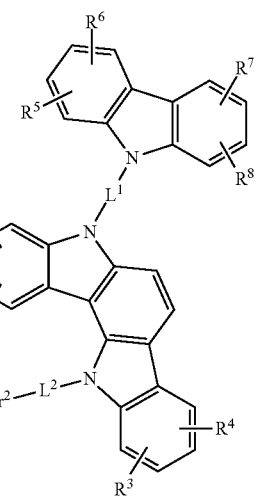
[Chemical Formula E2]
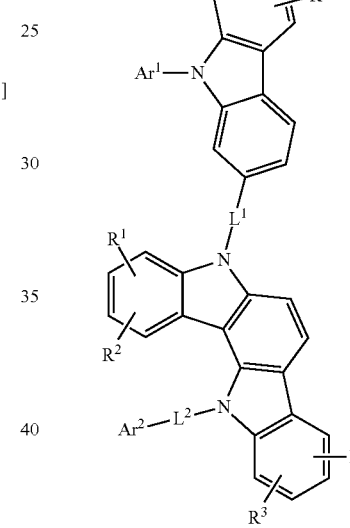
[Chemical Formula E3]
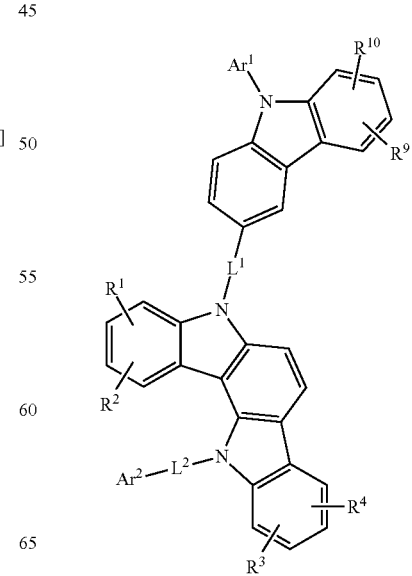

[Chemical Formula E4]

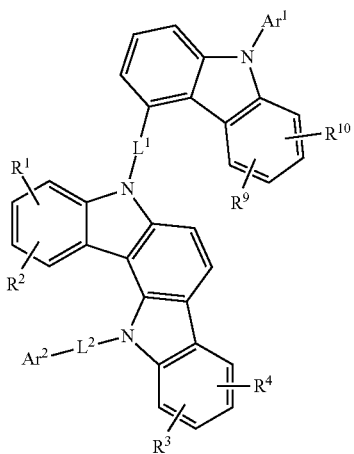

In Chemical Formula A1 to Chemical Formula A4, Chemical Formula B1 to Chemical Formula B4, Chemical Formula C1 to Chemical Formula C4, Chemical Formula D1 to Chemical Formula D4, and Chemical Formula E1 to Chemical Formula E4, $R^1$ to $R^{10}$, $L^1$, $L^2$, $Ar^1$, and $Ar^2$ are the same as described above.

In the most specific example embodiment, the first host compound may be represented by one of Chemical Formula A3, Chemical Formula B1 to Chemical Formula B4, Chemical Formula C1 to Chemical Formula C4, Chemical Formula D1, and Chemical Formula E1 to Chemical Formula E4, and more specifically one of Chemical Formula B1 to Chemical Formula B4, Chemical Formula C1 to Chemical Formula C4 and Chemical Formula E1 to Chemical Formula E4, and may be for example represented by one of Chemical Formula B1, Chemical Formula C1, Chemical Formula C2, Chemical Formula C3, Chemical Formula E1, Chemical Formula E2, and Chemical Formula E3.

As the most specific examples, the $L^1$ may be a phenylene group, or a biphenylene group, the $Ar^1$ may be a phenyl group, a biphenyl group, a terphenyl group, or a naphthyl group, the $L^2$ may be a single bond, or a phenylene group, the $Ar^2$ may be a phenyl group, a biphenyl group, or a terphenyl group, and the $R^1$ to $R^{10}$ may be all hydrogen.

In an example embodiment, in Chemical Formulae 1 and 2, the $L^1$ and $L^2$ may independently be a single bond, or a substituted or unsubstituted phenylene group, the $Ar^2$ may be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted fluorenyl group, and the "substituted" may refer to replacement of at least one hydrogen by deuterium, a C1 to C4 alkyl group, a C6 to C12 aryl group.

In an example embodiment, the first host compound may be for example compounds of Group 1, but is not limited thereto.

[Group 1]

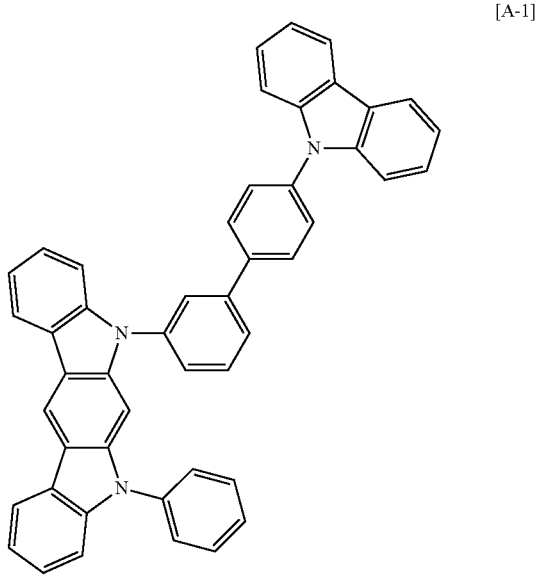

[A-1]

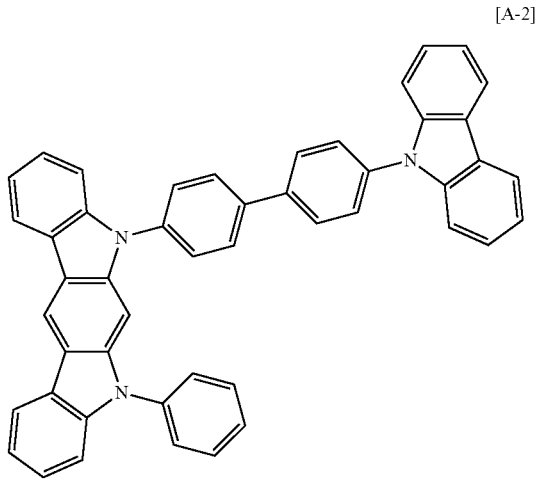

[A-2]

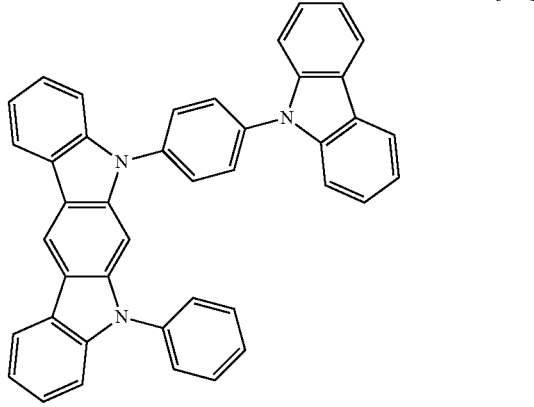

[A-3]

[A-4]
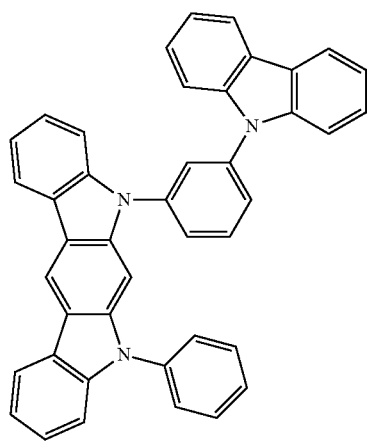
[A-7]
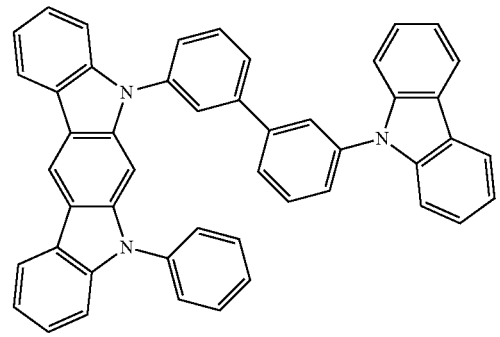
[A-5]
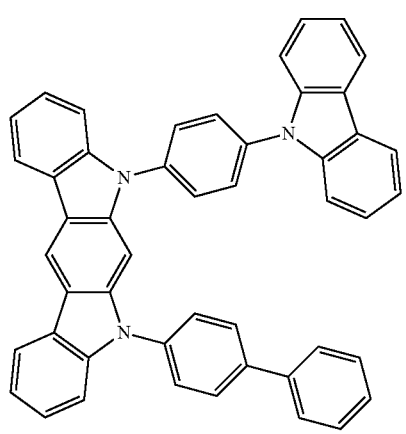
[A-8]
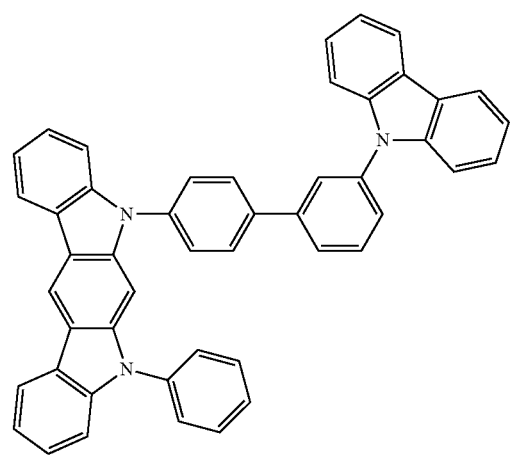
[A-6]
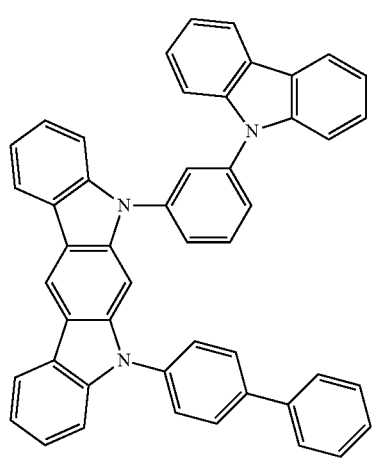
[A-9]
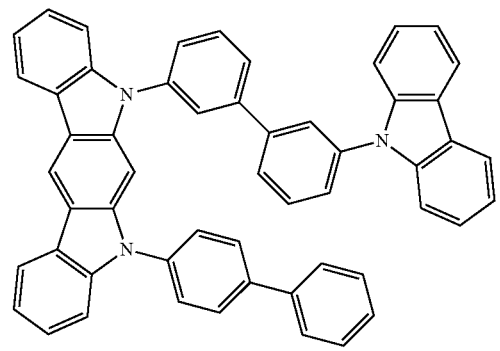

[A-10]
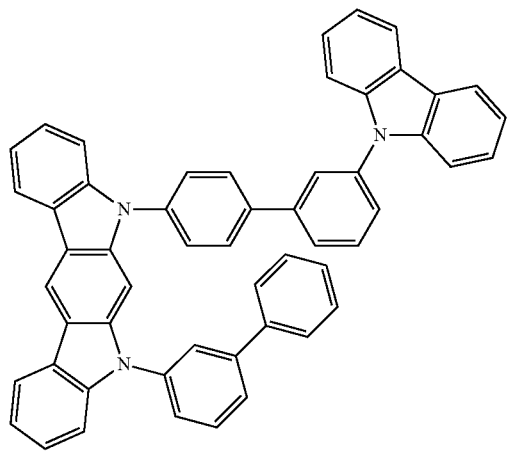
[A-11]
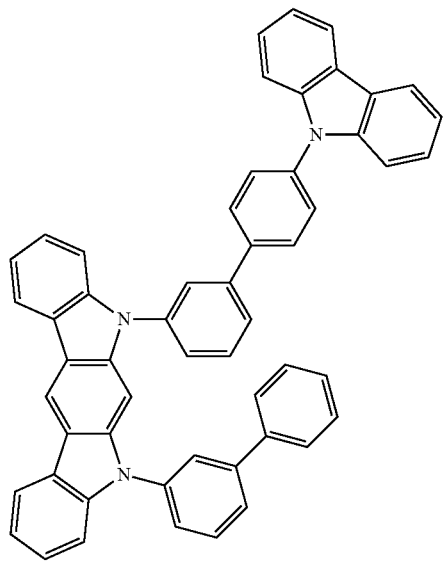
[A-12]
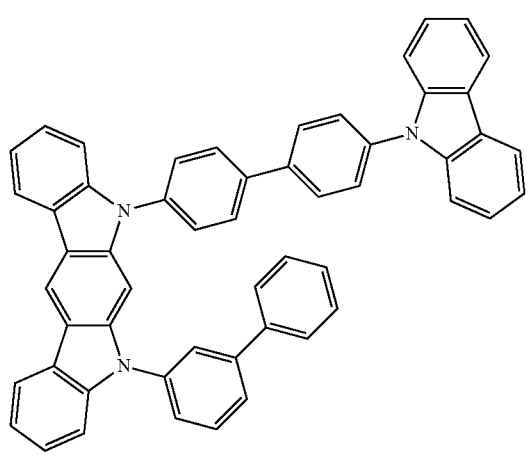
[A-13]
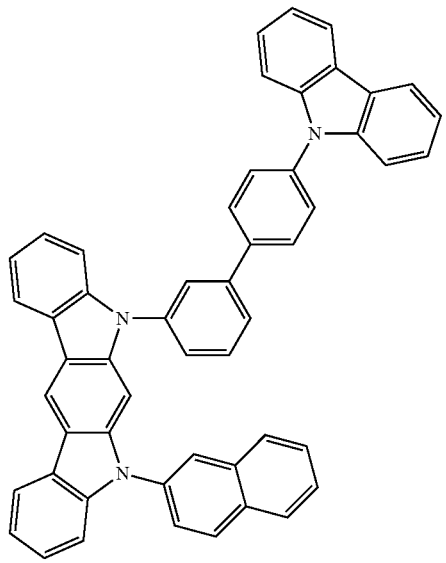
[A-14]
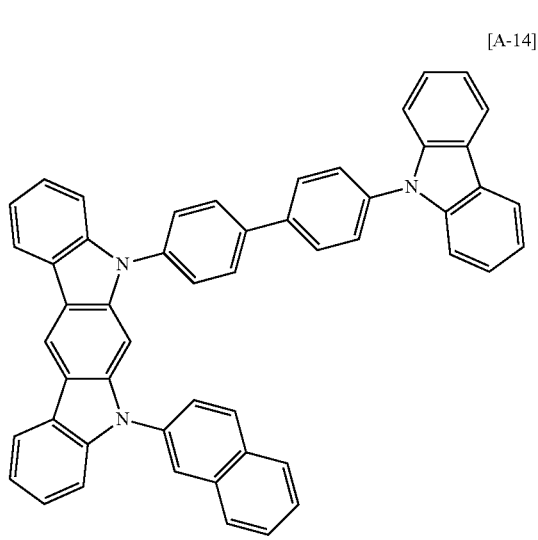
[A-15]
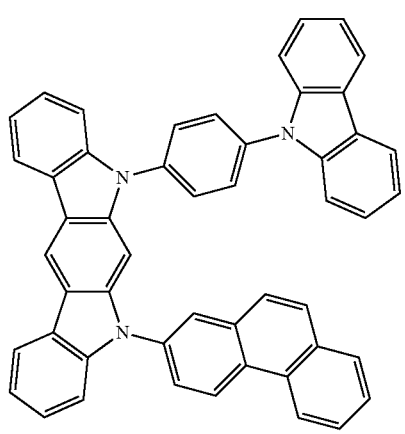

[A-16]
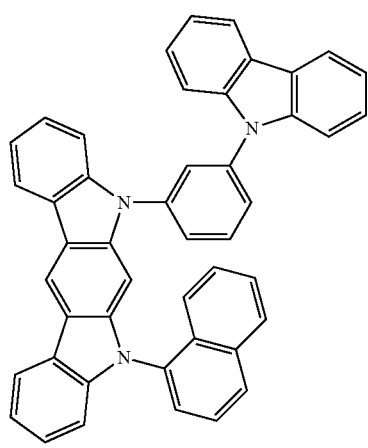
[A-17]
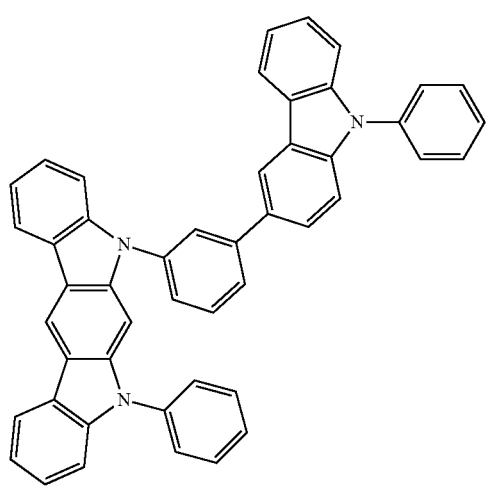
[A-18]
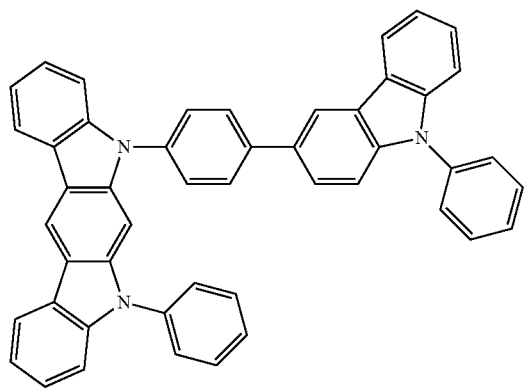
[A-19]
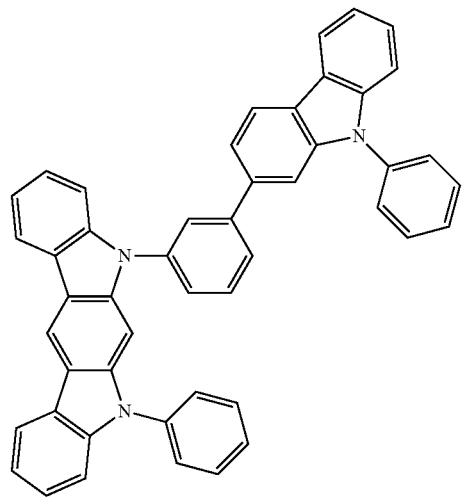
[A-20]
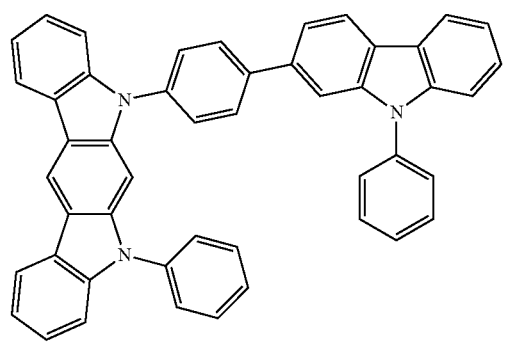
[A-21]
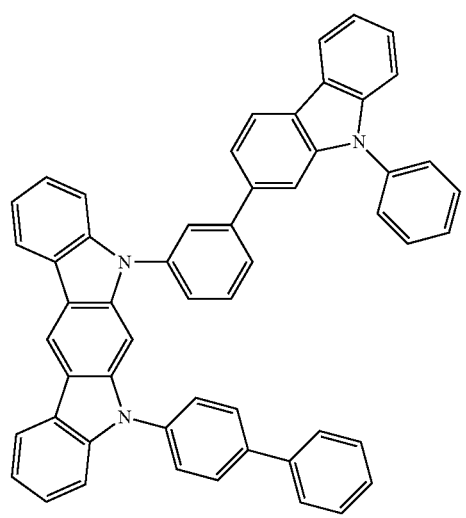

[A-22]
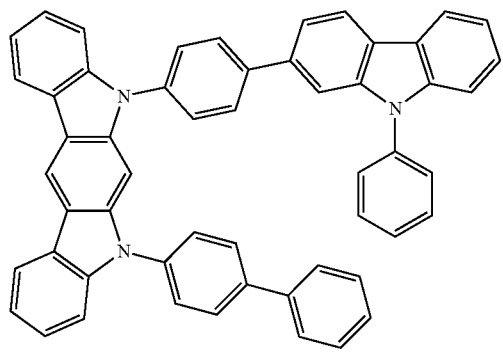
[A-23]
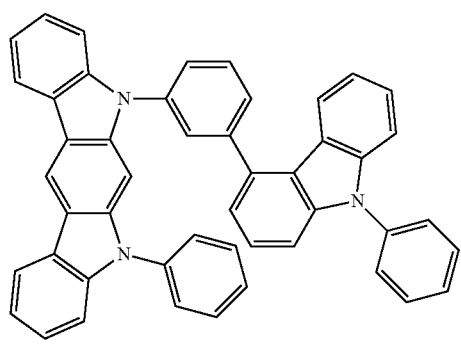
[A-24]
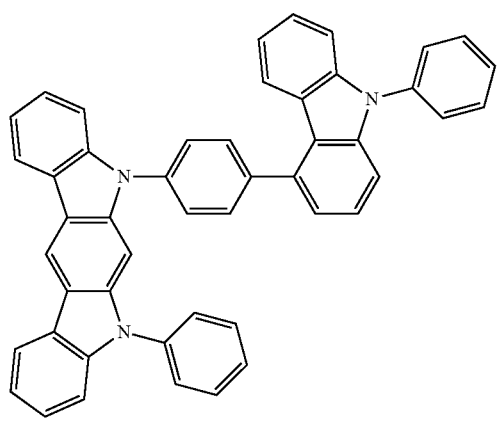
[A-25]
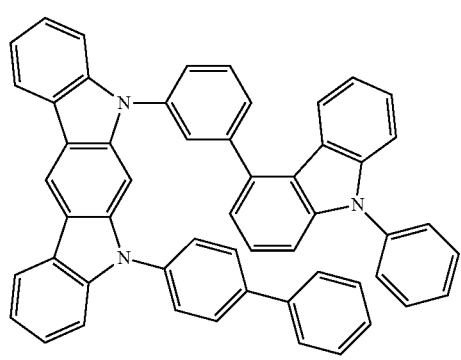
[A-26]
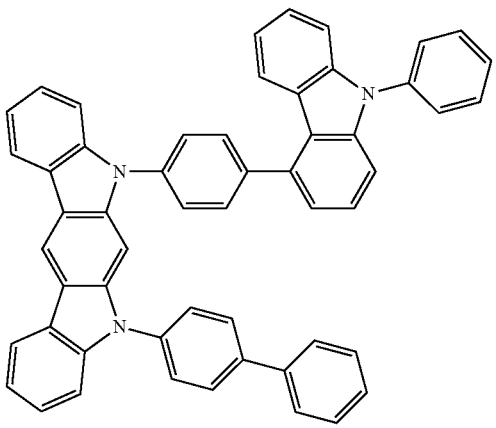
[A-27]
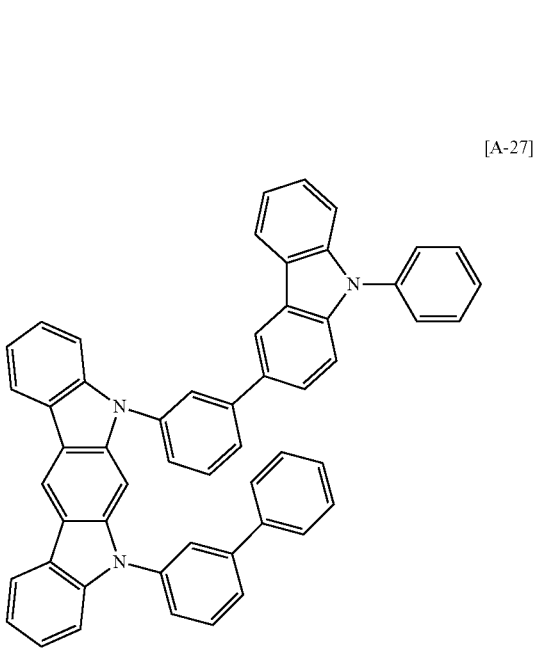
[A-28]
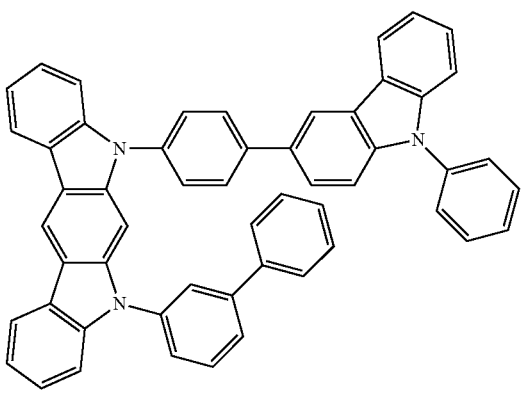

[A-29]
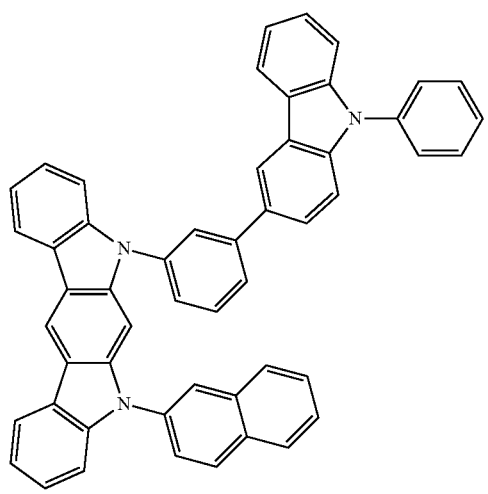
[A-30]
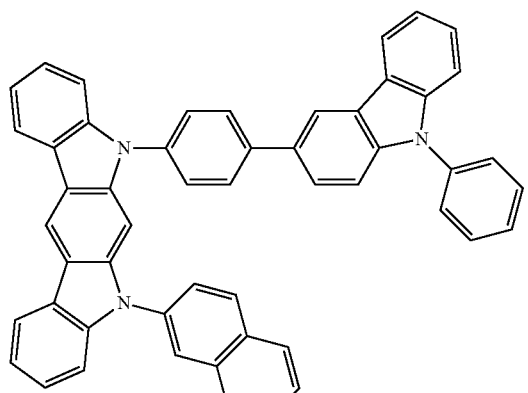
[A-31]
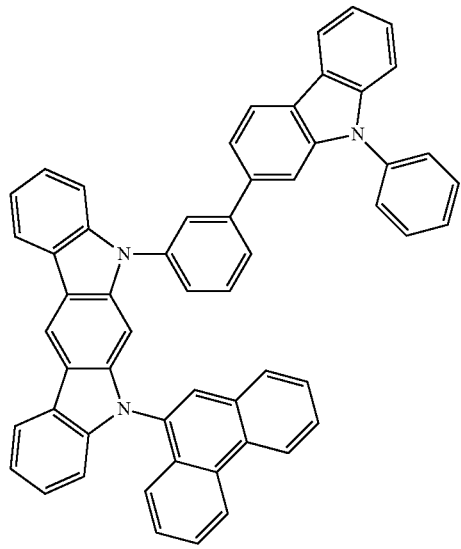
[A-32]
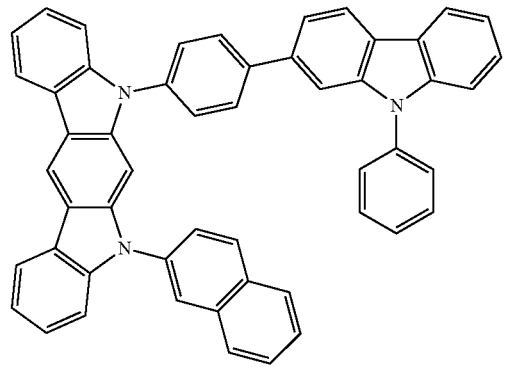
[A-33]
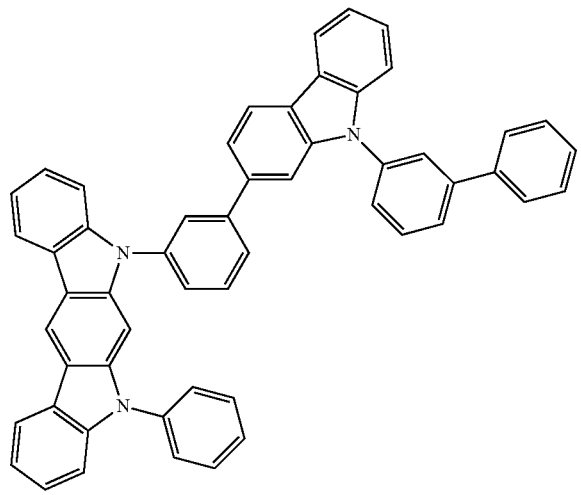
[A-34]
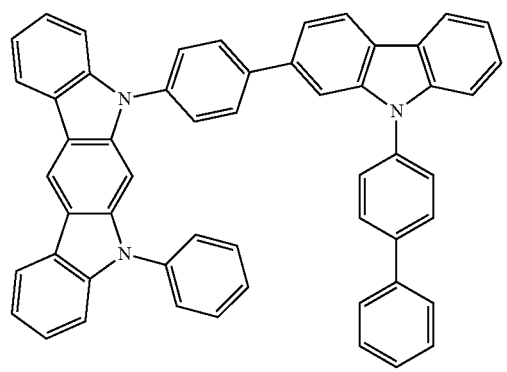

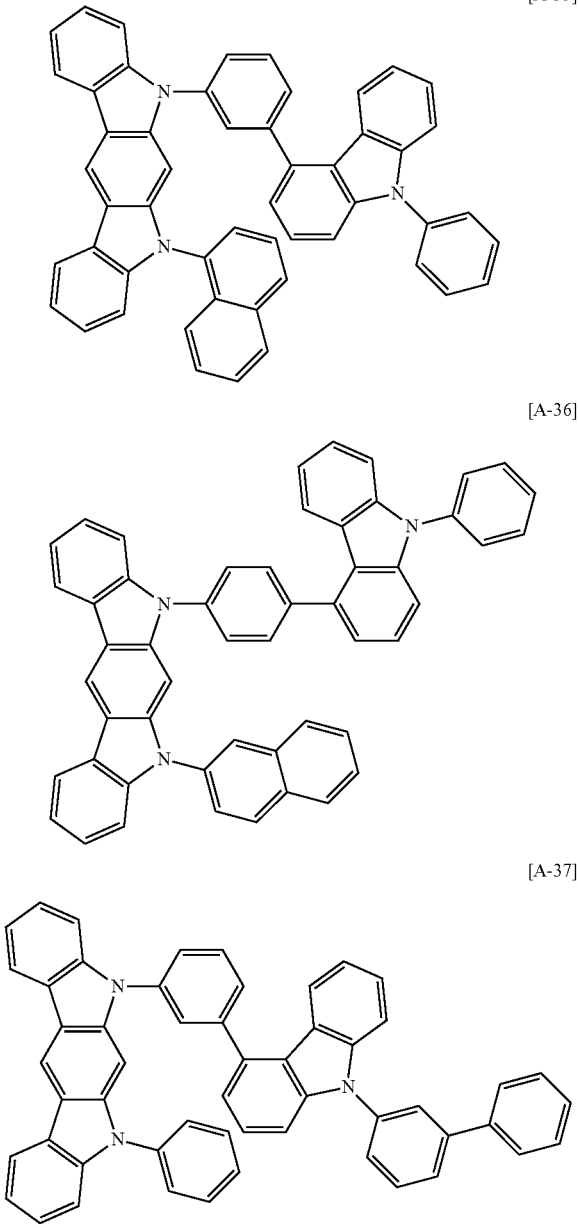
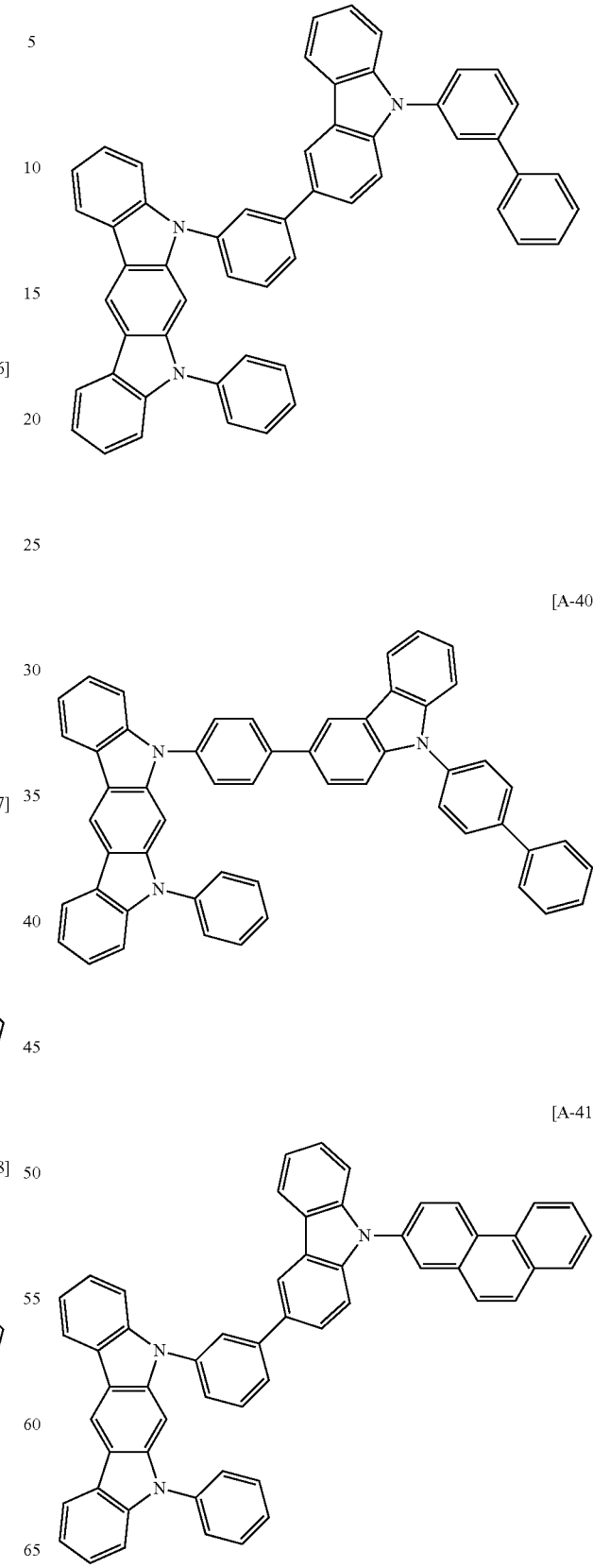

[A-42]
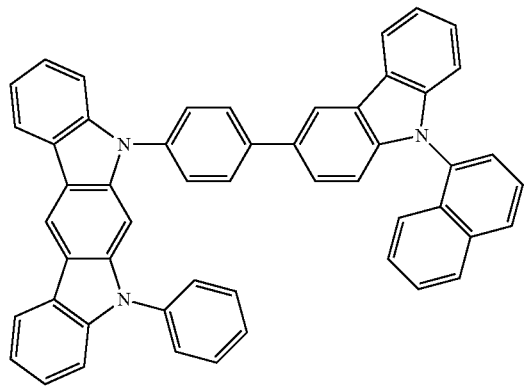
[A-43]
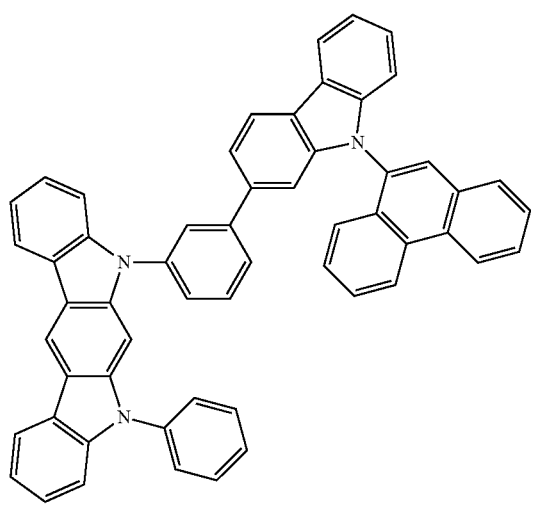
[A-44]
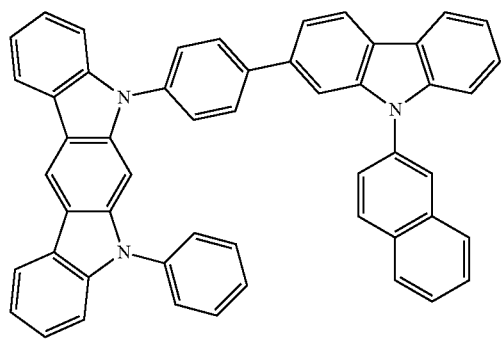
[A-45]
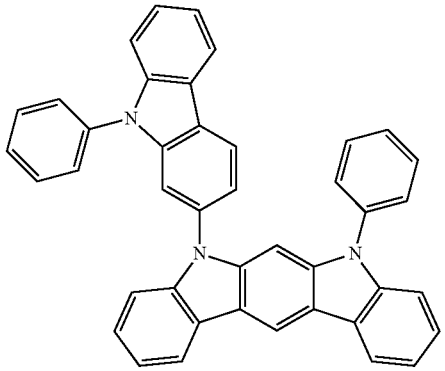
[A-46]
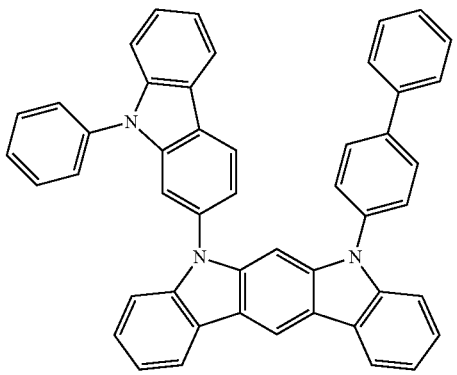
[A-47]
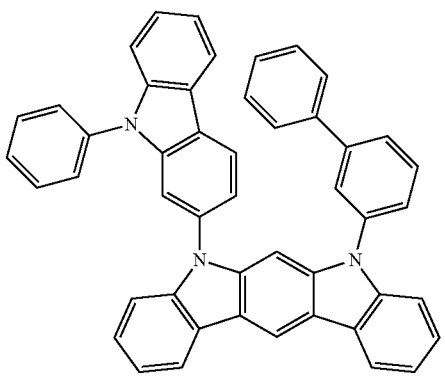
[A-48]
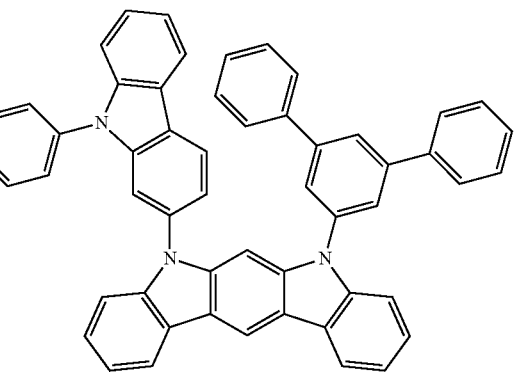

[A-49]
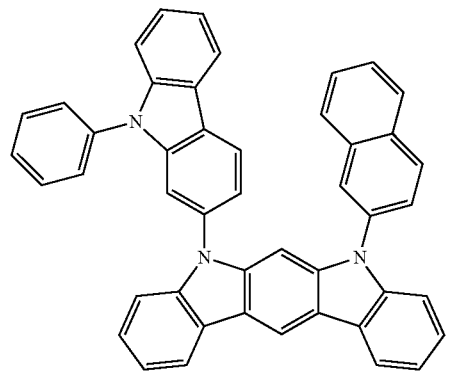
[A-50]
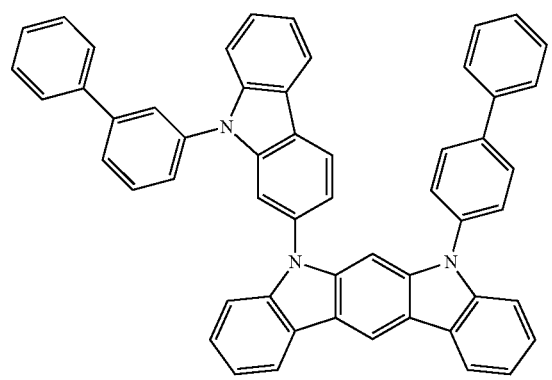
[A-51]
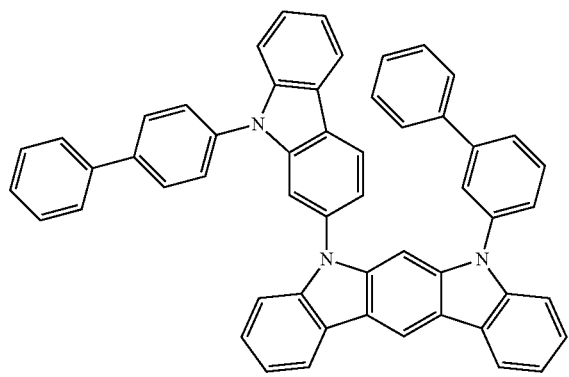
[A-52]
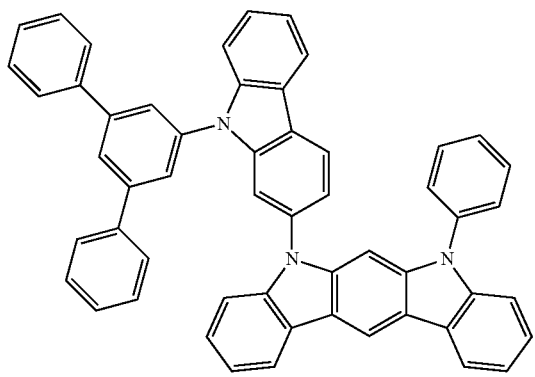
[A-53]
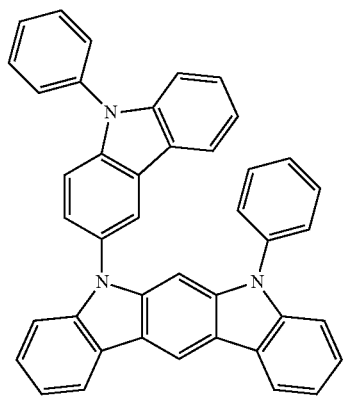
[A-54]
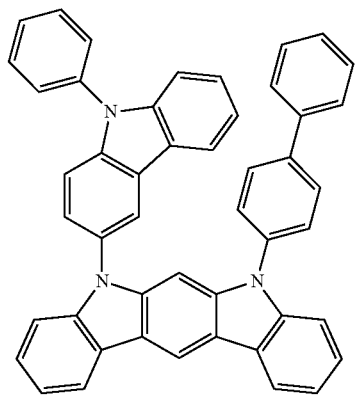
[A-55]
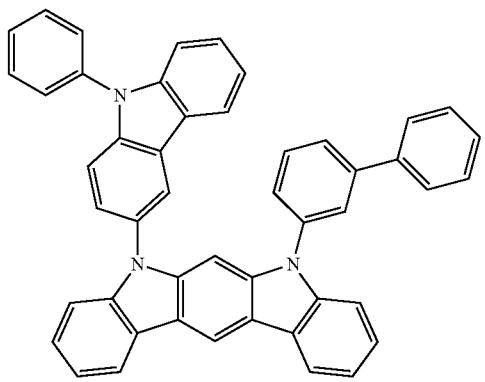
[A-56]
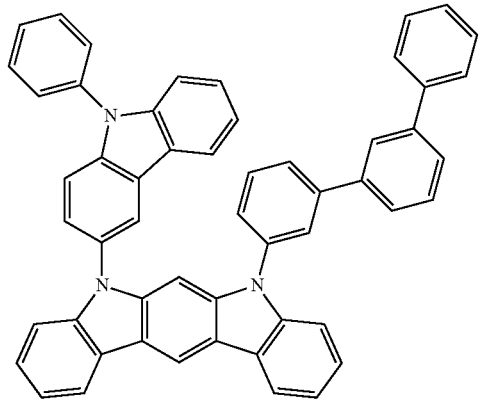

[A-57]
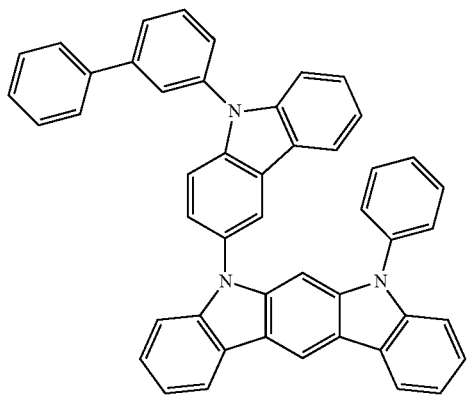
[A-58]
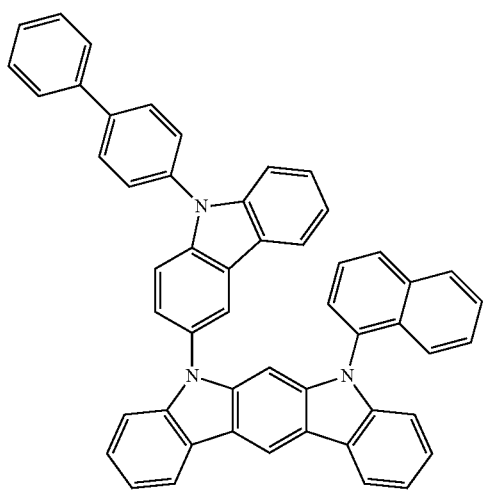
[A-59]
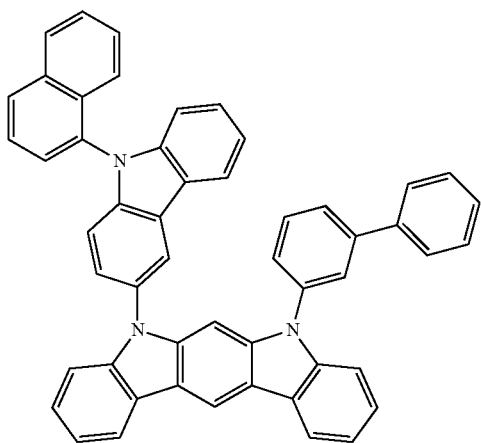
[A-60]
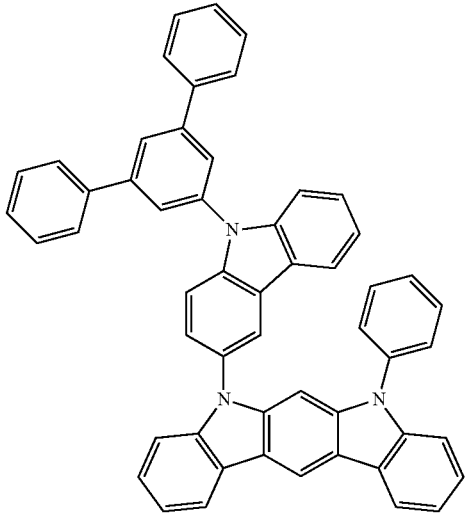
[A-61]
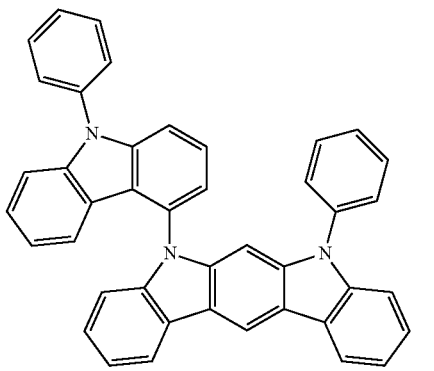
[A-62]
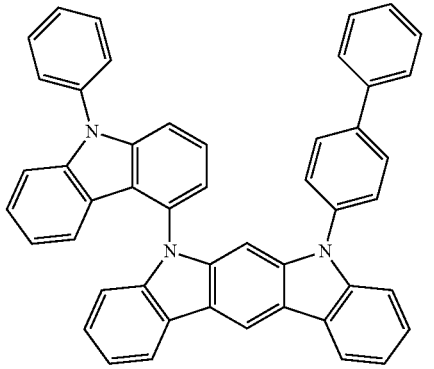
[A-63]
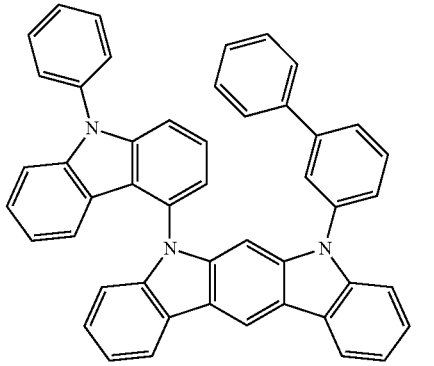

[A-64]
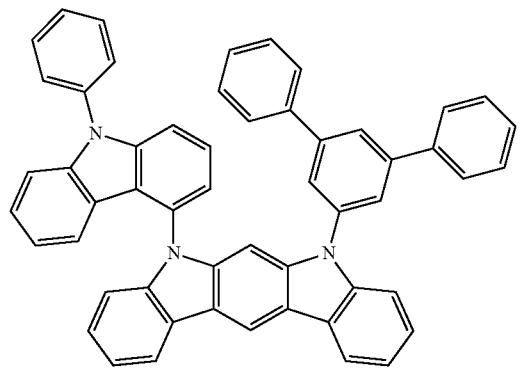
[A-65]
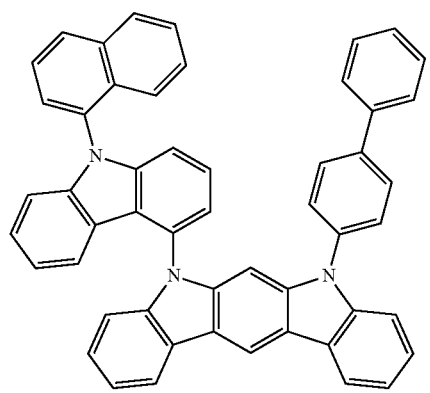
[A-66]
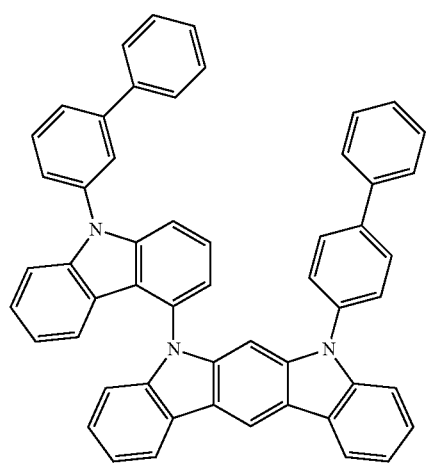
[A-67]
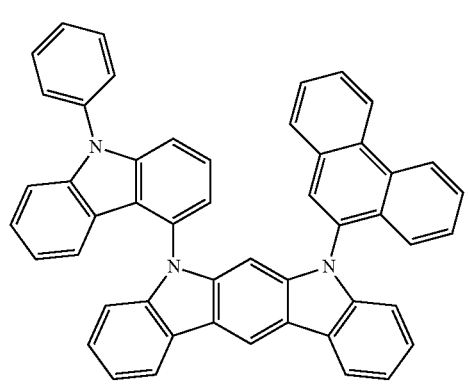
[A-68]
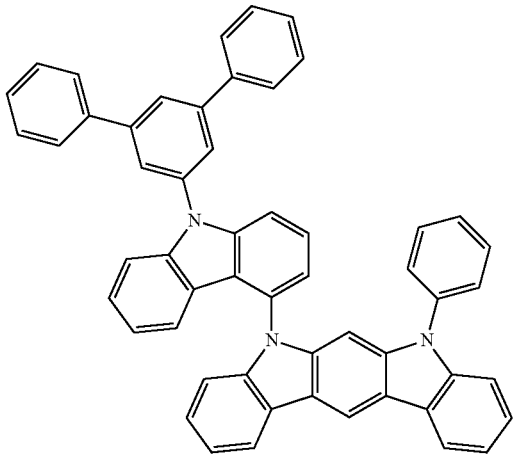
[A-69]
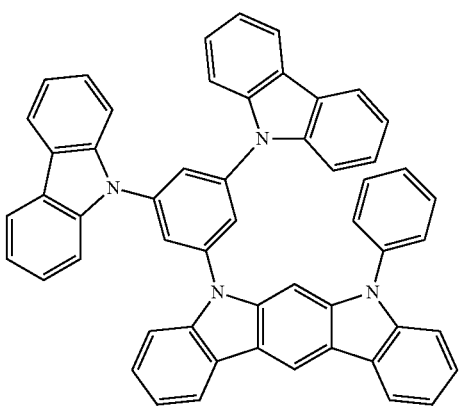
[A-70]
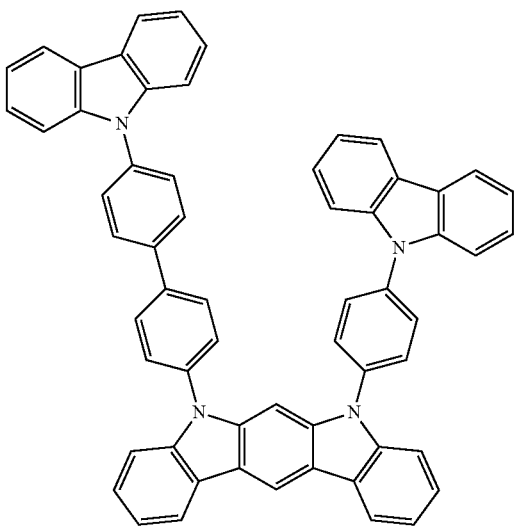

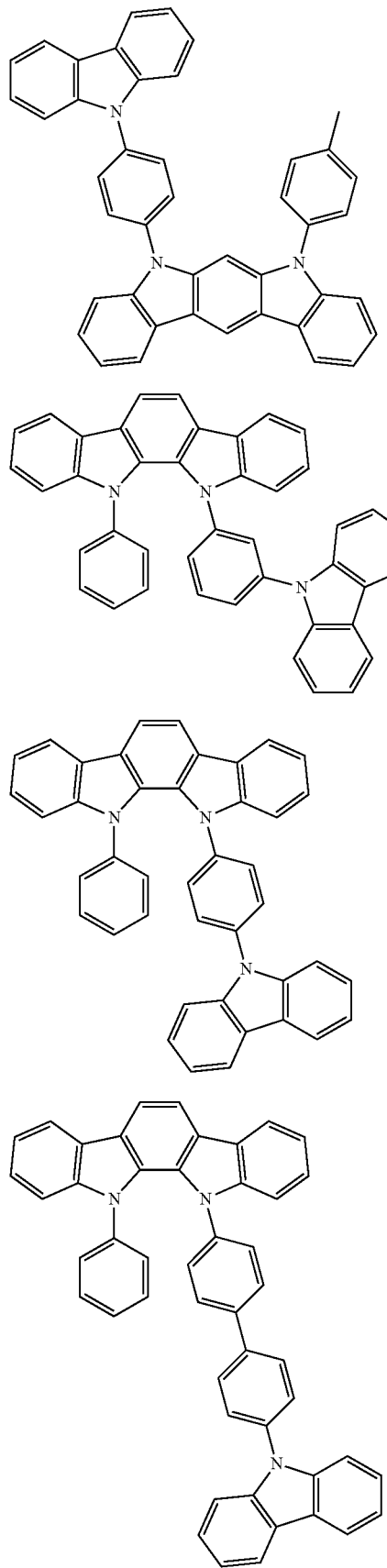
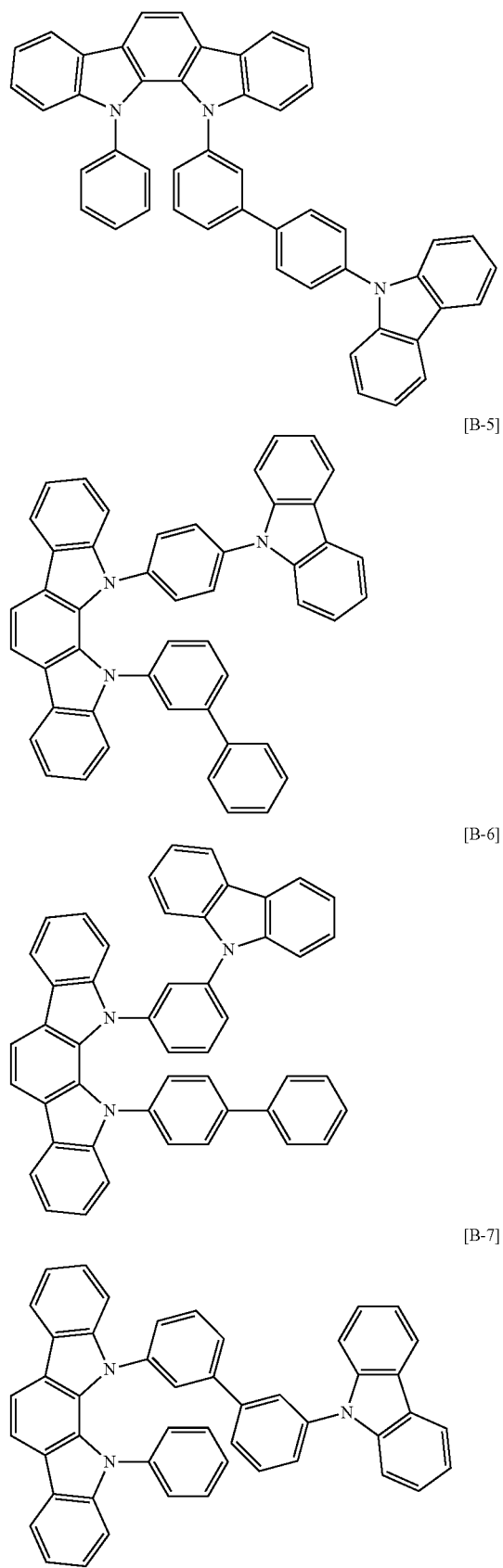

[B-8]
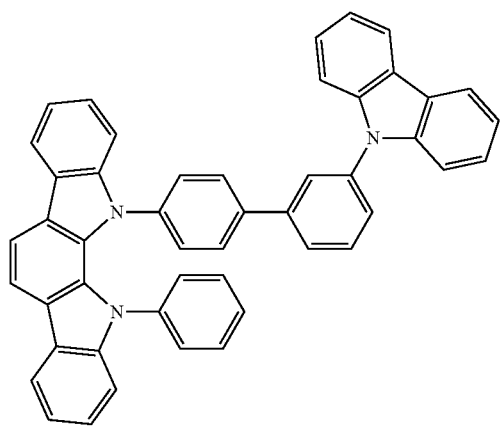
[B-9]
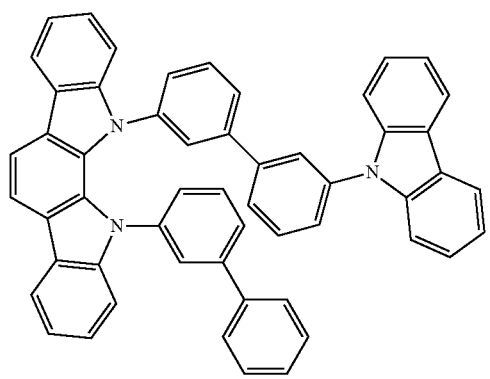
[B-10]
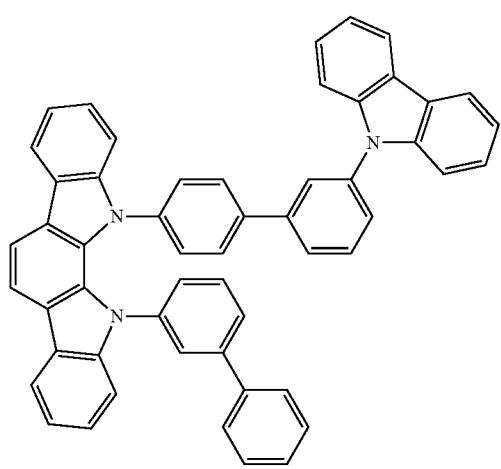
[B-11]
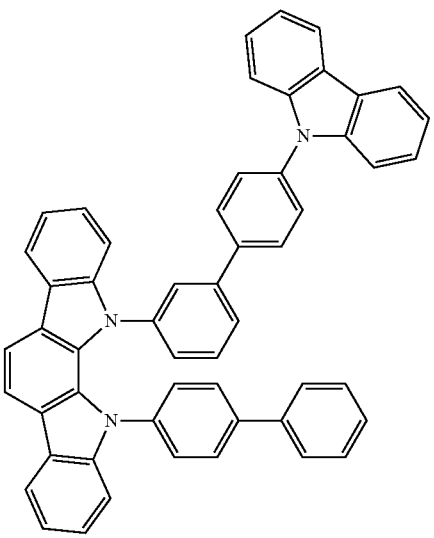
[B-12]
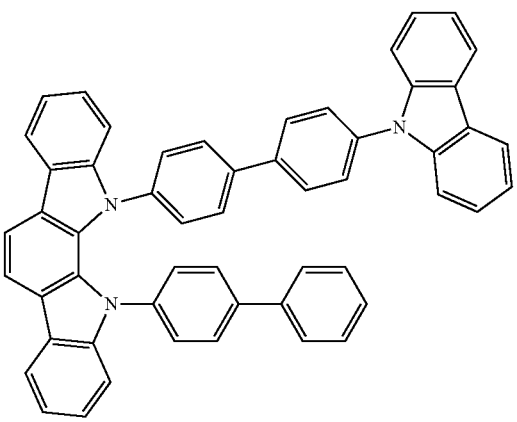
[B-13]
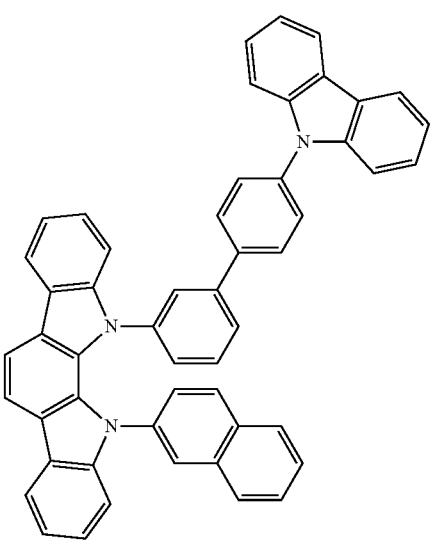

[B-14]
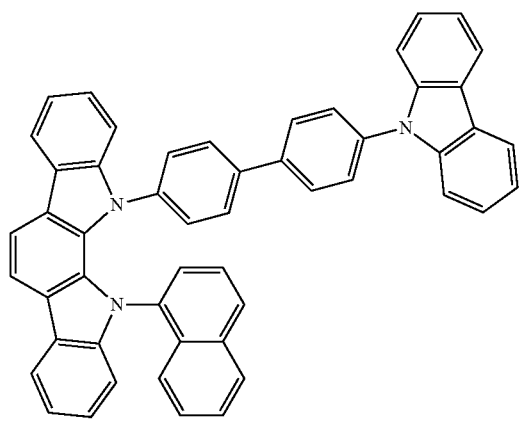
[B-17]
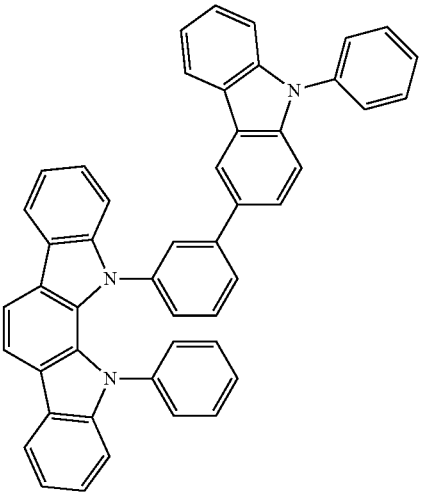
[B-15]
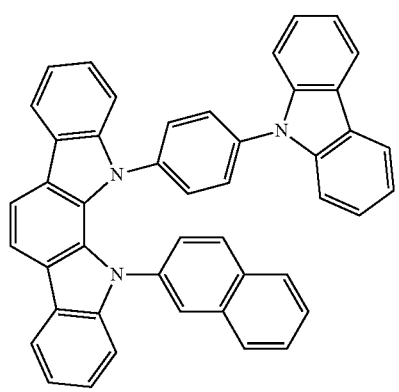
[B-18]
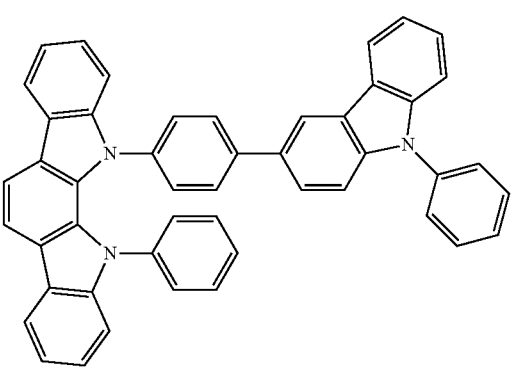
[B-16]
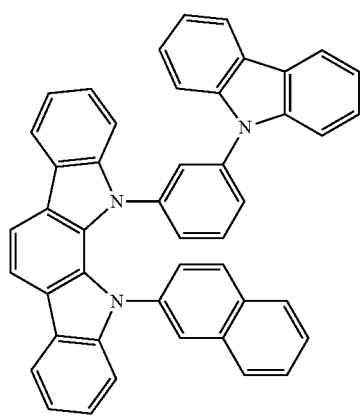
[B-19]
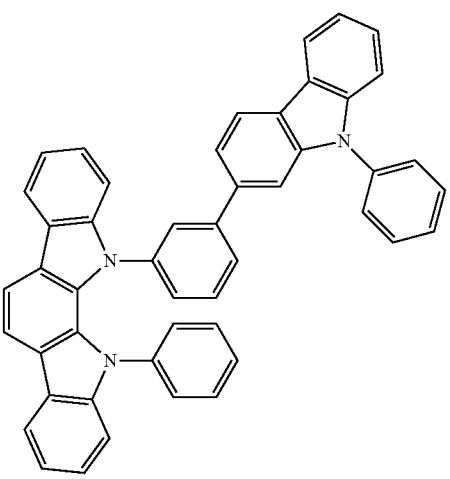

[B-20]
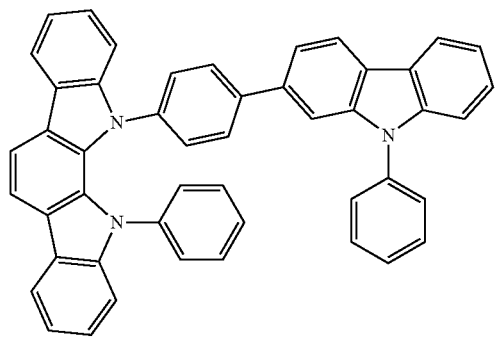
[B-21]
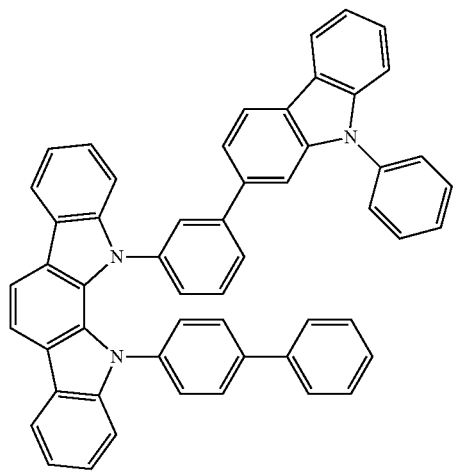
[B-22]
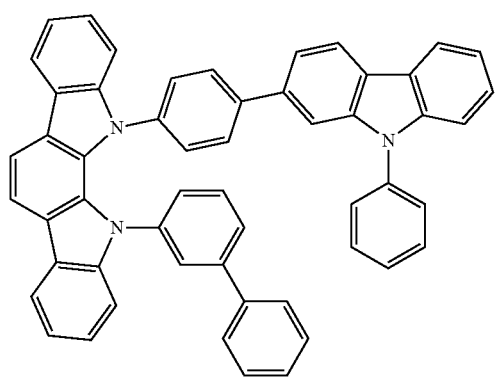
[B-23]
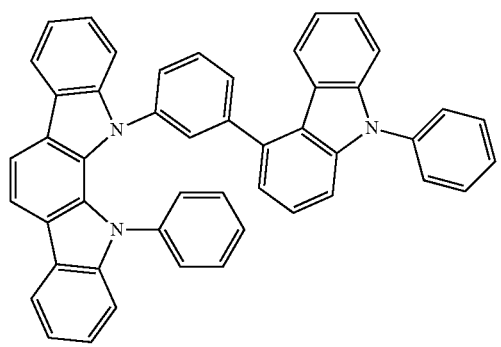
[B-24]
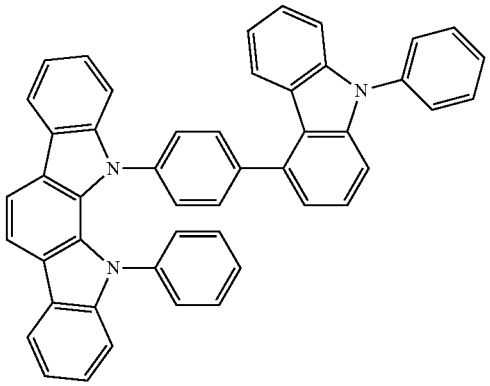
[B-25]
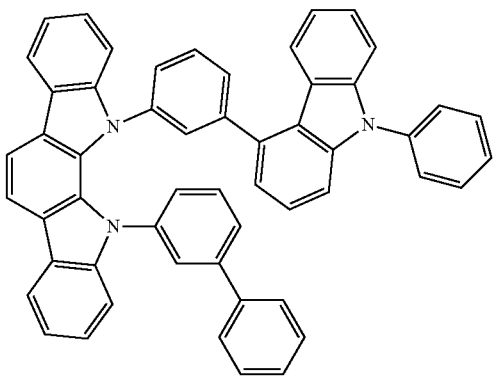
[B-26]
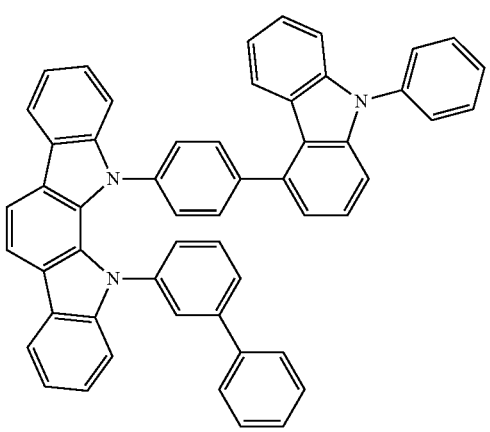

[B-27]
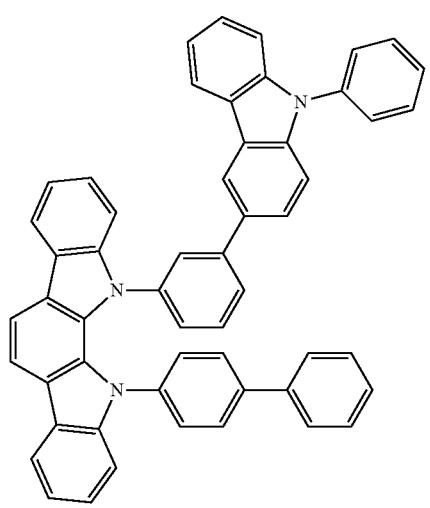
[B-30]
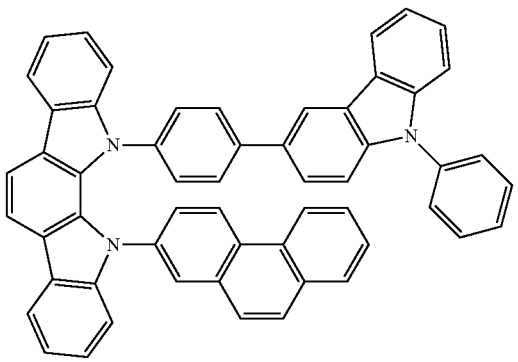
[B-28]
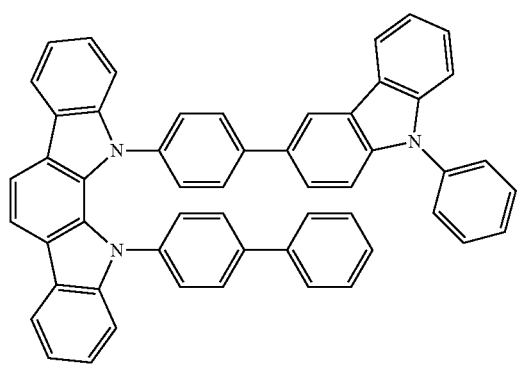
[B-31]
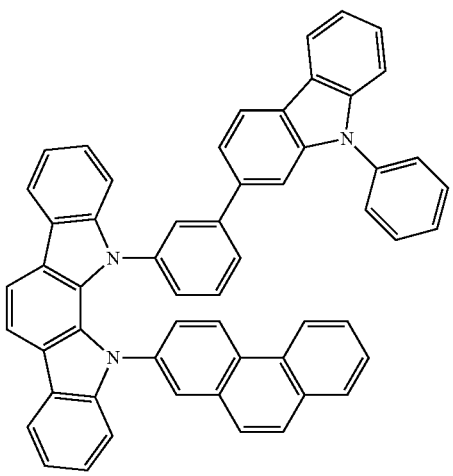
[B-29]
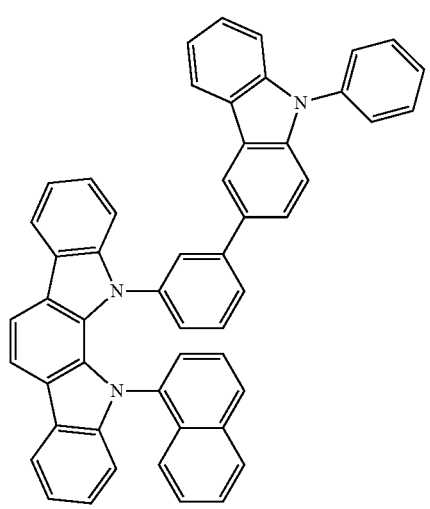
[B-32]
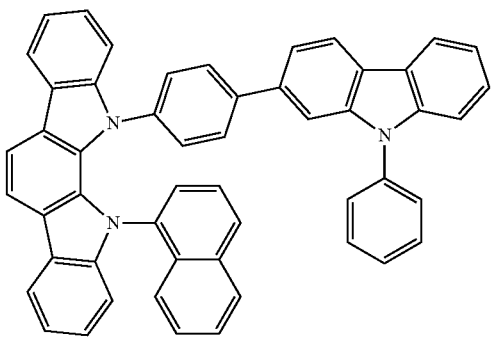

[B-33]
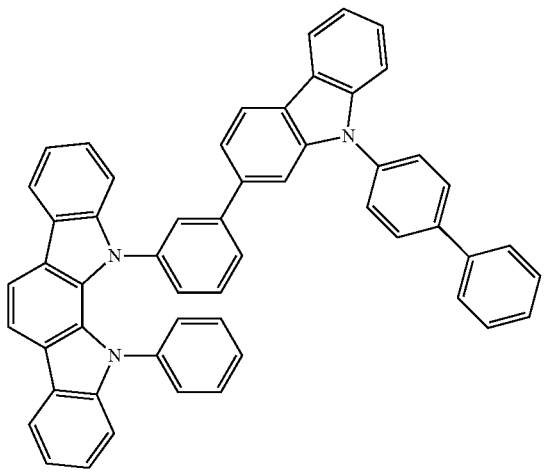
[B-34]
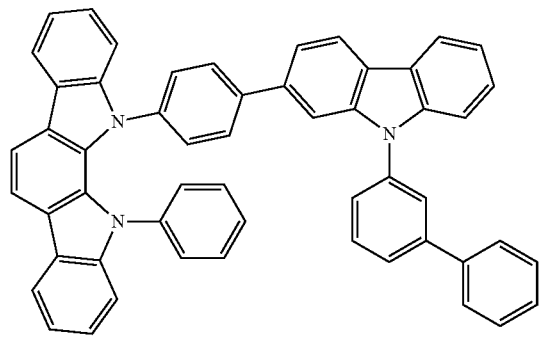
[B-35]
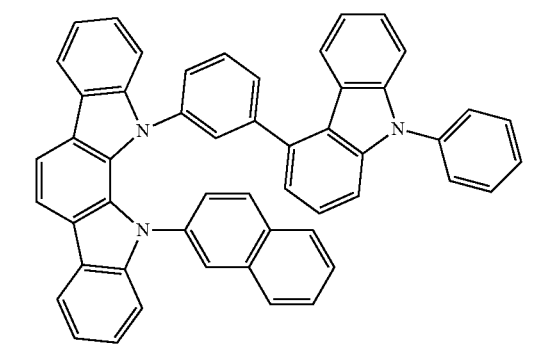
[B-36]
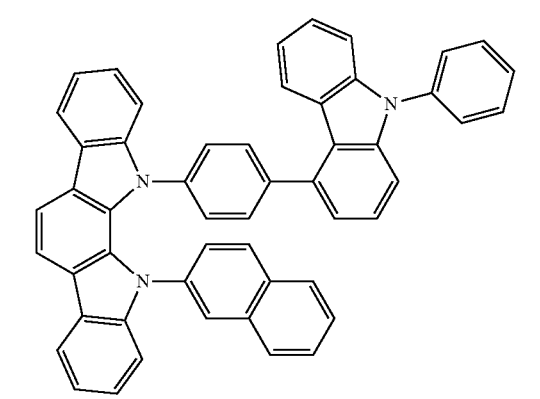
[B-37]
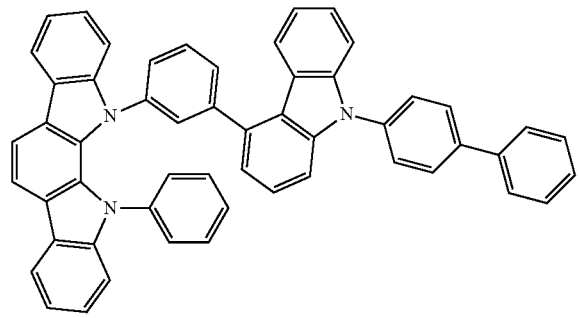
[B-38]
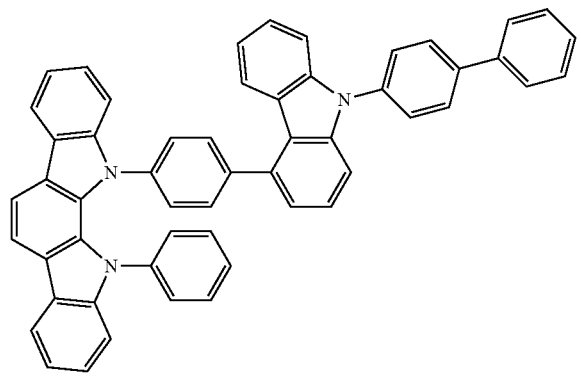
[B-39]
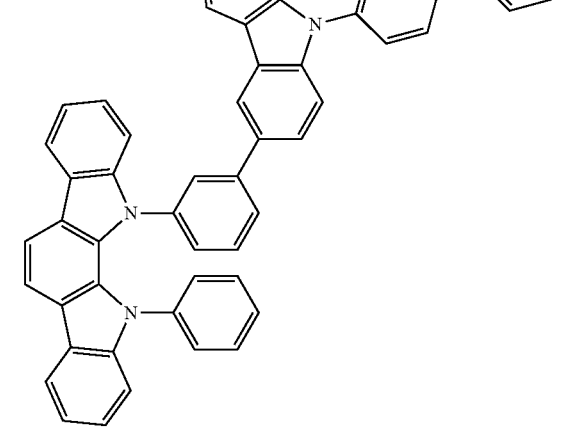
[B-40]
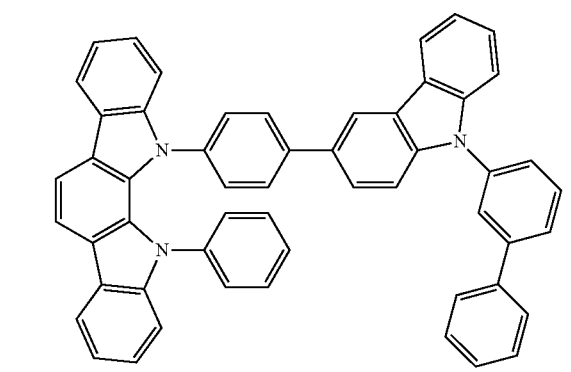

[B-41]
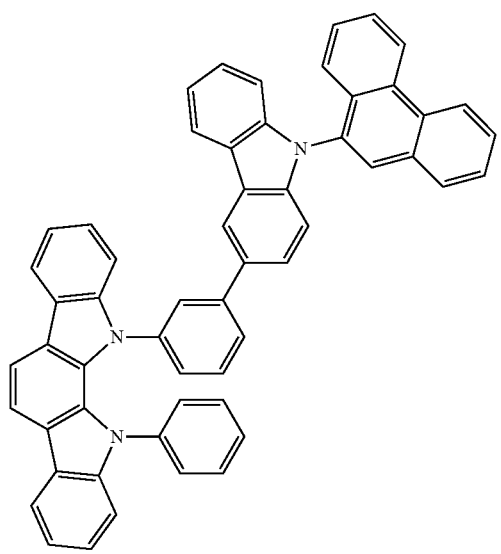
[B-42]
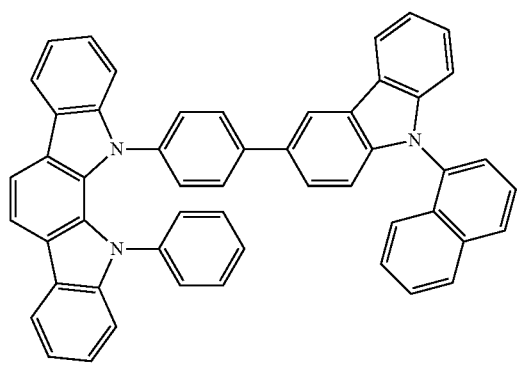
[B-43]
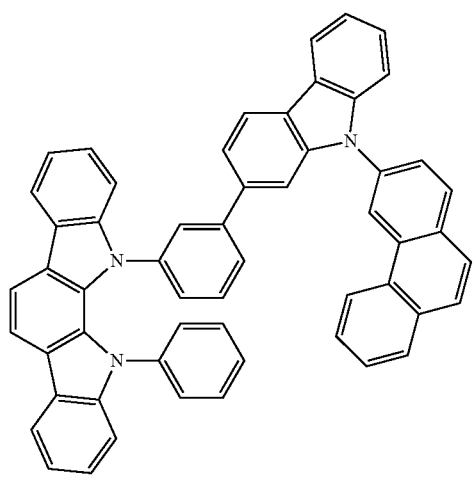
[B-44]
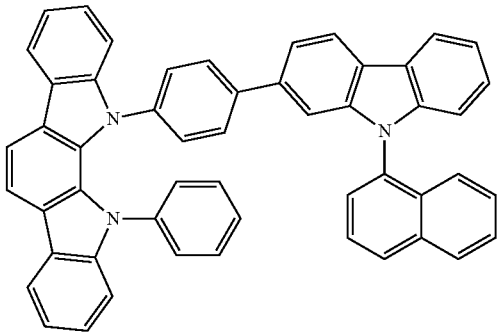
[B-45]
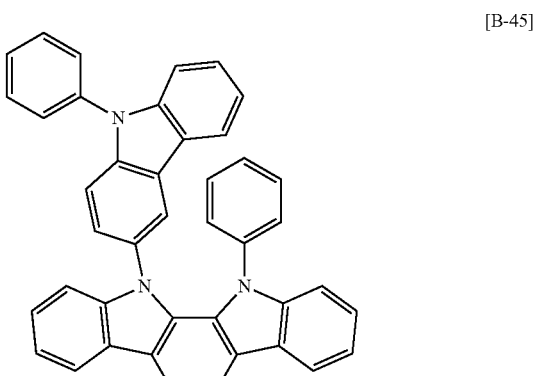
[B-46]
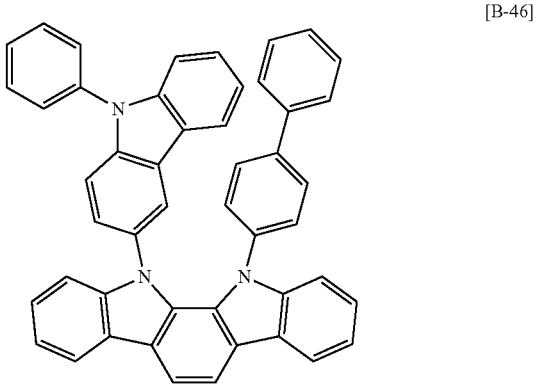
[B-47]
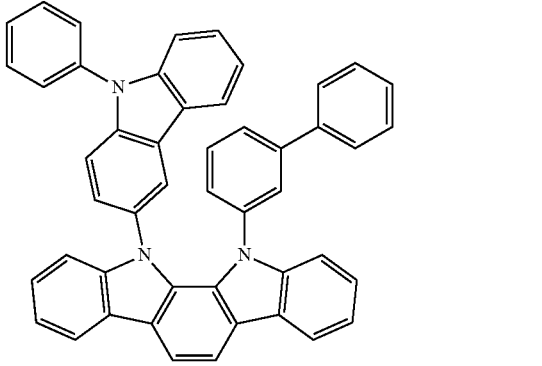

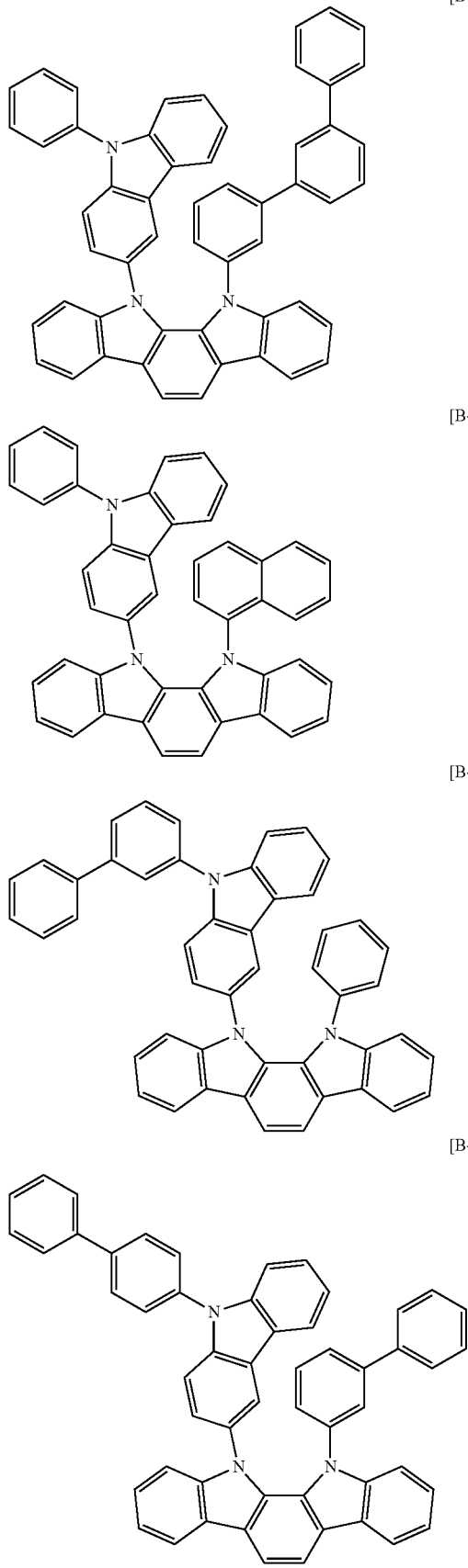
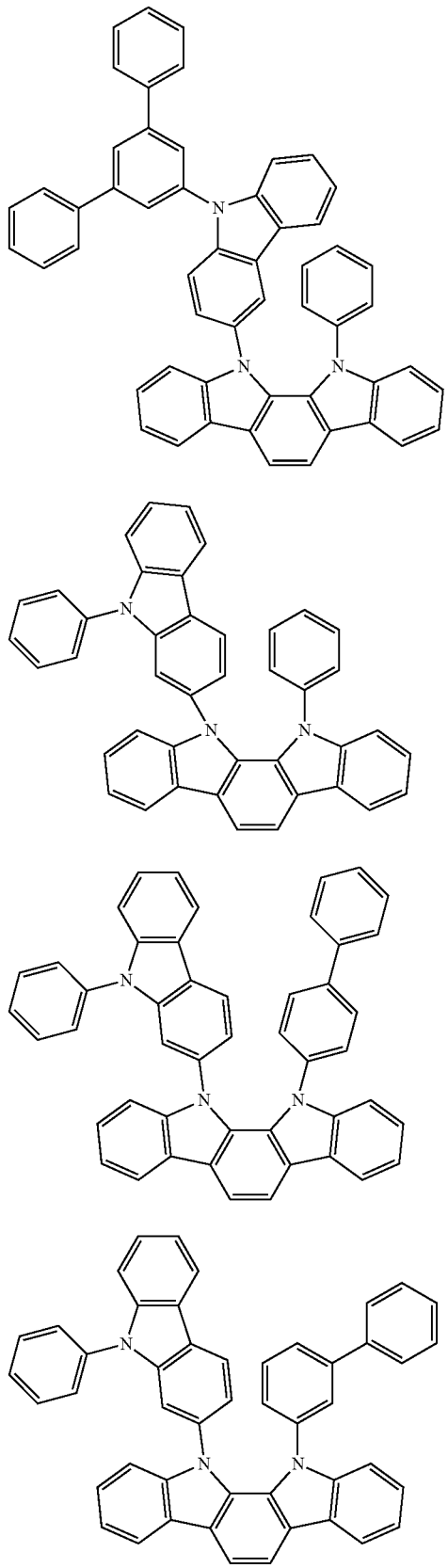

-continued
[B-56]
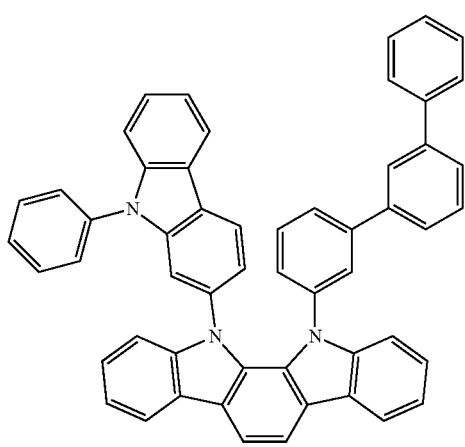
[B-57]
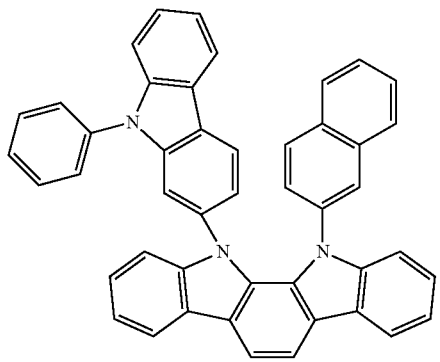
[B-58]
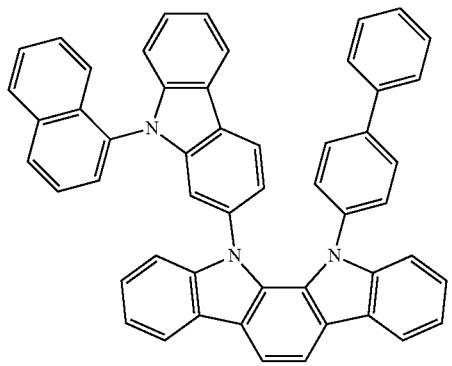
[B-59]
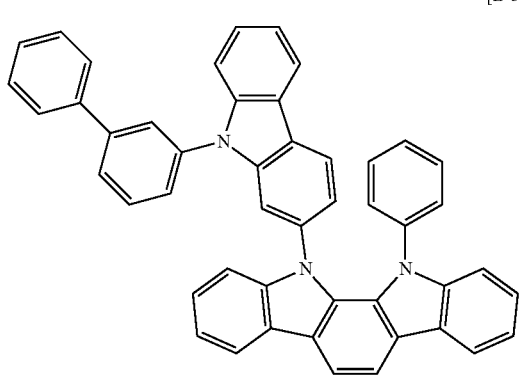
-continued
[B-60]
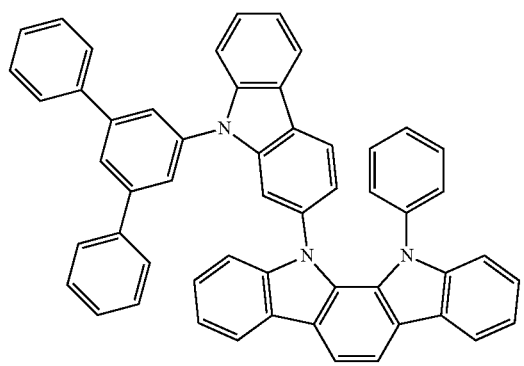
[B-61]
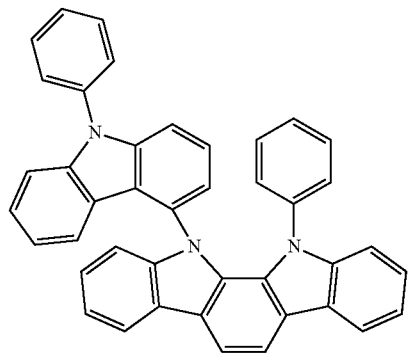
[B-62]
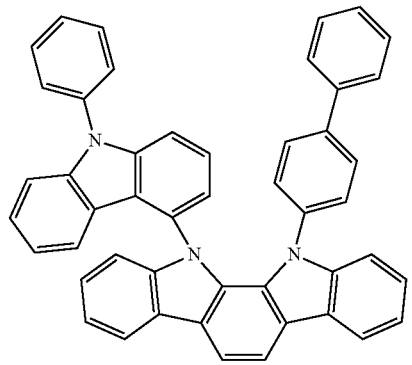
[B-63]
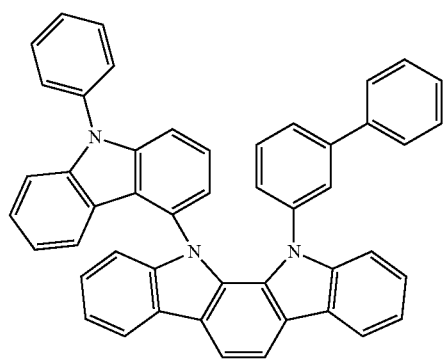

[B-64]
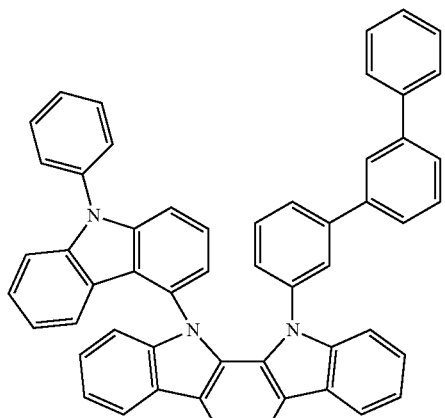
[C-3]
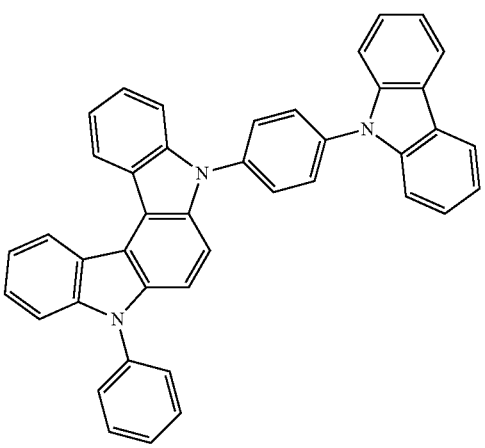
[C-1]
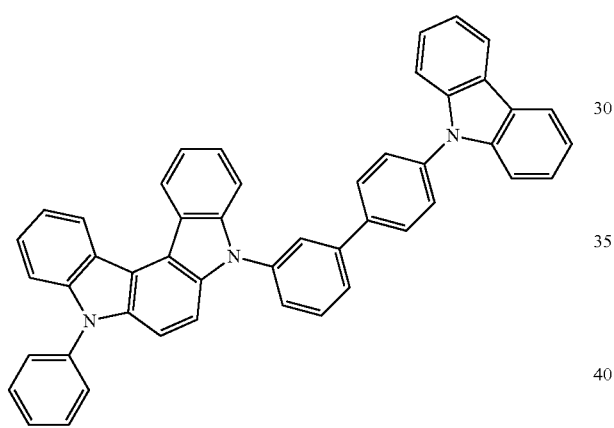
[C-4]
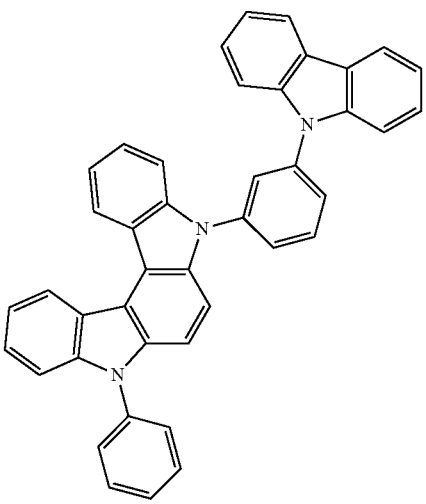
[C-2]
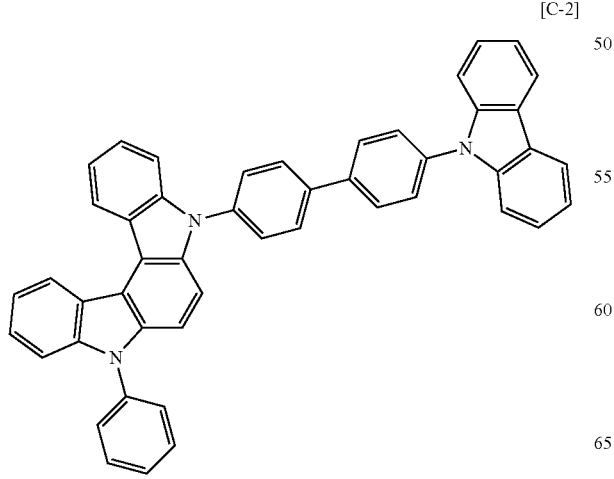
[C-5]
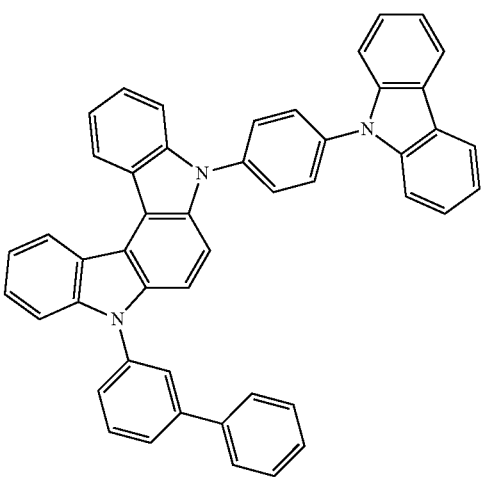

[C-6]
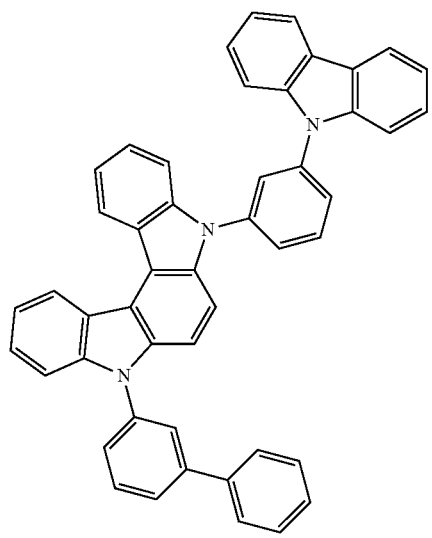
[C-9]
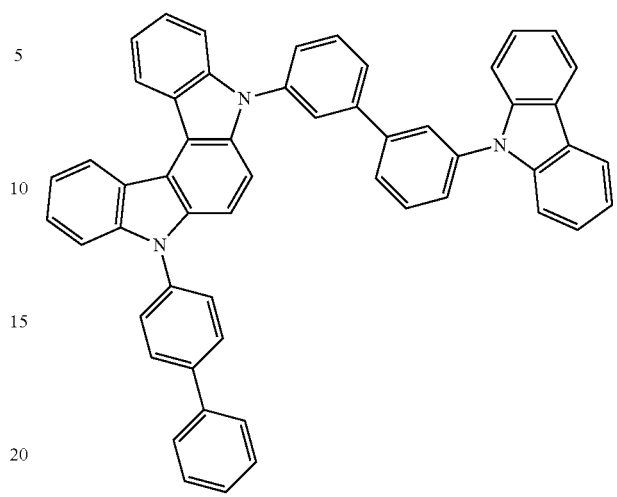
[C-7]
[C-10]
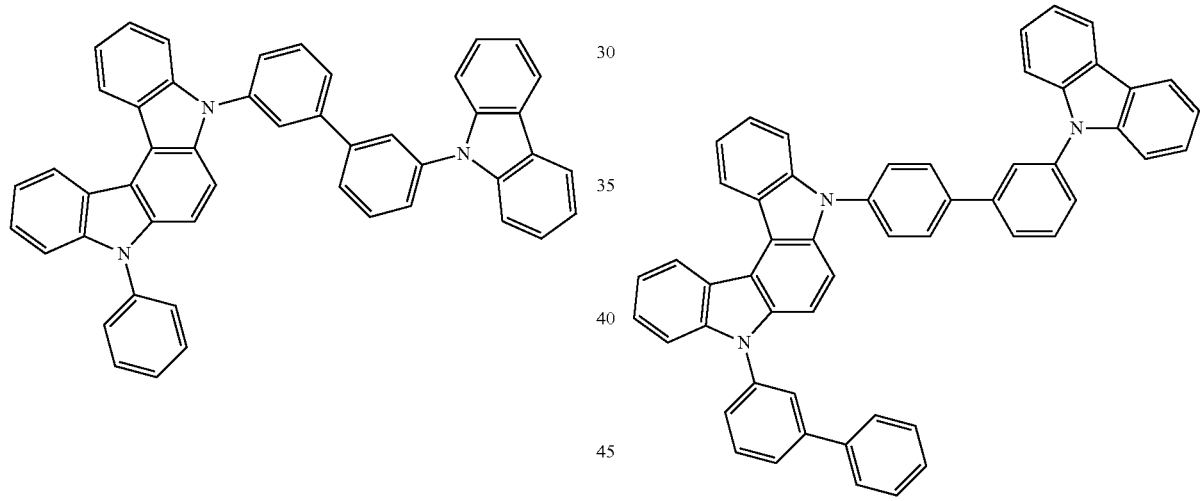
[C-8]
[C-11]
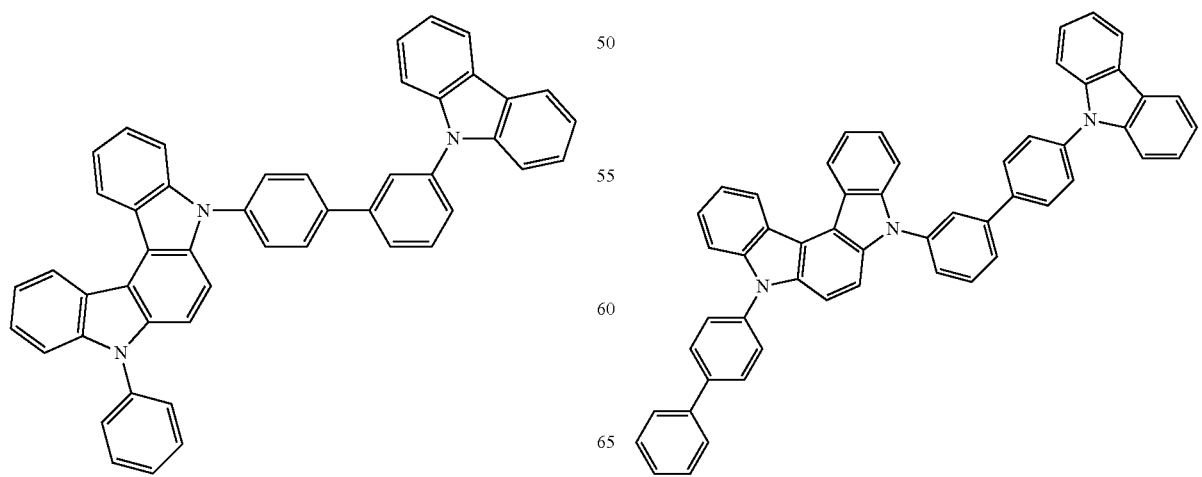

[C-12]
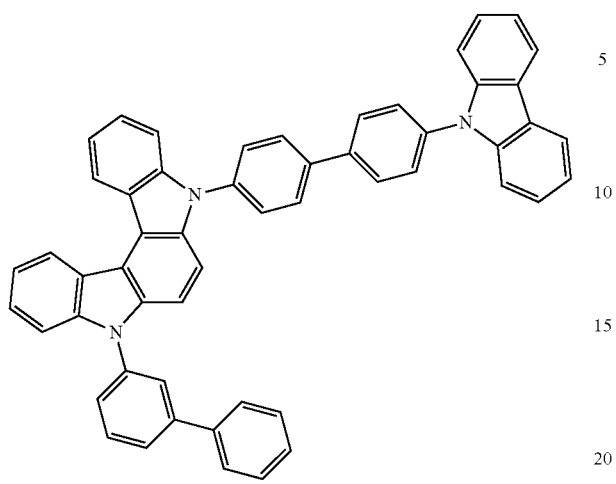
[C-15]
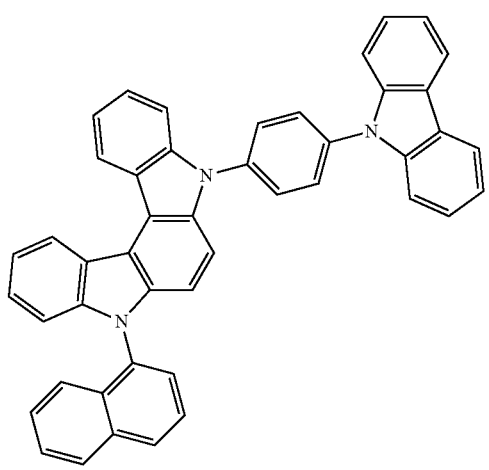
[C-13]
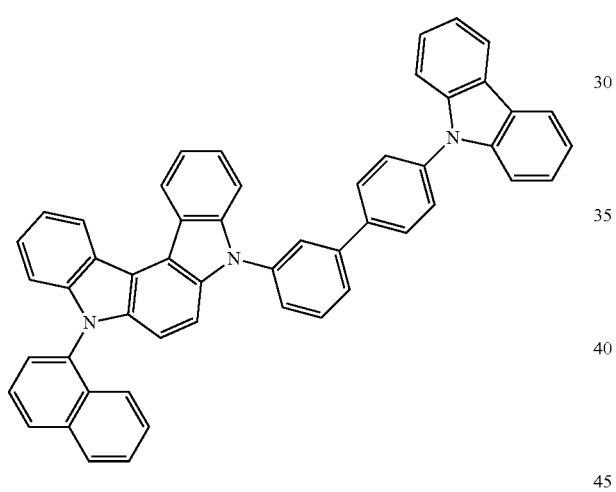
[C-16]
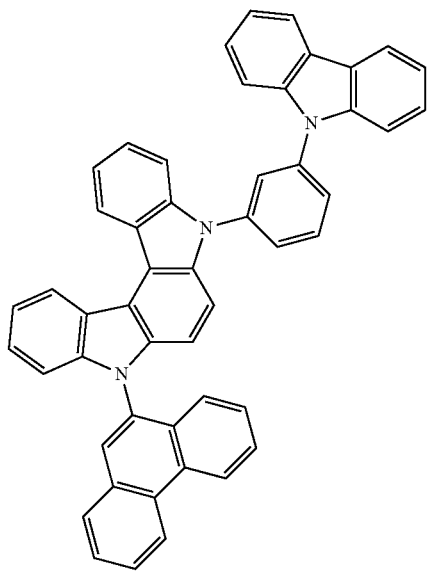
[C-14]
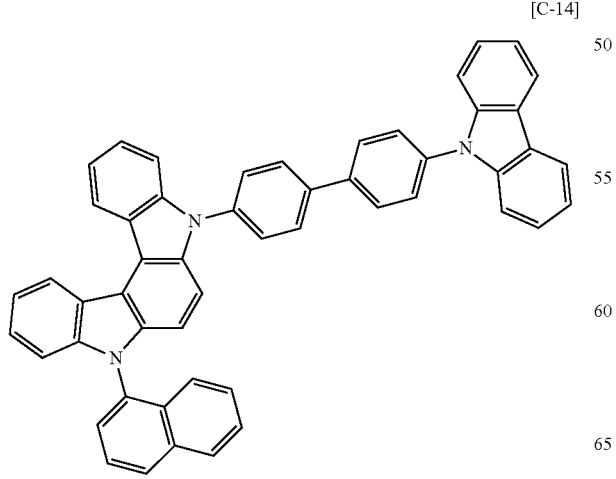
[C-17]
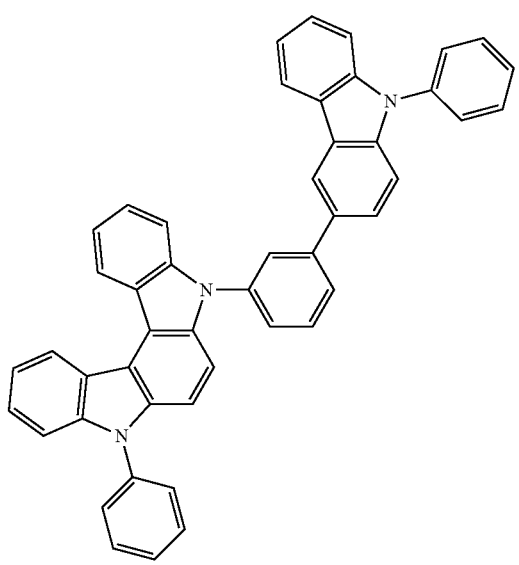

-continued
[C-18]
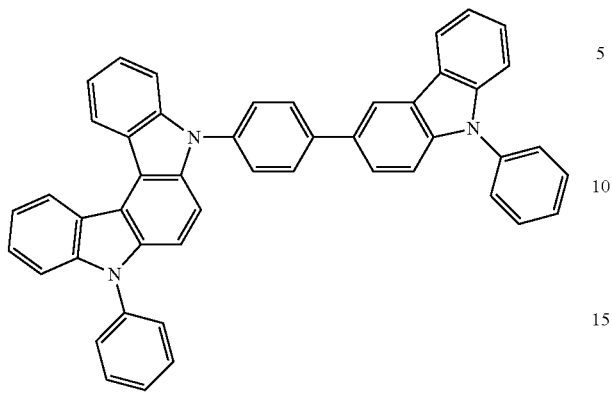
[C-19]
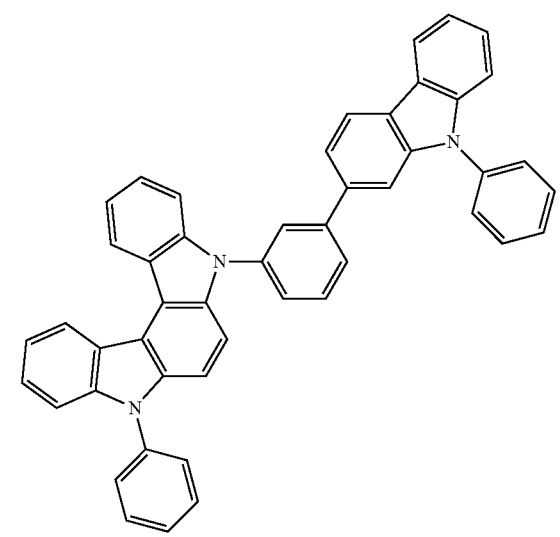
[C-20]
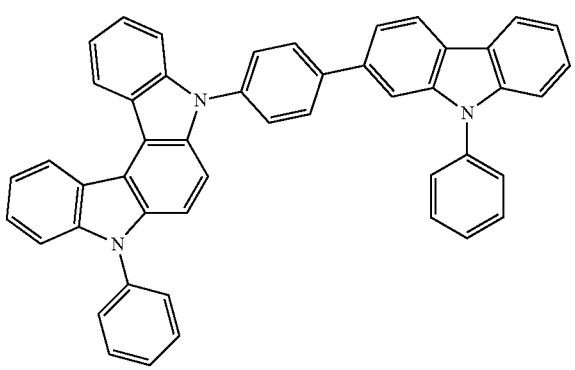
[C-21]
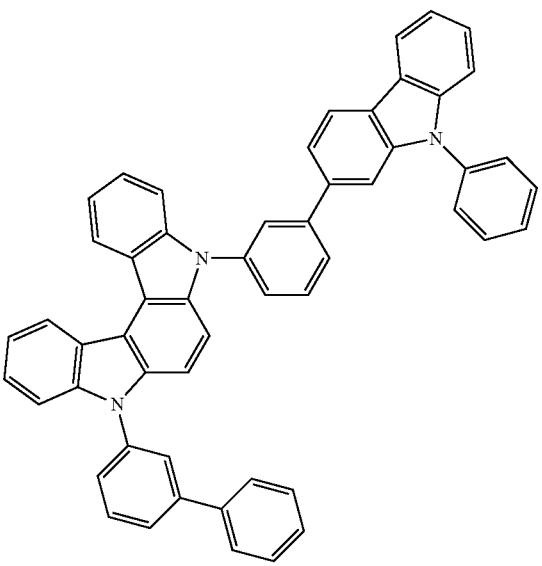
[C-22]
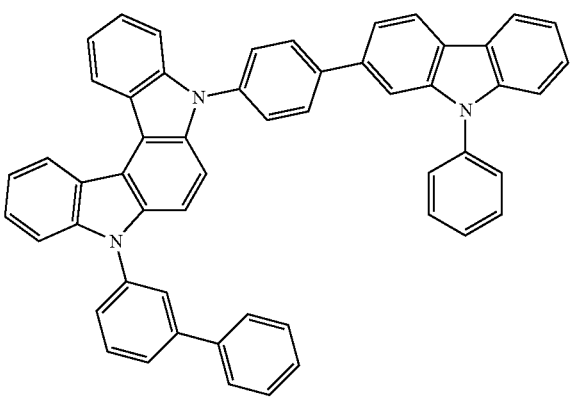
[C-23]
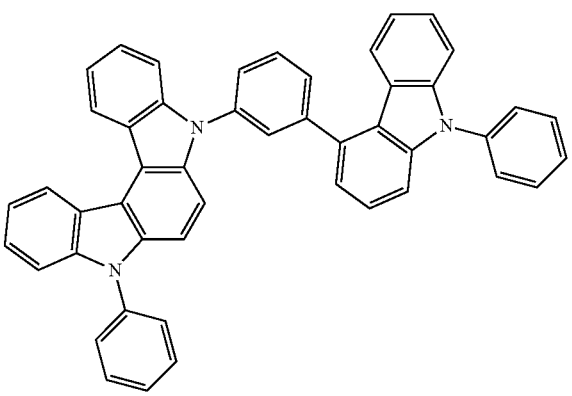

[C-24]
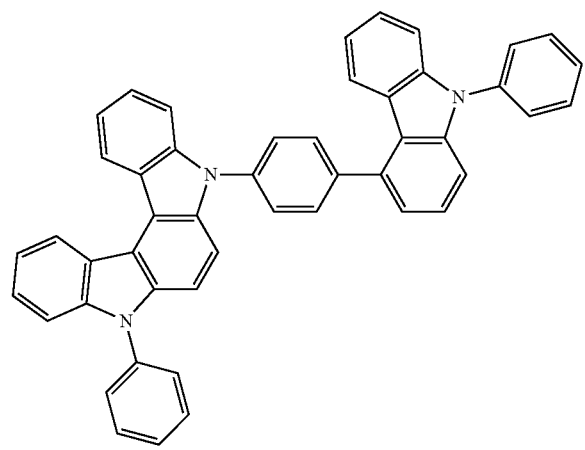
[C-27]
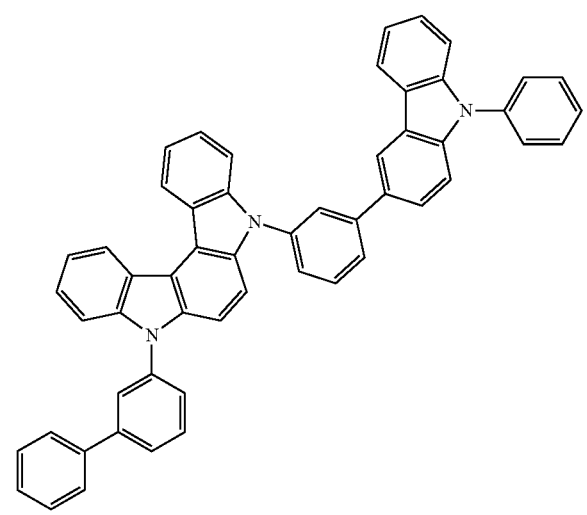
[C-25]
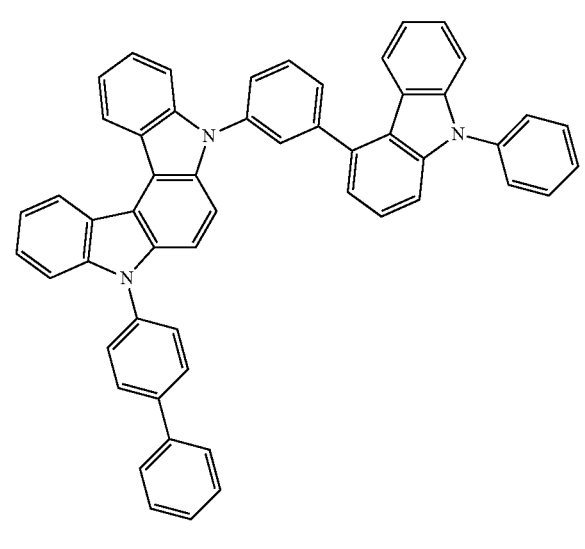
[C-28]
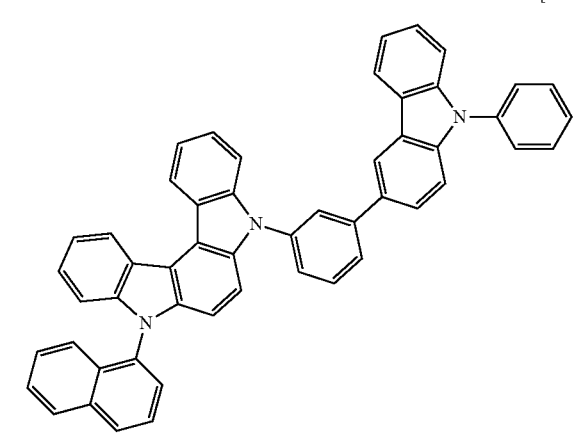
[C-26]
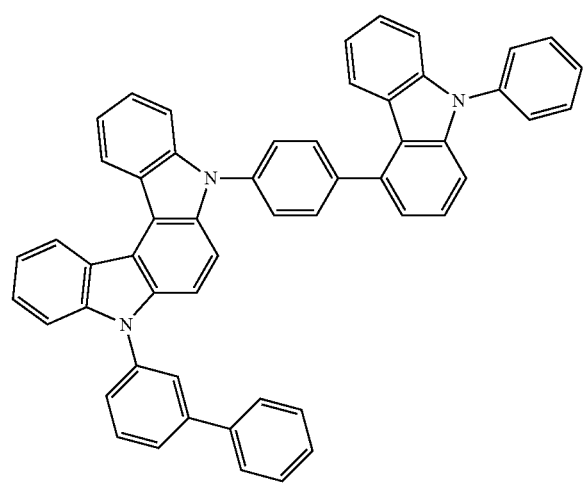
[C-29]

-continued
[C-30]
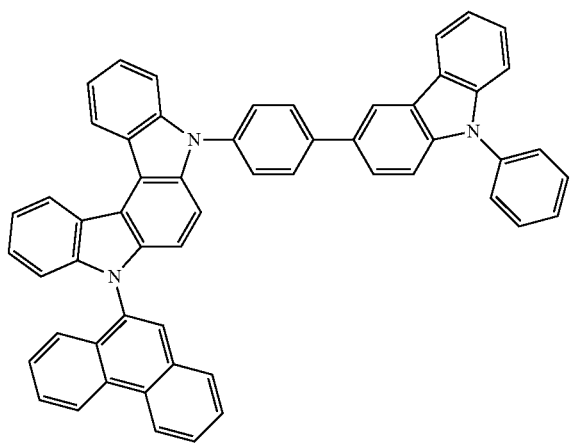
[C-33]
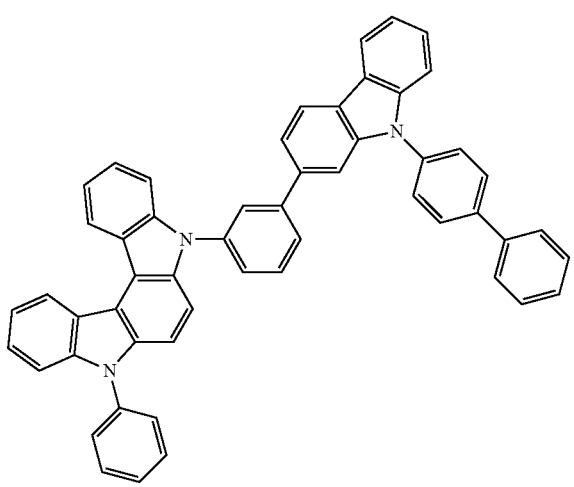
[C-31]
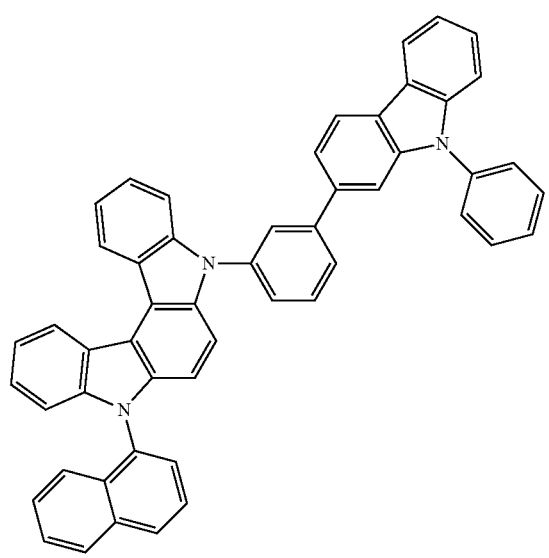
[C-34]
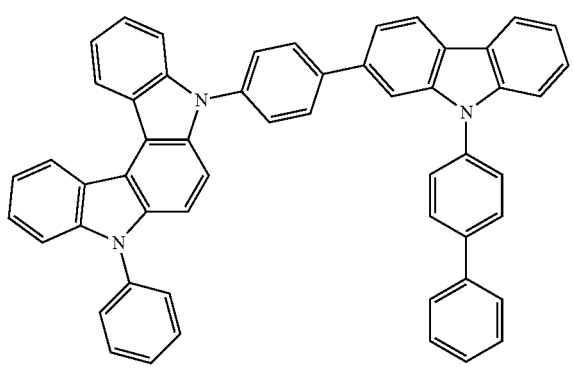
[C-32]
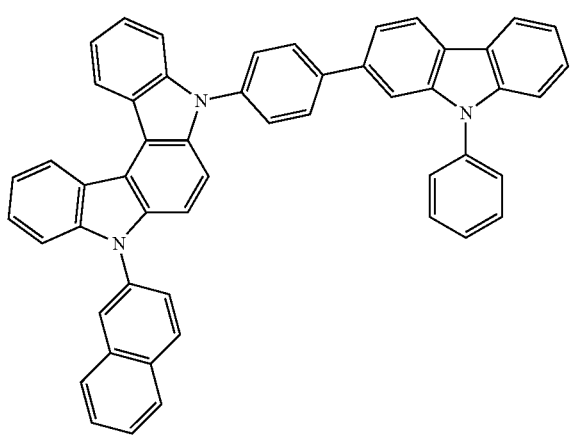
[C-35]
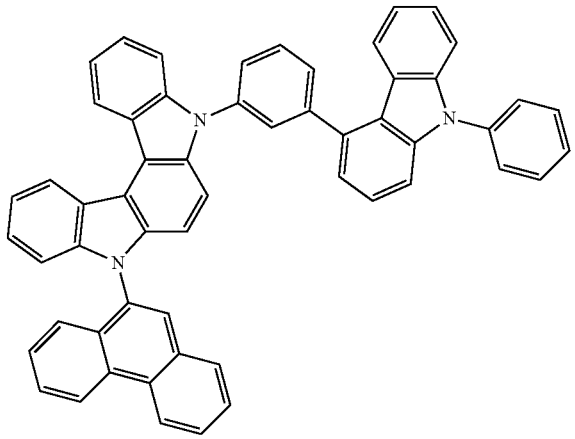

[C-36]
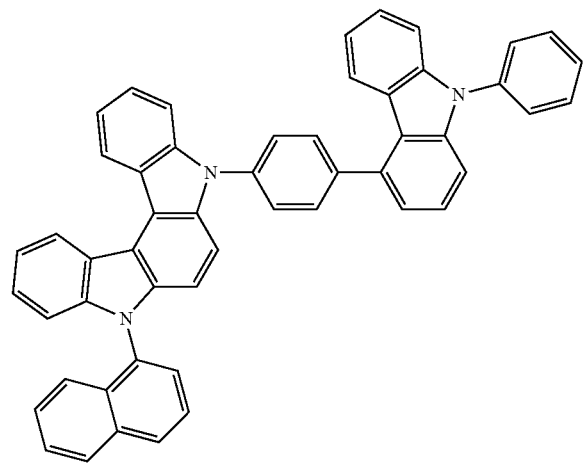
[C-37]
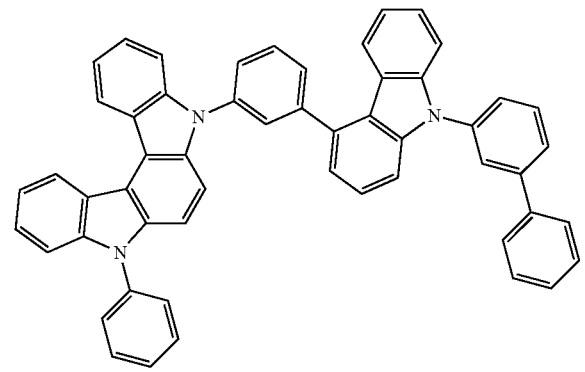
[C-38]
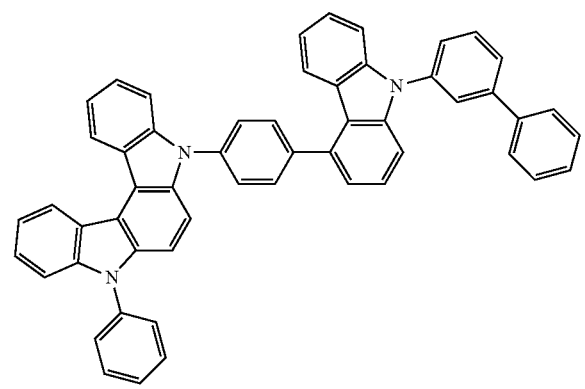
[C-39]
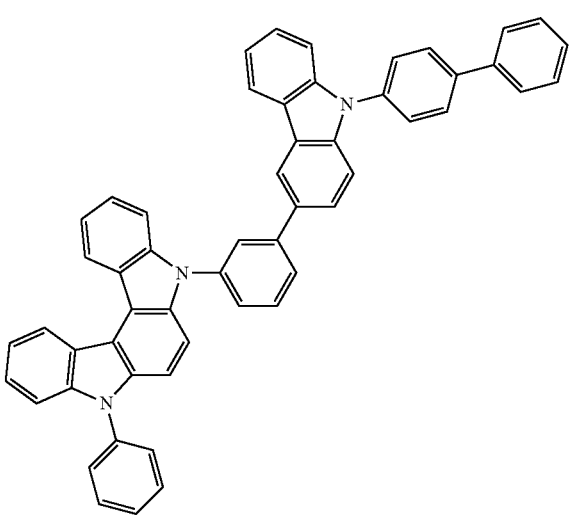
[C-40]
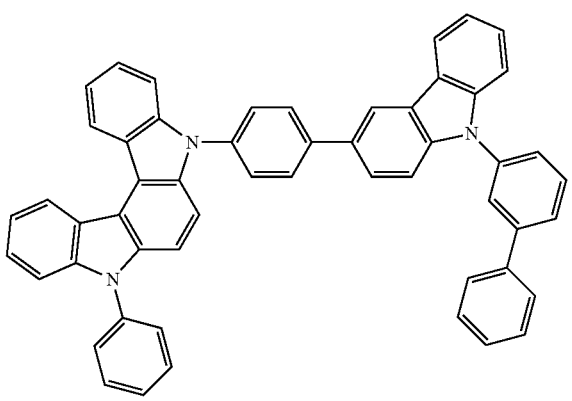
[C-41]
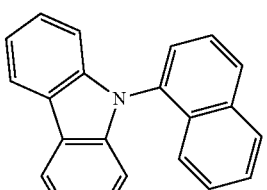
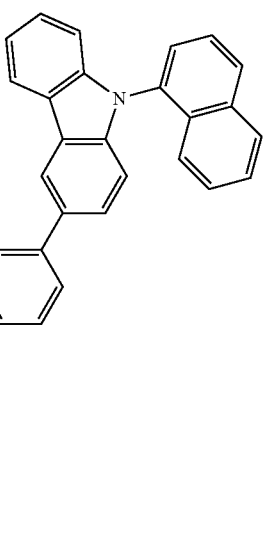

-continued
[C-42]
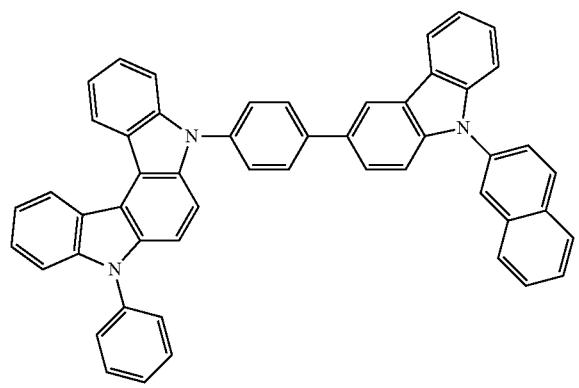
[C-43]
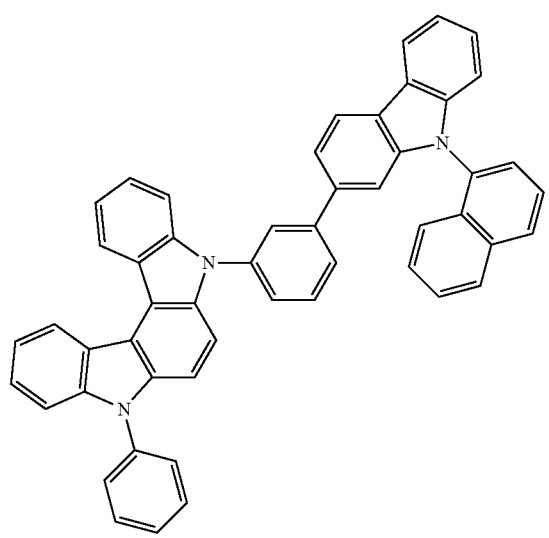
[C-44]
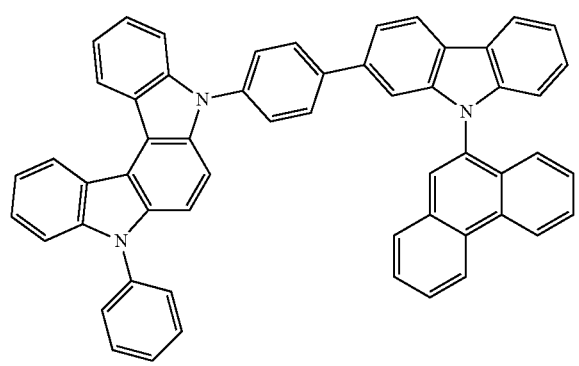
-continued
[C-45]
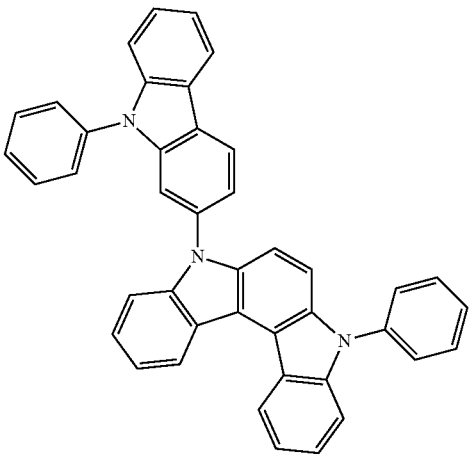
[C-46]
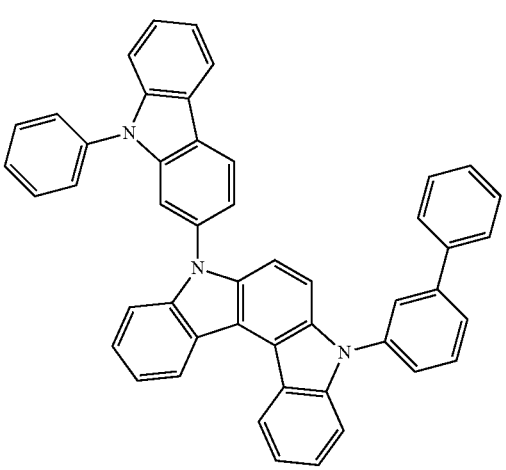
[C-47]
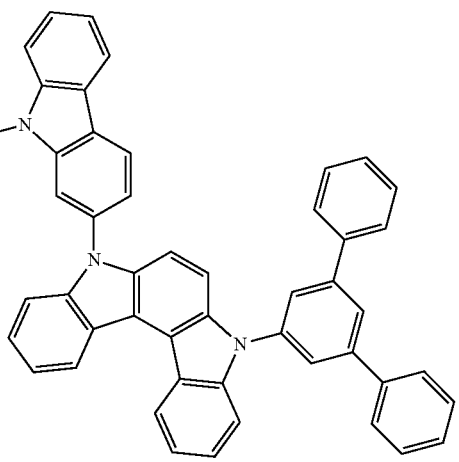

[C-48]
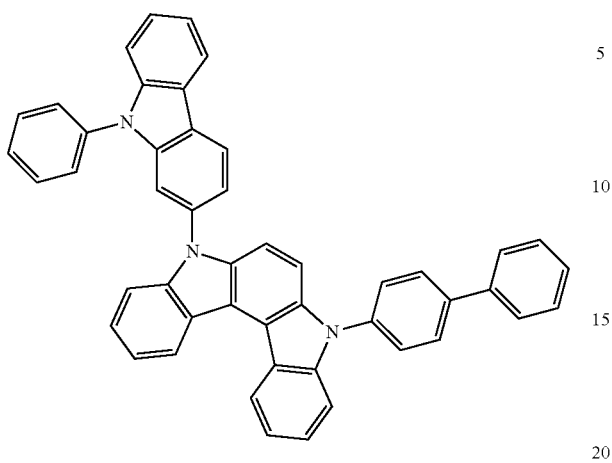
[C-51]
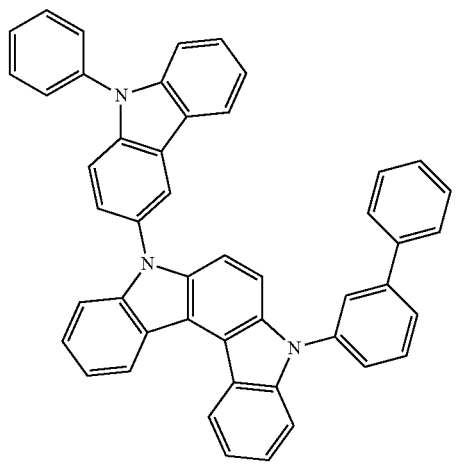
[C-49]
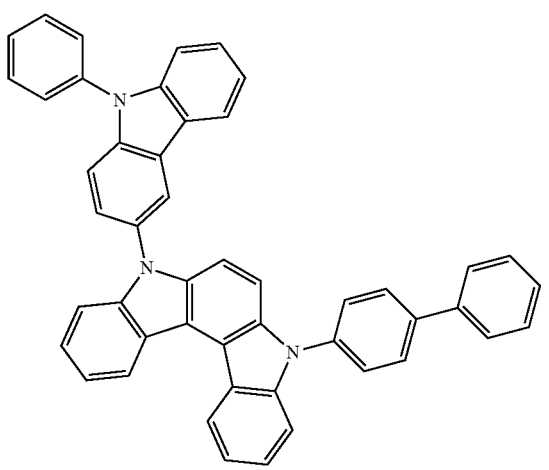
[C-52]
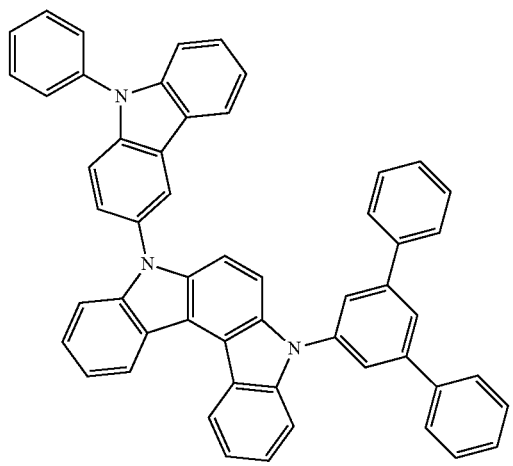
[C-50]
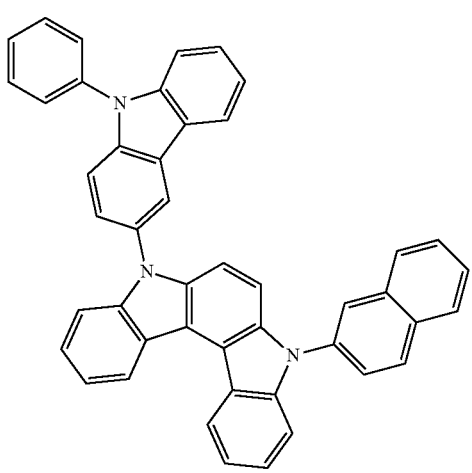
[C-53]
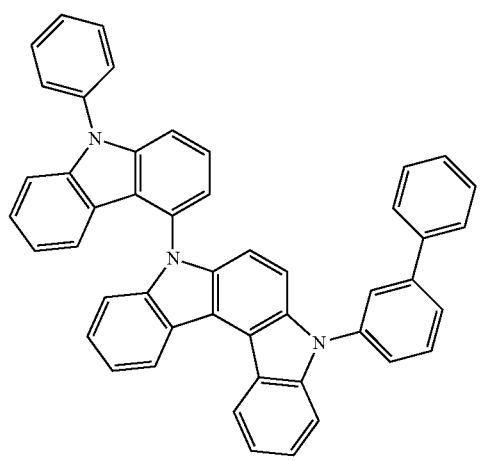

[C-54]
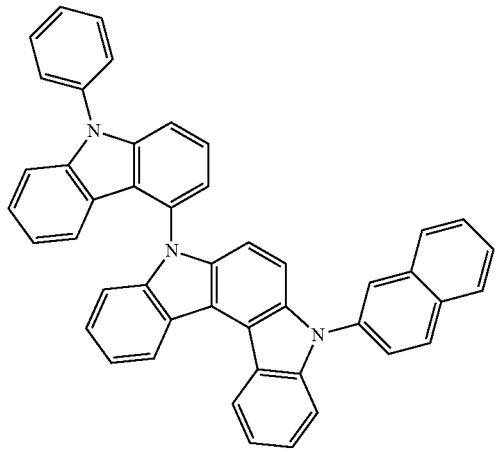
[C-55]
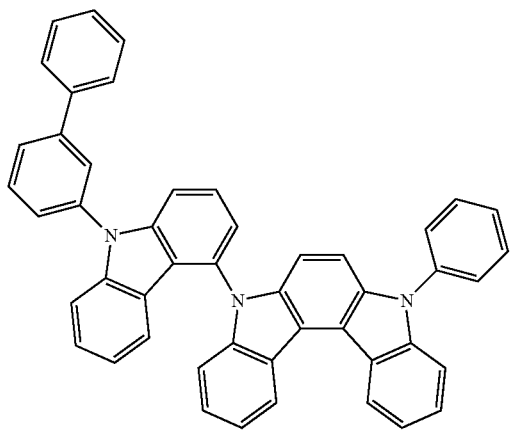
[C-56]
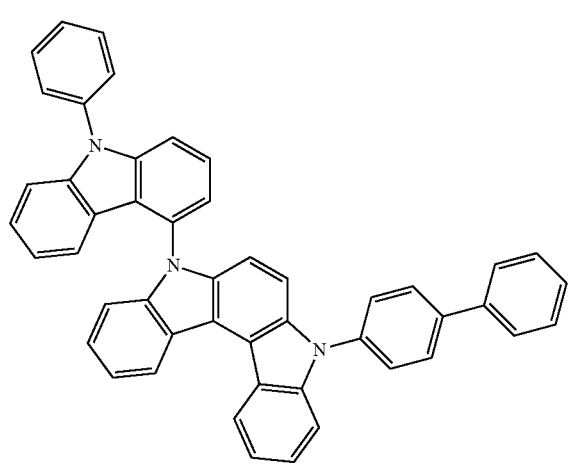
[D-1]
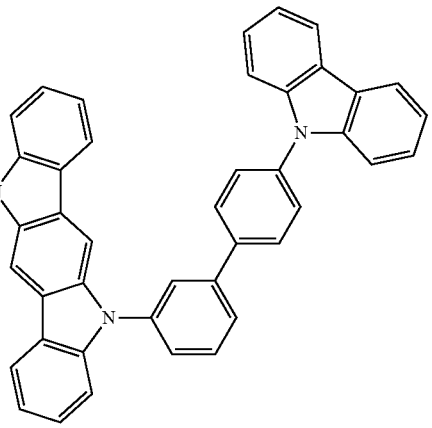
[D-2]
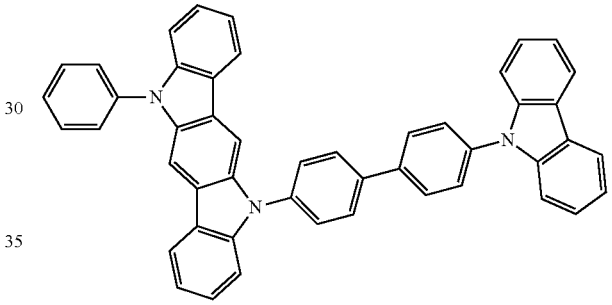
[D-3]
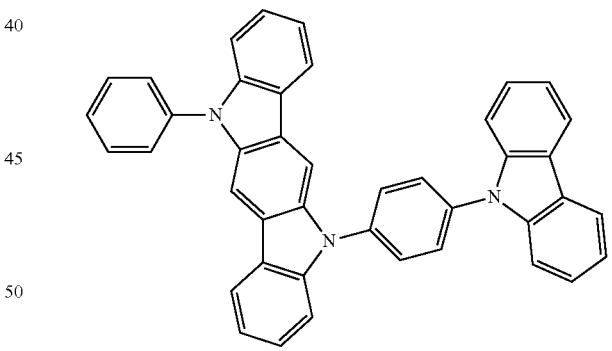
[D-4]
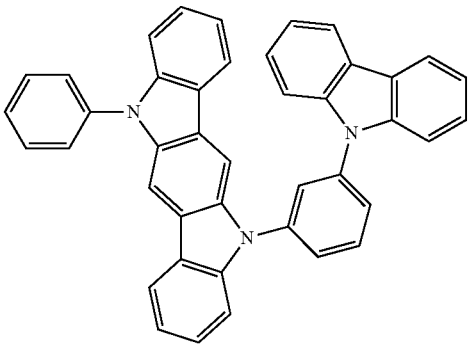

[D-5]
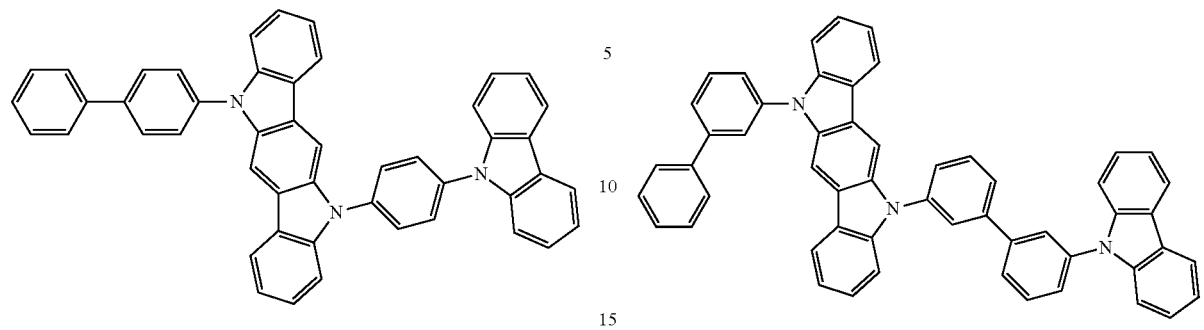
[D-9]
[D-6]
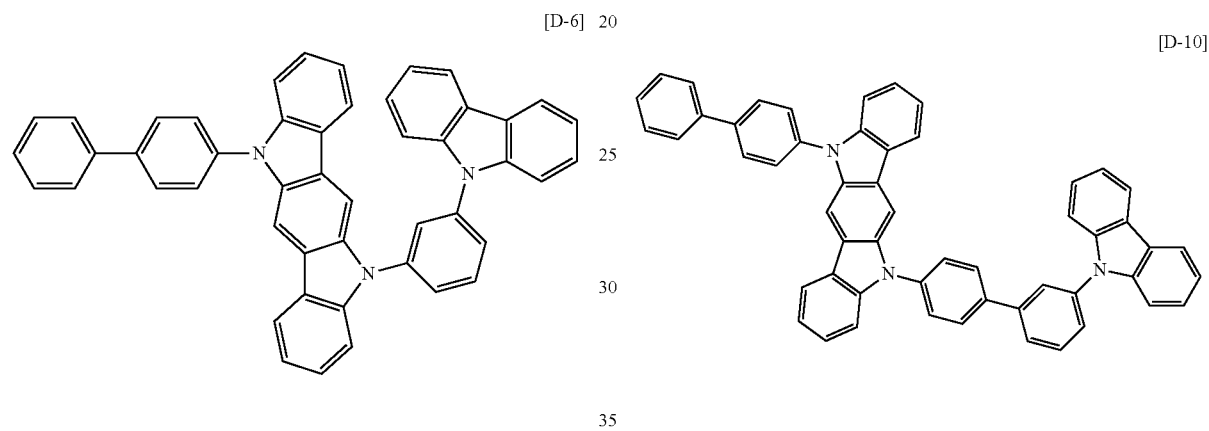
[D-10]
[D-7]
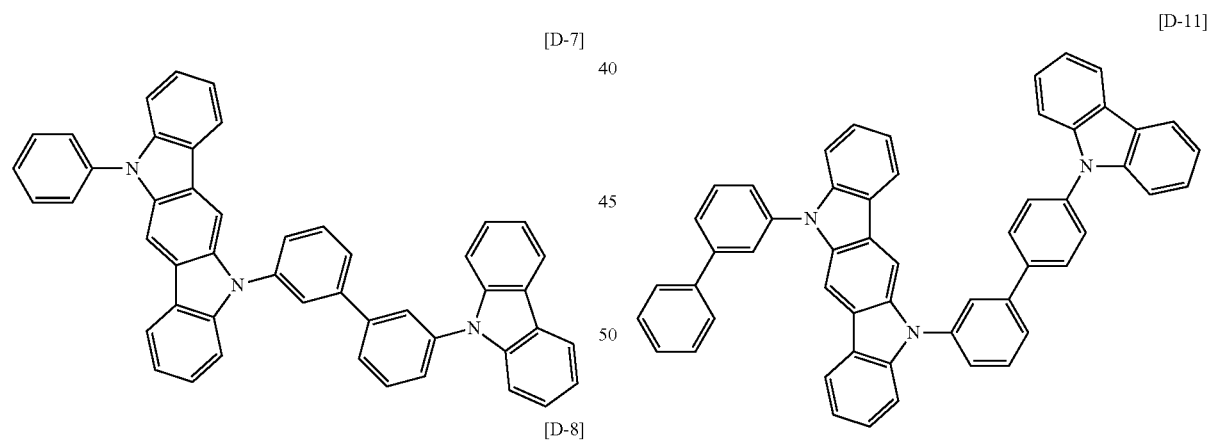
[D-11]
[D-8]
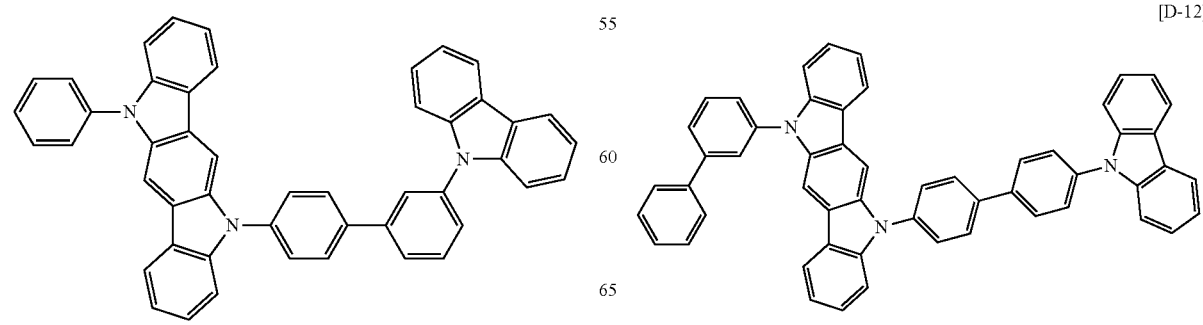
[D-12]

[D-13]
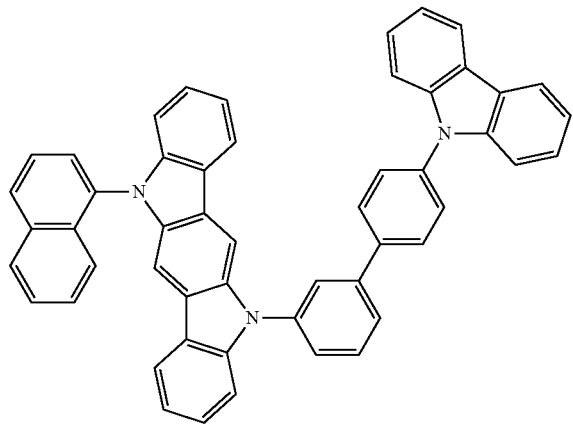
[D-17]
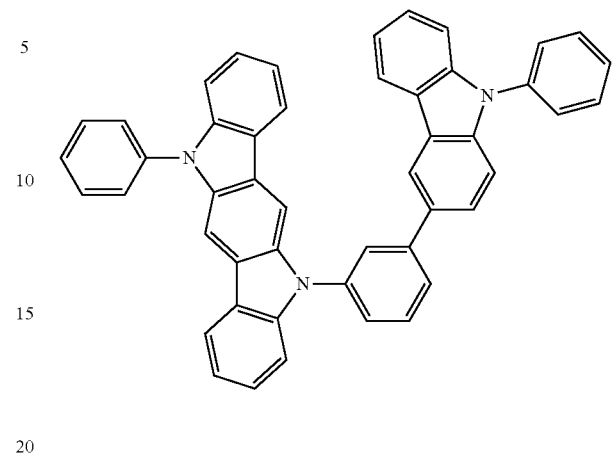
[D-14] [D-18]
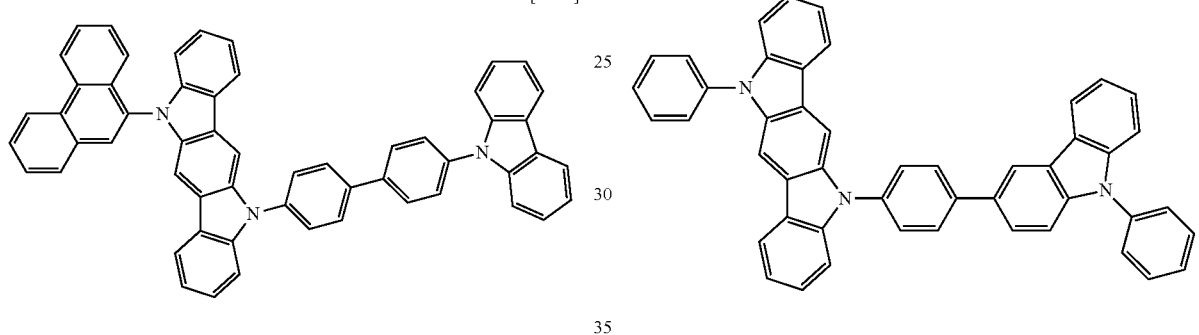
[D-15] [D-19]
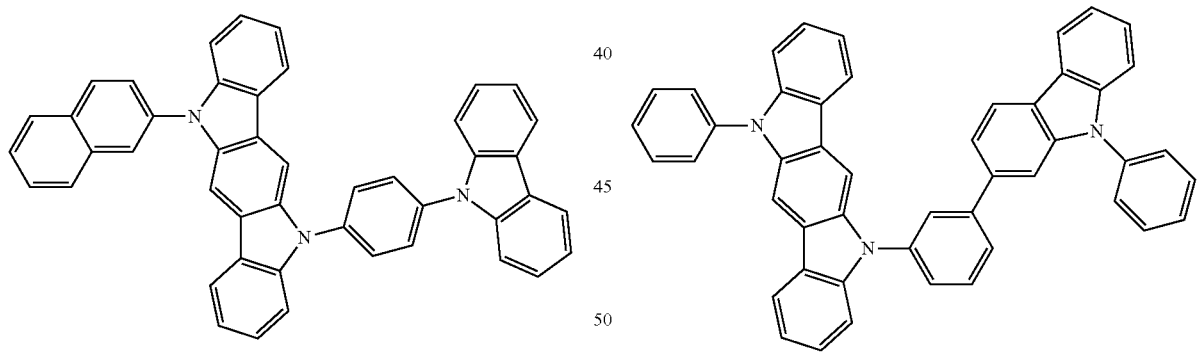
[D-16] [D-20]
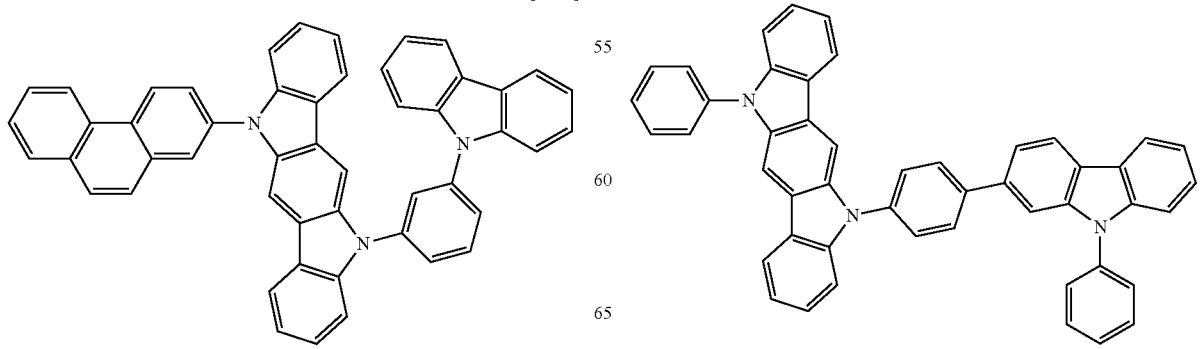

[D-21]
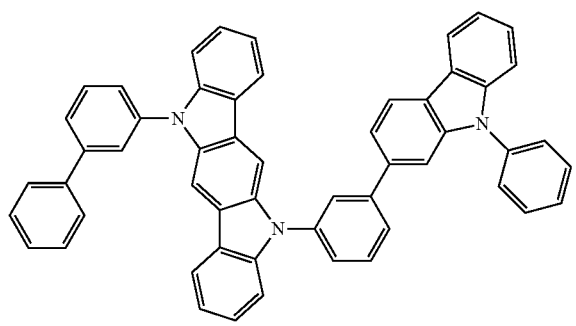
[D-25]
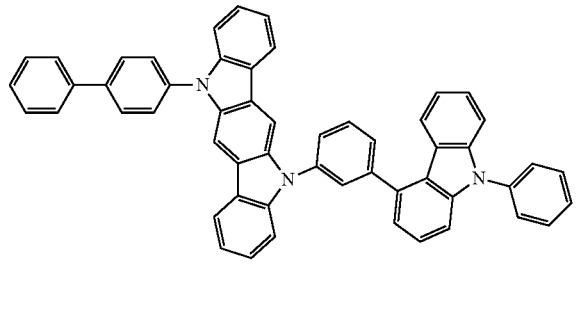
[D-22]
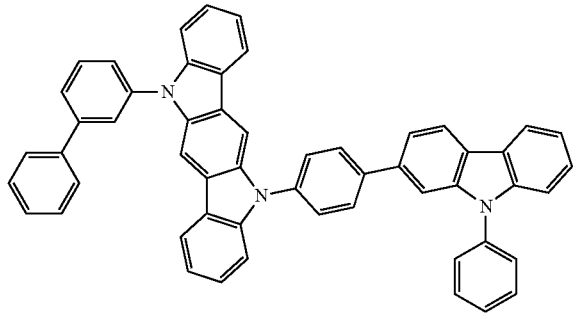
[D-26]
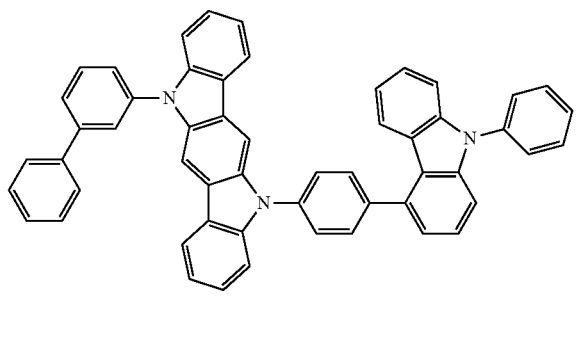
[D-23]
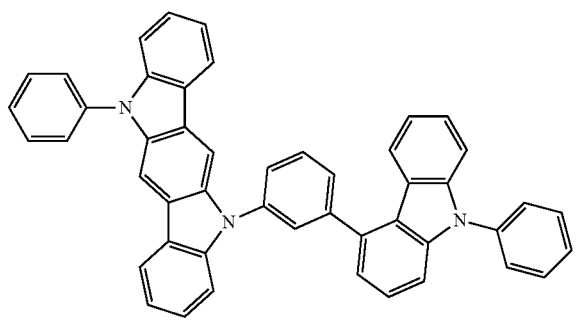
[D-27]
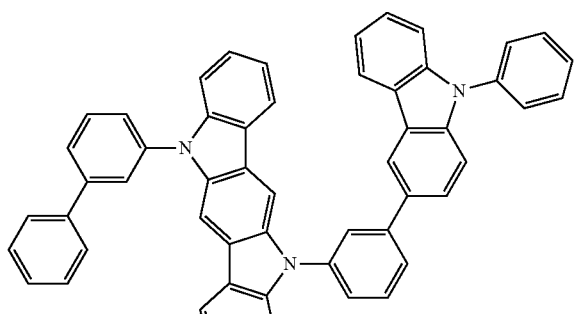
[D-24]
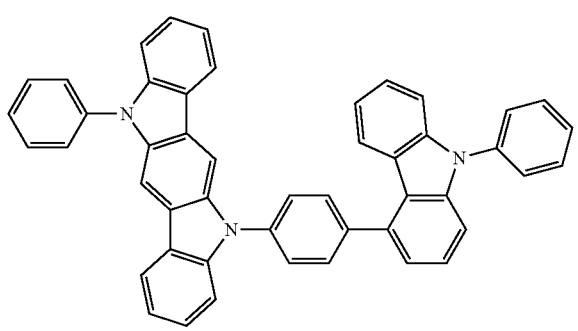
[D-28]
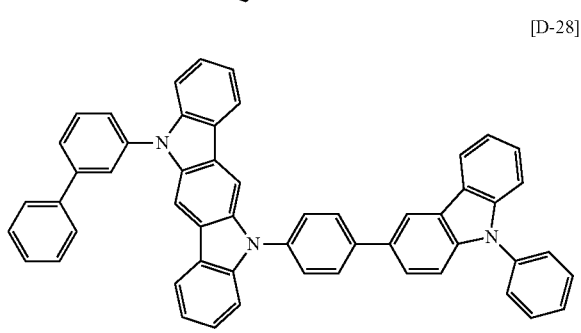

-continued
[D-29]
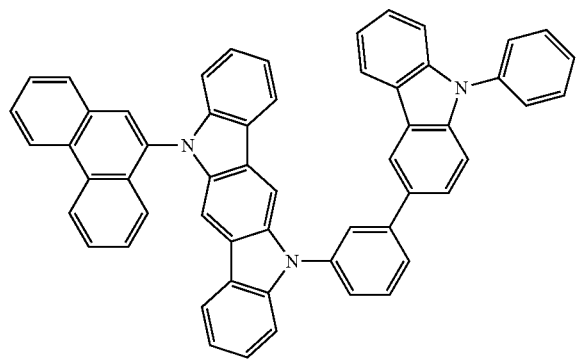
[D-30]
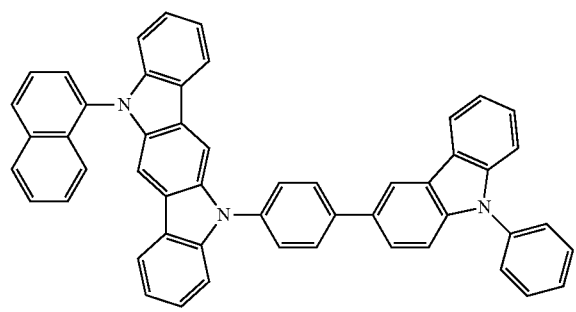
[D-31]
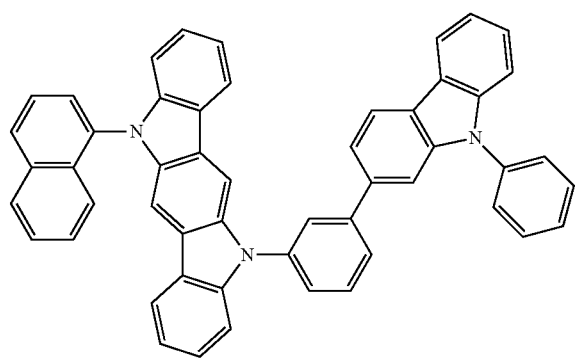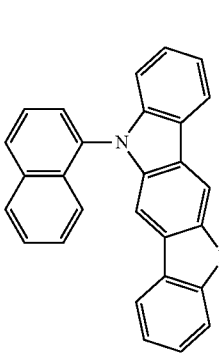
[D-32]
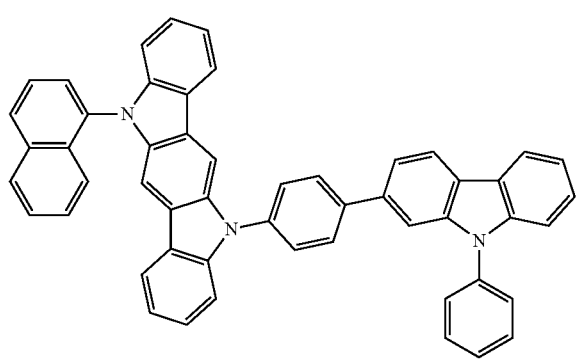
-continued
[D-33]
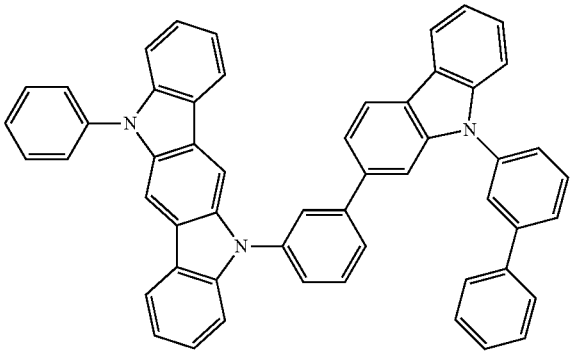
[D-34]
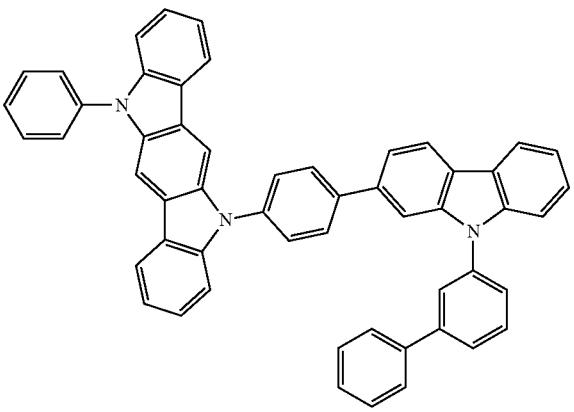
[D-35]
[D-36]
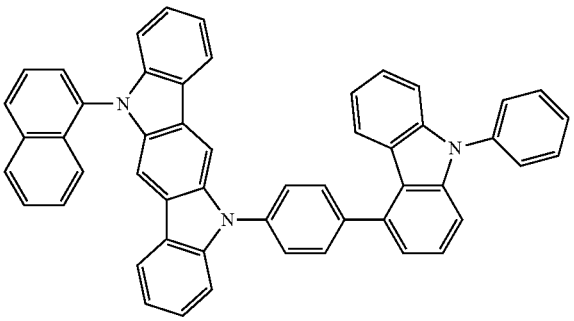

[D-37]
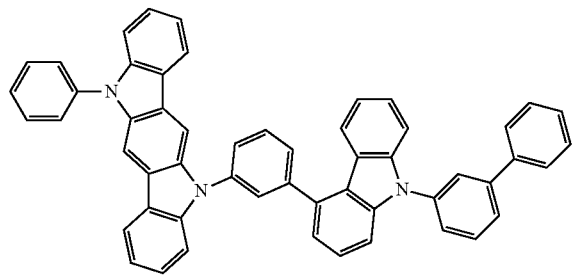
[D-41]
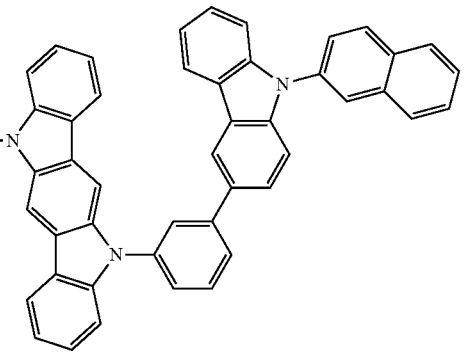
[D-38]
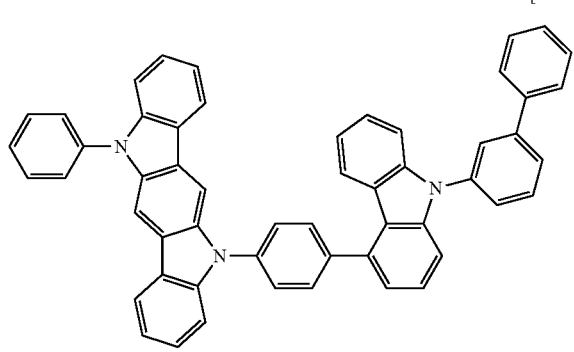
[D-42]
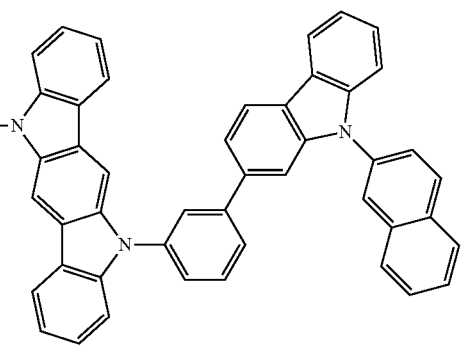
[D-39]
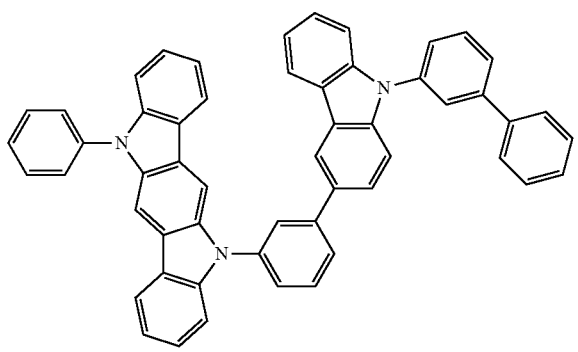
[D-43]
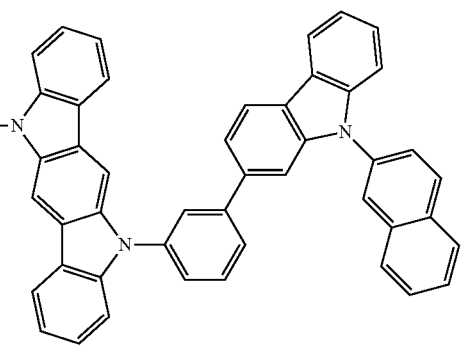
[D-40]
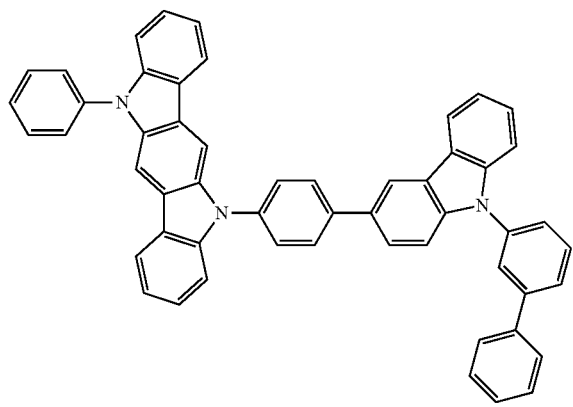
[D-44]
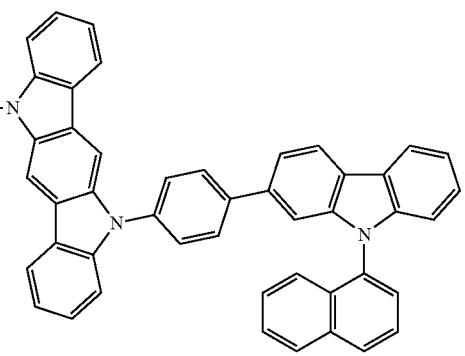

[D-45]
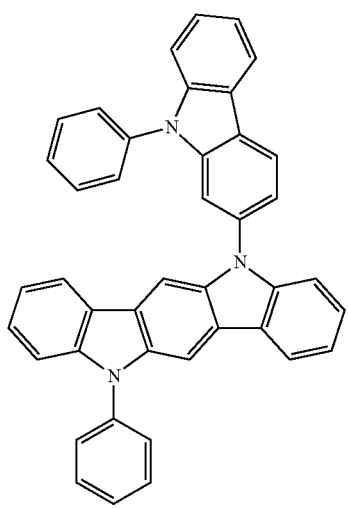
[D-46]
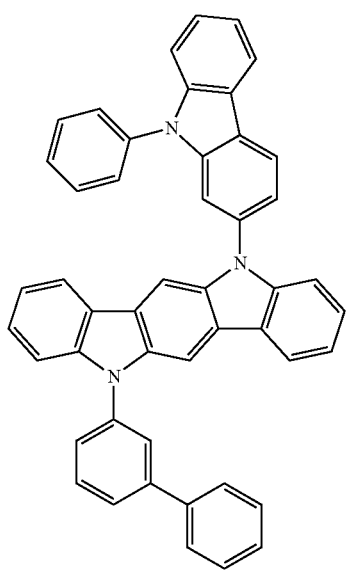
[D-47]
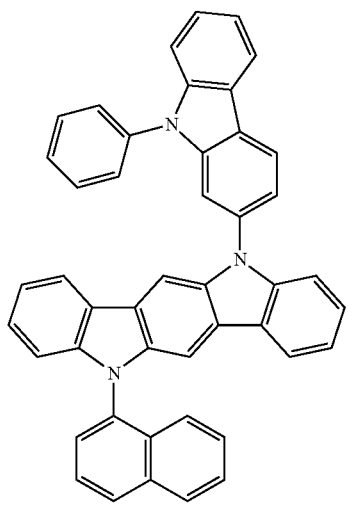
[D-48]
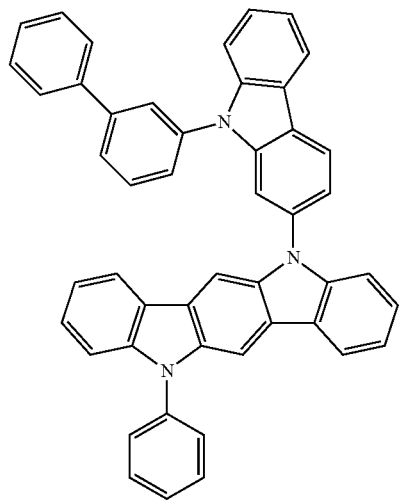
[D-49]
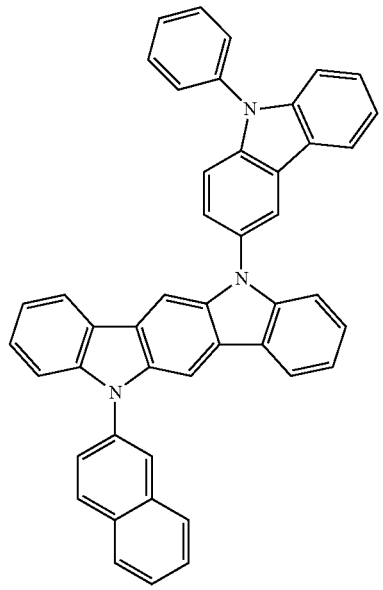
[D-50]
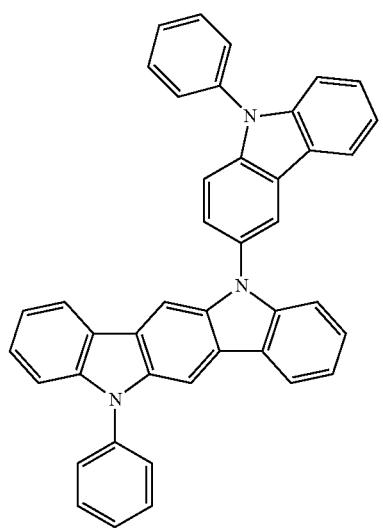

[D-51]
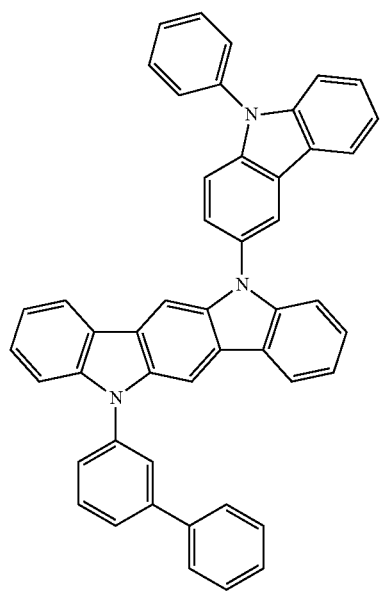
[D-52]
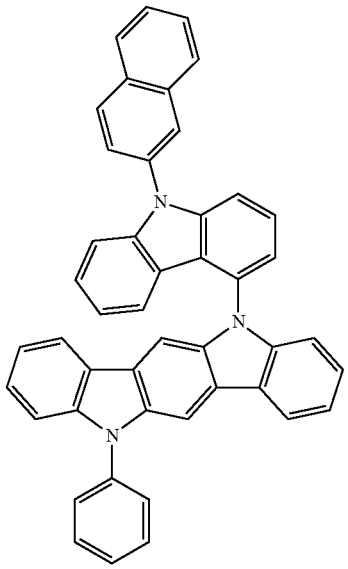
[D-53]
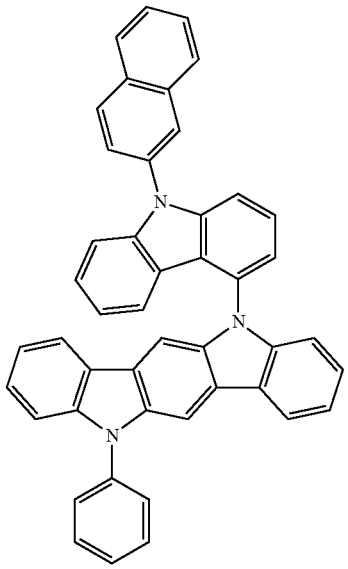
[D-54]
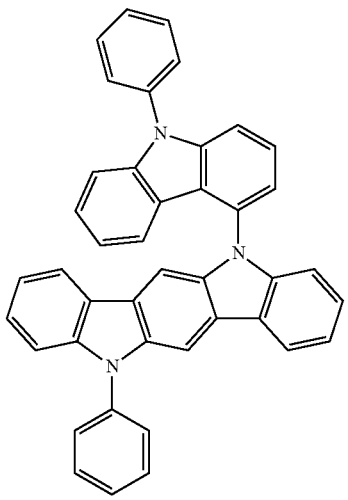
[D-55]
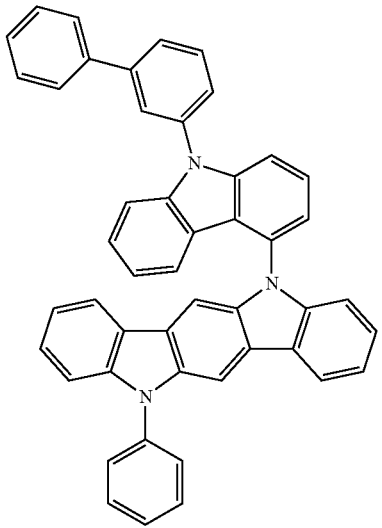

[D-56]
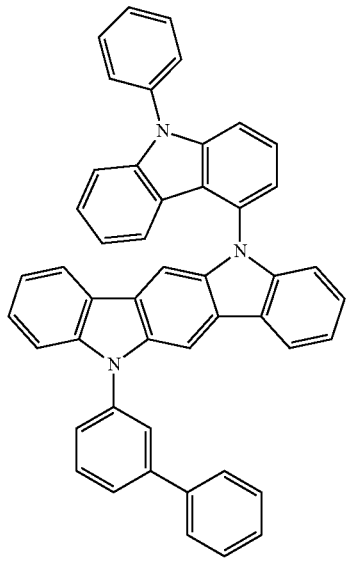
[E-1]
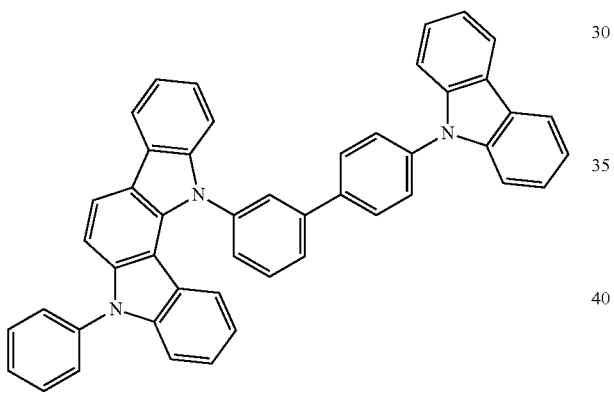
[E-2]
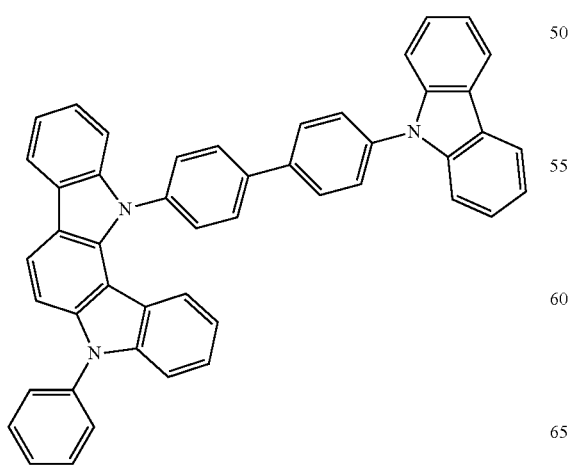
[E-3]
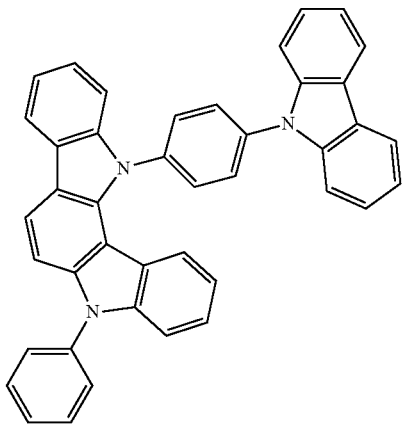
[E-4]
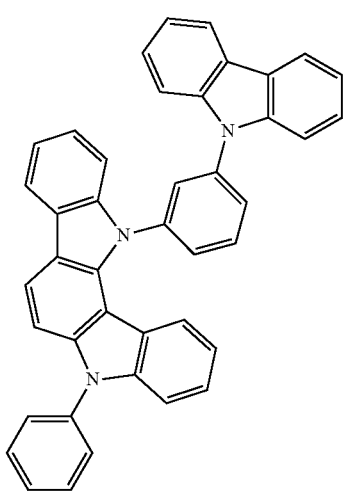
[E-5]
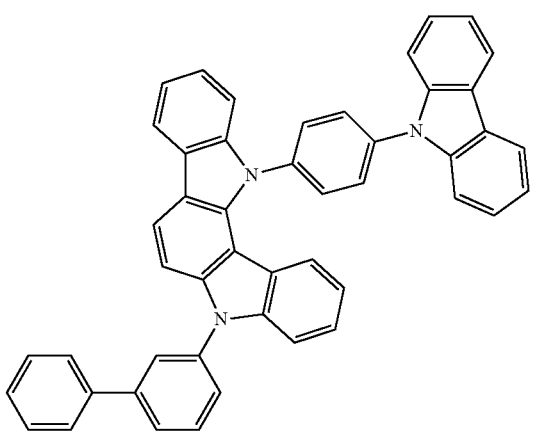

[E-6]
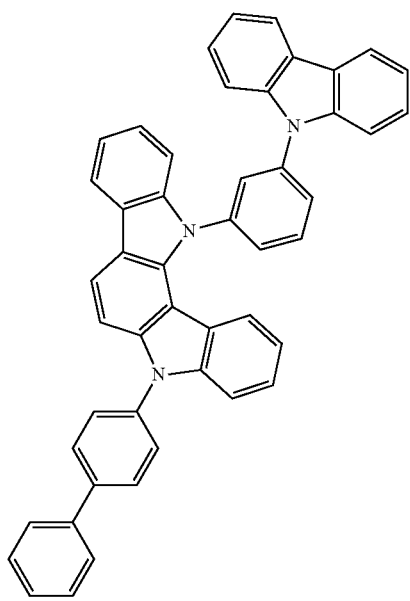
[E-9]
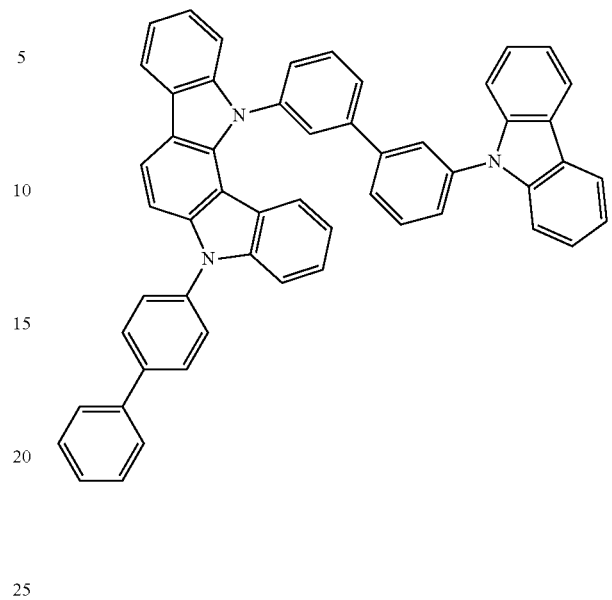
[E-7]
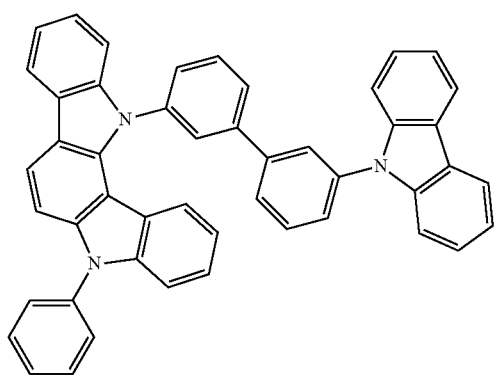
[E-10]
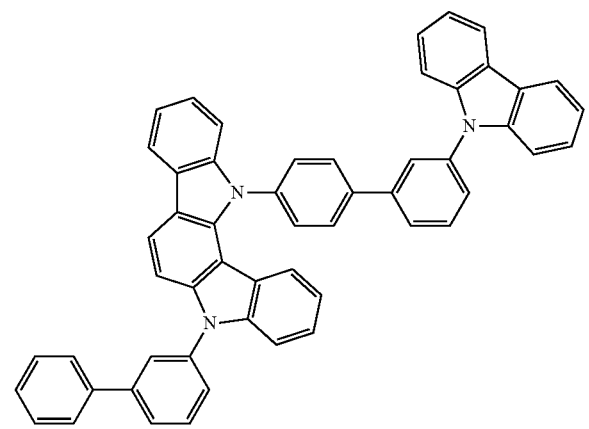
[E-8]
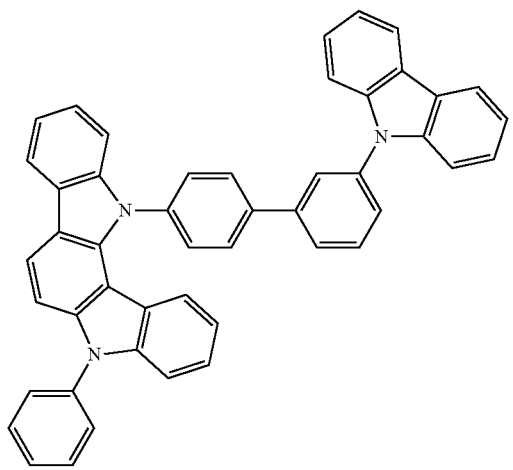
[E-11]
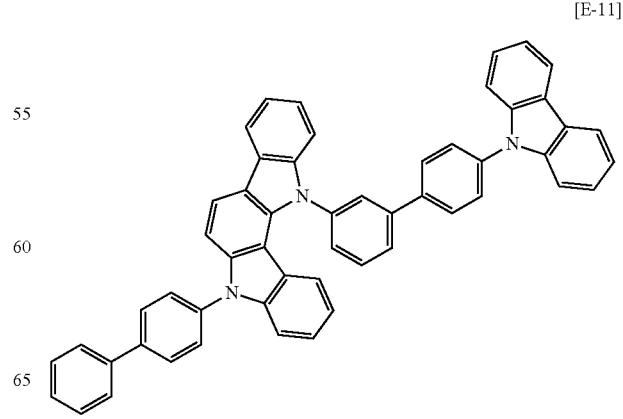

[E-12]
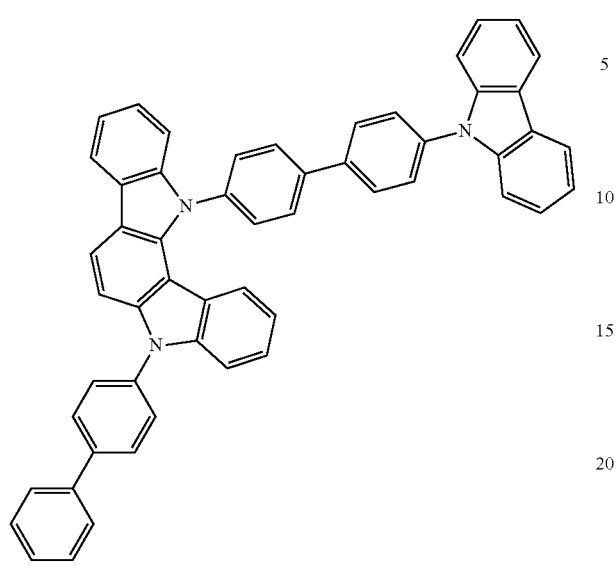
[E-15]
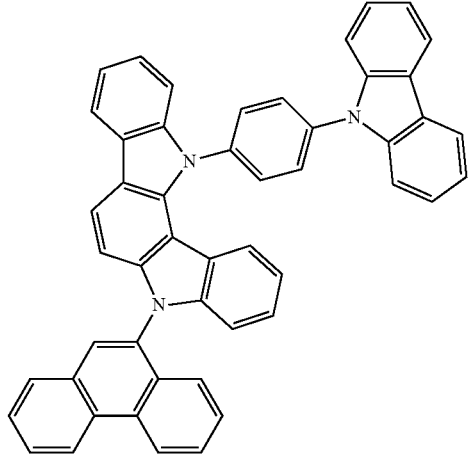
[E-13]
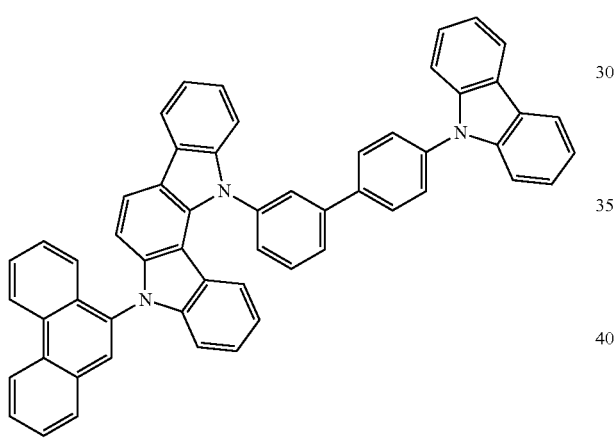
[E-16]
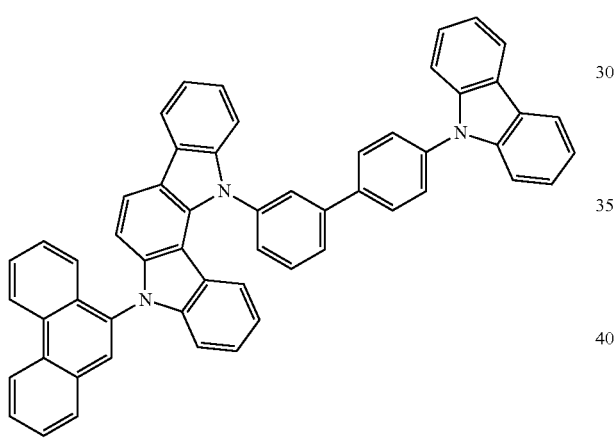
[E-14]
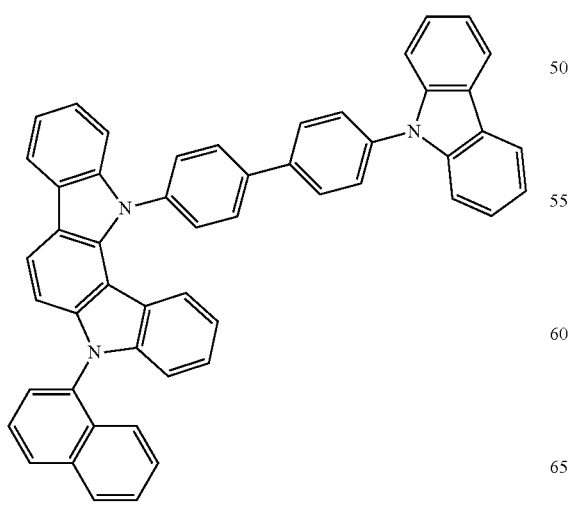
[E-17]
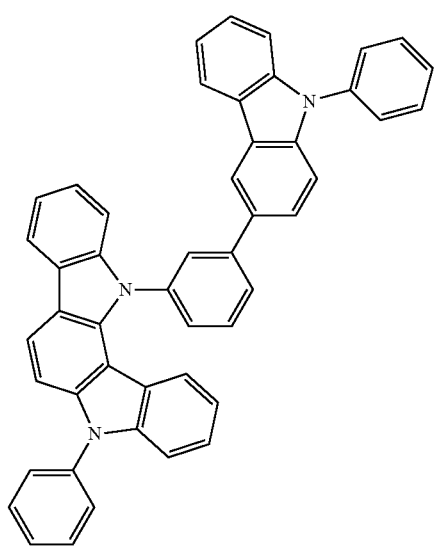

[E-18]
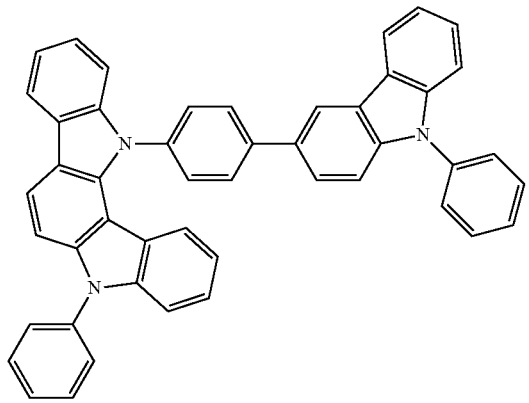
[E-21]
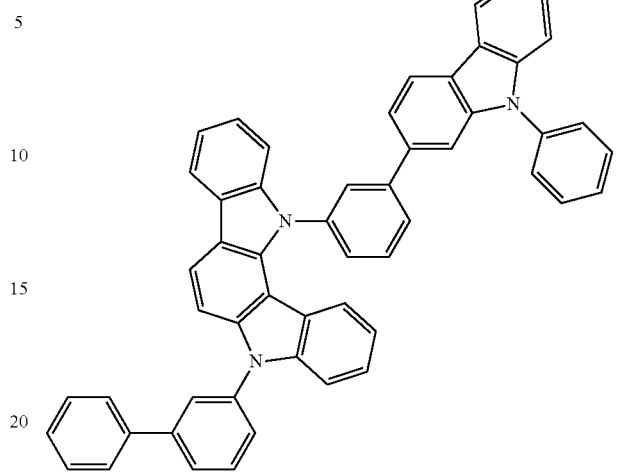
[E-19]
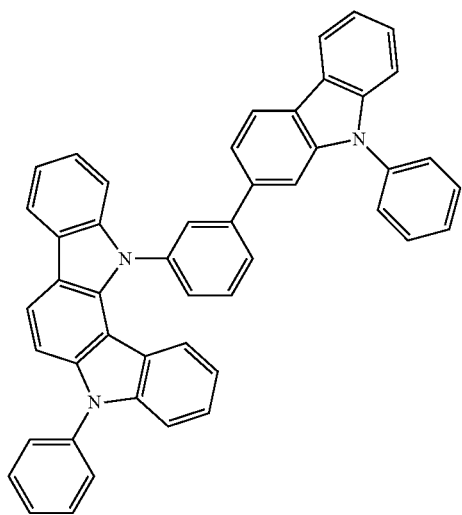
[E-22]
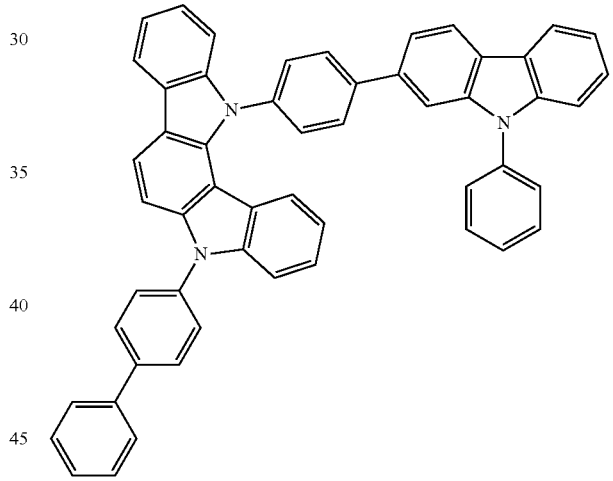
[E-20]
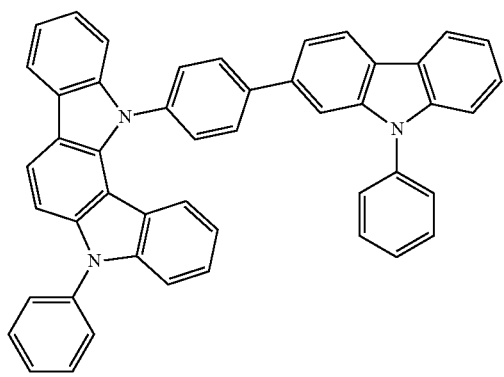
[E-23]
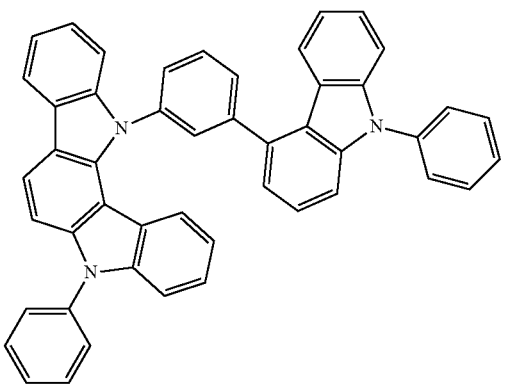

[E-24]
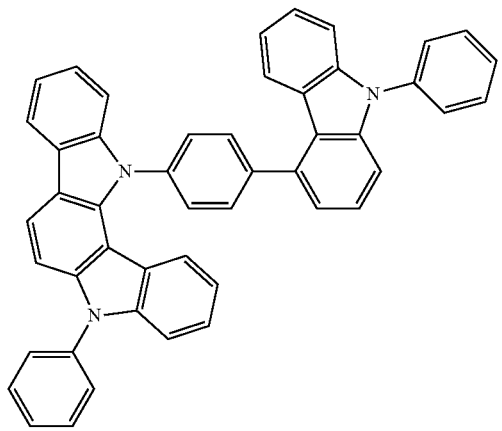
[E-27]
[E-25]
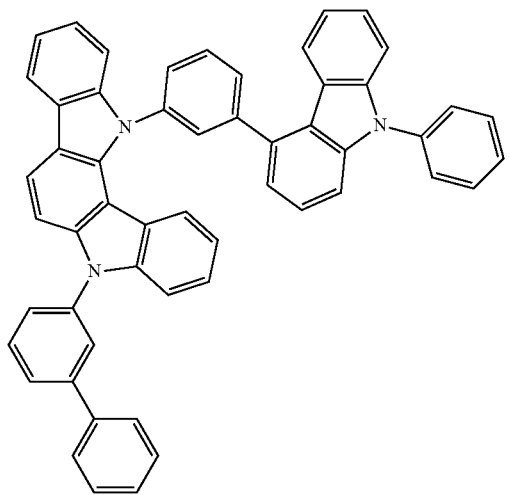
[E-28]
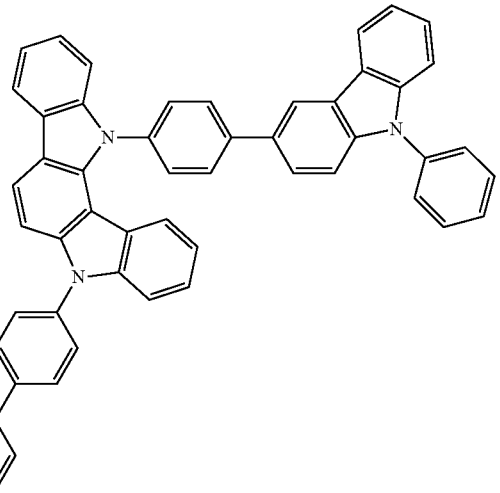
[E-26]
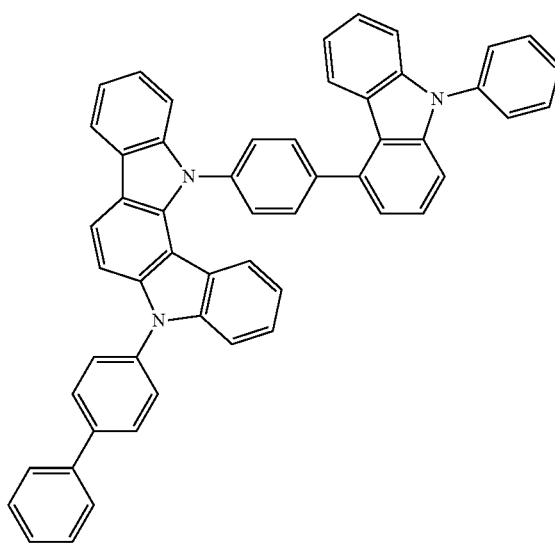
[E-29]
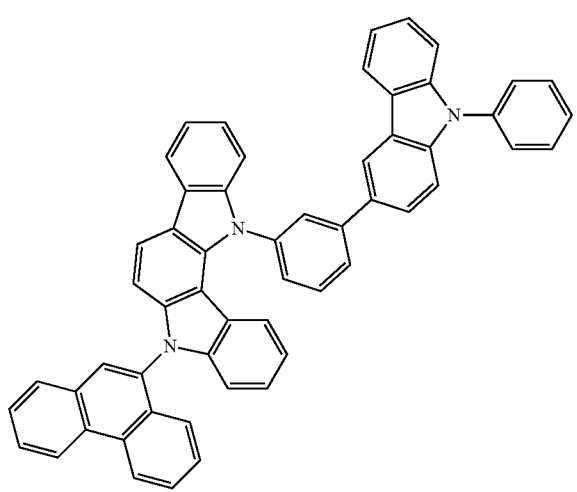

[E-30]
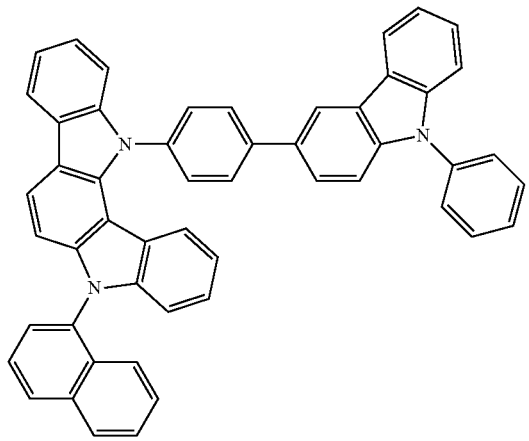
[E-31]
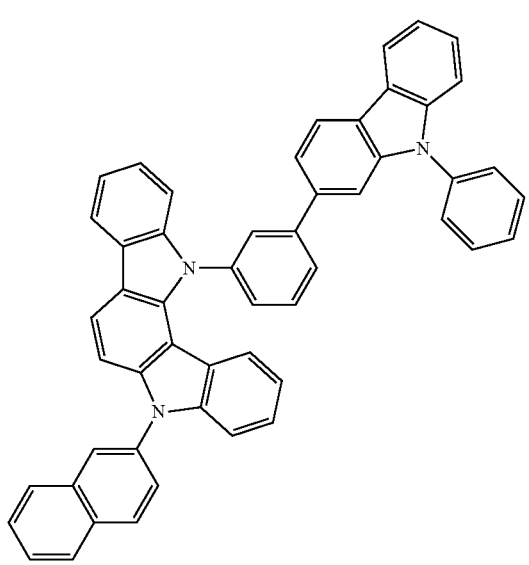
[E-32]
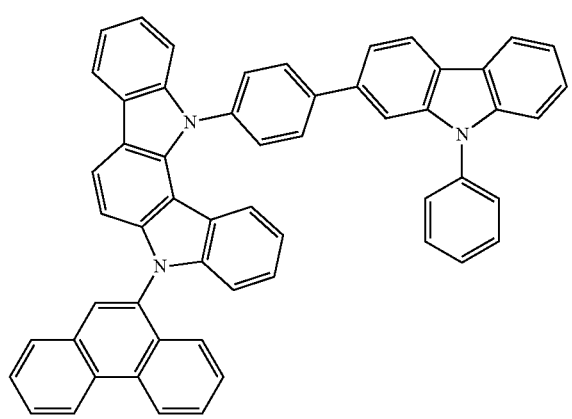
[E-33]
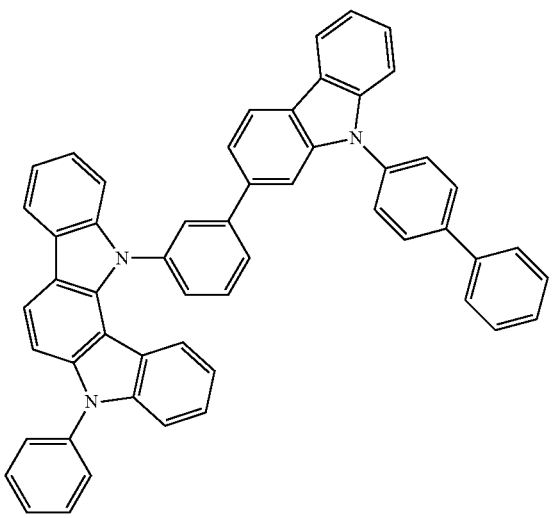
[E-34]
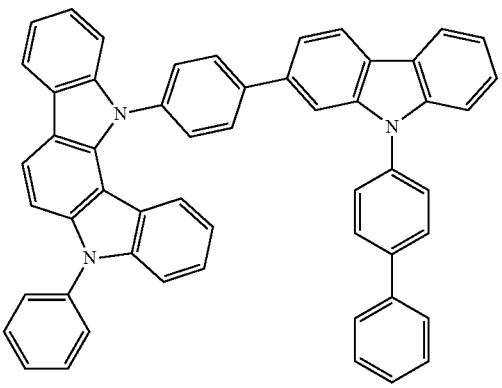
[E-35]
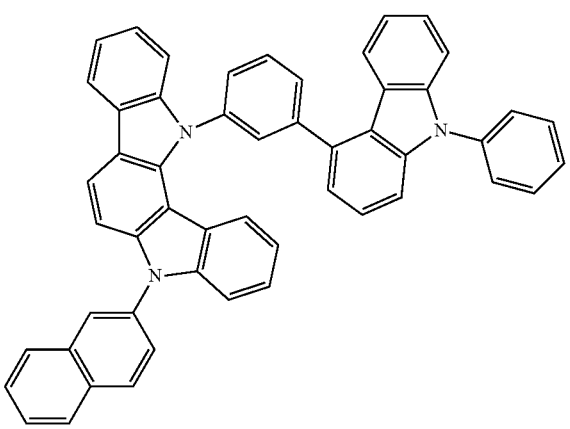

[E-36]
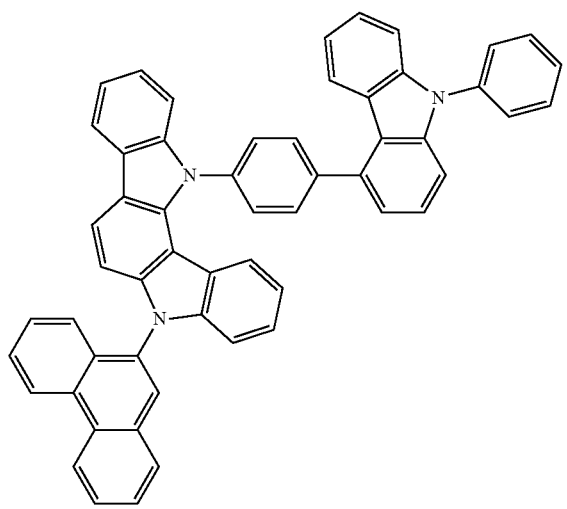
[E-39]
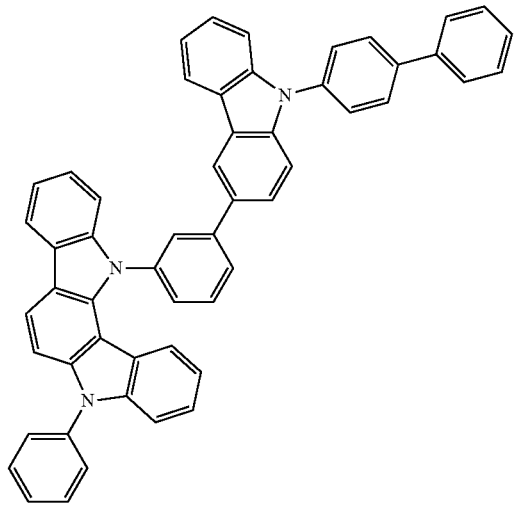
[E-37]
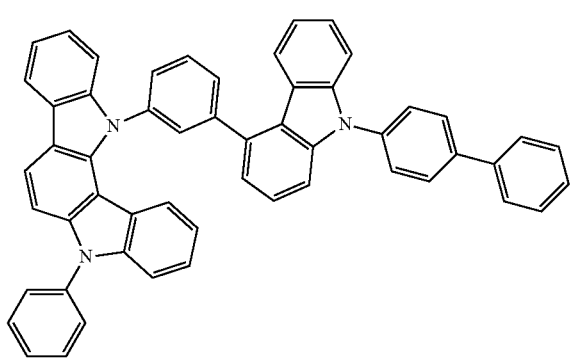
[E-40]
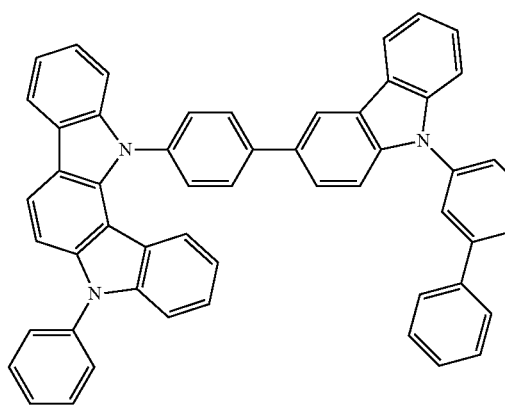
[E-38]
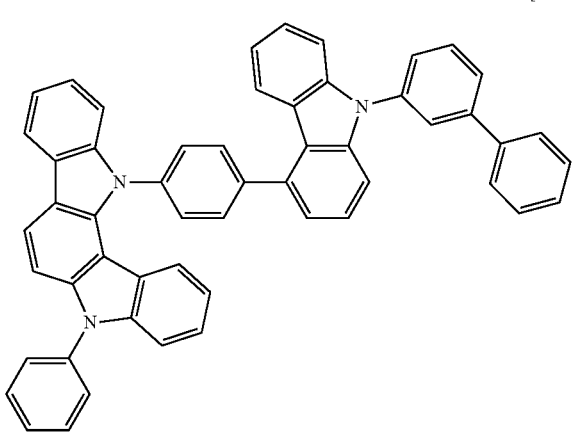
[E-41]
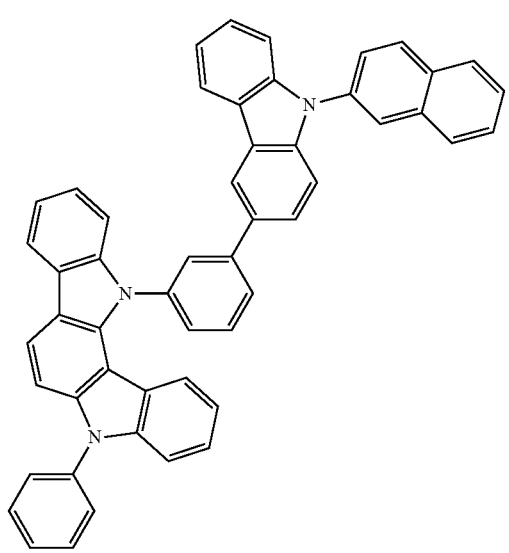

[E-42]
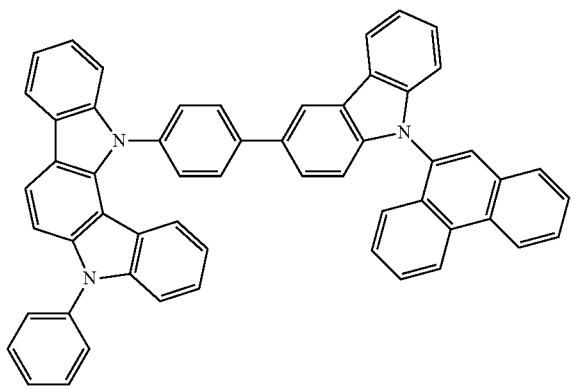
[E-45]
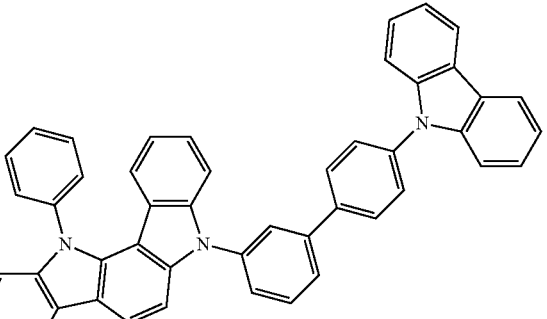
[E-46]
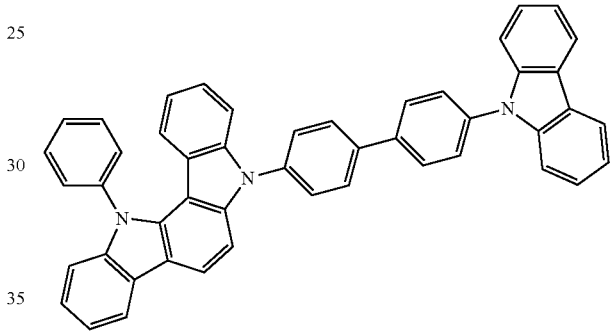
[E-43]
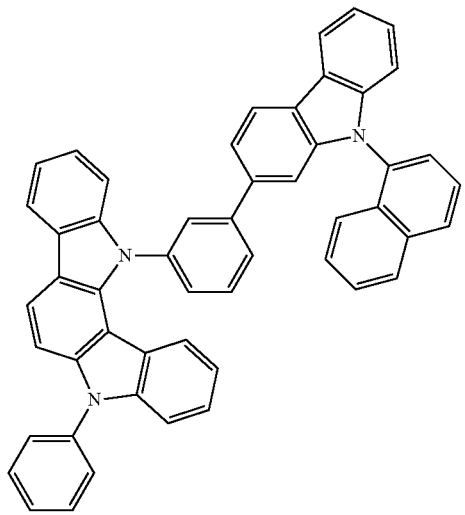
[E-47]
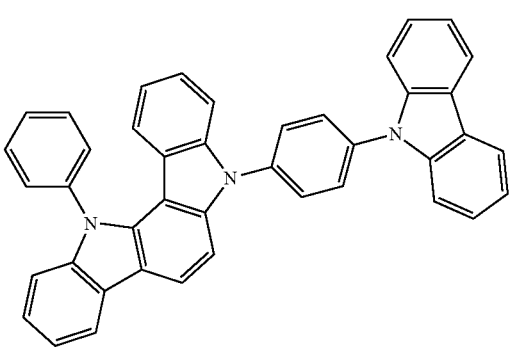
[E-44]
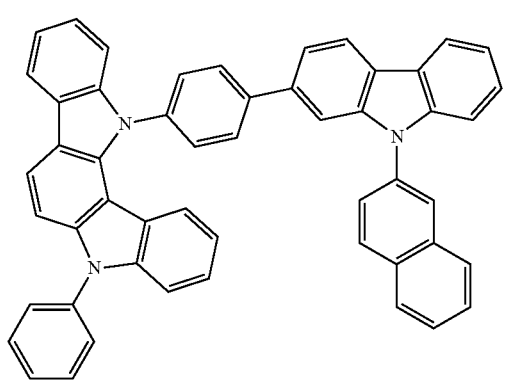
[E-48]
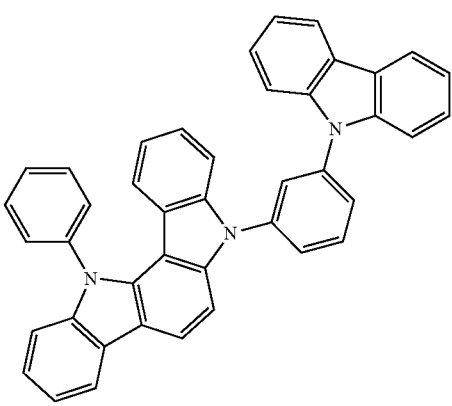

[E-49]
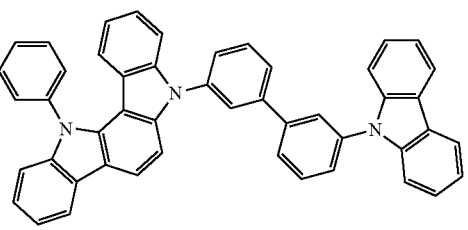
[E-50]
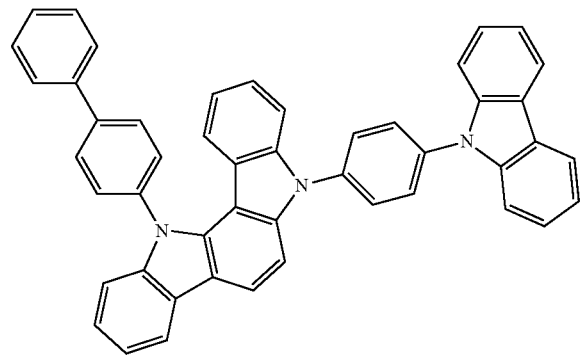
[E-51]
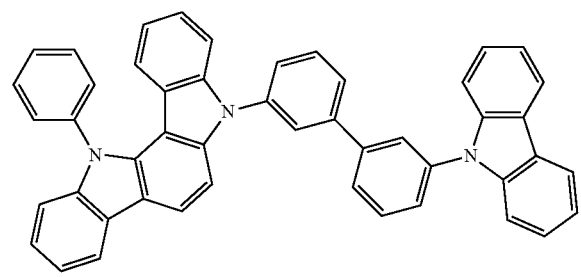
[E-52]
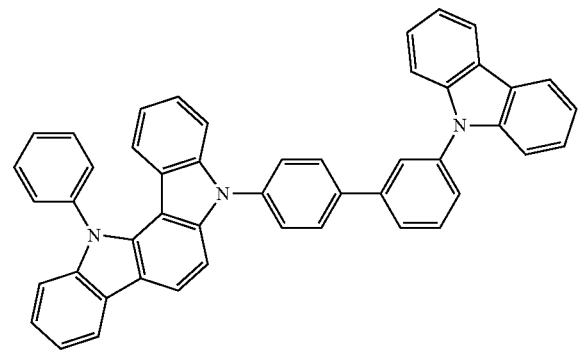
[E-53]
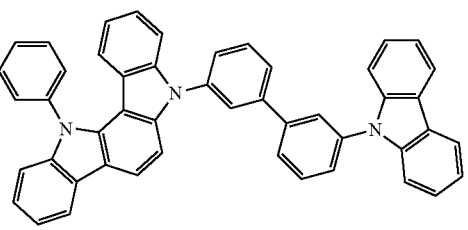
[E-54]
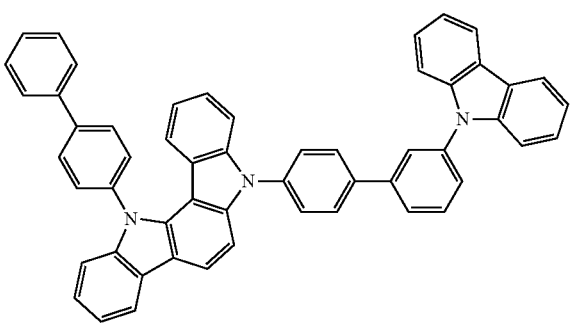
[E-55]
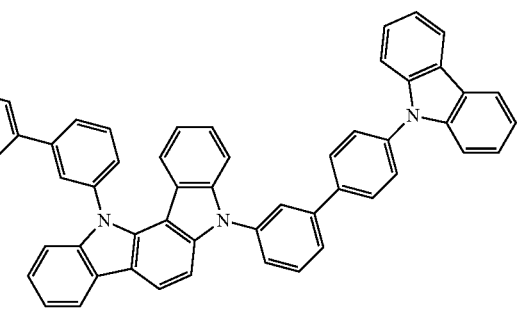
[E-56]
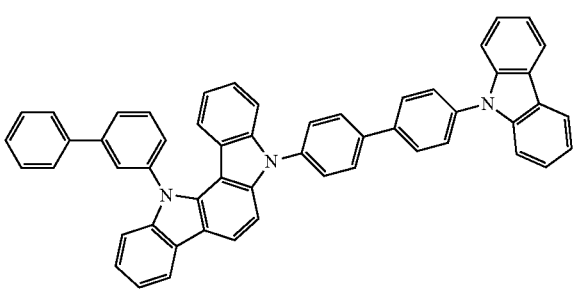
[E-57]
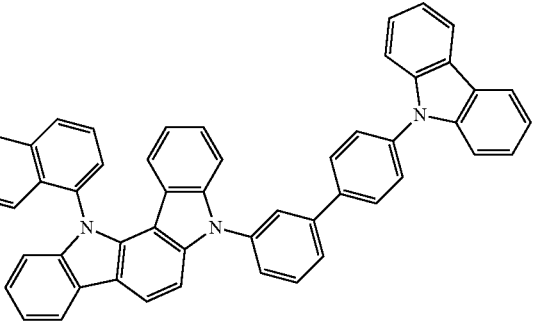

[E-58]
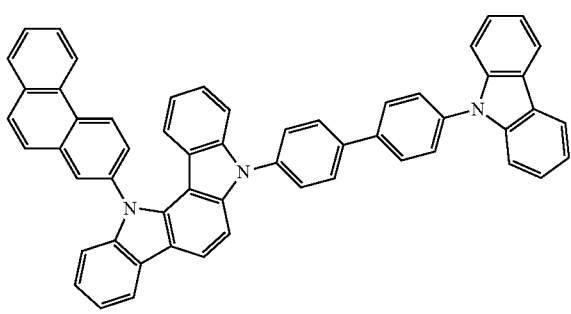
[E-59]
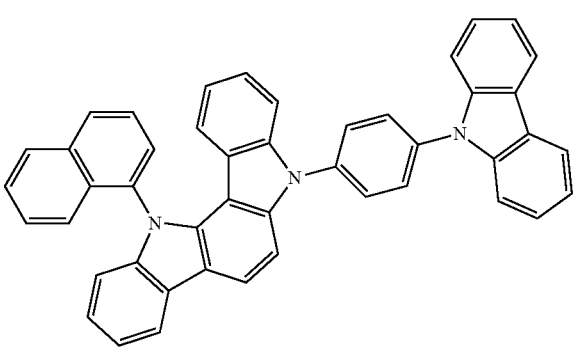
[E-60]
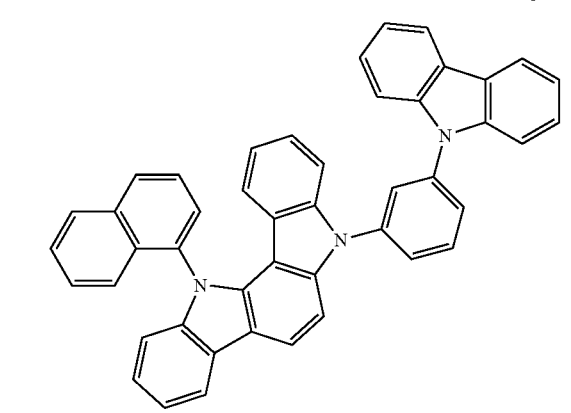
[E-61]
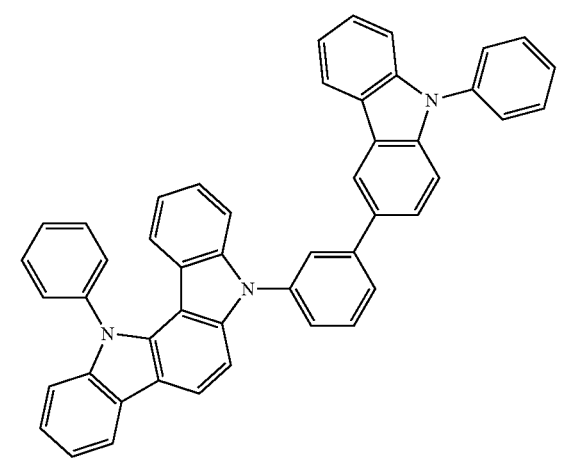
[E-62]
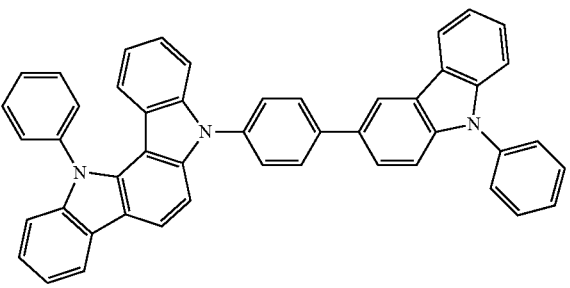
[E-63]
[E-64]
[E-65]

[E-66]
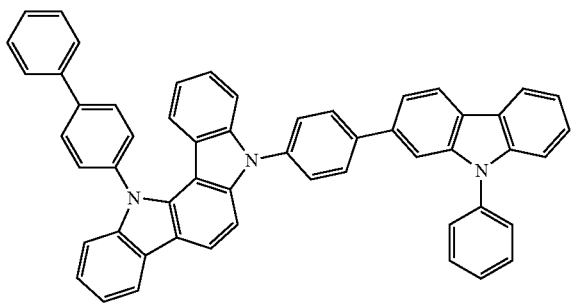
[E-67]
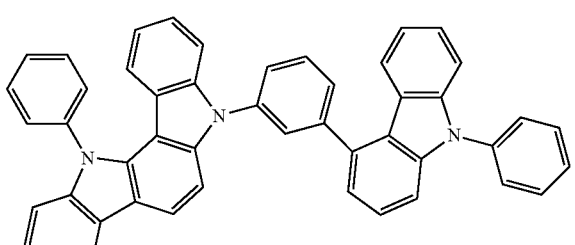
[E-68]
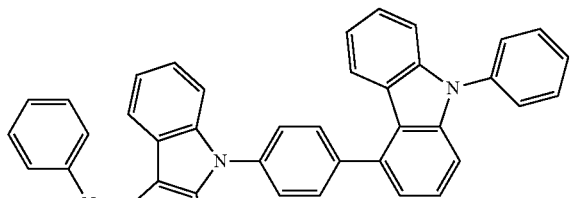
[E-69]
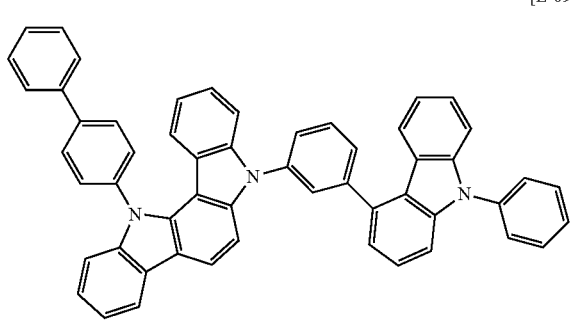
[E-70]
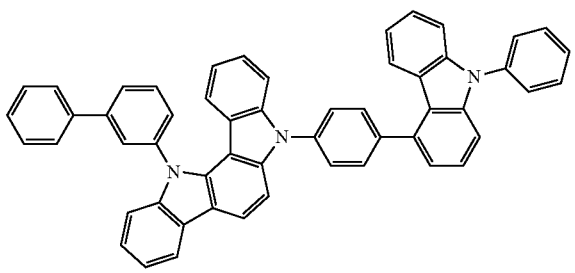
[E-71]
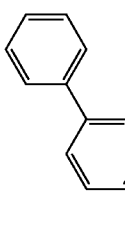
[E-72]
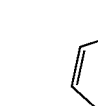
[E-73]
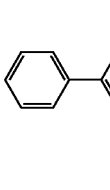
[E-74]

-continued
[E-75]
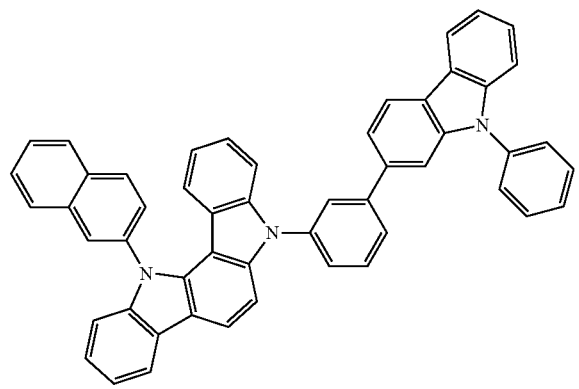
[E-76]
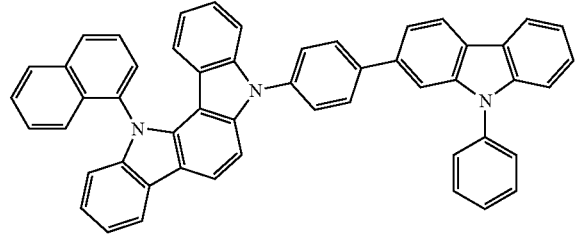
[E-77]
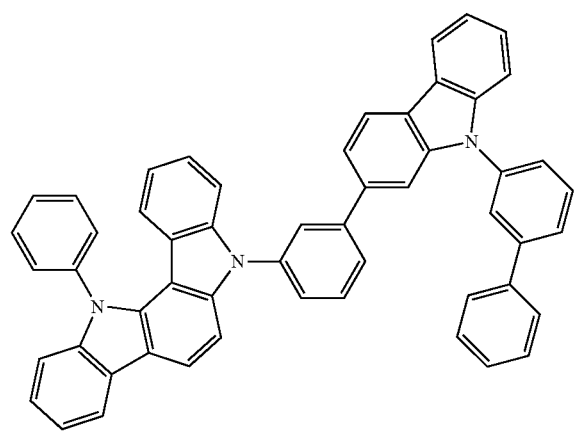
[E-78]
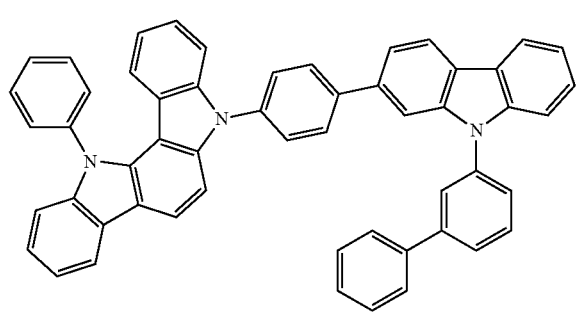
-continued
[E-79]
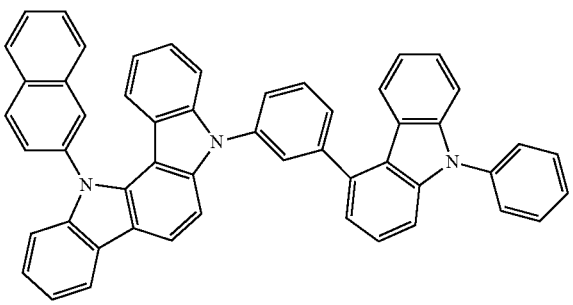
[E-80]
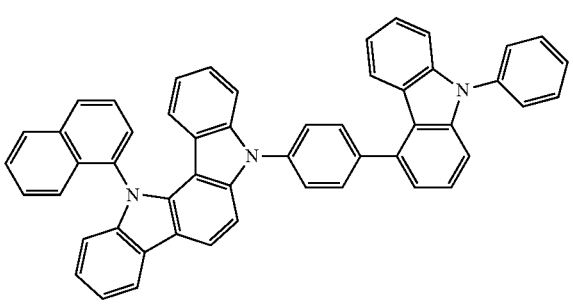
[E-81]
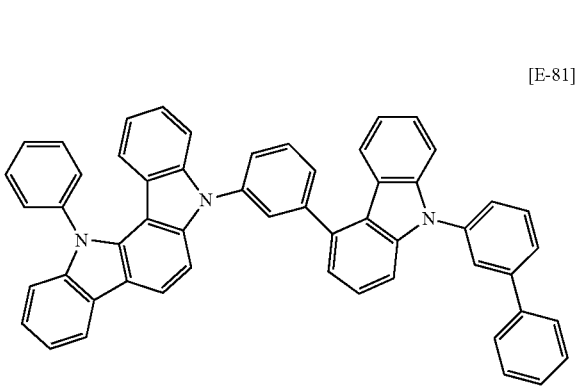
[E-82]
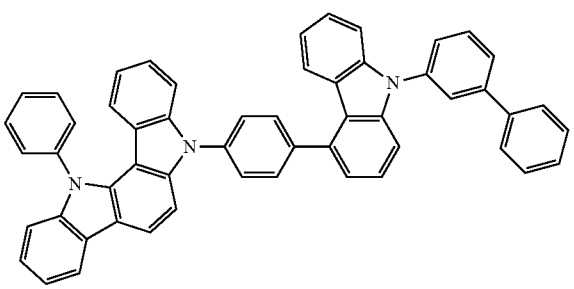

[E-83]
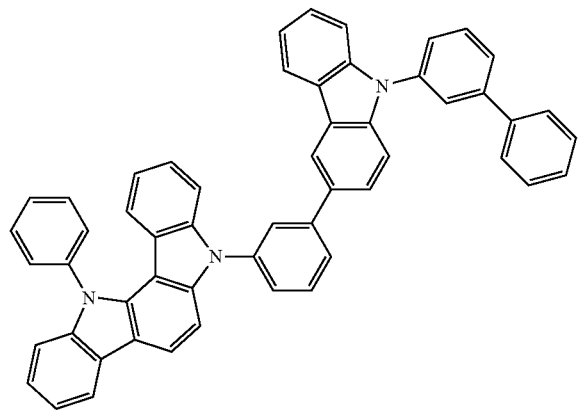
[E-84]
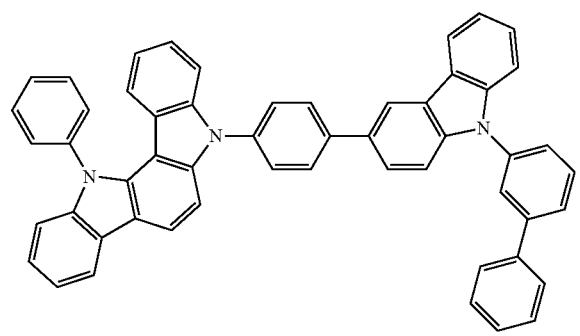
[E-85]
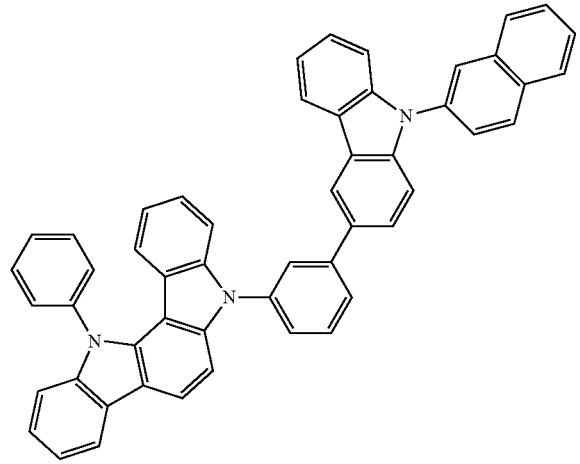
[E-86]
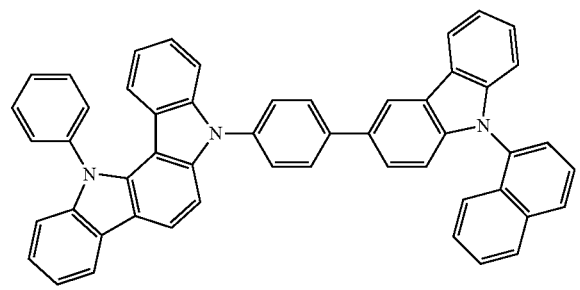
[E-87]
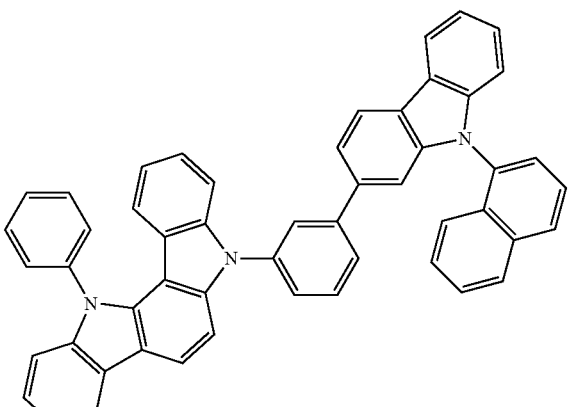
[E-88]
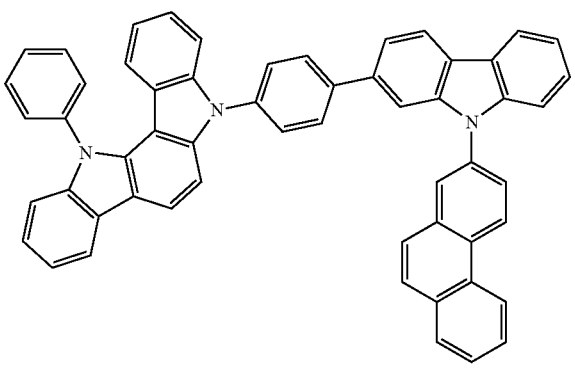
[E-89]
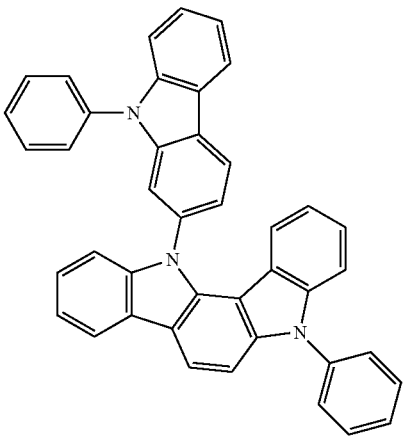

-continued
[E-90]
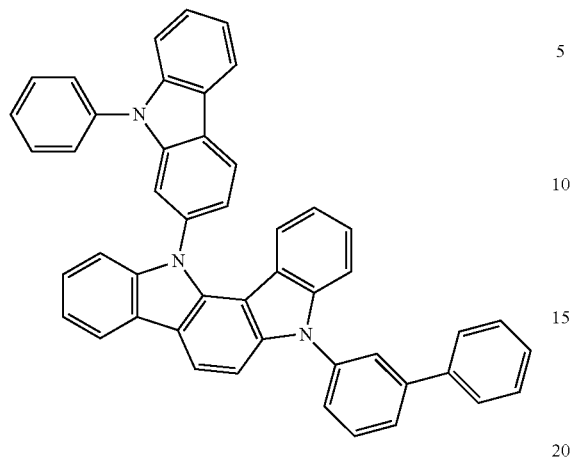
[E-91]
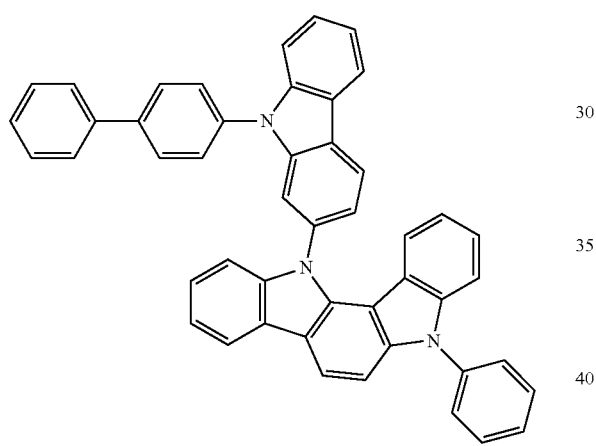
[E-92]
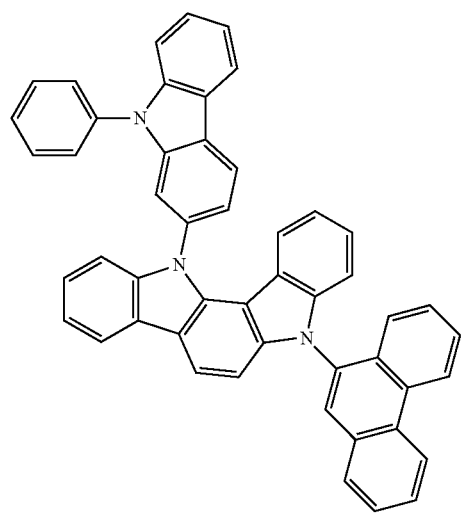
-continued
[E-93]
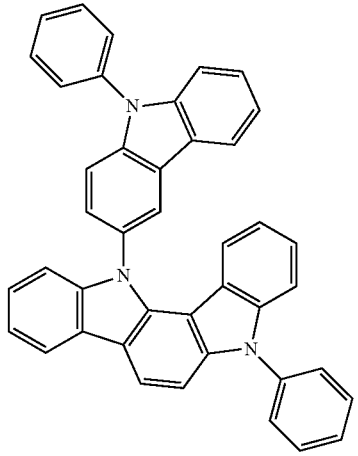
[E-94]
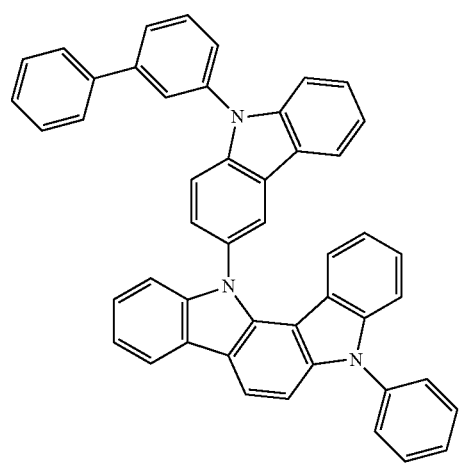
[E-95]
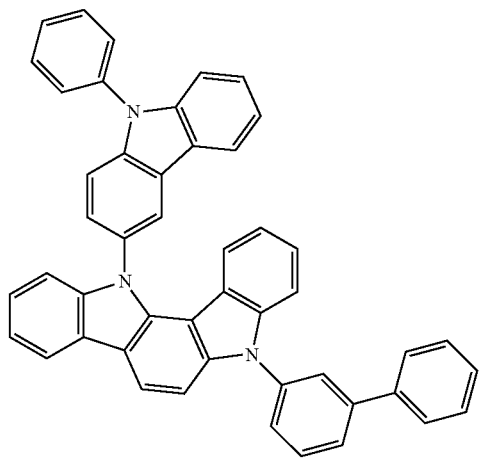

[E-96]
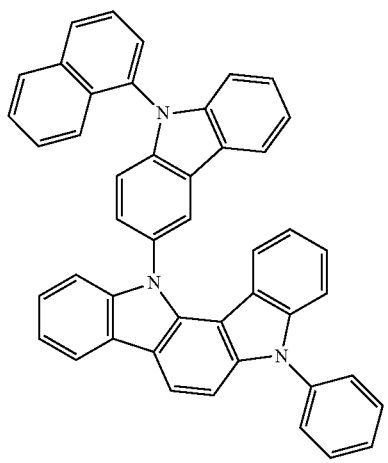
[E-97]
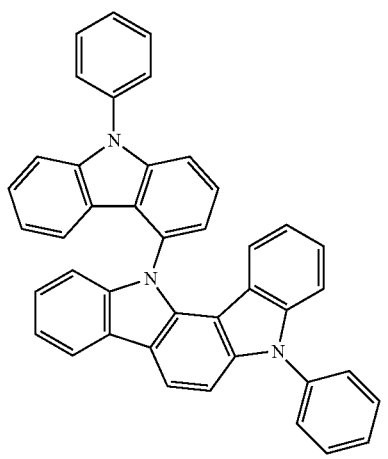
[E-98]
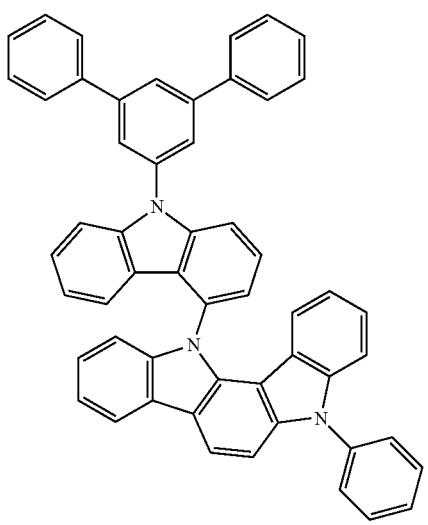
[E-99]
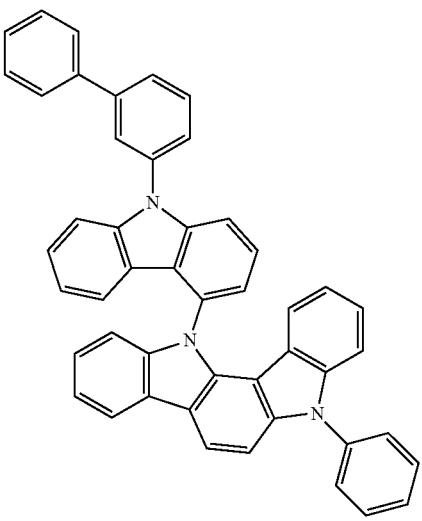
[E-100]
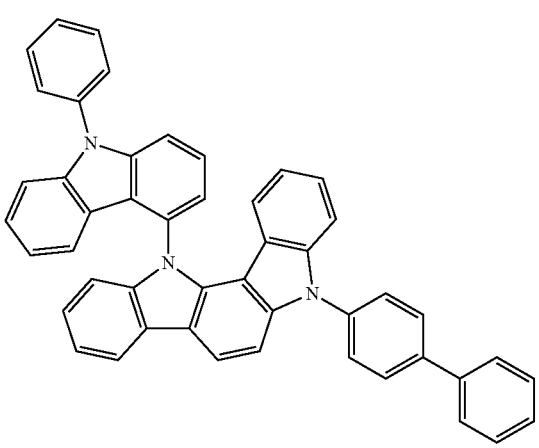
[E-101]
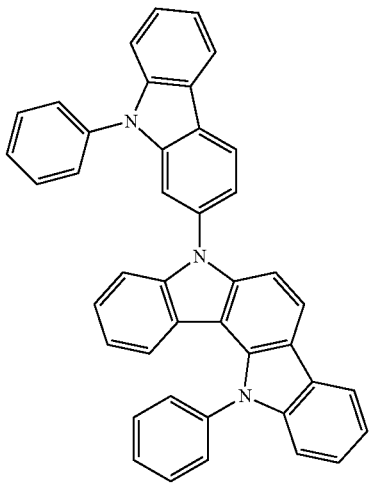

-continued
[E-102]
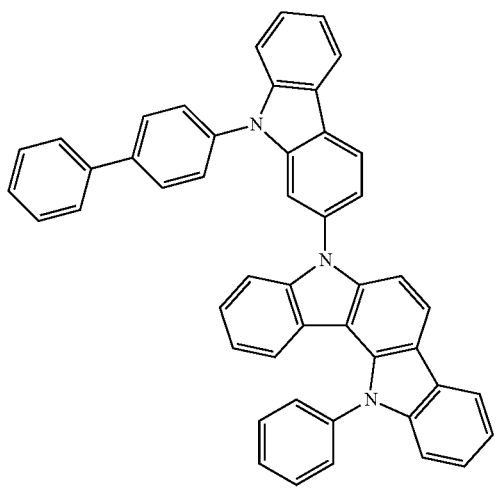
[E-103]
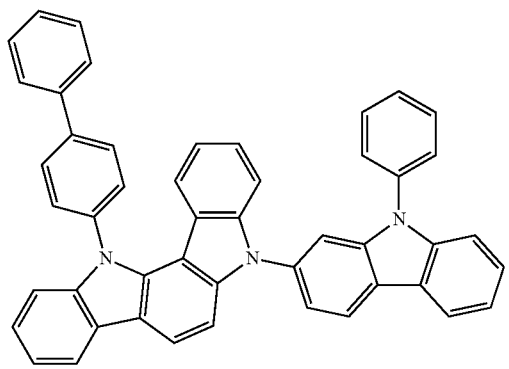
[E-104]
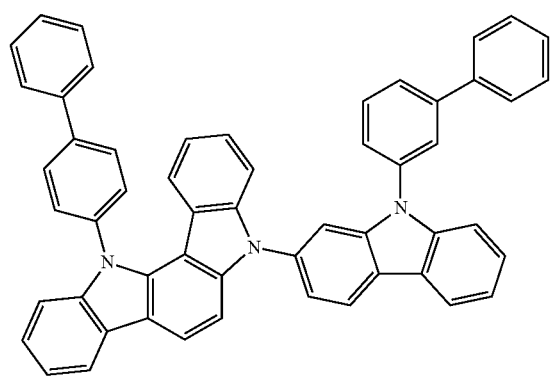
-continued
[E-105]
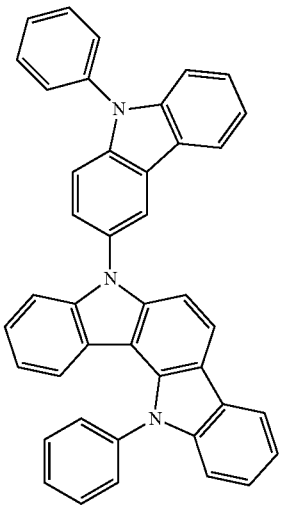
[E-106]
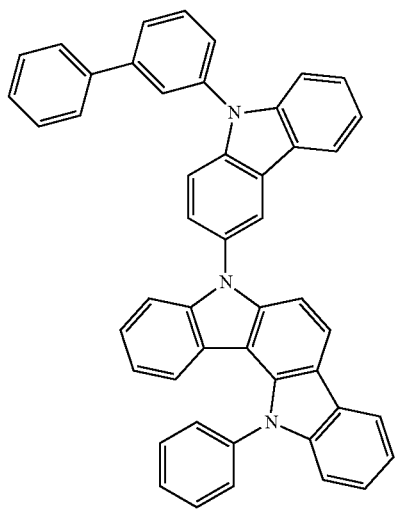
[E-107]
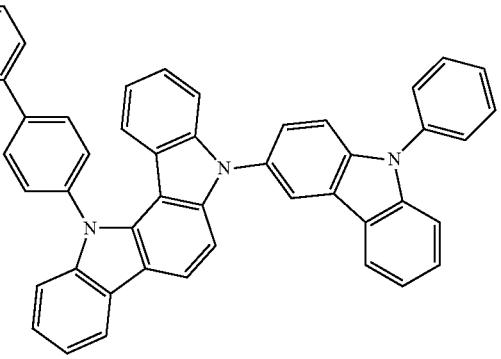

[E-108]
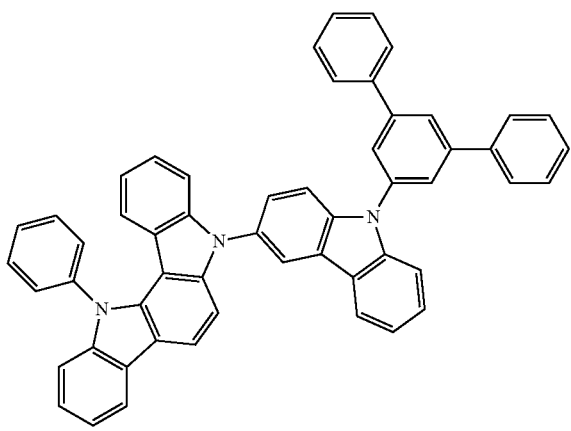

[E-109]
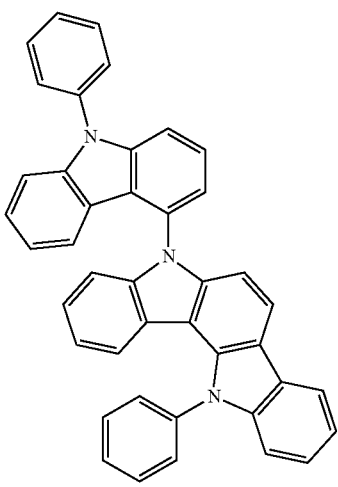

[E-110]
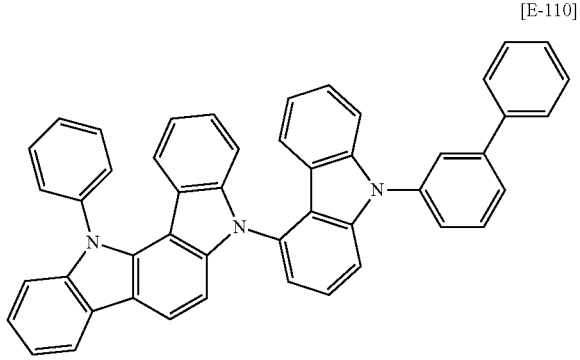

[E-111]
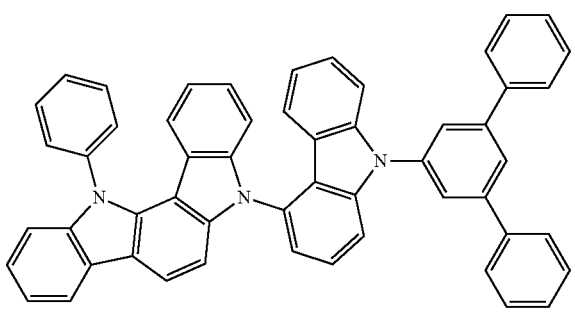

[E-112]
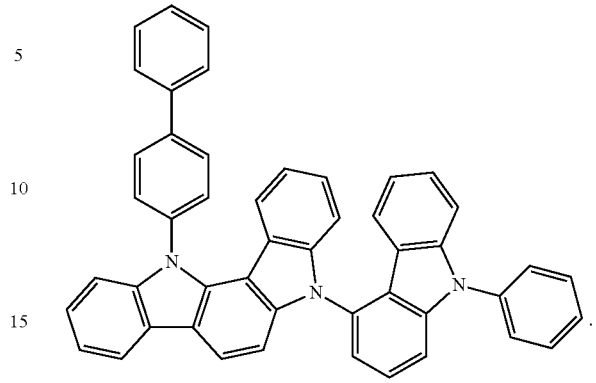

The second host compound is a compound having relatively strong electron transport characteristics and is represented by a combination of Chemical Formula 3 and Chemical Formula 4.

[Chemical Formula 3]
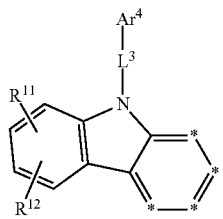

[Chemical Formula 4]
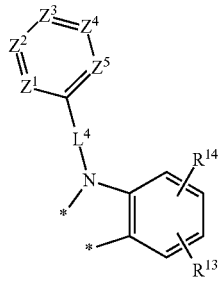

In Chemical Formula 3 and Chemical Formula 4, two adjacent *'s of Chemical Formula 3 are bound to two adjacent *'s of Chemical Formula 4 and the remainder *'s of Chemical Formula 3 not being bound to *'s of Chemical Formula 4 are $CR^b$, $Ar^3$ is a substituted or unsubstituted C6 to C30 aryl group, or a substituted or unsubstituted C2 to C30 heterocyclic group, $L^3$ and $L^4$ are independently a single bond or a substituted or unsubstituted C6 to C30 arylene group, $Z^1$ to $Z^5$ are independently N or $CR^c$, at least two of $Z^1$ to $Z^5$ are N, $R^b$, $R^c$ and $R^{11}$ to $R^{14}$ are independently hydrogen, deuterium, a substituted or unsubstituted C1 to C10 alkyl group, a substituted or unsubstituted C6 to C20 aryl group, a substituted or unsubstituted C2 to C30 heterocyclic group, or a combination thereof, and $R^c$'s are independently present alone or adjacent groups thereof are linked with each other to form a substituted or unsubstituted aliphatic, aromatic, or heteroaromatic monocyclic or polycyclic ring.

In an example embodiment, $R^c$ may independently be hydrogen, deuterium, methyl group, a substituted or unsubstituted phenyl group, a substituted or unsubstituted biphenyl group, a substituted or unsubstituted naphthyl group, a substituted or unsubstituted terphenyl group, a substituted or unsubstituted triphenylene group, a substituted or unsubstituted dibenzofuranyl group, a substituted or unsubstituted dibenzothiophenyl group, a substituted or unsubstituted fluorenyl group, or a combination thereof, or $R^c$ may independently present alone or adjacent groups thereof may be linked with each other to form a substituted or unsubstituted quinazolyl group.

In an example embodiment, $R^b$ may be hydrogen, deuterium, a methyl group, or a phenyl group, specifically hydrogen, or a phenyl group, and more specifically hydrogen.

The second host compound includes a substituent having electron characteristics and including a nitrogen-containing hexagonal ring in the indolocarbazole moiety, thereby the compound may become a structure capable of accepting electrons when an electric field is applied, and accordingly a driving voltage of an organic optoelectronic device may be lowered with the first host compound.

In the present disclosure, "substituted" of Chemical Formulae 3 and 4 refers to replacement of at least one hydrogen by deuterium, a C1 to C4 alkyl group, a C6 to C12 aryl group, or a C2 to C20 heterocyclic group.

In addition, in an example embodiment, "substituted" of Chemical Formulae 3 and 4 may refer to replacement of at least one hydrogen by deuterium, a C6 to C12 aryl group, or a C2 to C20 heterocyclic group, for example the "substituted" refers to replacement of at least one hydrogen by a phenyl group, a para-biphenyl group, a meta-biphenyl group, a pyridinyl group, a pyrimidinyl group, a triazinyl group, a quinazolinyl group, a dibenzofuranyl group, or a dibenzothiophenyl group.

In an example embodiment, the $R^{11}$ to $R^{14}$ may independently be hydrogen, deuterium, a substituted or unsubstituted C1 to C4 alkyl group, or a substituted or unsubstituted C6 to C12 aryl group, specifically hydrogen, deuterium, or a substituted or unsubstituted C6 to C12 aryl group, and more specifically hydrogen, a phenyl group, or a biphenyl group. In the most specific example embodiment, they may be all hydrogen.

In an example embodiment, $Ar^3$ may be a substituted or unsubstituted C6 to C30 aryl group, $L^3$ and $L^4$ may independently be a single bond, a substituted or unsubstituted phenylene group, or a substituted or unsubstituted biphenylene group, $Z^1$ to $Z^5$ may independently be N or $CR^c$, at least two of $Z^1$ to $Z^5$ may be N, $R^{b1}$ to $R^{b4}$ and $R^{11}$ to $R^{14}$ may independently be hydrogen, deuterium, a substituted or unsubstituted C1 to C4 alkyl group, a substituted or unsubstituted C6 to C12 aryl group, or a combination thereof, and $R^c$ may independently be hydrogen, deuterium, methyl group, a substituted or unsubstituted phenyl group, a substituted or unsubstituted biphenyl group, a substituted or unsubstituted naphthyl group, a substituted or unsubstituted terphenyl group, a substituted or unsubstituted triphenylene group, a substituted or unsubstituted dibenzofuranyl group, a substituted or unsubstituted dibenzothiophenyl group, a substituted or unsubstituted fluorenyl group, or a combination thereof, and $R^c$'s are independently present alone or adjacent groups thereof are linked with each other to form a substituted or unsubstituted quinazolyl group.

In an example embodiment, the second host compound may be for example represented by one of Chemical Formula A-ET, Chemical Formula B-ET, Chemical Formula C-ET, Chemical Formula D-ET and Chemical Formula E-ET according to a fusion point of Chemical Formula 3 and Chemical Formula 4.

[Chemical Formula A-ET]

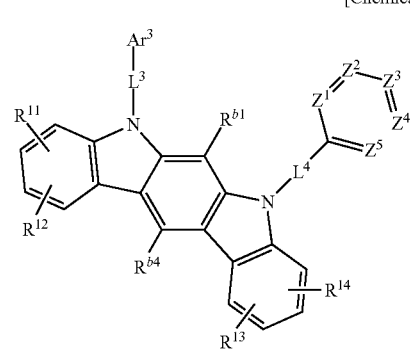

[Chemical Formula B-ET]

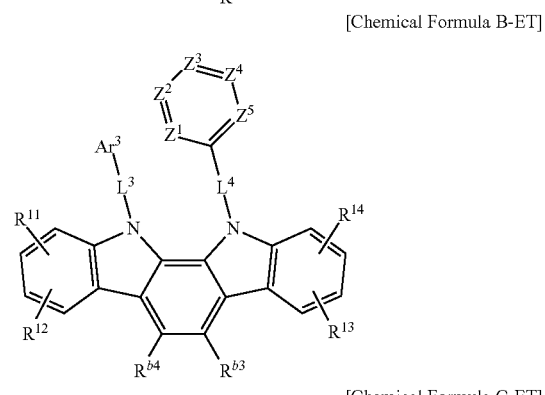

[Chemical Formula C-ET]

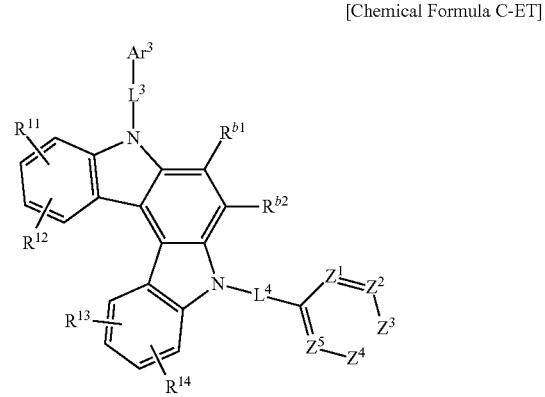

[Chemical Formula D-ET]

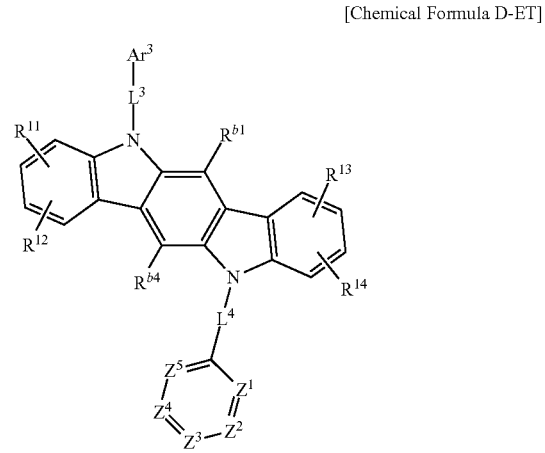

[Chemical Formula E-ET]

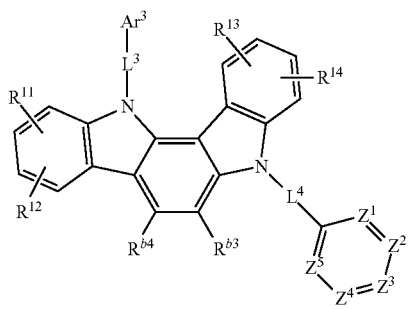

In Chemical Formula A-ET, Chemical Formula B-ET, Chemical Formula C-ET, Chemical Formula D-ET, and Chemical Formula E-ET, $Ar^3$, $L^3$, $L^4$, $Z^1$ to $Z^5$, and $R^{11}$ to $R^{14}$ are the same as described above, and $R^{b1}$ to $R^{b4}$ are the same as the definition of $R^b$.

In an example embodiment, the $R^b$ and $R^{b1}$ to $R^{b4}$ may independently be hydrogen, deuterium, a substituted or unsubstituted C1 to C4 alkyl group, or a substituted or unsubstituted C6 to C12 aryl group, specifically hydrogen, deuterium, or a substituted or unsubstituted C6 to C12 aryl group, and more specifically hydrogen, a phenyl group, or a biphenyl group. In the most specific example embodiment, they may be all hydrogen.

In the present disclosure, "linking of the adjacent groups" in the definition of $R^c$ means that a phenyl group linked with each $R^c$ and two substituents of the adjacent $R^c$'s are fused with each other to provide a substituted or unsubstituted aliphatic, aromatic, or heteroaromatic monocyclic or polycyclic ring. For example, when $Z^1$ is $CR^{c1}$ and $Z^2$ is $CR^{c2}$, $R^{c1}$ and $R^{c2}$ may form a heteroaromatic polycyclic ring with a phenyl group linked with them. Herein, examples of the heteroaromatic polycyclic ring may be a substituted or unsubstituted quinazolinyl group, a substituted or unsubstituted quinoxalinyl group, and the like, for example a substituted or unsubstituted quinazolinyl group.

In an example embodiment, when the $R^c$'s are independently present, the hexagonal ring consisting of $Z^1$ to $Z^5$ may be a substituted or unsubstituted pyrimidine, a substituted or unsubstituted triazine, a substituted or unsubstituted pyrazinyl, or a substituted or unsubstituted pyridazinyl, and specifically a substituted or unsubstituted pyrimidine, or a substituted or unsubstituted triazine, and Chemical Formula 4 may be for example represented by one of Chemical Formula 4a to Chemical Formula 4c.

[Chemical Formula 4a]

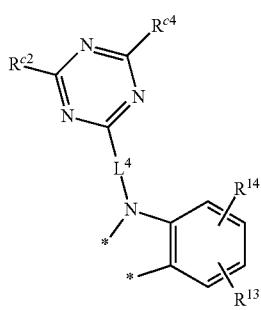

[Chemical Formula 4b]

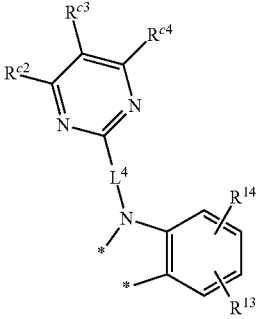

[Chemical Formula 4c]

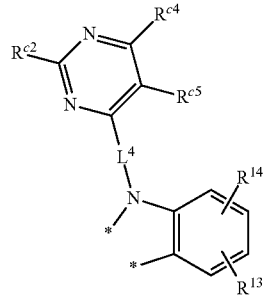

In addition, in another example embodiment, the adjacent groups of the $R^c$'s may be linked with each other to form a substituted or unsubstituted heteroaromatic polycyclic ring, wherein a polycyclic ring consisting of the $Z^1$ to $Z^5$ may be for example a substituted or unsubstituted quinazolinyl group, and Chemical Formula 4 may be represented by Chemical Formula 4d or Chemical Formula 4e.

[Chemical Formula 4d]

[Chemical Formula 4e]

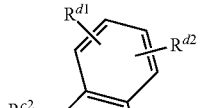

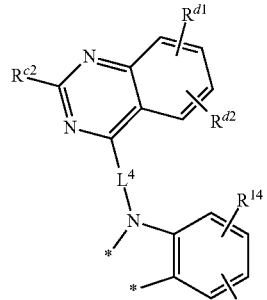

In Chemical Formula 4a to Chemical Formula 4e, $R^{13}$ and $R^{14}$ are the same as described above, and $R^{c2}$ to $R^{c5}$, $R^{d1}$, and $R^{d2}$ are independently hydrogen, deuterium, a substituted or unsubstituted C1 to C10 alkyl group, a substituted or unsubstituted C6 to C20 aryl group, or a combination thereof.

In an example embodiment, the $R^{c2}$ to $R^{c5}$ may independently be hydrogen, a substituted or unsubstituted C1 to C10 alkyl group, or a substituted or unsubstituted C6 to C20 aryl group, specifically hydrogen, or a substituted or unsubstituted C6 to C20 aryl group, and more specifically hydrogen, a substituted or unsubstituted phenyl group, a substituted or unsubstituted para-biphenyl group, a substituted or unsubstituted meta-biphenyl group, a substituted or unsubstituted terphenyl group, a substituted or unsubstituted dibenzofuranyl group, or a substituted or unsubstituted dibenzothiophenyl group.

For example, the $R^{c2}$ and $R^{c4}$ may independently be a substituted or unsubstituted phenyl group, a substituted or unsubstituted para-biphenyl group, a substituted or unsubstituted meta-biphenyl group, a substituted or unsubstituted terphenyl group, a substituted or unsubstituted dibenzofuranyl group, or a substituted or unsubstituted dibenzothiophenyl group, and the $R^{c3}$ and $R^{c5}$ may be all hydrogen.

In a more specific example embodiment,

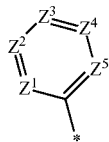

of Chemical Formula 4 may be selected from substituents of Group IV.

[Group IV]

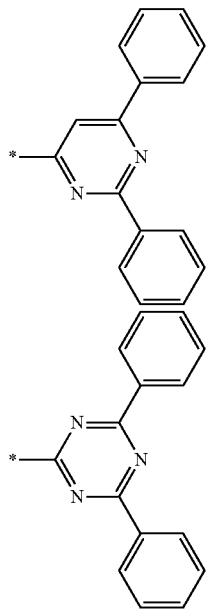
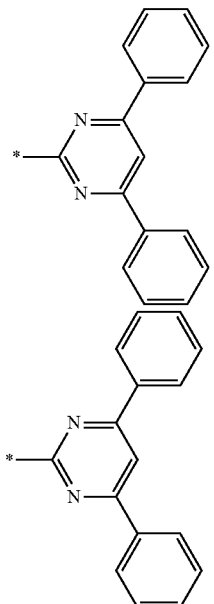
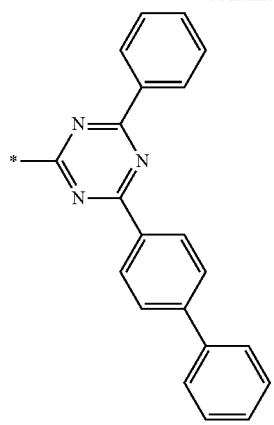
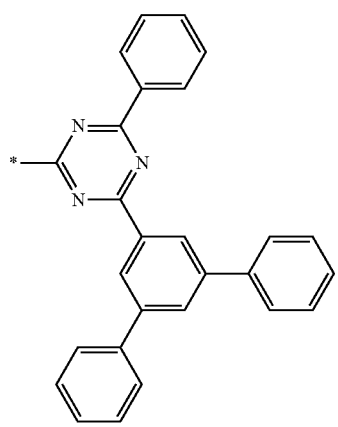
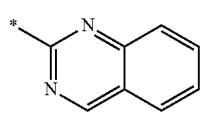
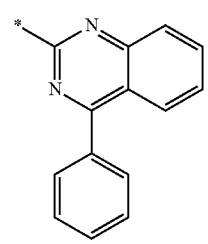
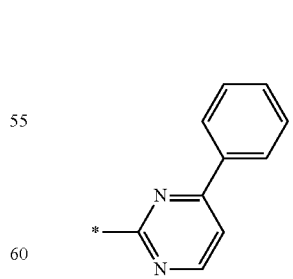
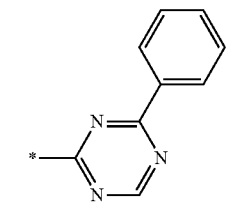
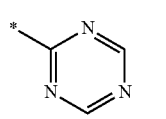

-continued
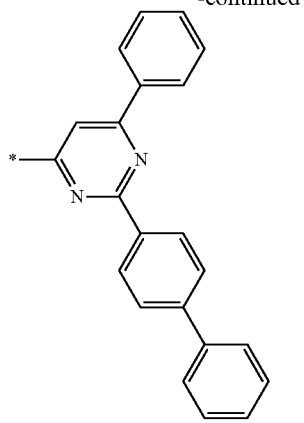
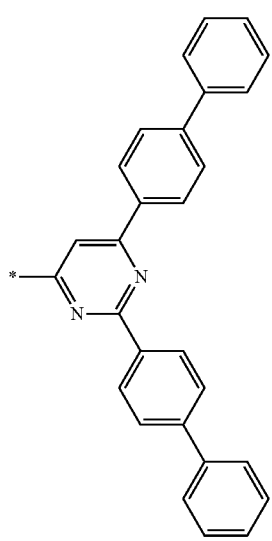
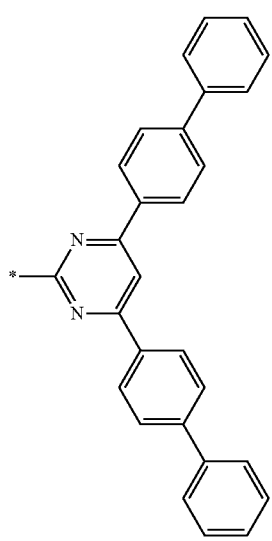
-continued
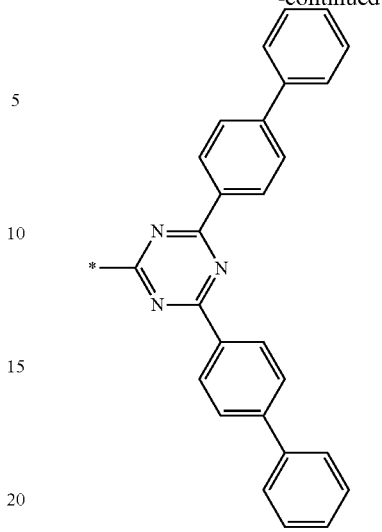
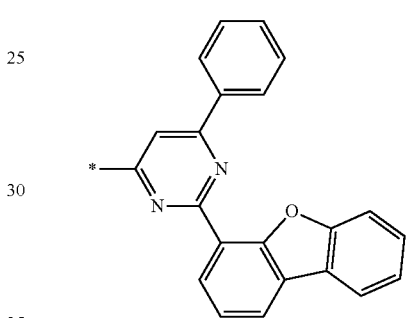
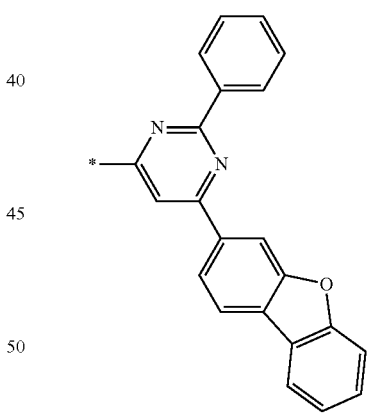
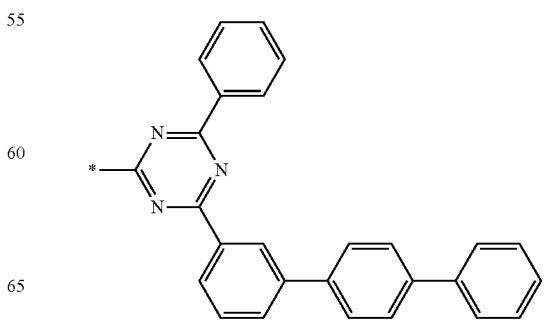

-continued
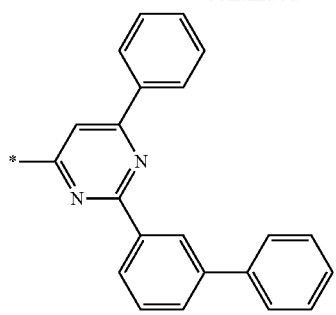
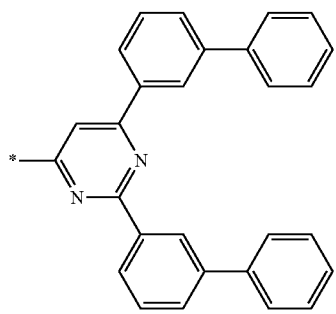
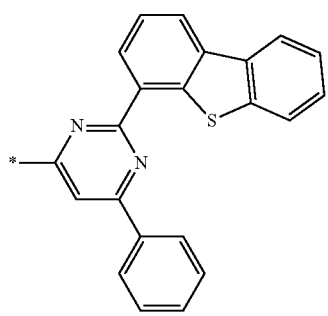
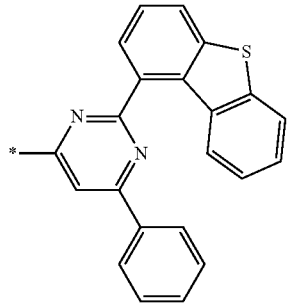
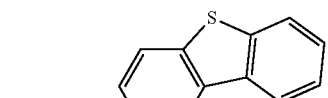
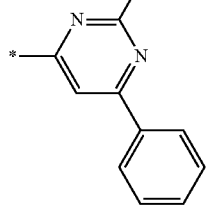
-continued
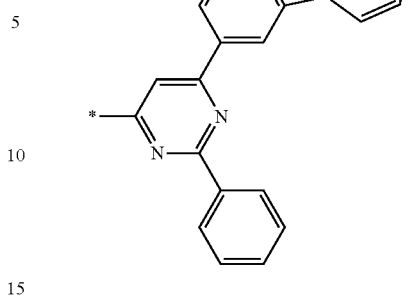
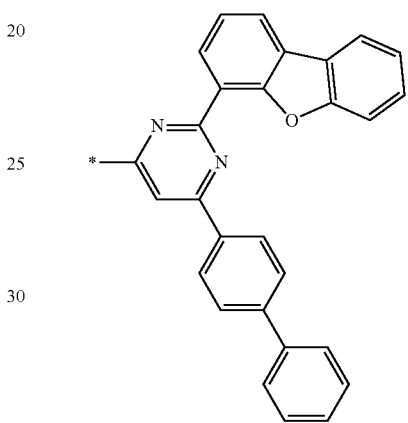
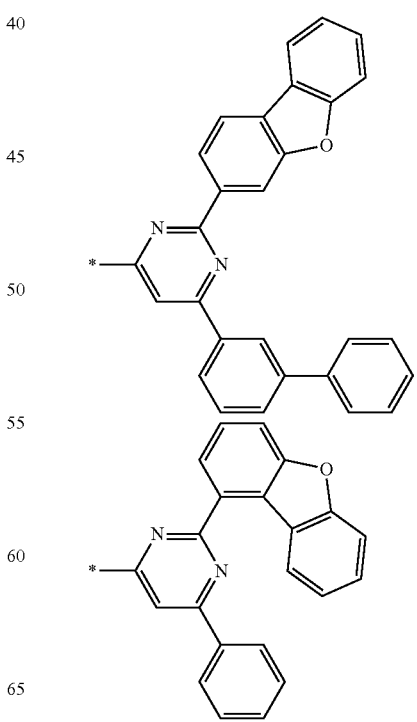

141
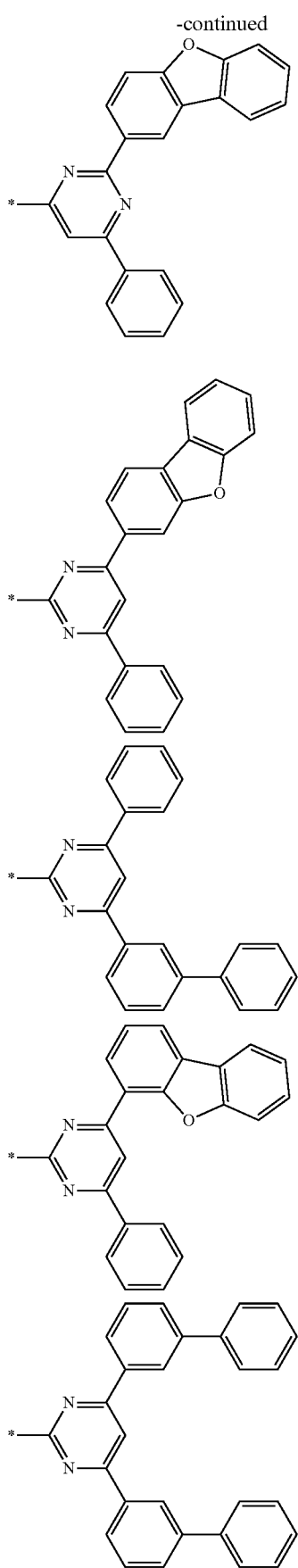
142
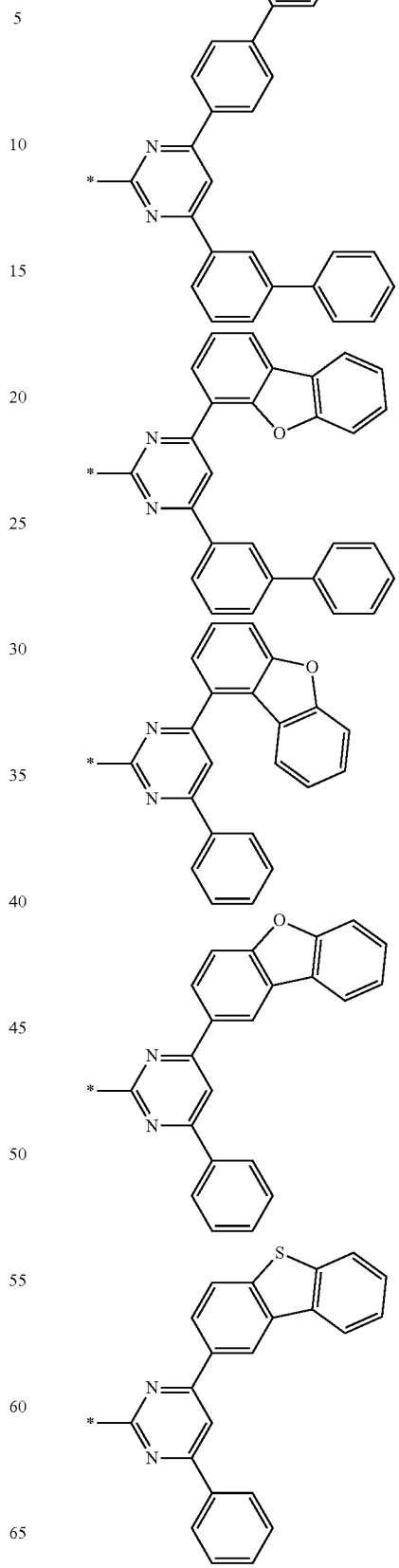

143
-continued
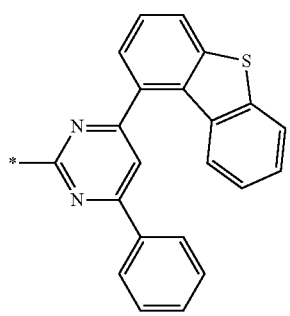
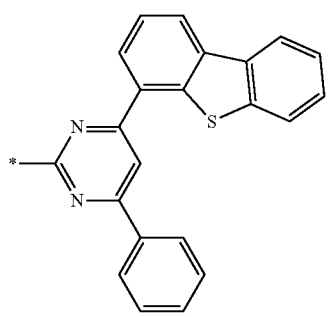
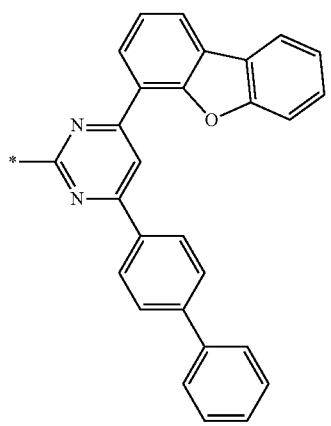
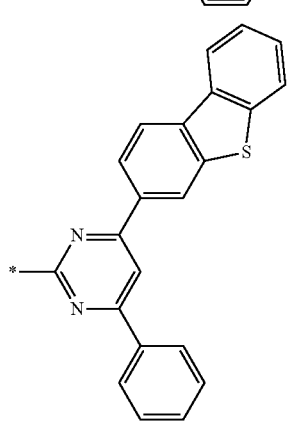
144
-continued
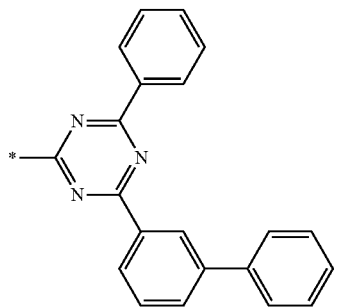
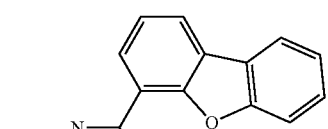
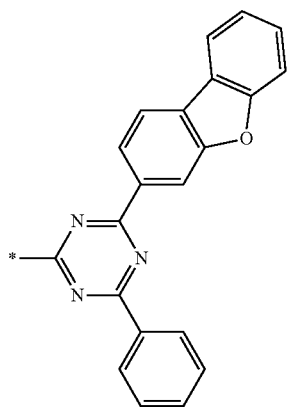
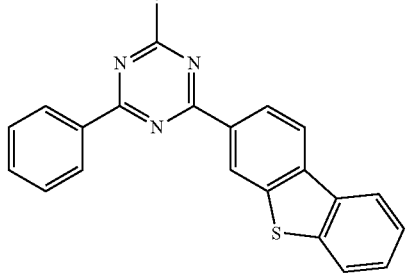

145
-continued
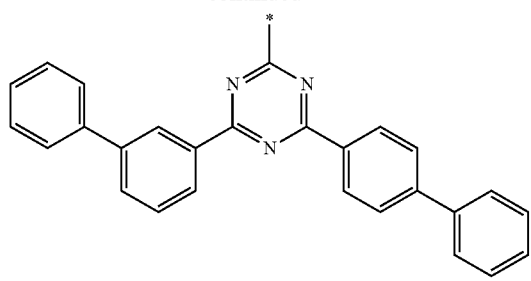
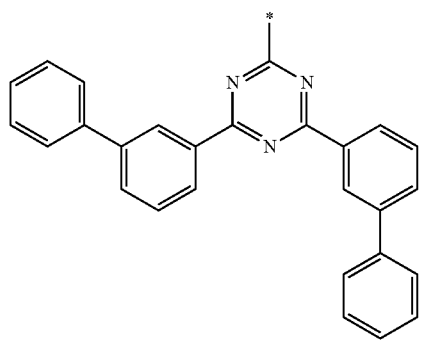
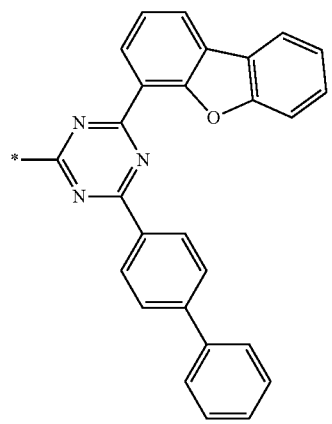
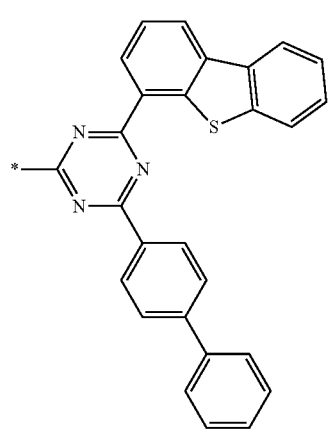
146
-continued
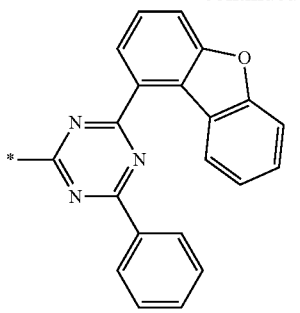
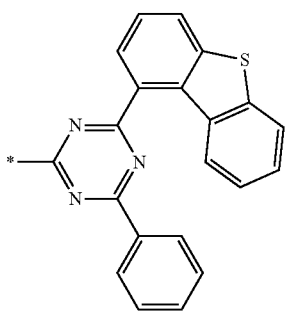
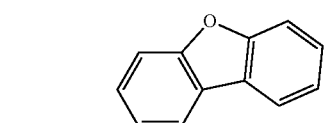
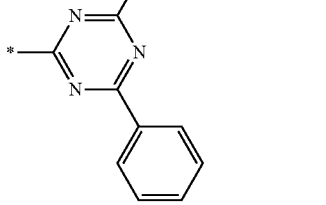
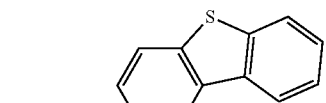
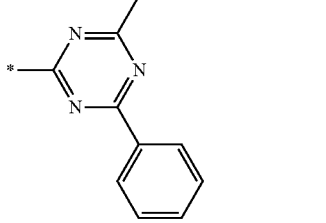
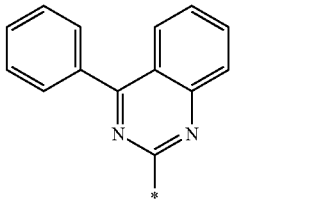

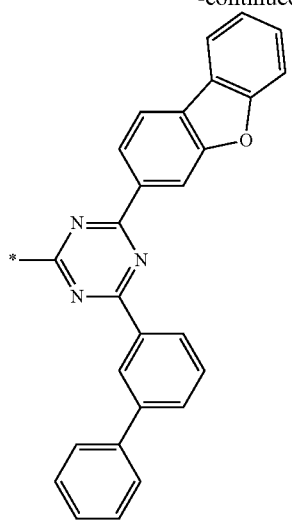
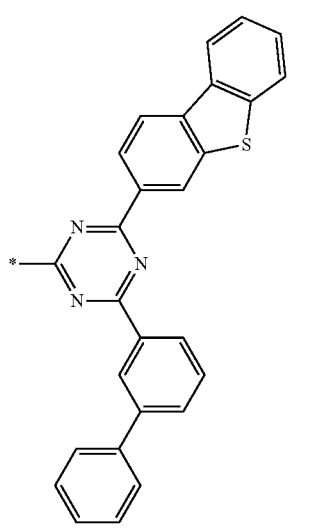
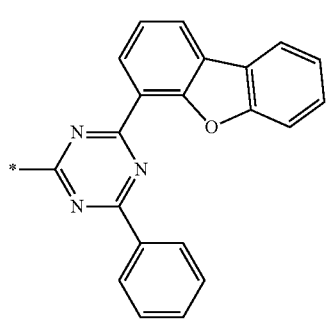
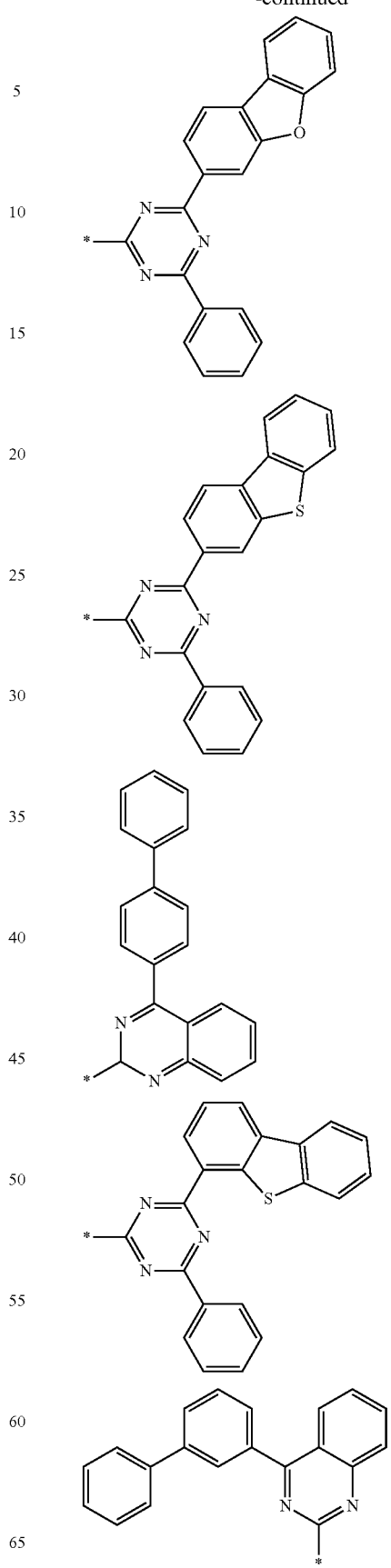

-continued

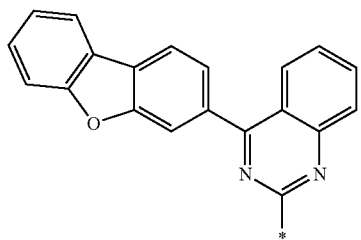

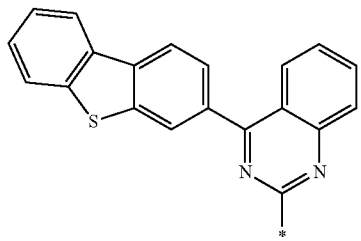 [SMILES: *c1nc(-c2ccc3c(c2)sc2ccccc23)c2ccccc2n1]

In Group IV, * is a linking point with an adjacent atom.

In an example embodiment, the $R^{d1}$ and $R^{d2}$ may independently be hydrogen, deuterium, a substituted or unsubstituted C1 to C4 alkyl group, a substituted or unsubstituted C6 to C12 aryl group, specifically hydrogen, deuterium, or a substituted or unsubstituted C6 to C12 aryl group, and more specifically hydrogen, a phenyl group, or a biphenyl group. In addition, in the most specific example embodiment, they may be all hydrogen.

In an example embodiment, the $L^3$ and $L^4$ may independently be a single bond, or a substituted or unsubstituted C6 to C12 arylene group, and specifically a single bond or a substituted or unsubstituted phenylene group, and they may be for example all single bonds.

In an example embodiment, the $Ar^3$ may be a substituted or unsubstituted C6 to C12 aryl group, for example a substituted or unsubstituted phenyl group.

In a more specific example embodiment, the second host compound may be represented by one of Chemical Formula B-ET, and specifically one of Chemical Formula B-ET-a, Chemical Formula B-ET-b, Chemical Formula B-ET-c, Chemical Formula B-ET-d, and Chemical Formula B-ET-e.

[Chemical Formula B-ET-a]

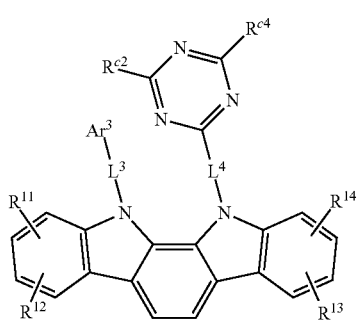

-continued

[Chemical Formula B-ET-b]

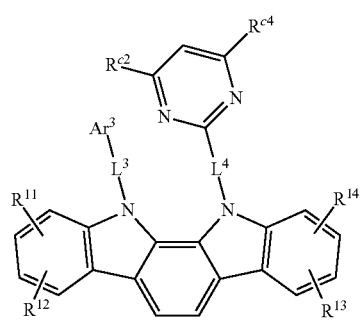

[Chemical Formula B-ET-c]

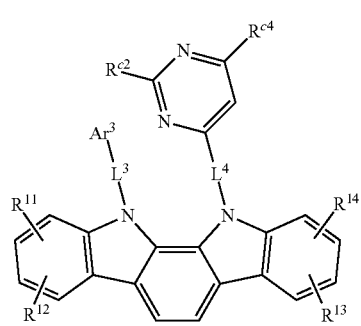

[Chemical Formula B-ET-d]

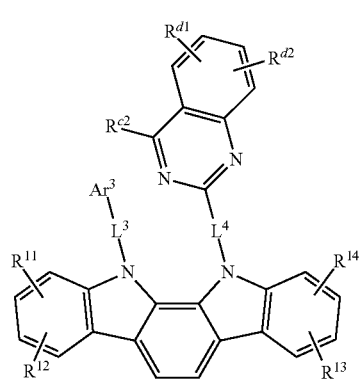

[Chemical Formula B-ET-e]

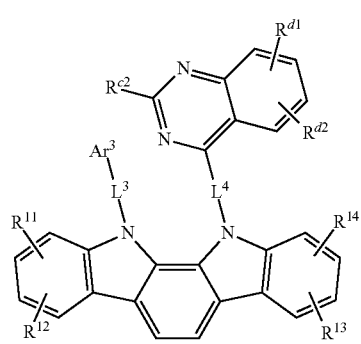

In Chemical Formula B-ET-a, Chemical Formula B-ET-b, Chemical Formula B-ET-c, Chemical Formula B-ET-d, and Chemical Formula B-ET-e, $Ar^3$, $L^3$ and $L^4$, $R^{c2}$ to $R^{c5}$, $R^{d1}$, $R^{d2}$, and $R^{11}$ to $R^{14}$ are the same as described above.

In addition, in the most specific example embodiment, the second host compound may be represented by Chemical Formula B-ET-a.

The second host compound may be for example compounds of Group 2, but is not limited thereto.

[Group 2]
[A-ET 1]
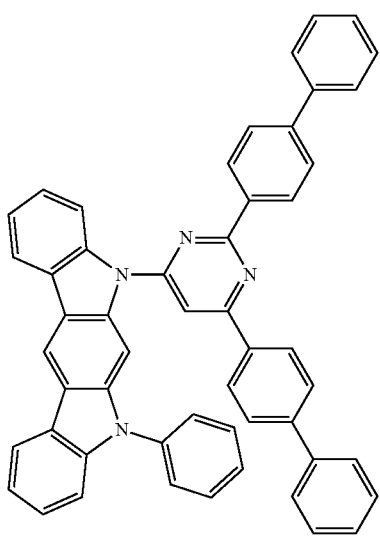
[A-ET 2]
[A-ET 3]
[A-ET 4]
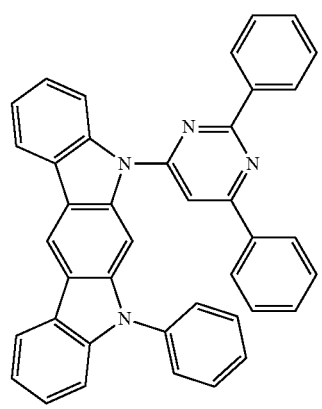
[A-ET 5]
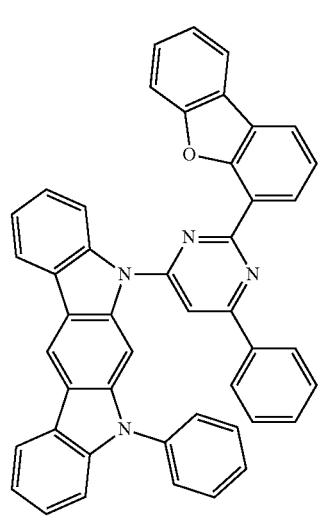
[A-ET 6]
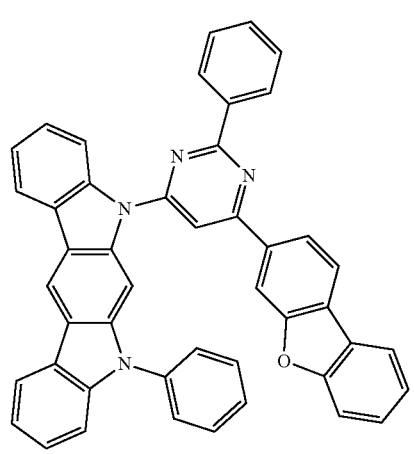

[A-ET 7]
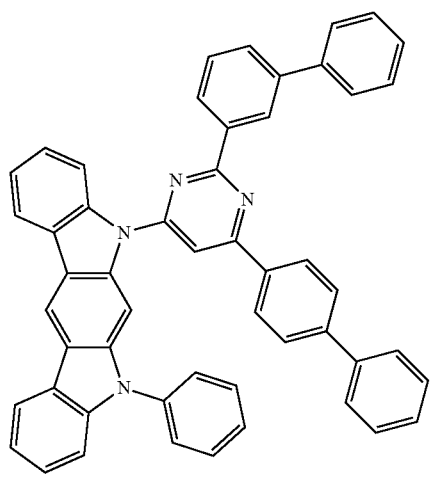
[A-ET 10]
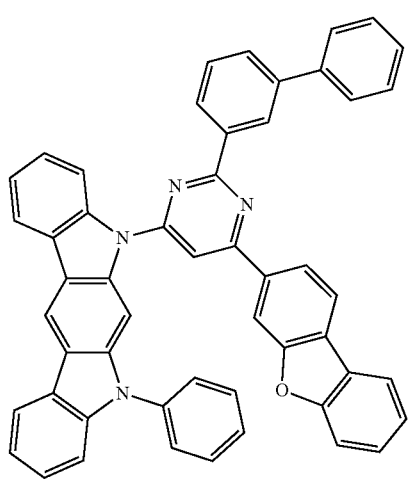
[A-ET 8]
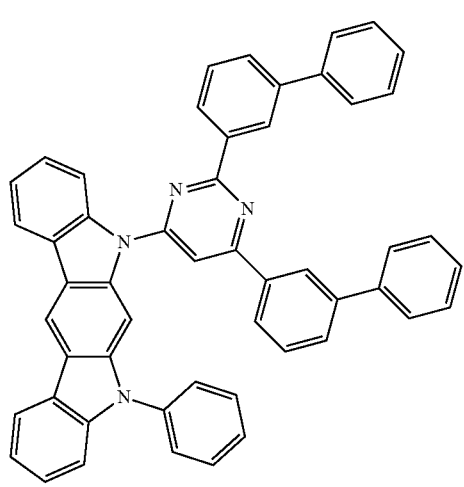
[A-ET 11]
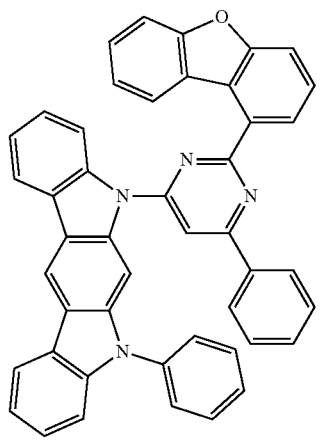
[A-ET 9]
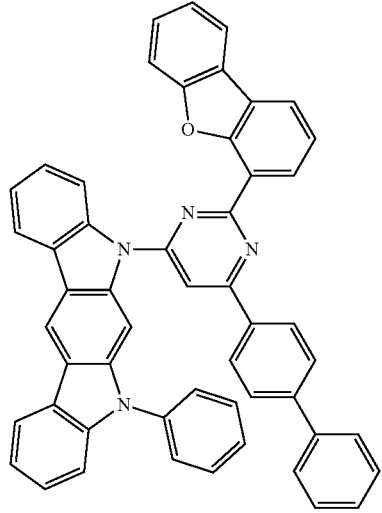
[A-ET 12]
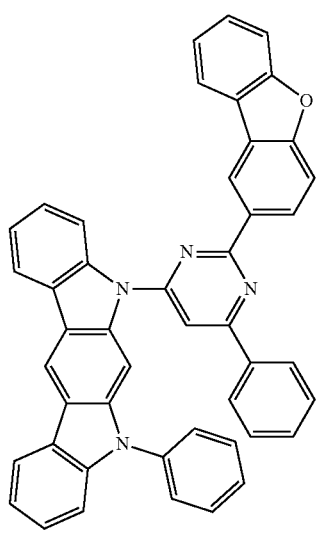

[A-ET 13]
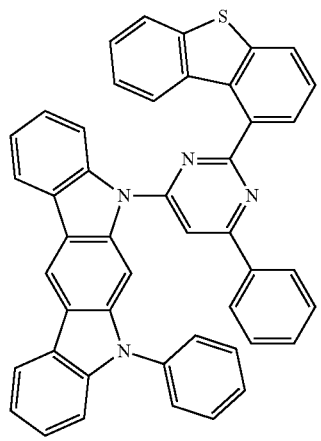
[A-ET 14]
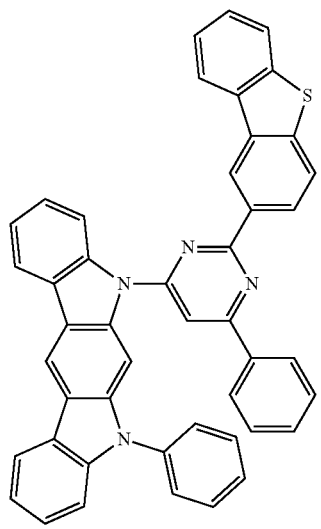
[A-ET 15]
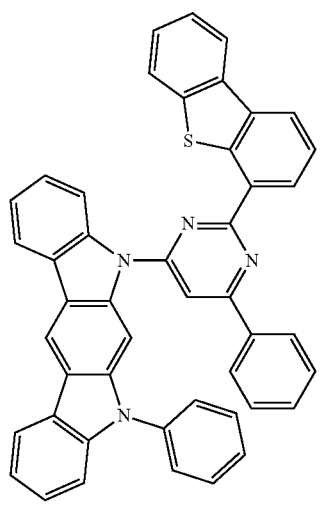
[A-ET 16]
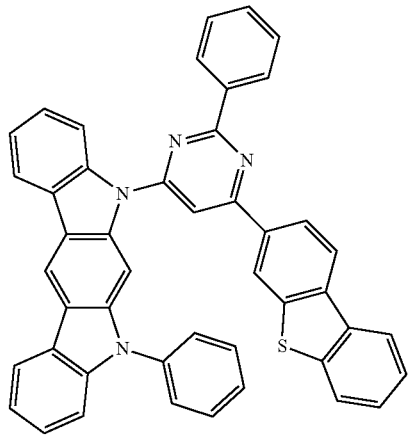
[A-ET 17]
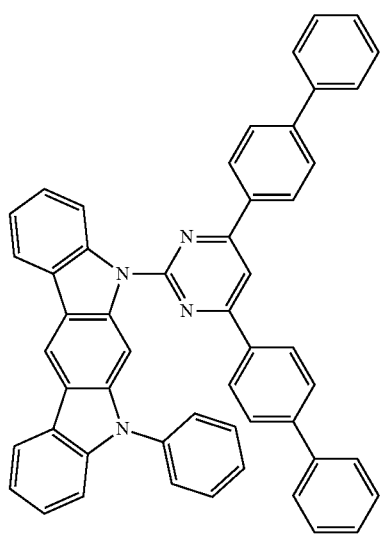
[A-ET 18]
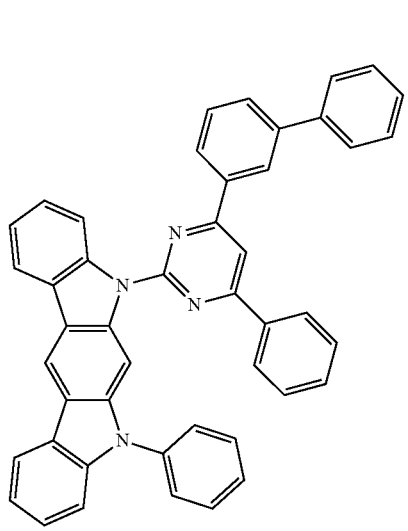

[A-ET 19]
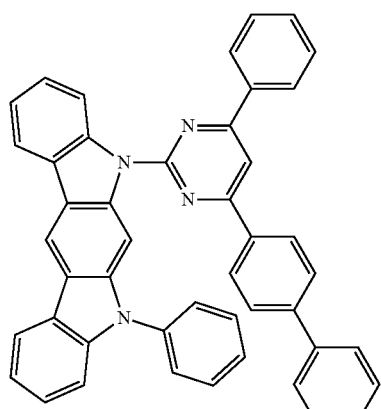
[A-ET 22]
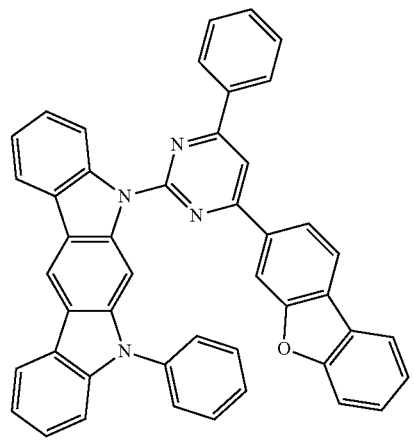
[A-ET 20]
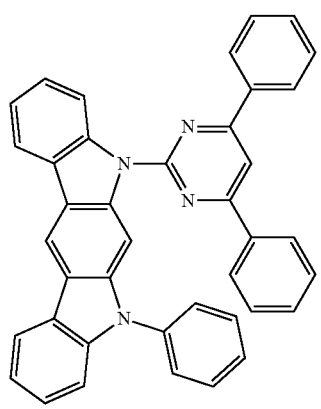
[A-ET 23]
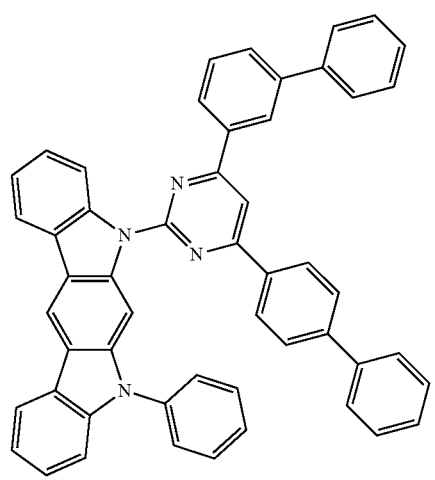
[A-ET 21]
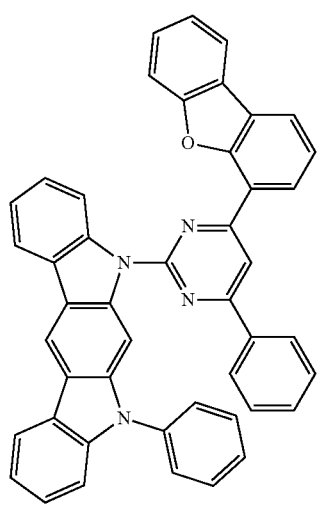
[A-ET 24]
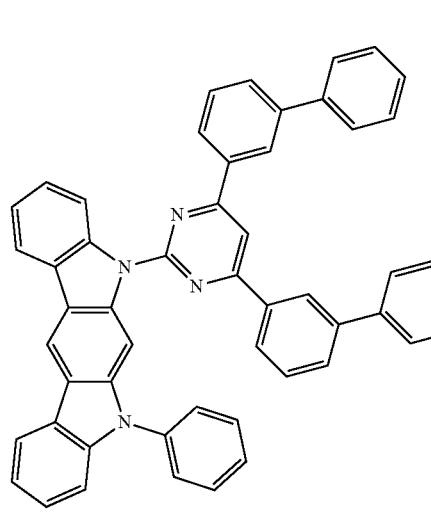

-continued
[A-ET 25]
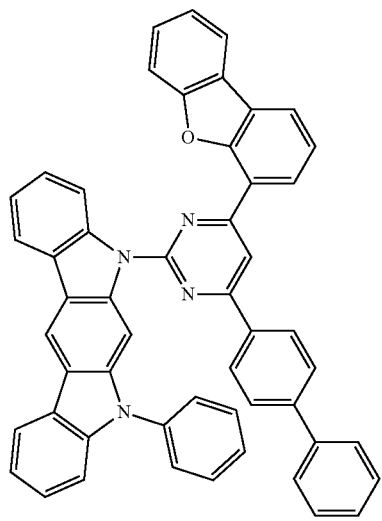
[A-ET 26]
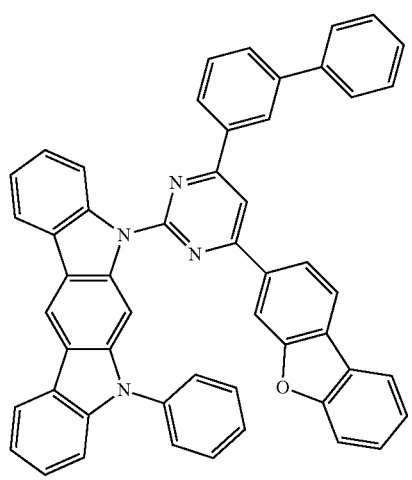
[A-ET 27]
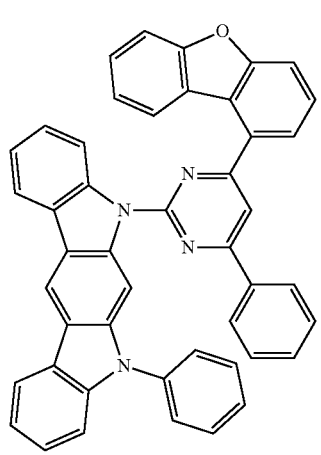
[A-ET 28]
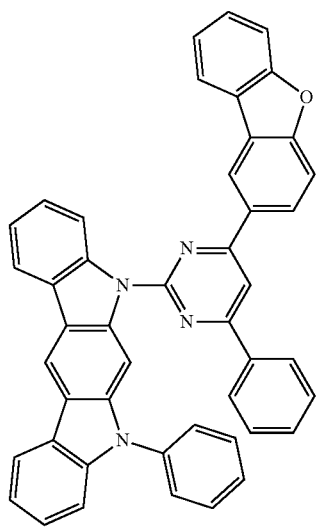
[A-ET 29]
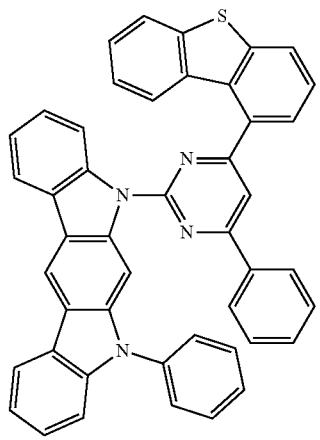
[A-ET 30]
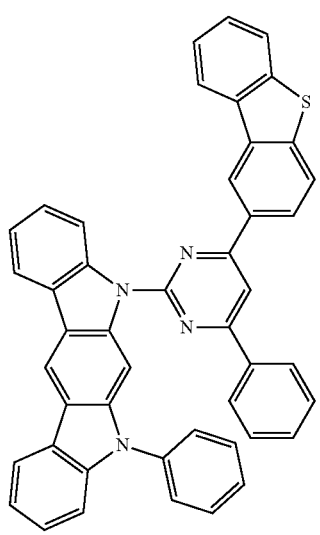

[A-ET 31]
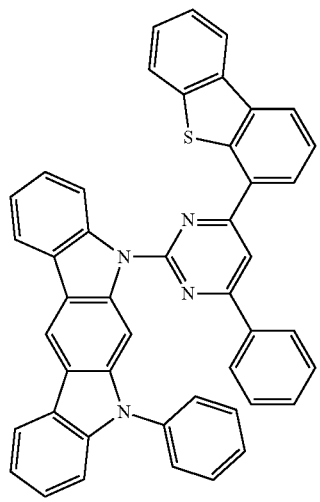
[A-ET 32]
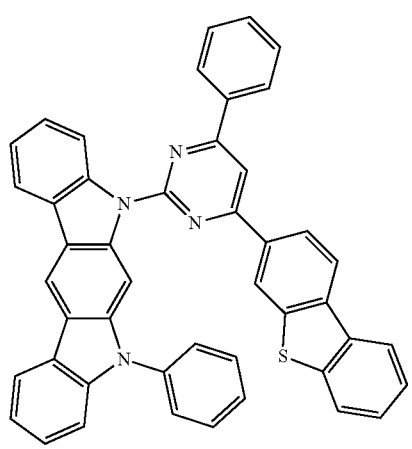
[A-ET 33]
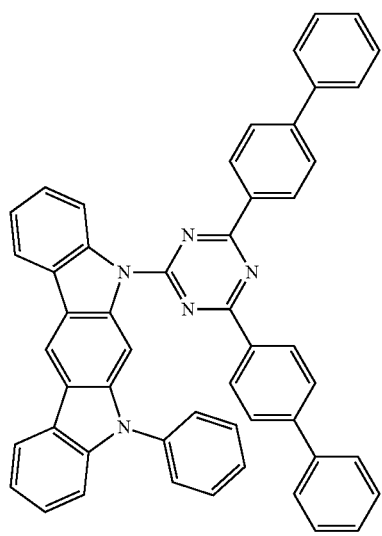
[A-ET 34]
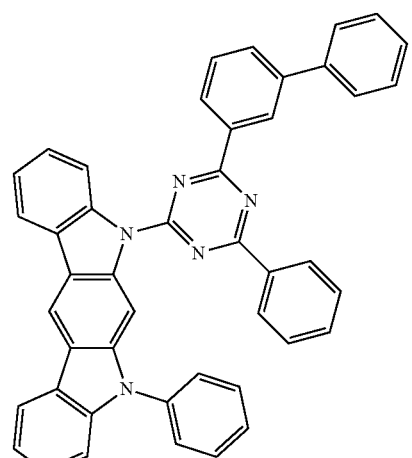
[A-ET 35]
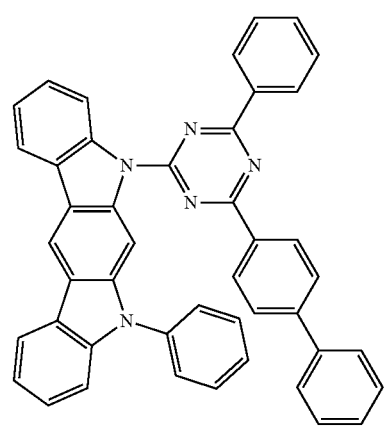
[A-ET 36]
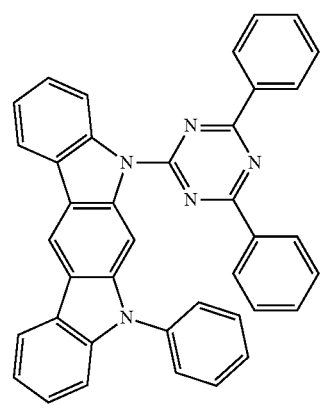

[A-ET 37]
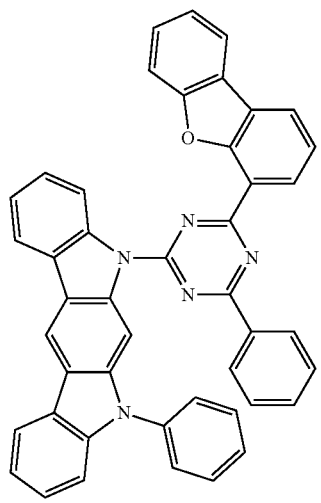
[A-ET 38]
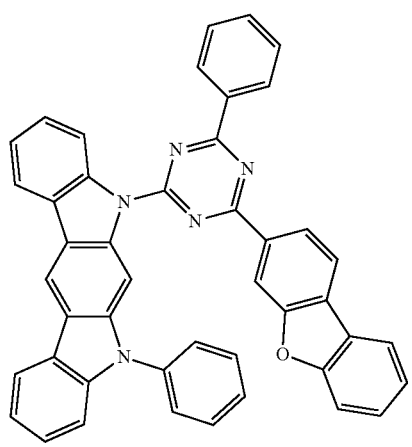
[A-ET 39]
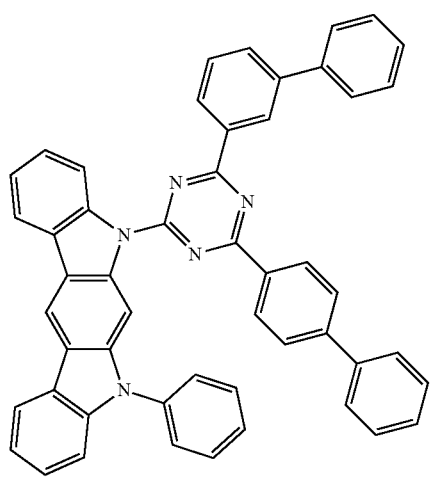
[A-ET 40]
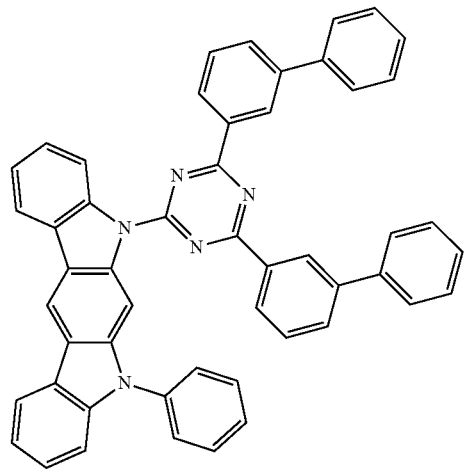
[A-ET 41]
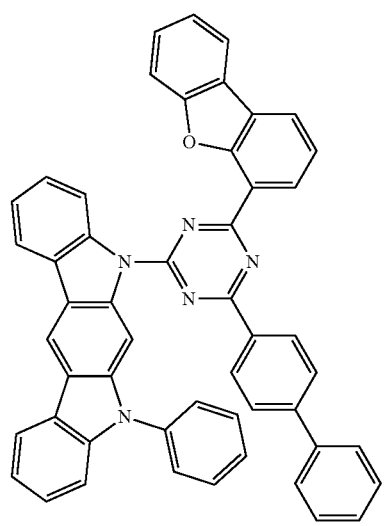
[A-ET 42]
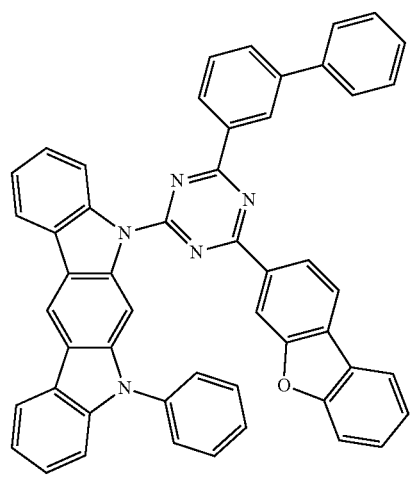

[A-ET 43]
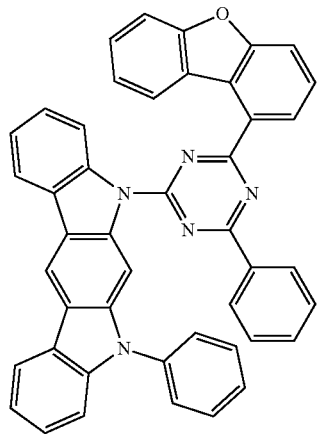
[A-ET 46]
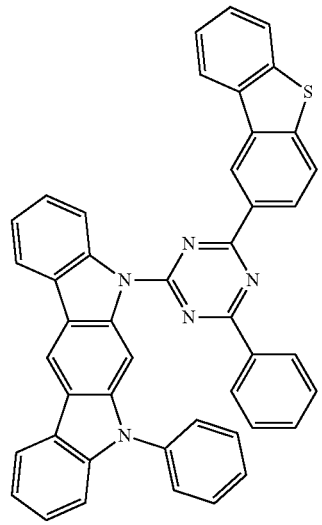
[A-ET 44]
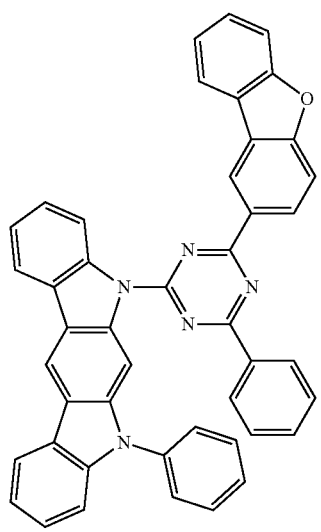
[A-ET 47]
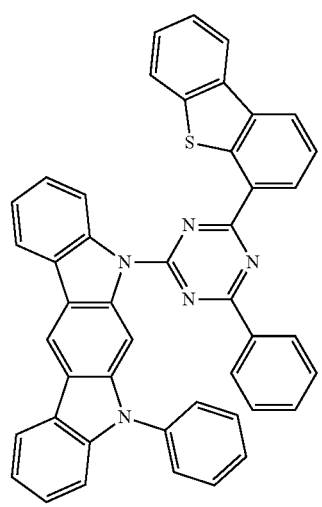
[A-ET 45]
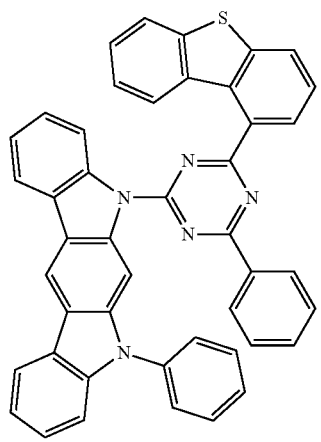
[A-ET 48]
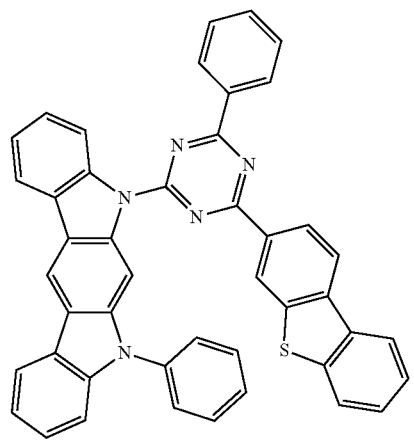

-continued
[A-ET 49]
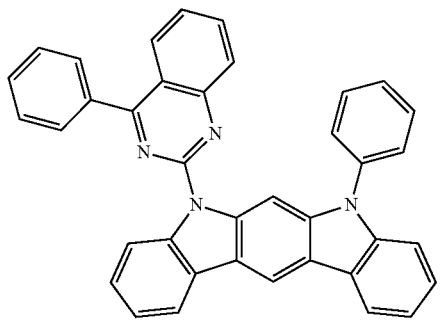
[A-ET 50]
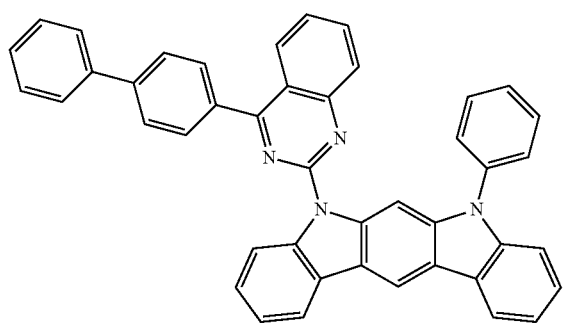
[A-ET 51]
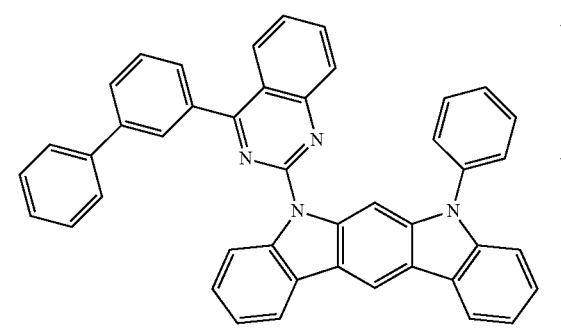
[A-ET 52]
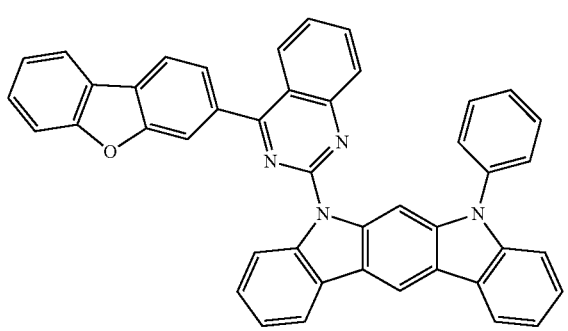
-continued
[B-ET 1]
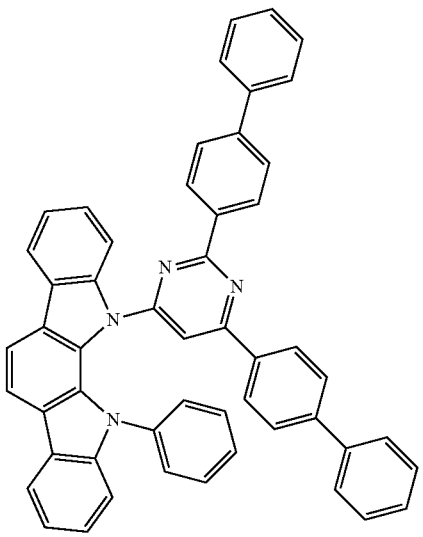
[B-ET 2]
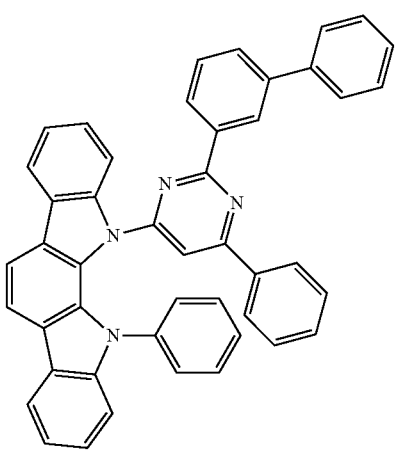
[B-ET 3]
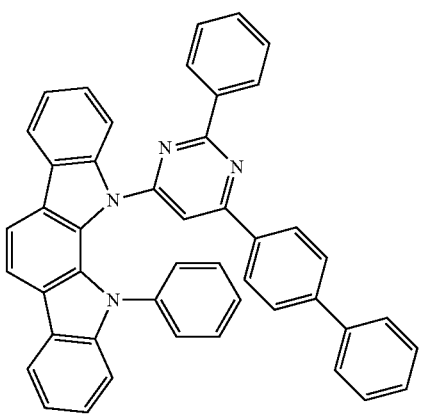

[B-ET 4]
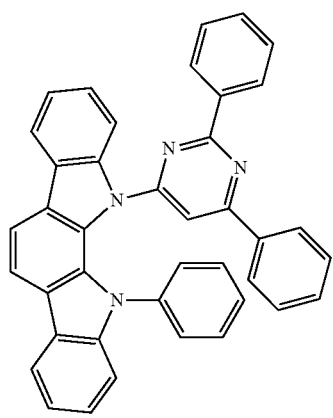
[B-ET 5]
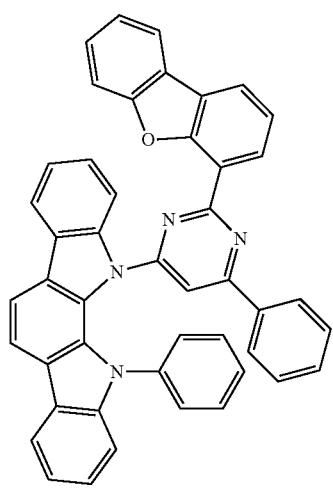
[B-ET 6]
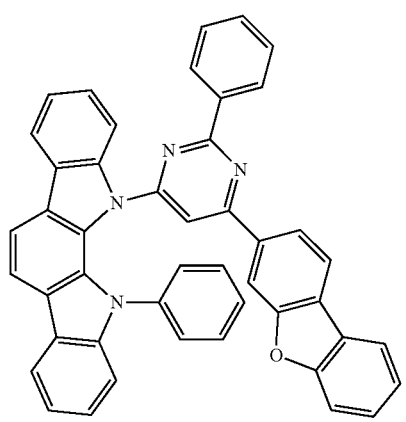
[B-ET 7]
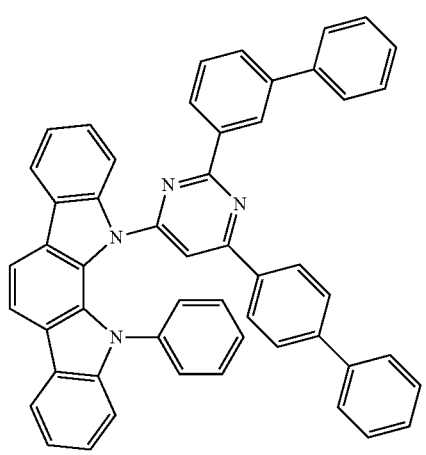
[B-ET 8]
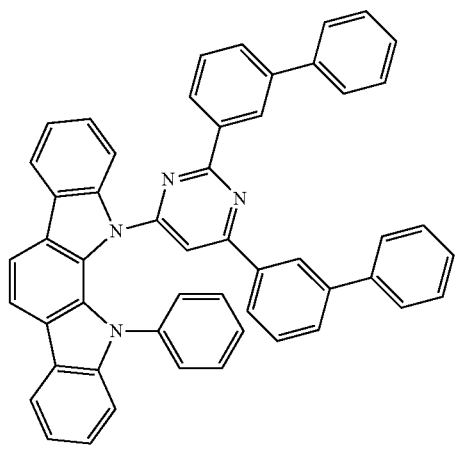
[B-ET 9]
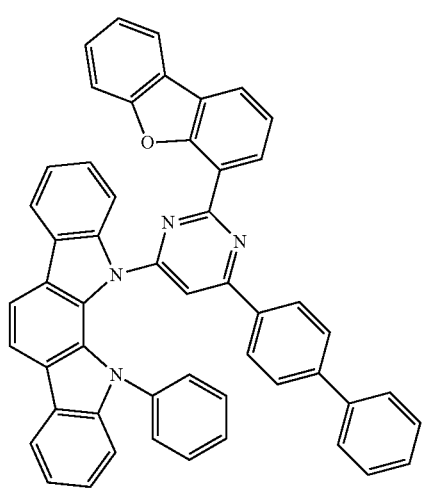

[B-ET 10]
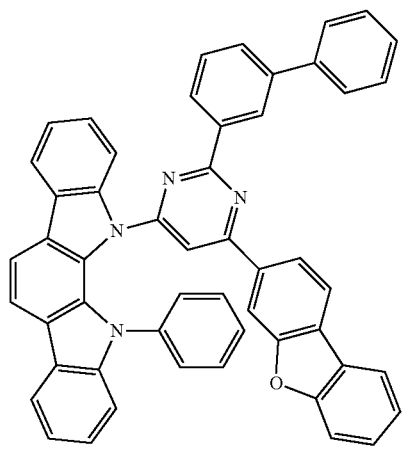
[B-ET 13]
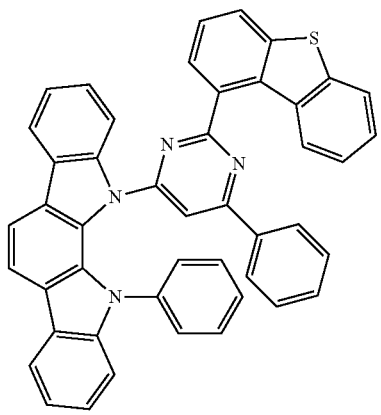
[B-ET 11]
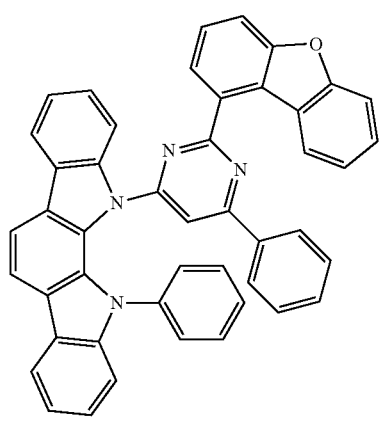
[B-ET 14]
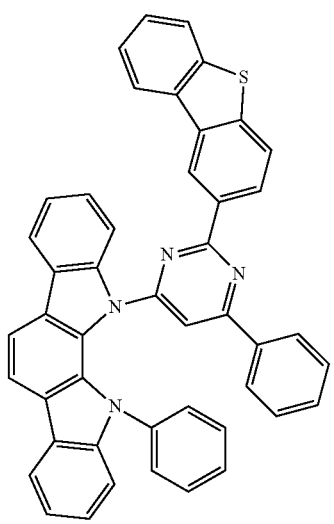
[B-ET 12]
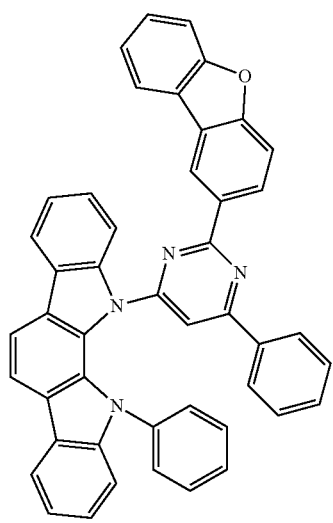
[B-ET 15]
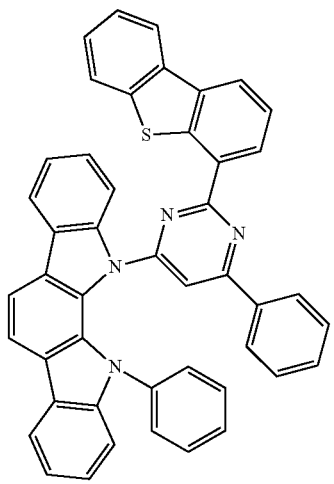

[B-ET 16]
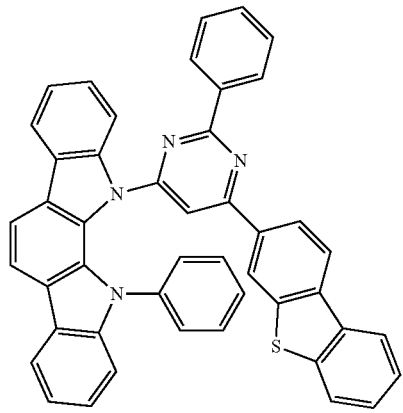
[B-ET 17]
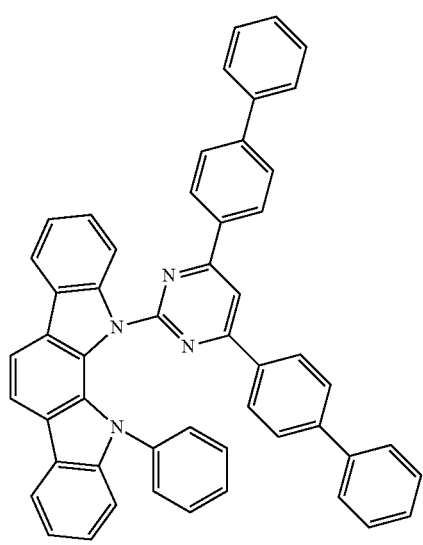
[B-ET 18]
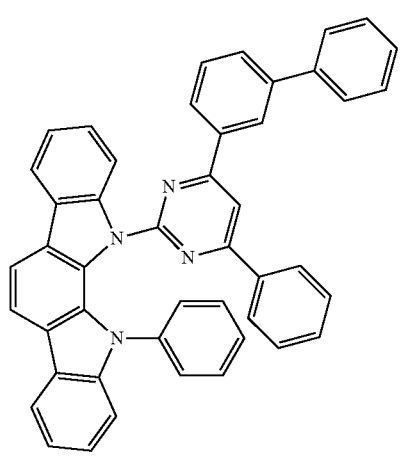
[B-ET 19]
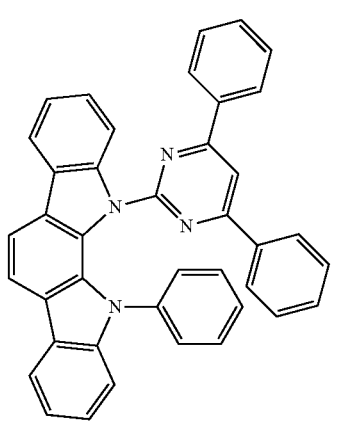
[B-ET 20]
[B-ET 21]
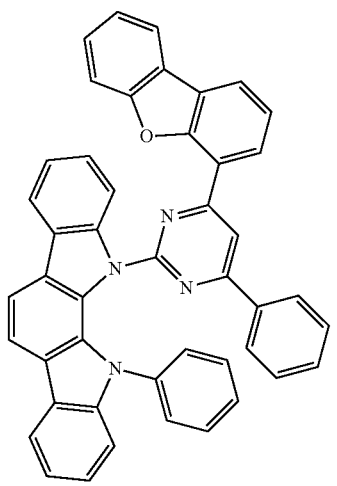

[B-ET 22]
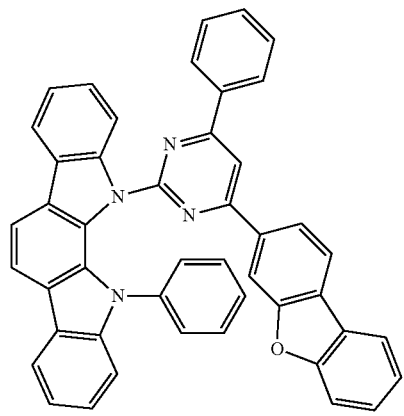
[B-ET 25]
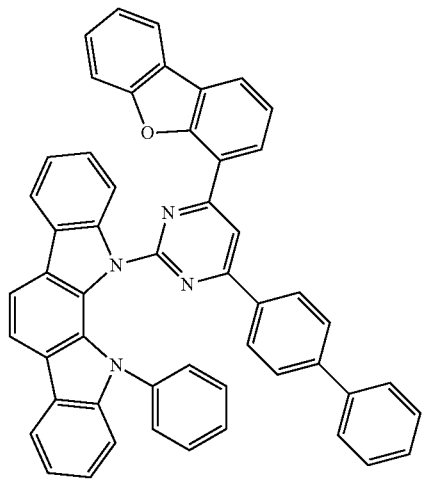
[B-ET 23]
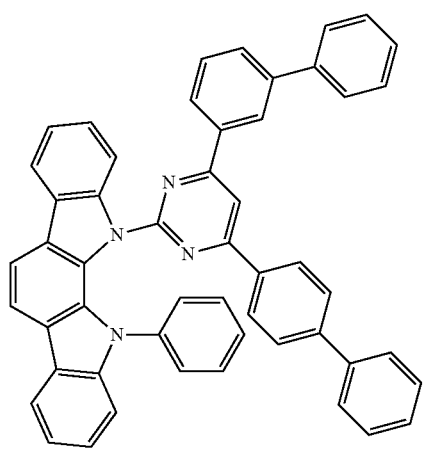
[B-ET 26]
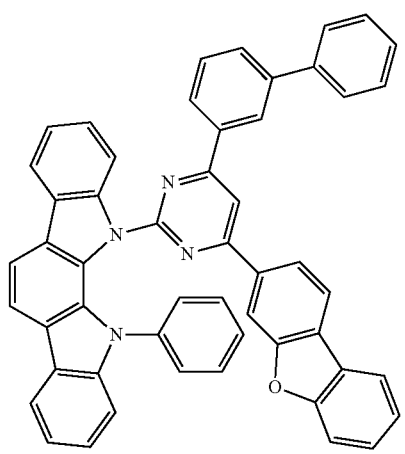
[B-ET 24]
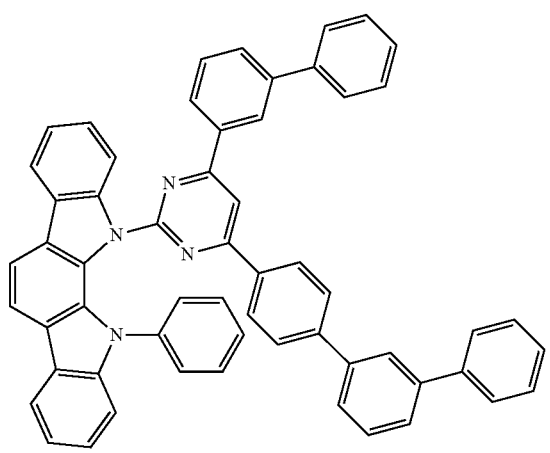
[B-ET 27]
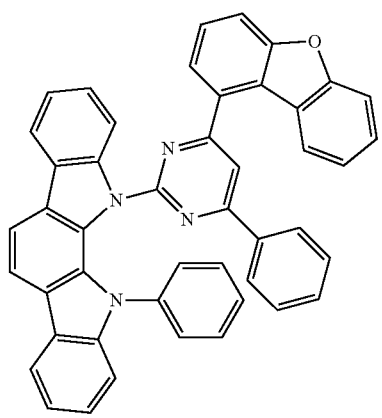

[B-ET 28]
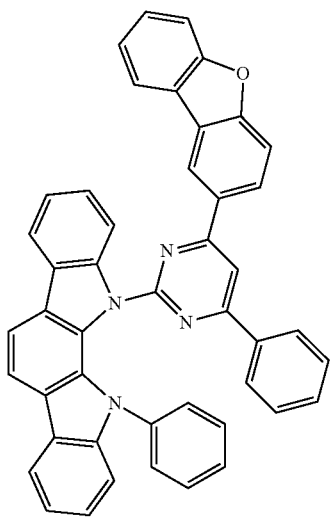
[B-ET 29]
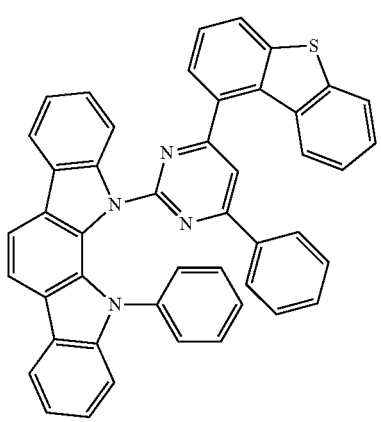
[B-ET 30]
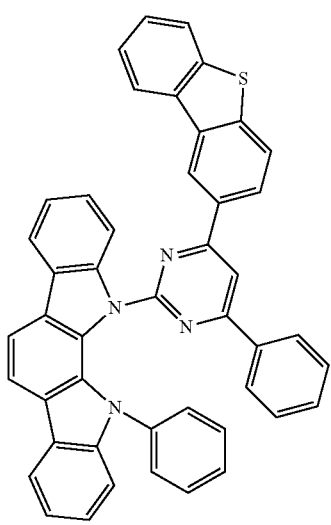
[B-ET 31]
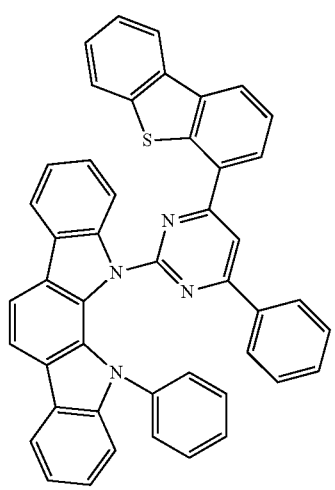
[B-ET 32]
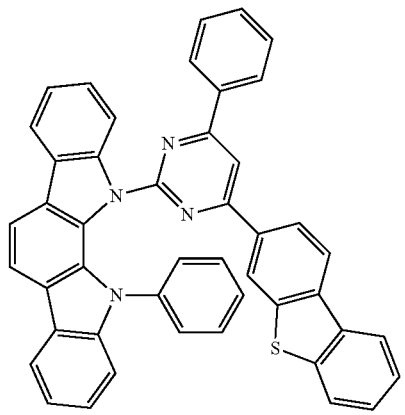
[B-ET 33]
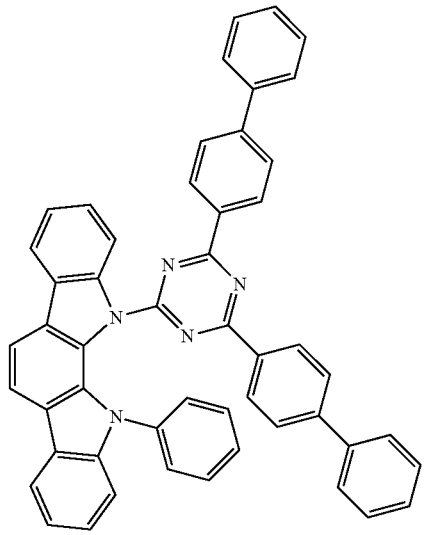

-continued
[B-ET 34]
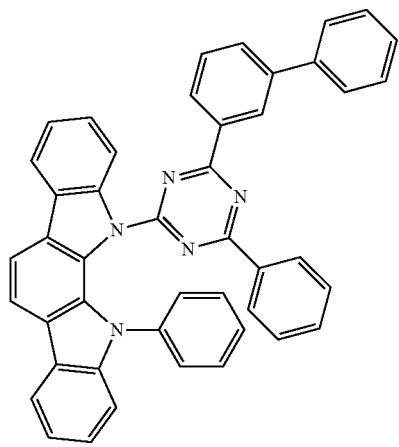
[B-ET 37]
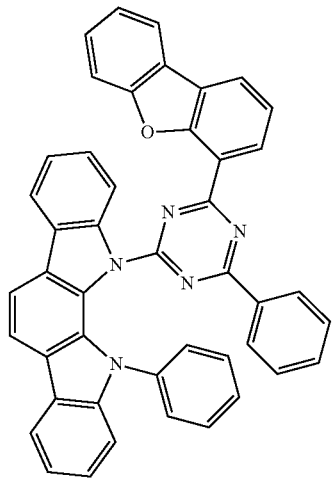
[B-ET 35]
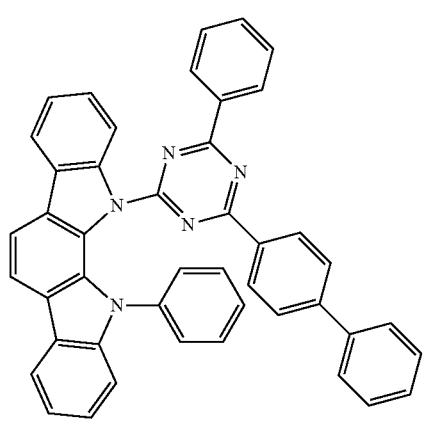
[B-ET 38]
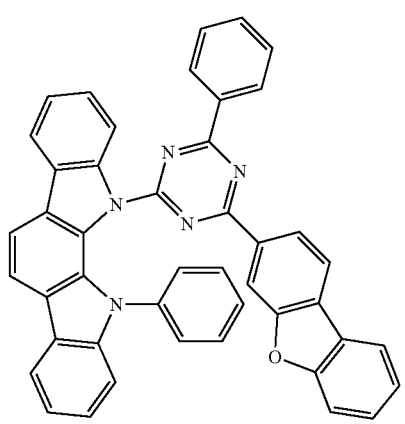
[B-ET 36]
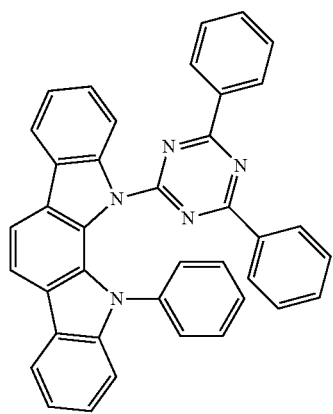
[B-ET 39]
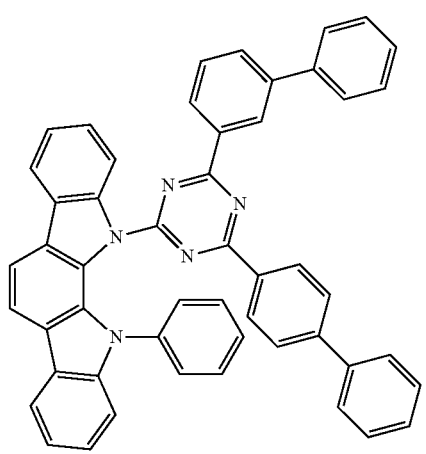

-continued
[B-ET 40]
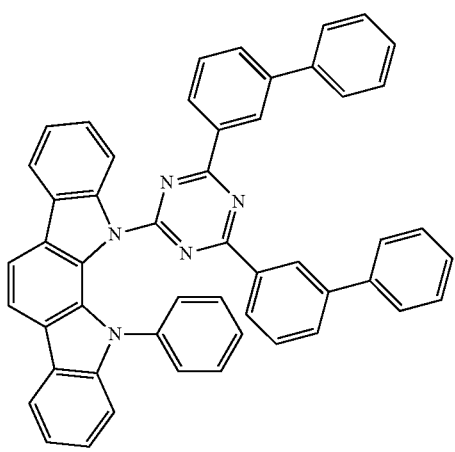
[B-ET 41]
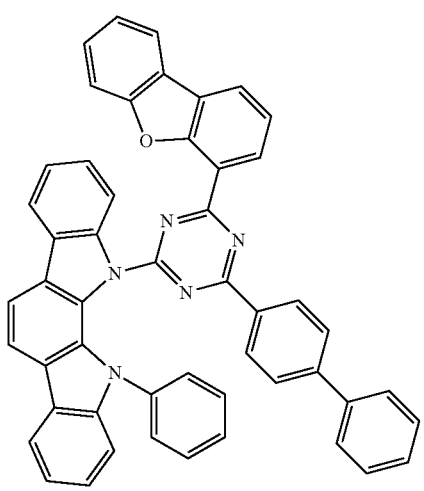
[B-ET 42]
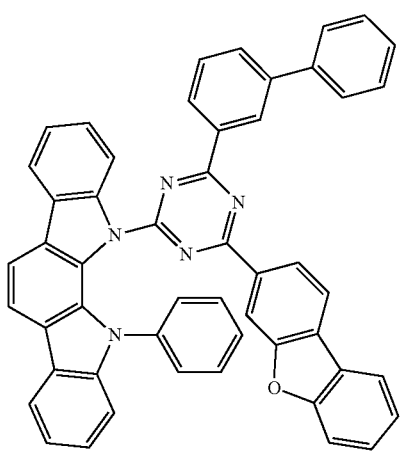
-continued
[B-ET 43]
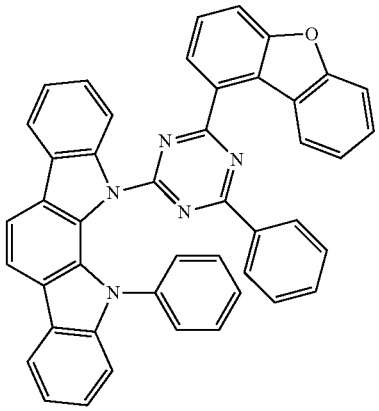
[B-ET 44]
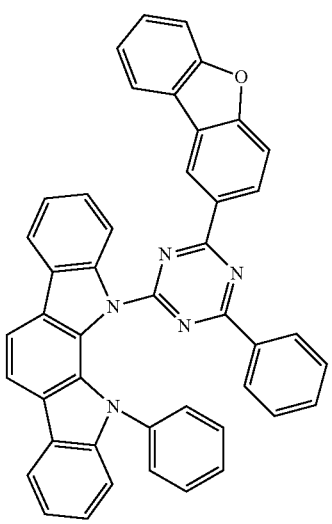
[B-ET 45]
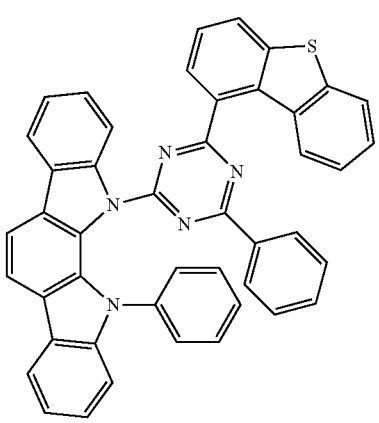

[B-ET 46]
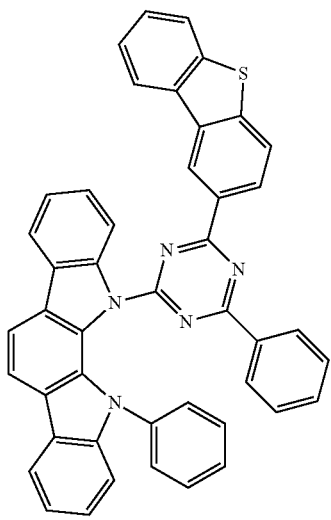
[B-ET 47]
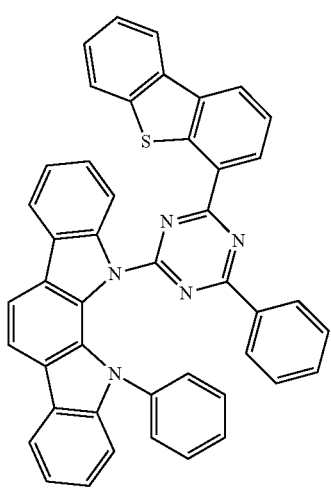
[B-ET 48]
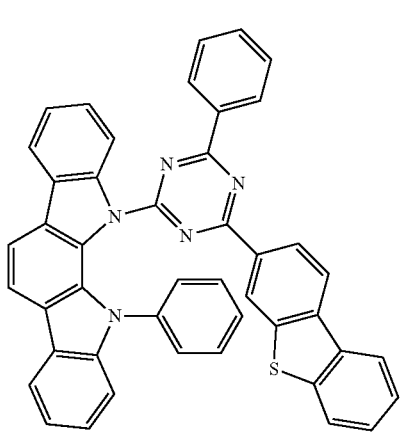
[B-ET 49]
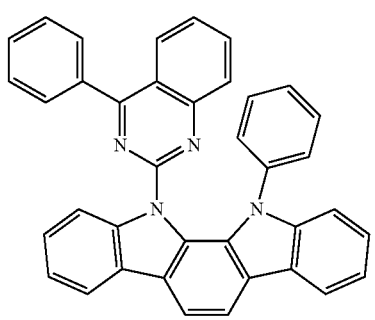
[B-ET 50]
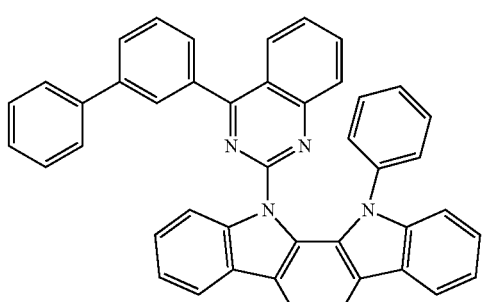
[B-ET 51]
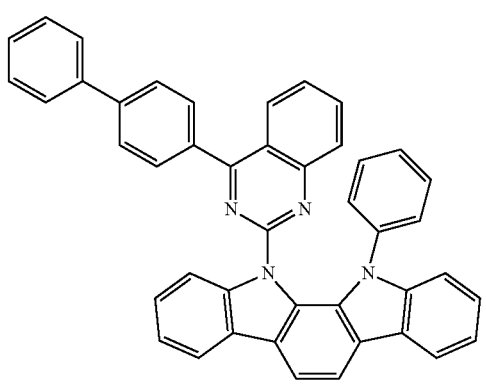
[B-ET 52]
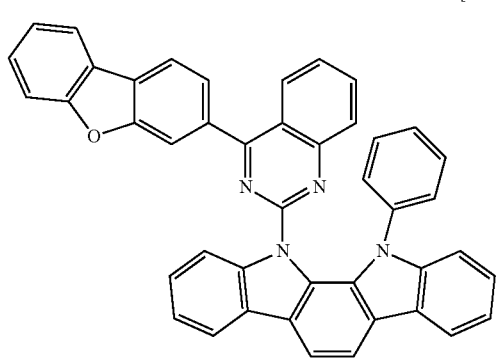

[C-ET 1]
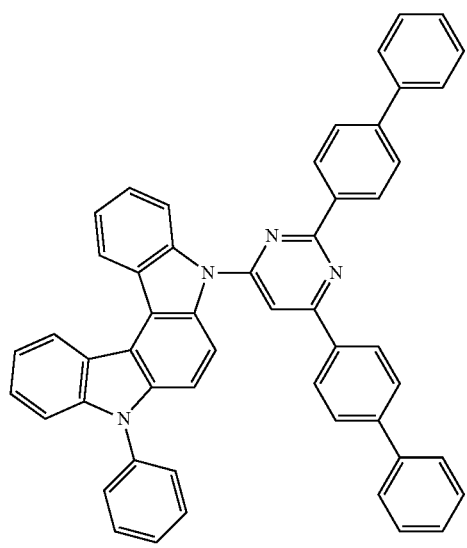
[C-ET 2]
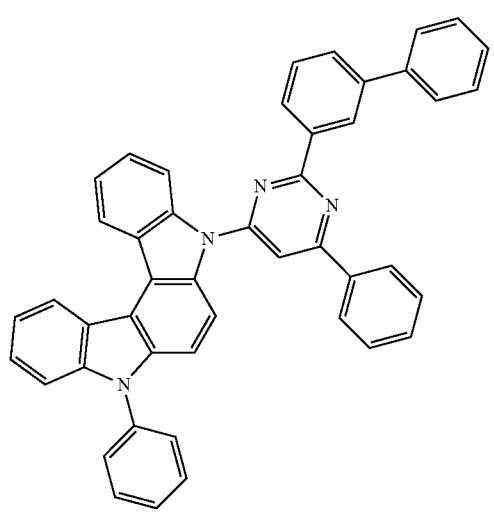
[C-ET 3]
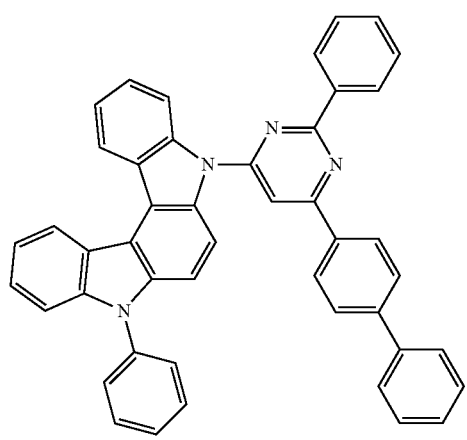
[C-ET 4]
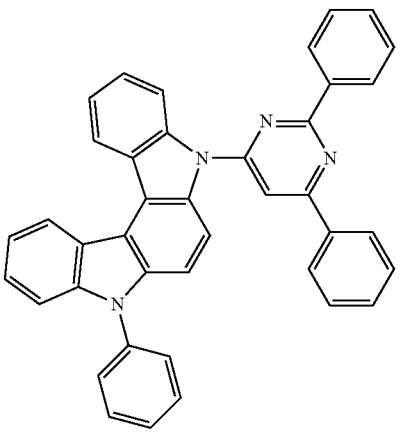
[C-ET 5]
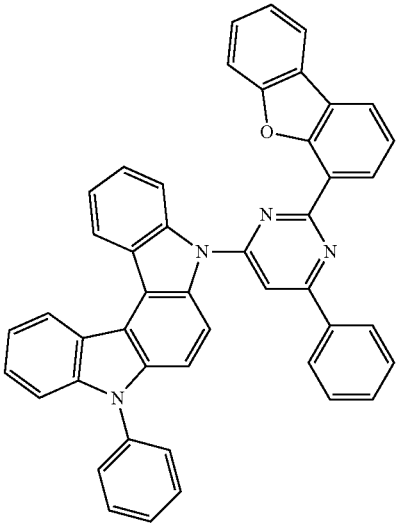
[C-ET 6]
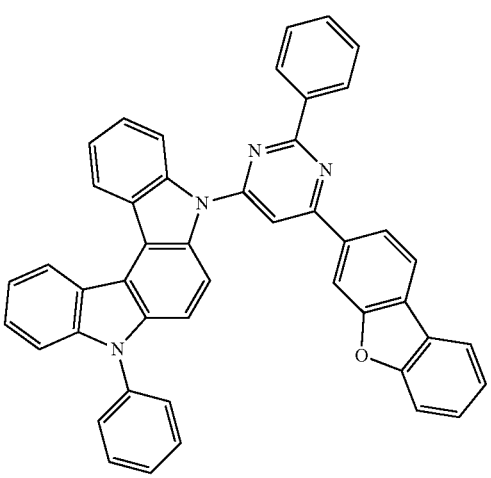

[C-ET 7]
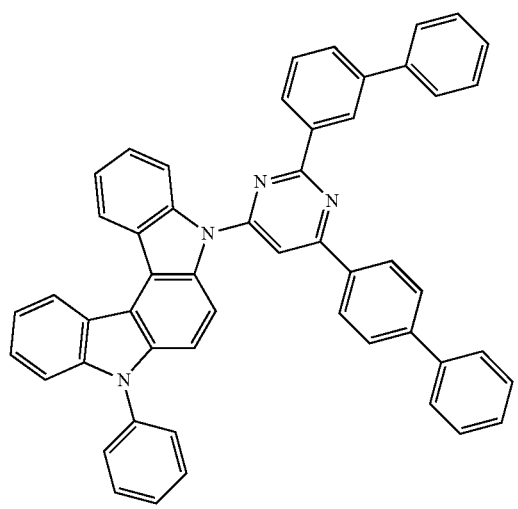
[C-ET 8]
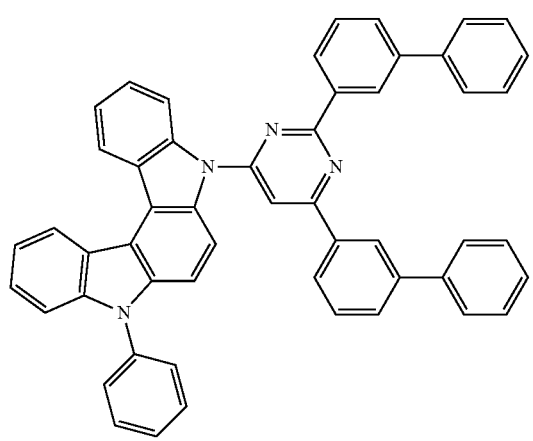
[C-ET 9]
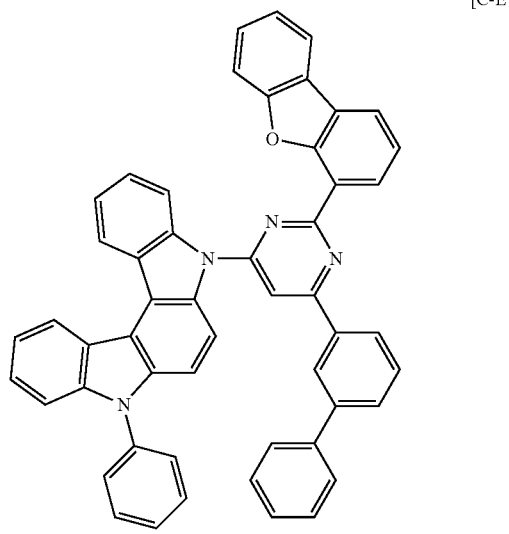
[C-ET 10]
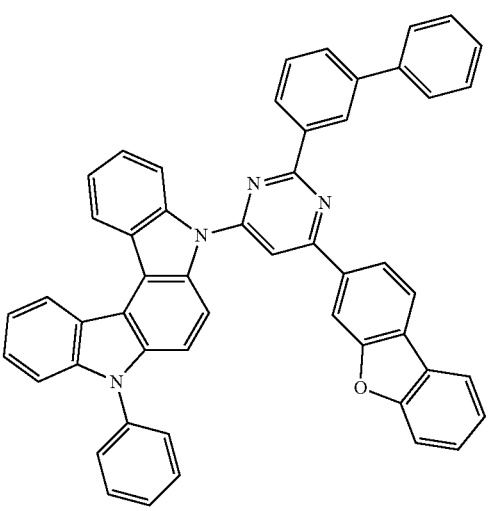
[C-ET 11]
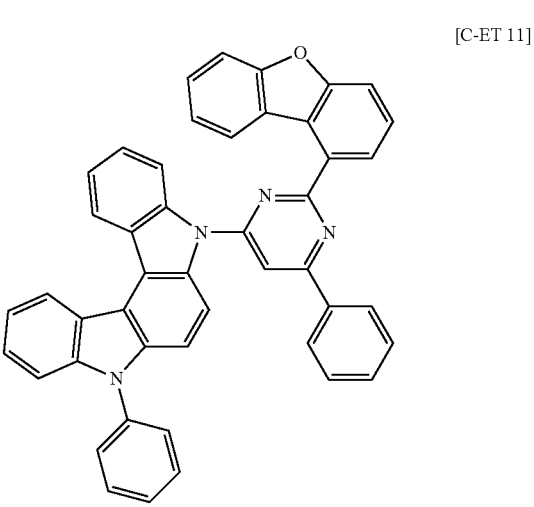
[C-ET 12]
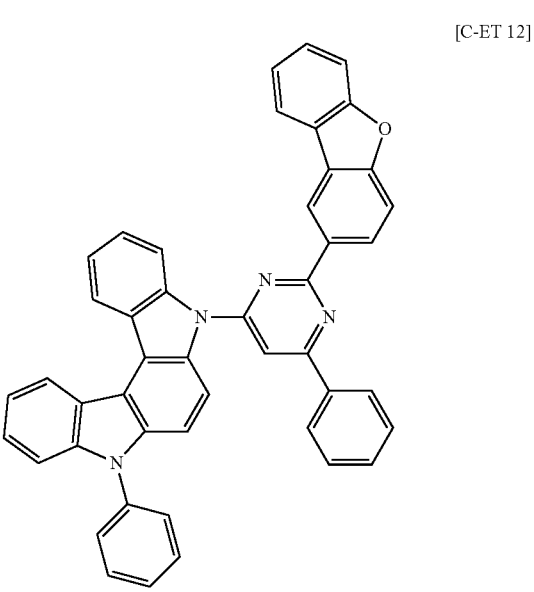

[C-ET 13]
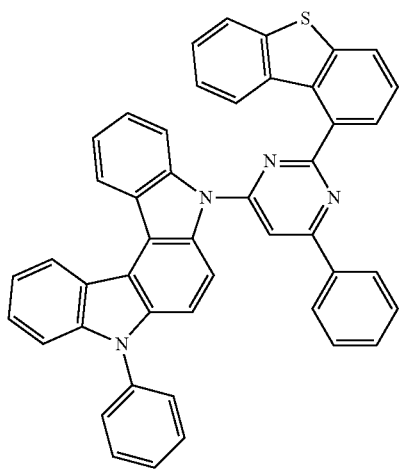
[C-ET 14]
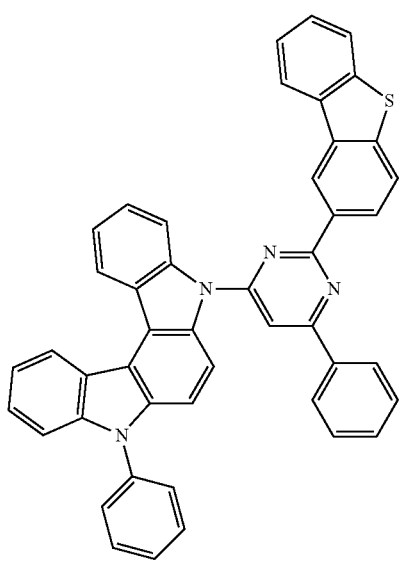
[C-ET 15]
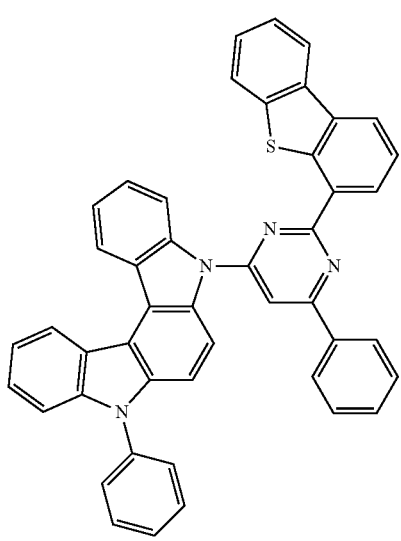
[C-ET 16]
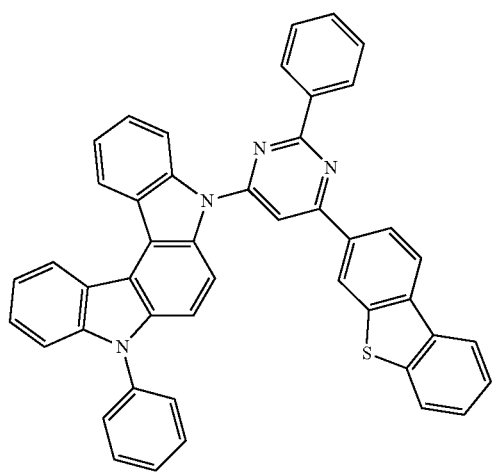
[C-ET 17]
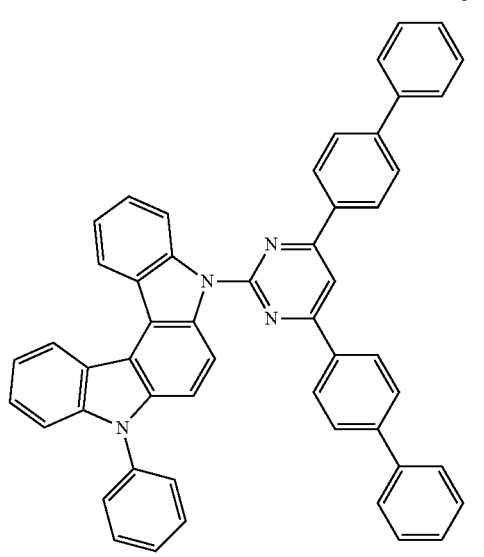
[C-ET 18]
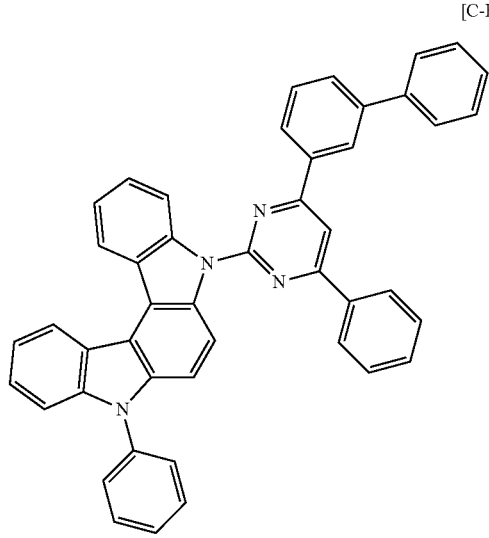

[C-ET 19]
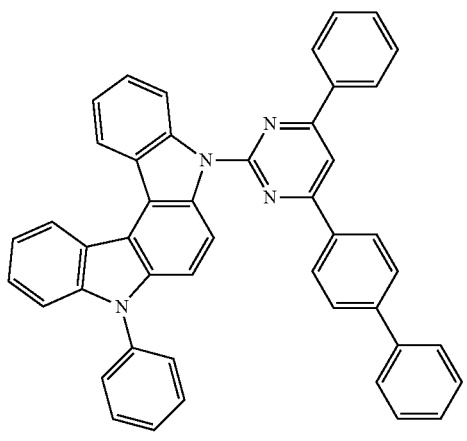
[C-ET 20]
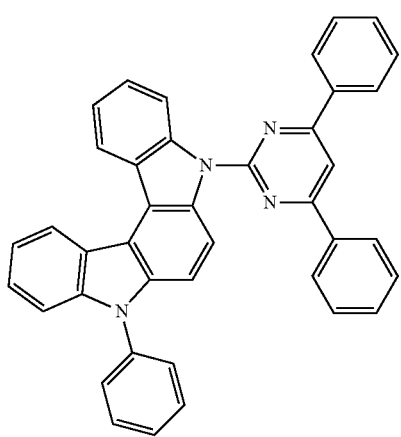
[C-ET 21]
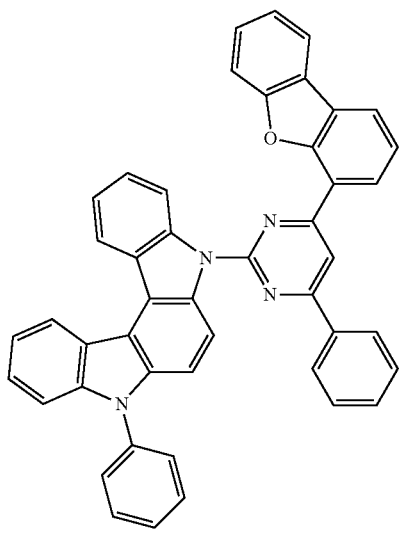
[C-ET 22]
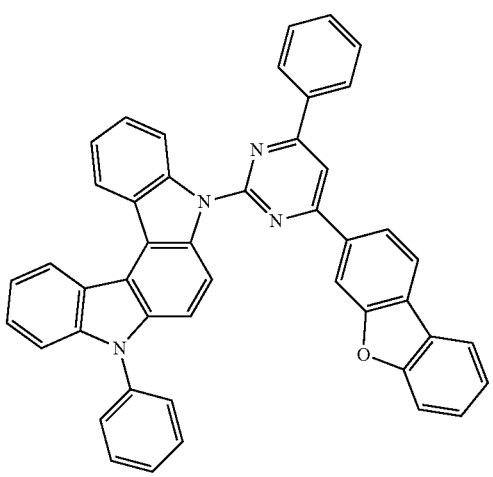
[C-ET 23]
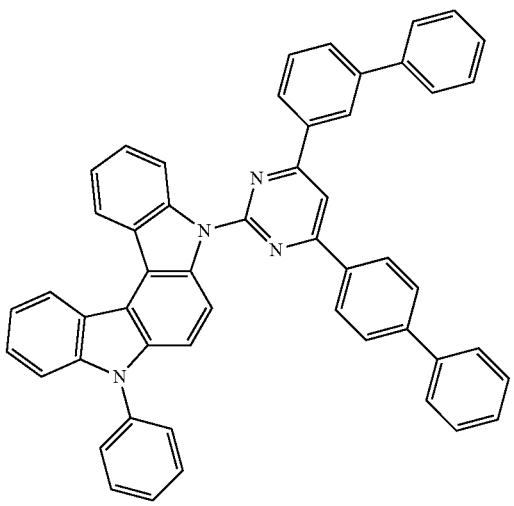
[C-ET 24]
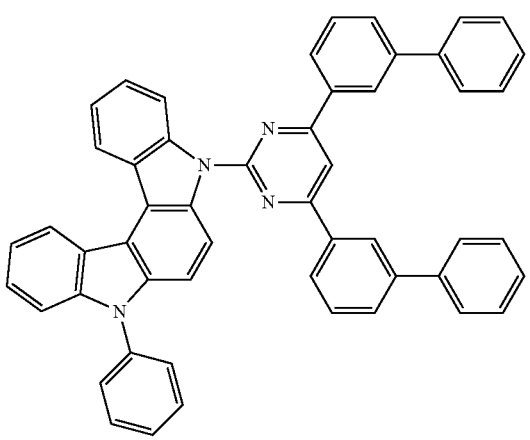

[C-ET 25]
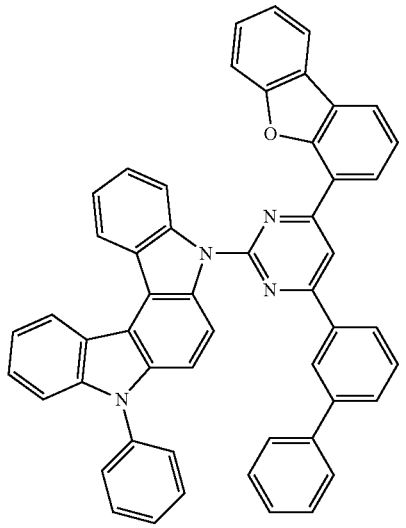
[C-ET 28]
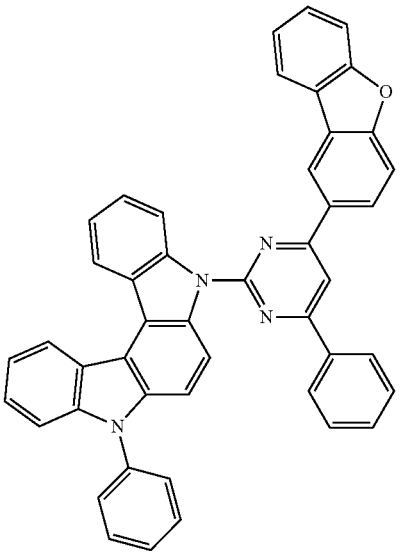
[C-ET 26]
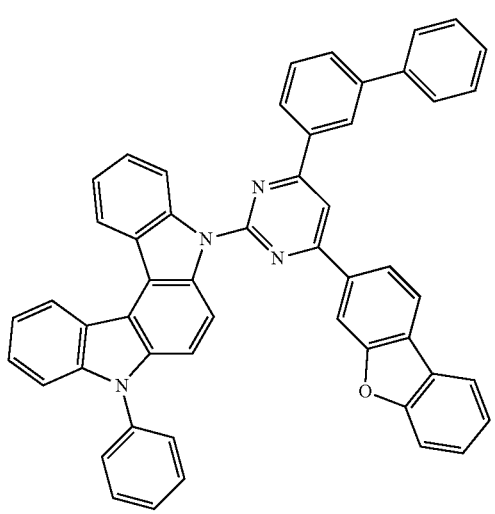
[C-ET 29]
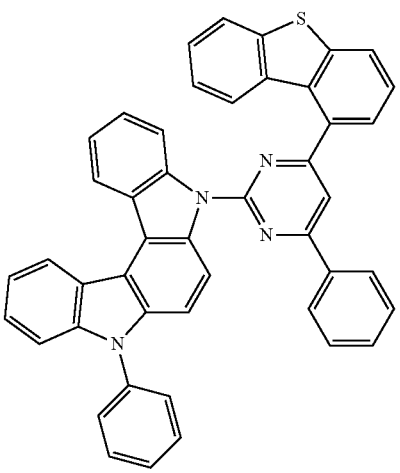
[C-ET 27]
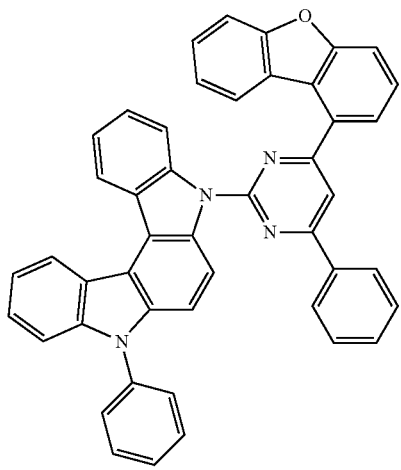
[C-ET 30]
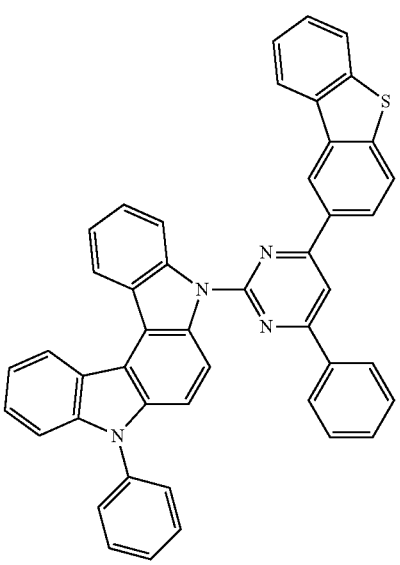

[C-ET 31]
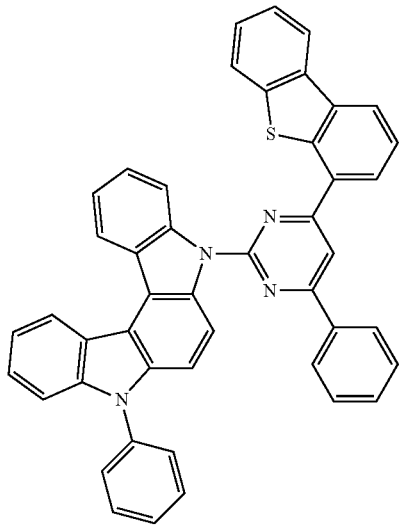
[C-ET 32]
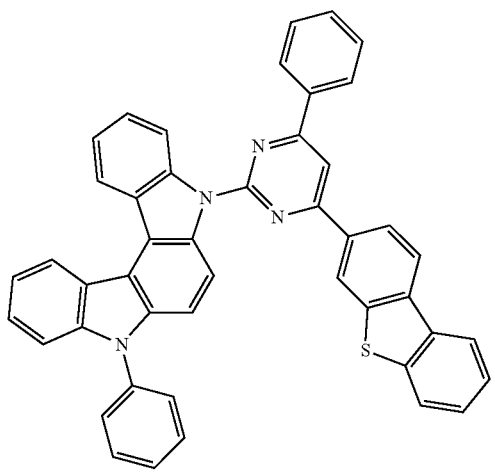
[C-ET 33]
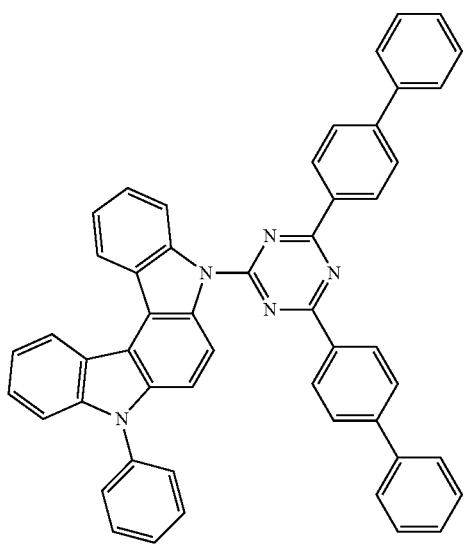
[C-ET 34]
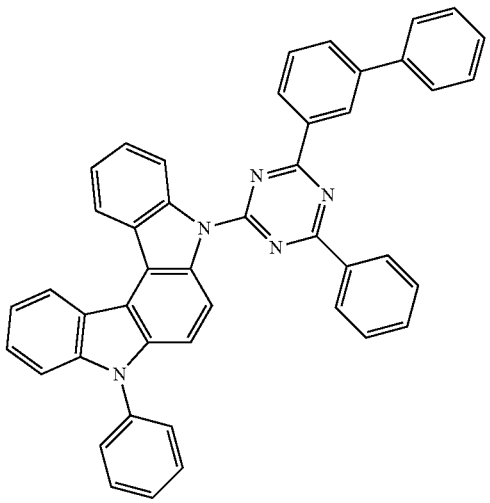
[C-ET 35]
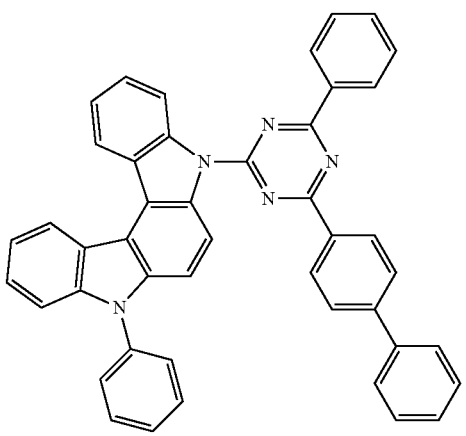
[C-ET 36]
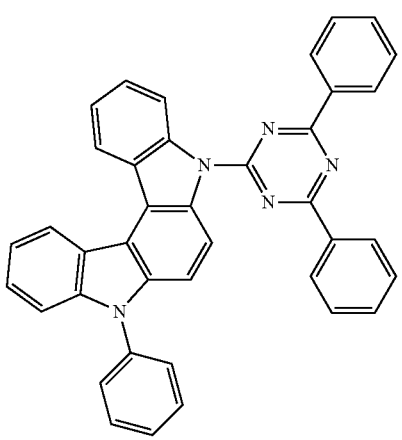

[C-ET 37]
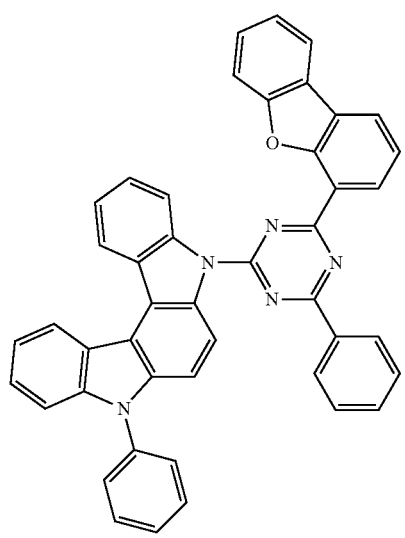
[C-ET 38]
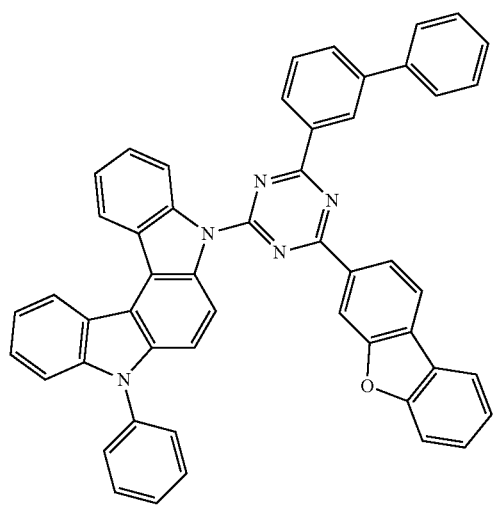
[C-ET 39]
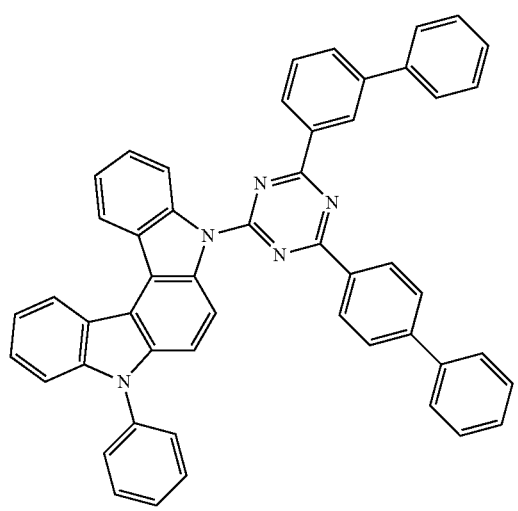
[C-ET 40]
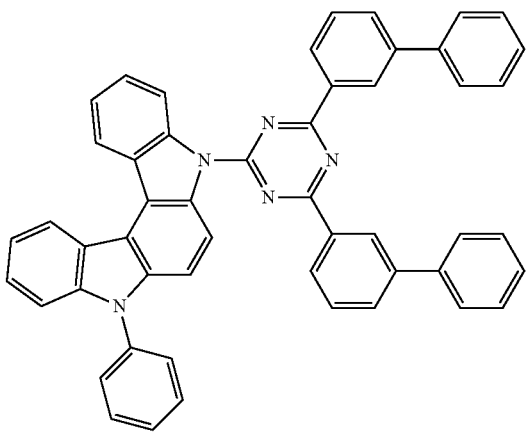
[C-ET 41]
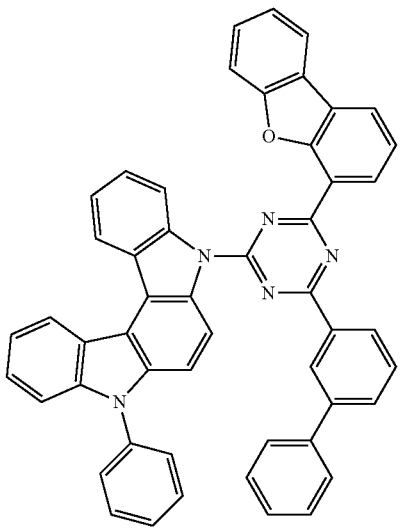
[C-ET 42]
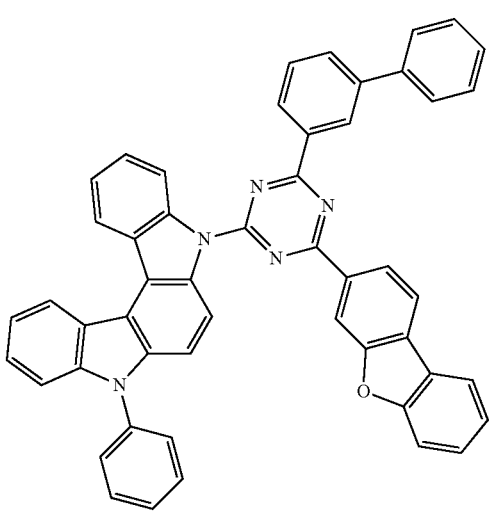

-continued
[C-ET 43]
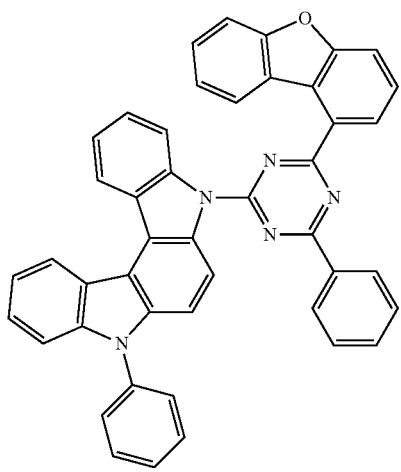
[C-ET 44]
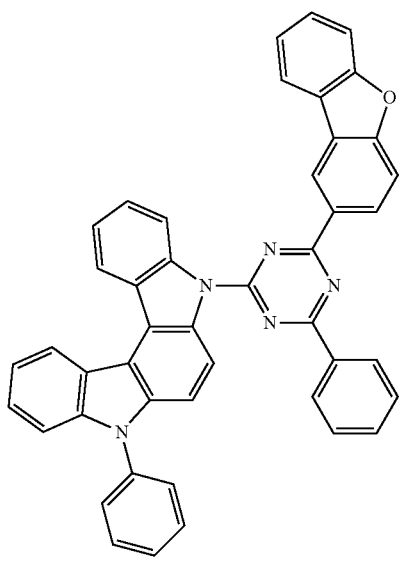
[C-ET 45]
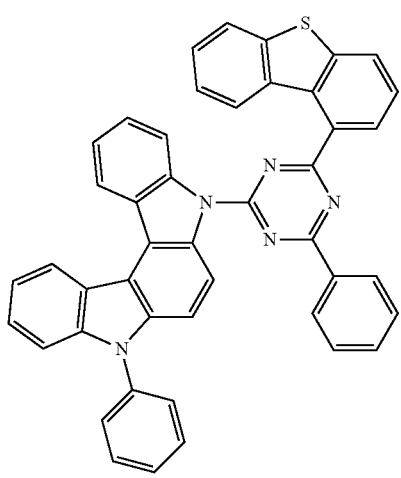
-continued
[C-ET 46]
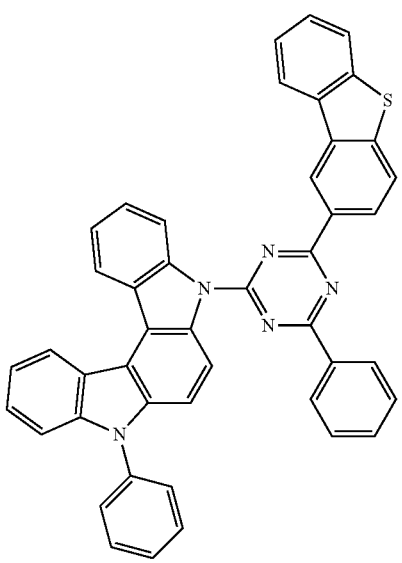
[C-ET 47]
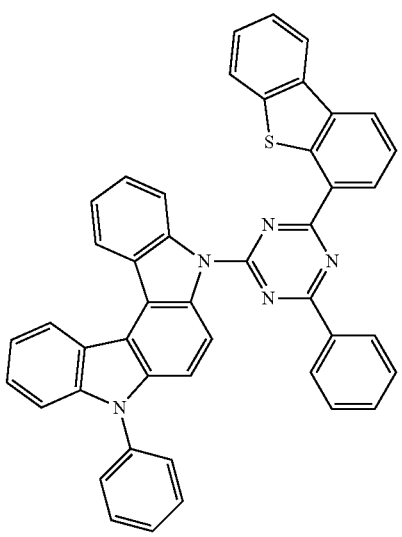
[C-ET 48]
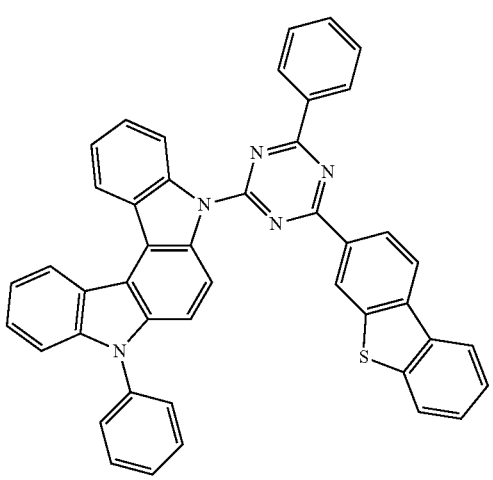

201
-continued
[C-ET 49]
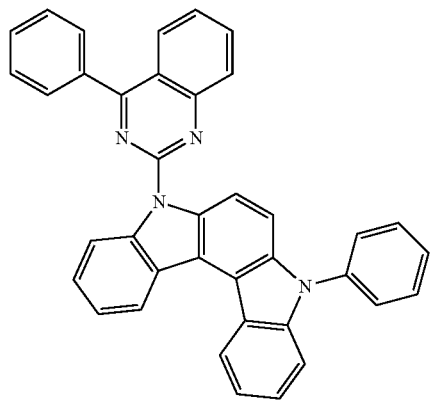
[C-ET 50]
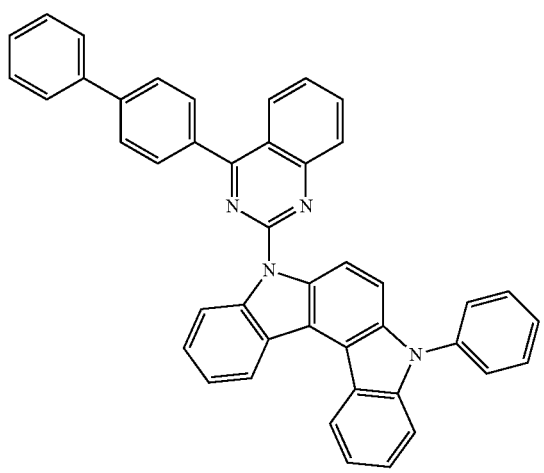
[C-ET 51]
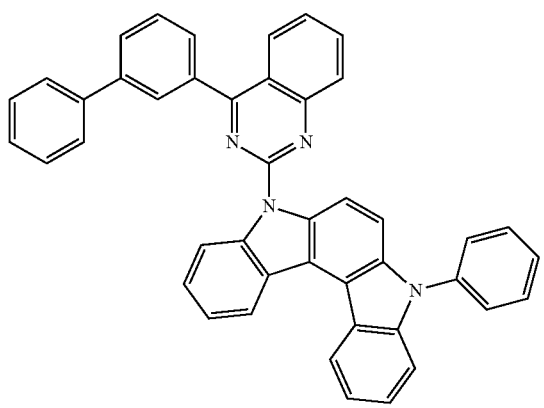
202
-continued
[C-ET 52]
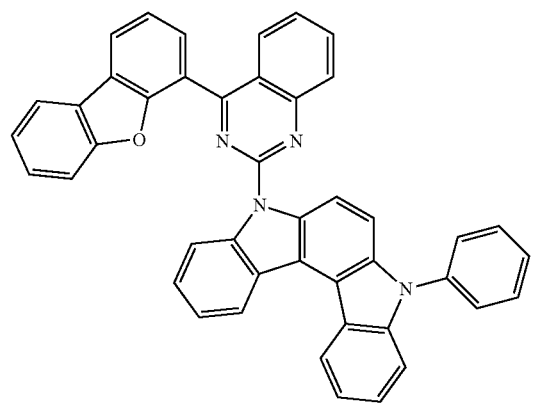
[D-ET 1]
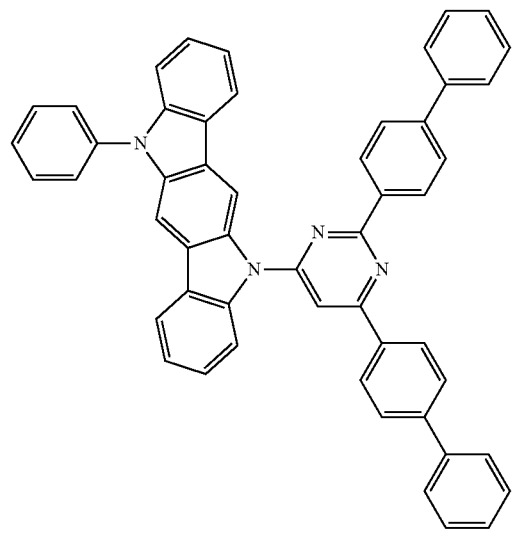
[D-ET 2]
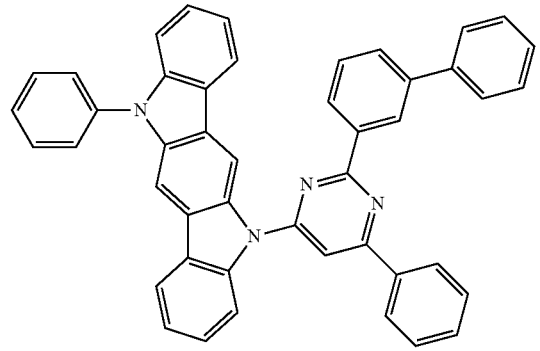

[D-ET 3]
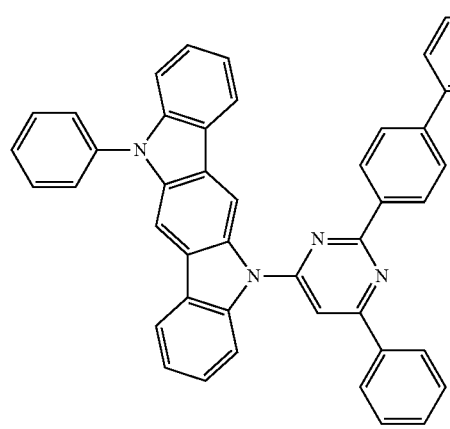
[D-ET 4]
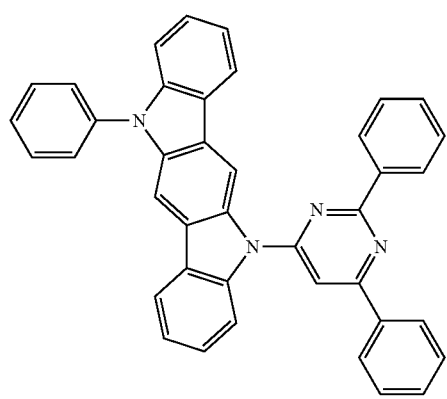
[D-ET 5]
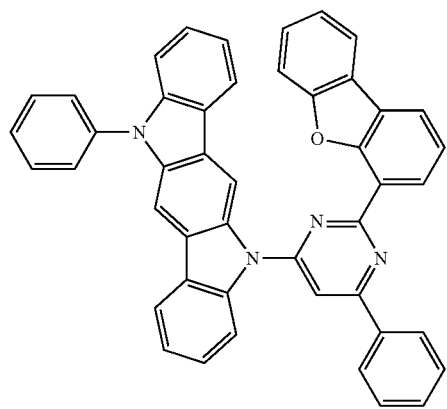
[D-ET 6]
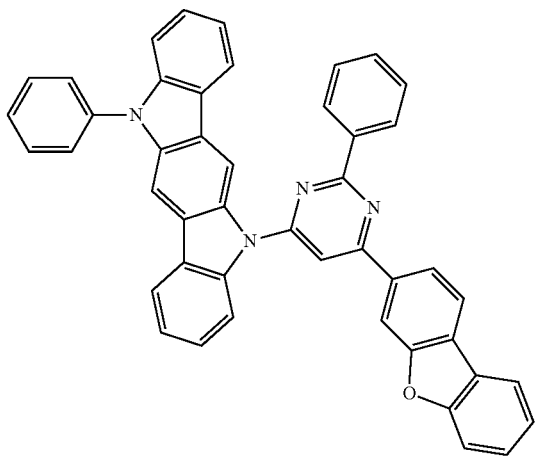
[D-ET 7]
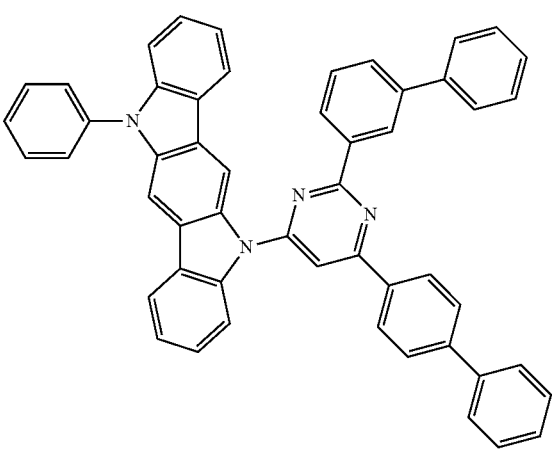
[D-ET 8]
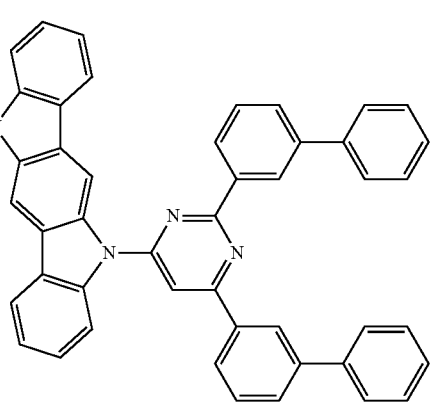

[D-ET 9]
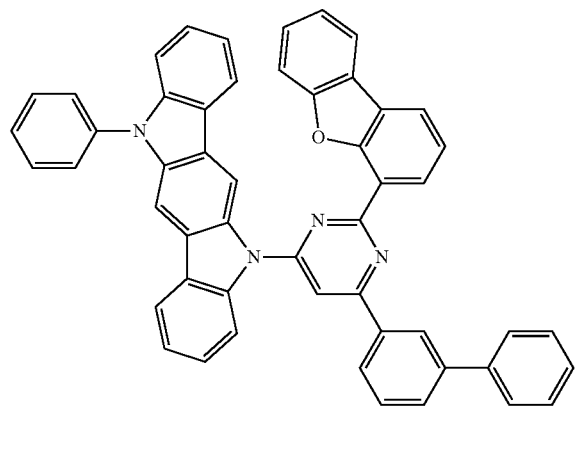
[D-ET 12]
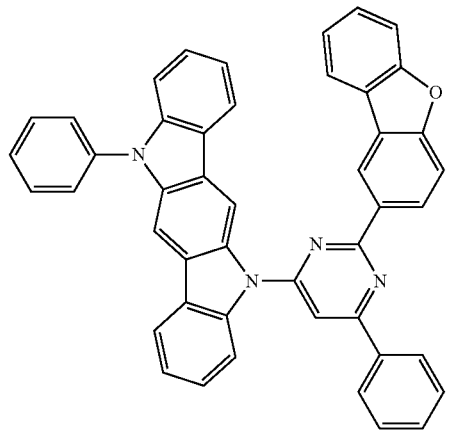
[D-ET 10]
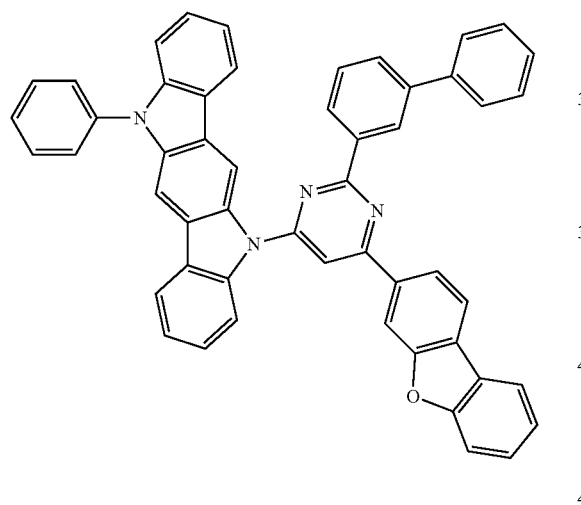
[D-ET 13]
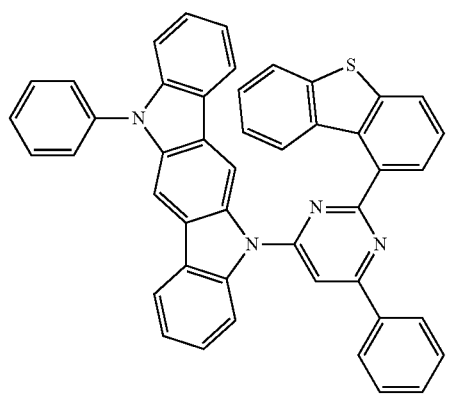
[D-ET 11]
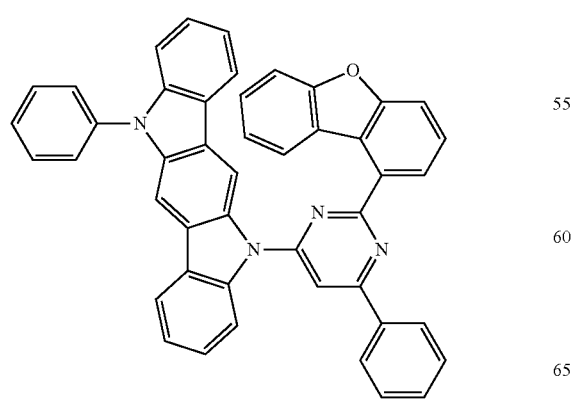
[D-ET 14]
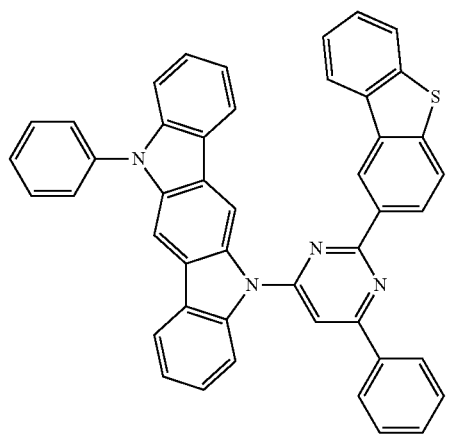

[D-ET 15]
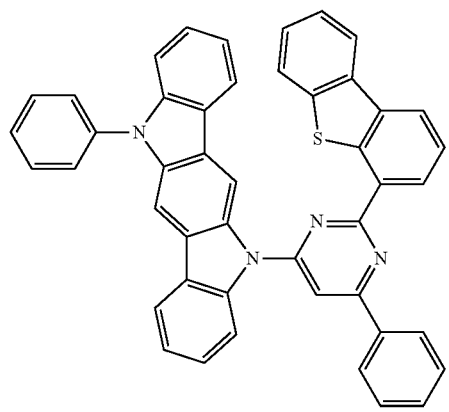
[D-ET 16]
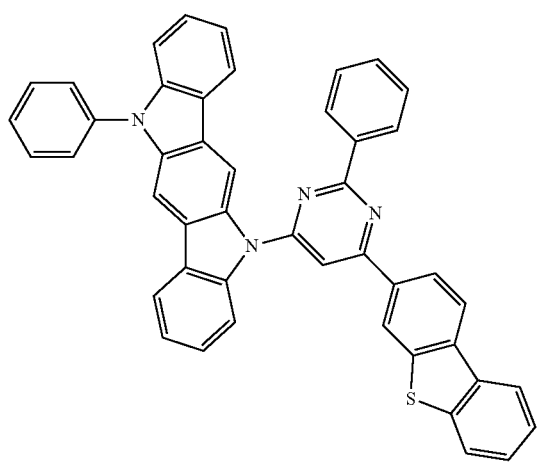
[D-ET 17]
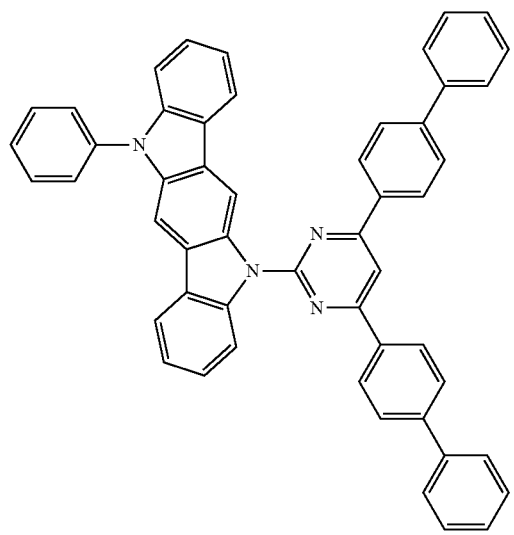
[D-ET 18]
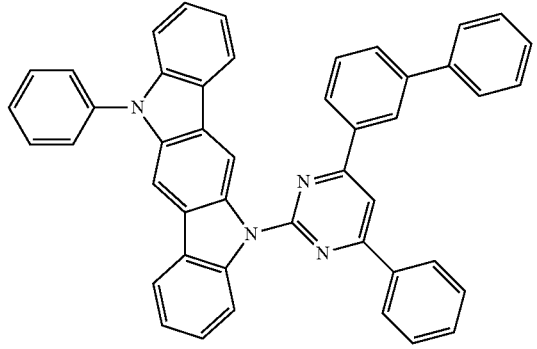
[D-ET 19]
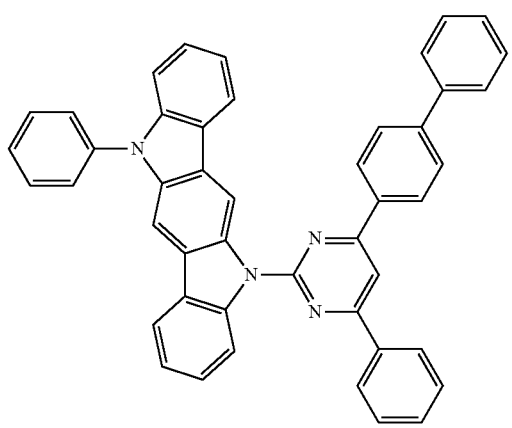
[D-ET 20]
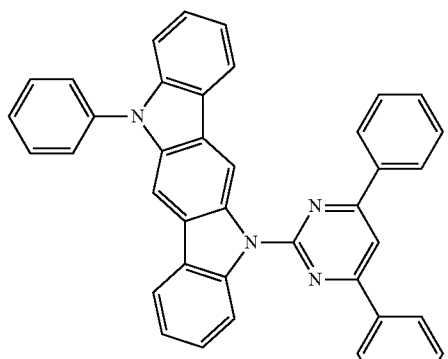
[D-ET 21]
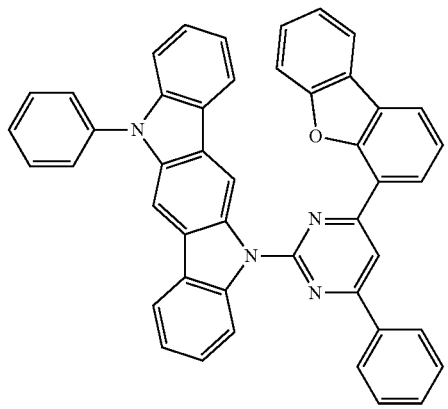

[D-ET 22]
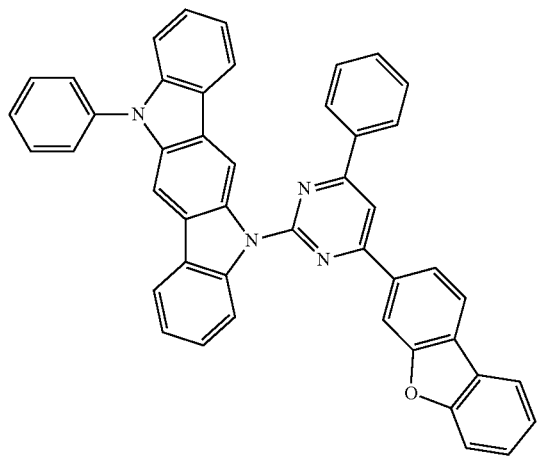
[D-ET 25]
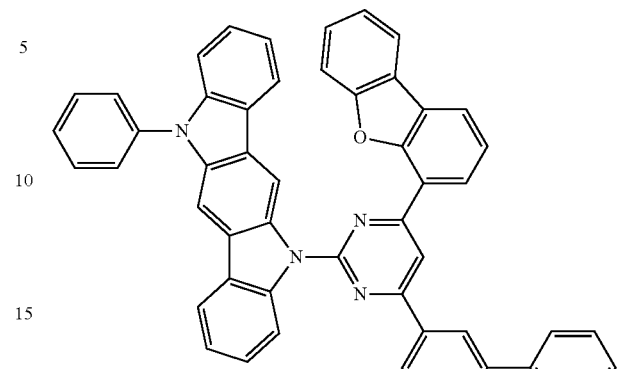
[D-ET 23]
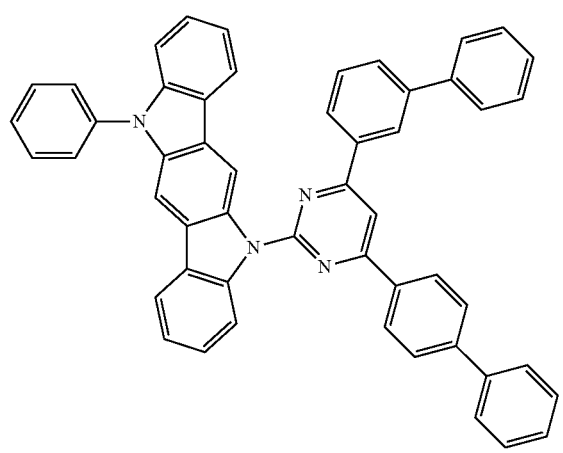
[D-ET 26]
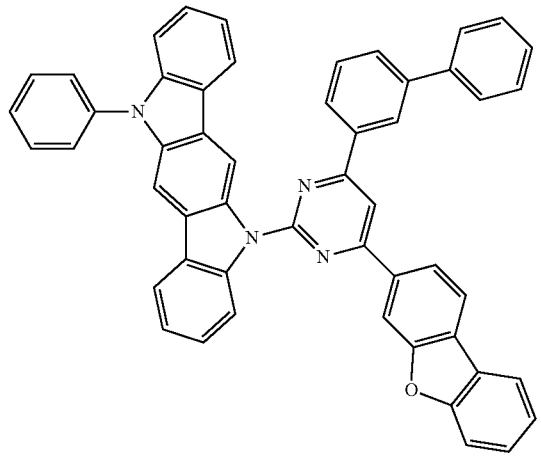
[D-ET 24]
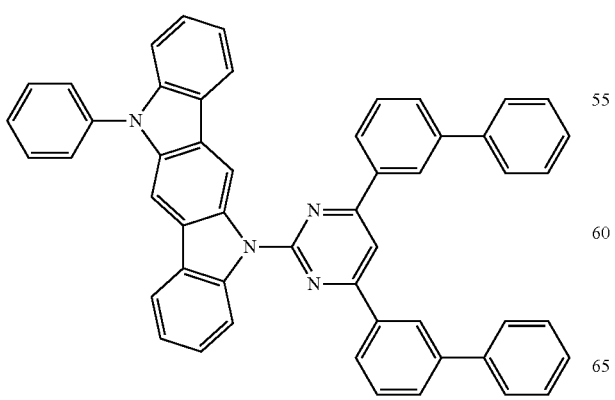
[D-ET 27]
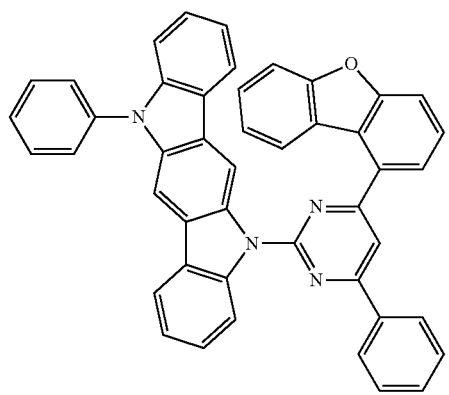

[D-ET 28]
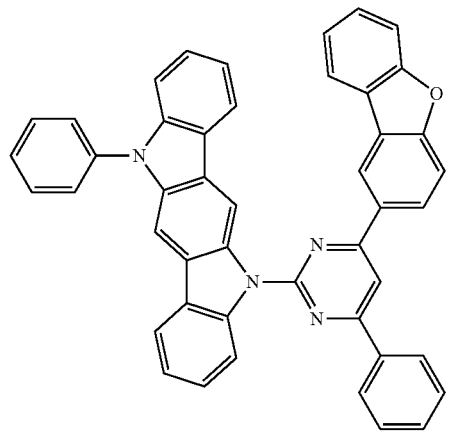
[D-ET 29]
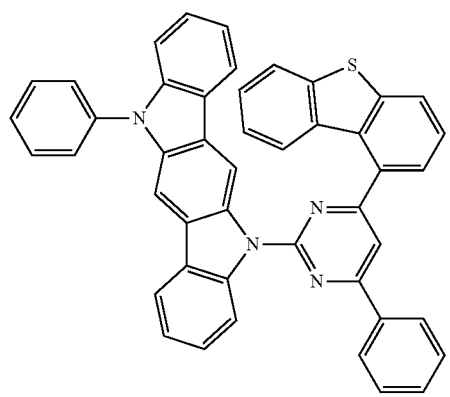
[D-ET 30]
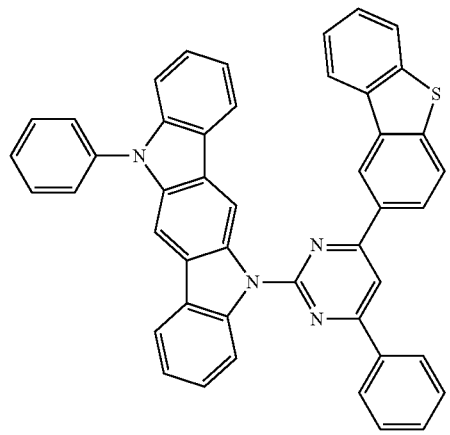
[D-ET 31]
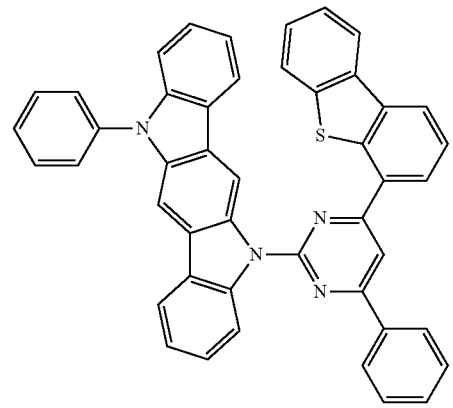
[D-ET 32]
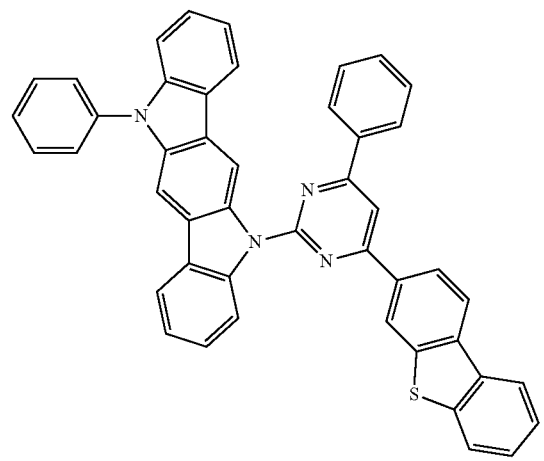
[D-ET 33]
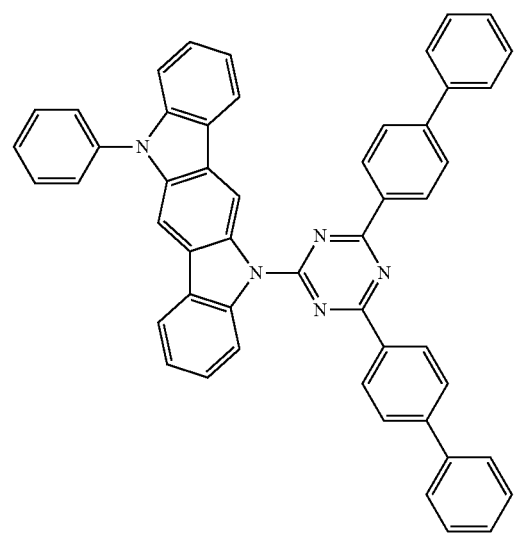

-continued
[D-ET 34]
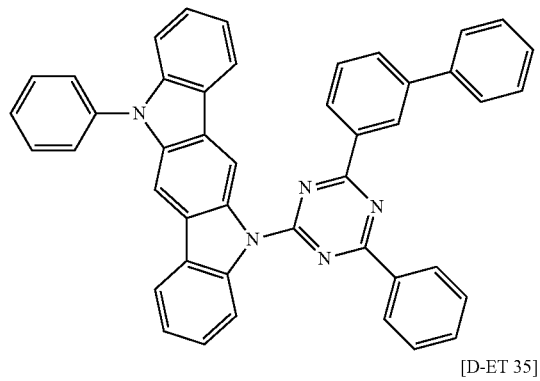
[D-ET 35]
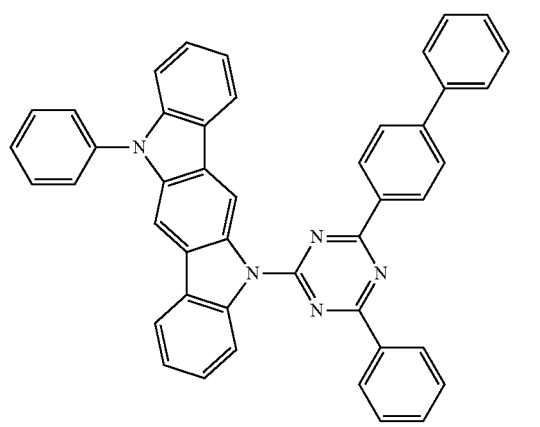
[D-ET 36]
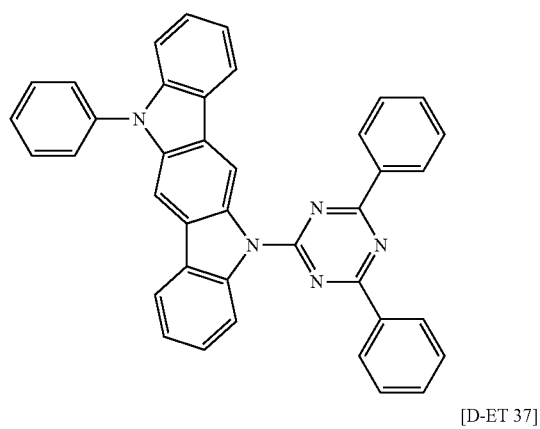
[D-ET 37]
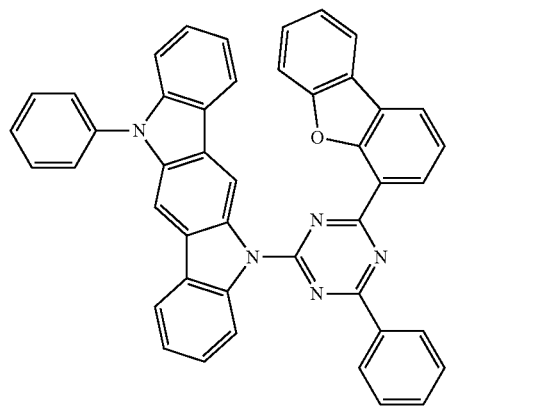
-continued
[D-ET 38]
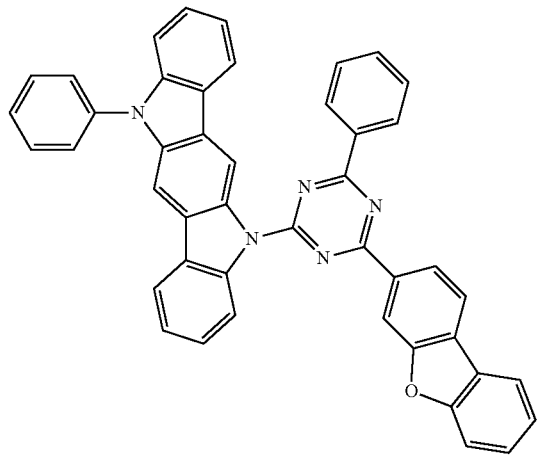
[D-ET 39]
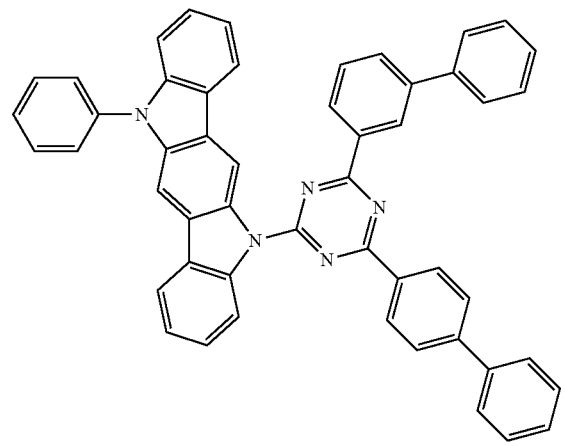
[D-ET 40]
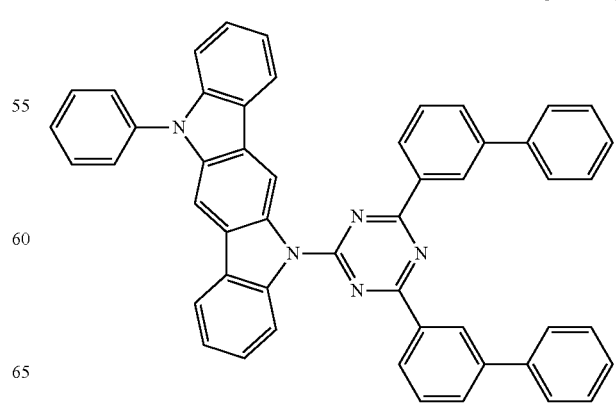

[D-ET 41]
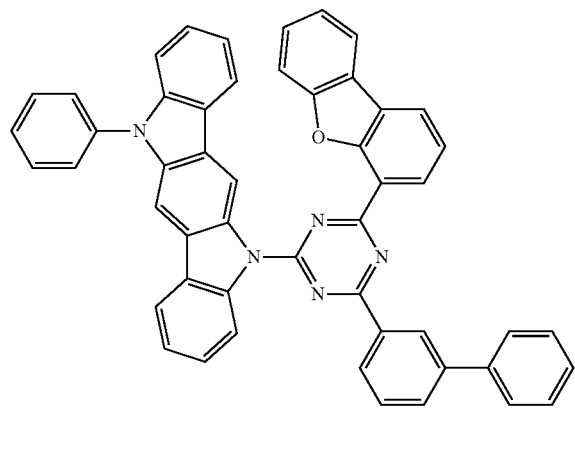
[D-ET 42]
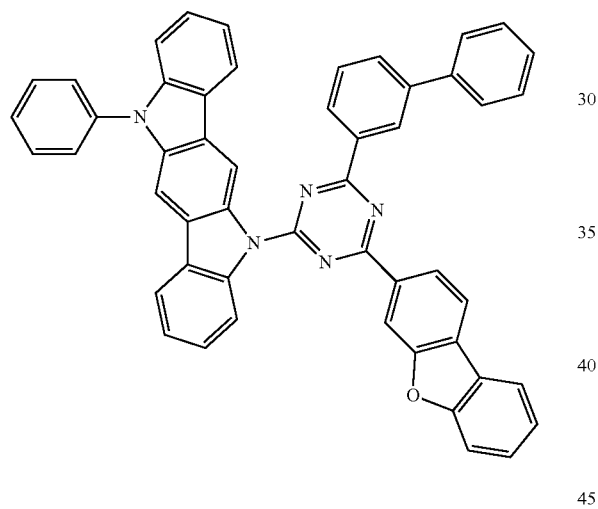
[D-ET 43]
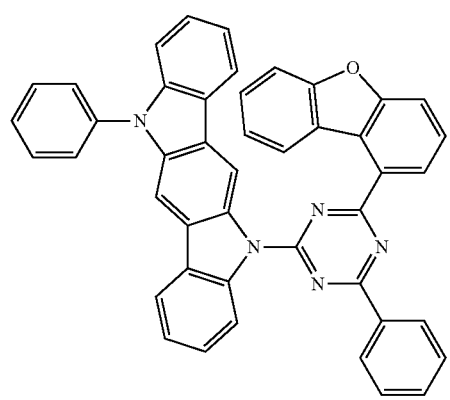
[D-ET 44]
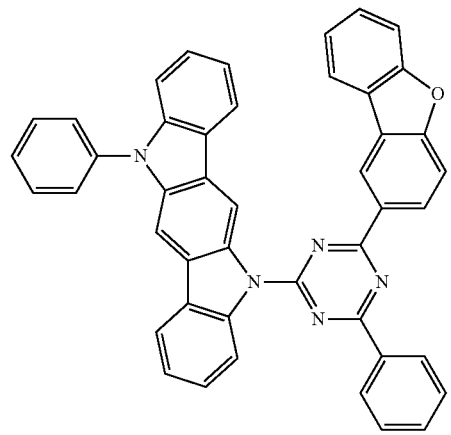
[D-ET 45]
[D-ET 46]
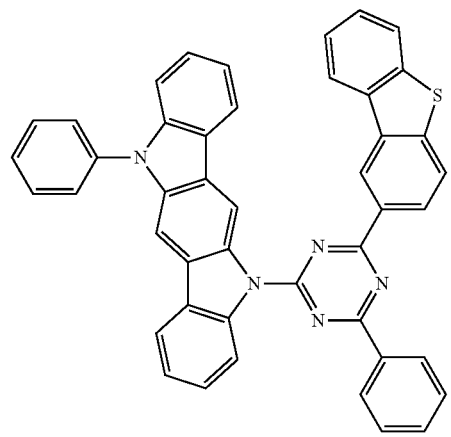

[D-ET 47]
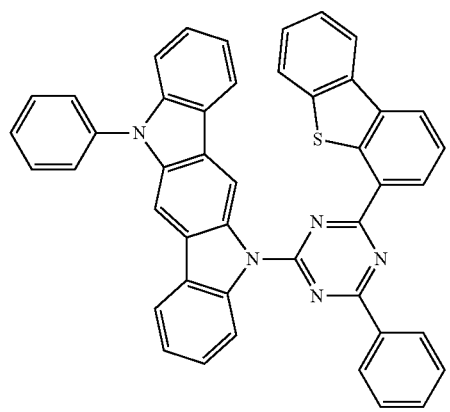
[D-ET 48]
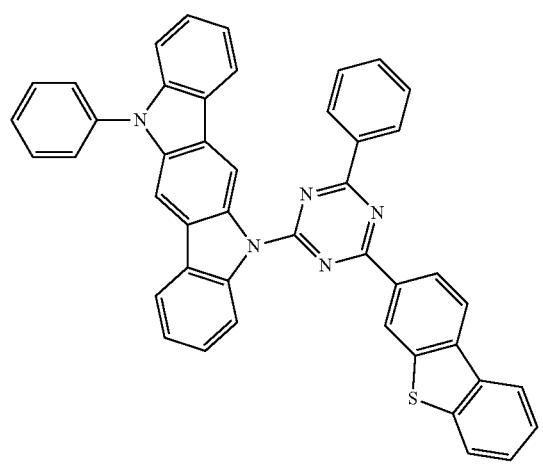
[D-ET 49]
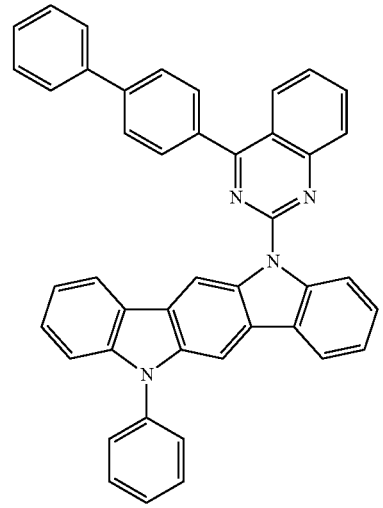
[D-ET 50]
[D-ET 51]
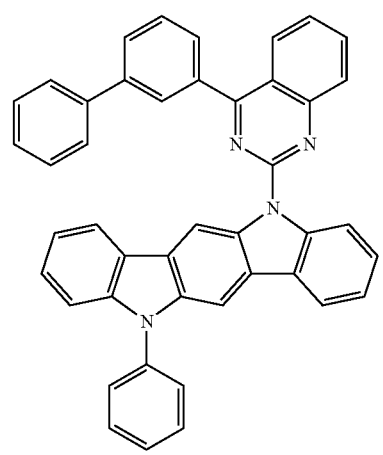
[D-ET-52]
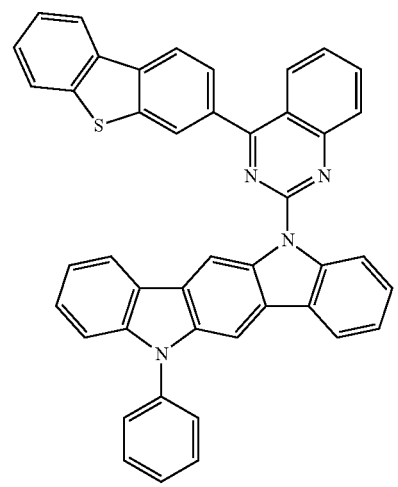

[E-ET 1]
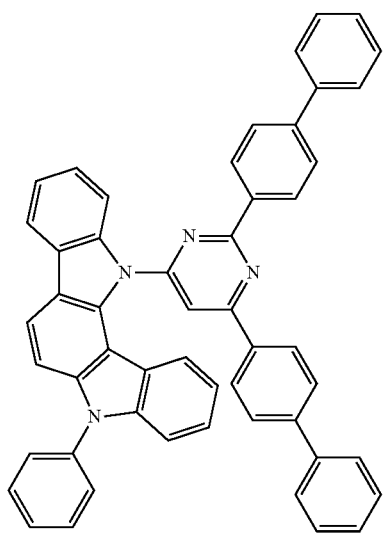
[E-ET 2]
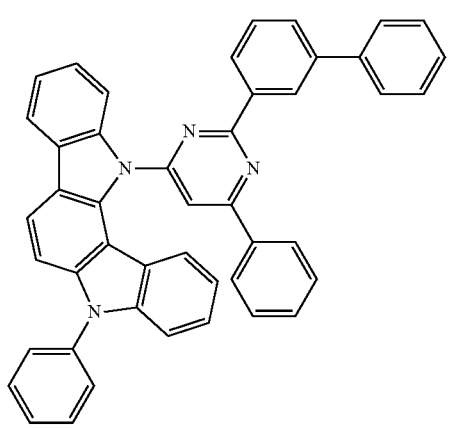
[E-ET 3]
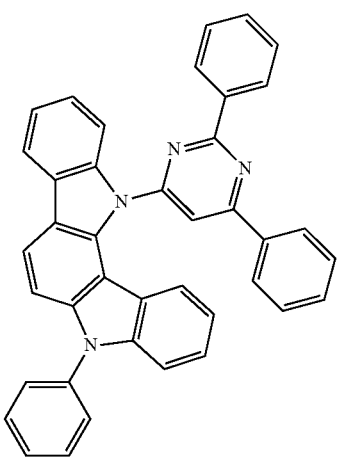
[E-ET 4]
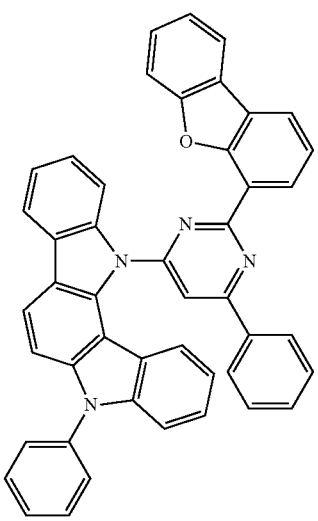
[E-ET 5]
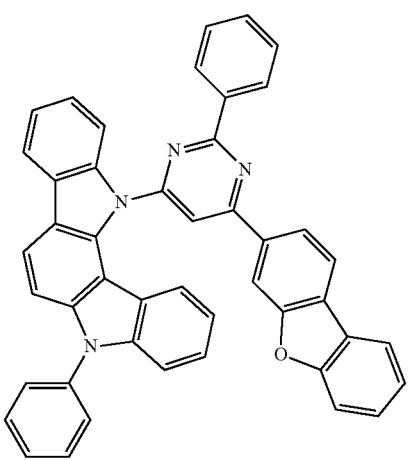
[E-ET 6]

[E-ET 7]
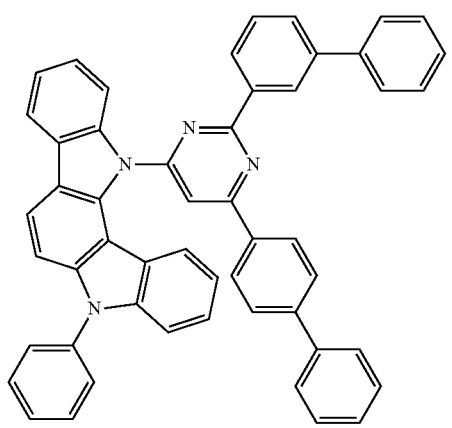
[E-ET 10]
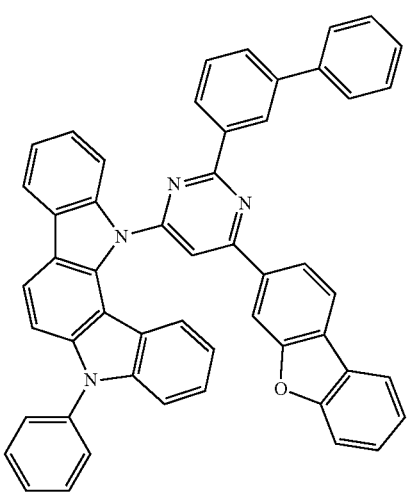
[E-ET 8]
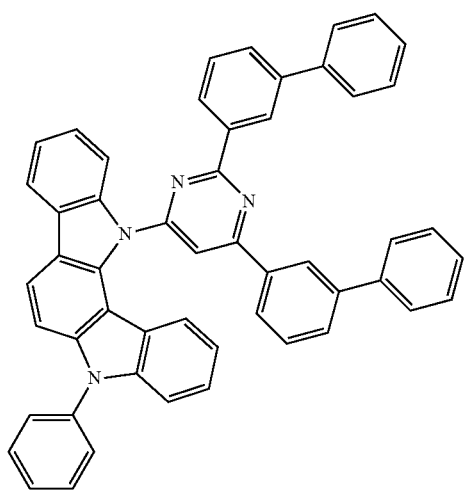
[E-ET 11]
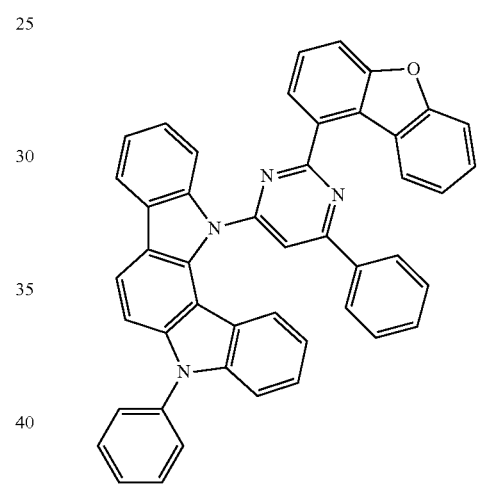
[E-ET 9]
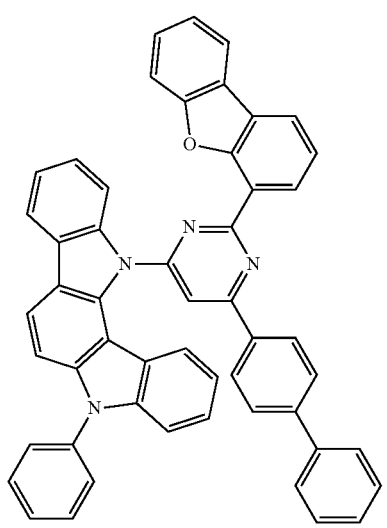
[E-ET 12]
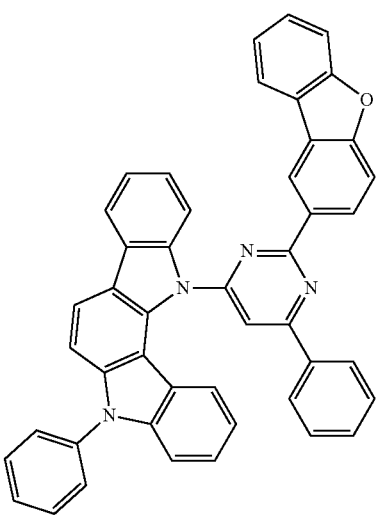

[E-ET 13]
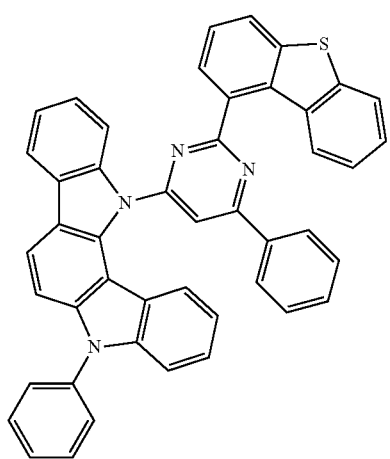
[E-ET 14]
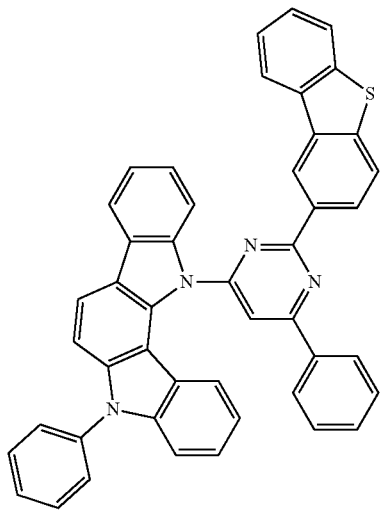
[E-ET 15]
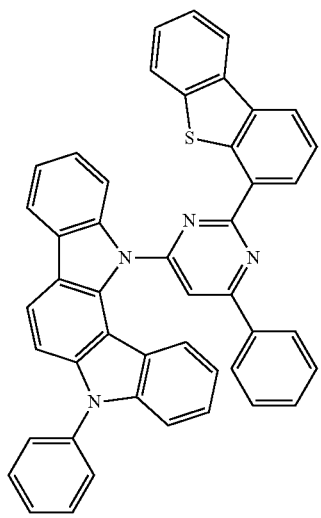
[E-ET 16]
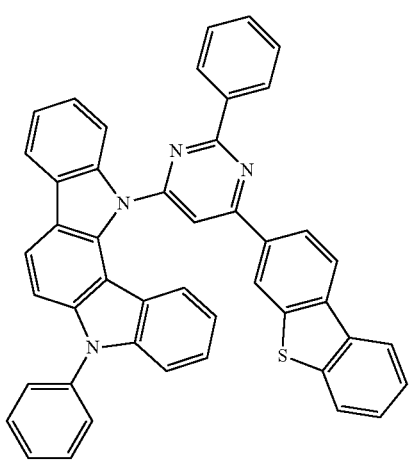
[E-ET 17]
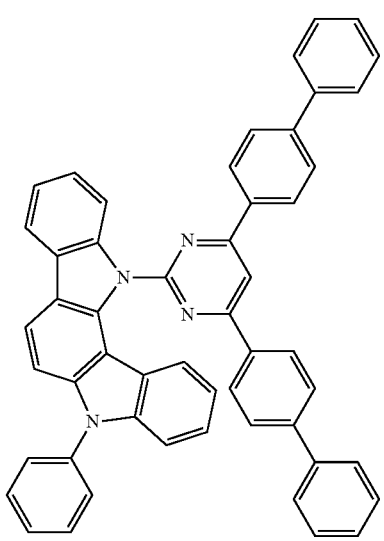
[E-ET 18]
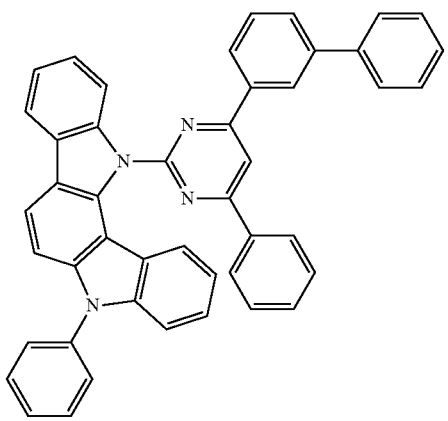

[E-ET 19]
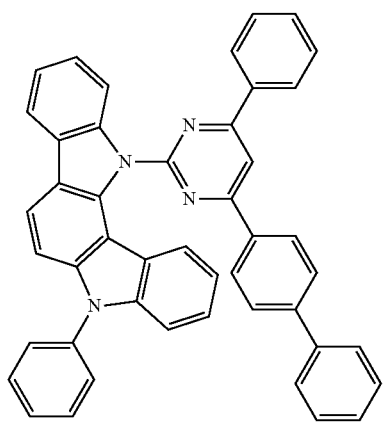
[E-ET 20]
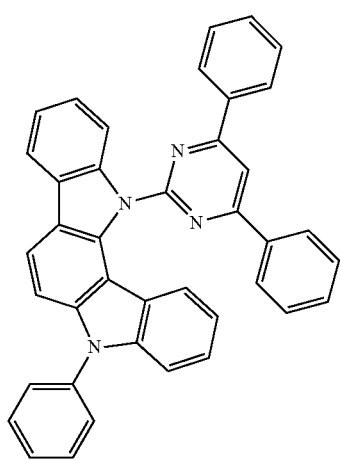
[E-ET 21]
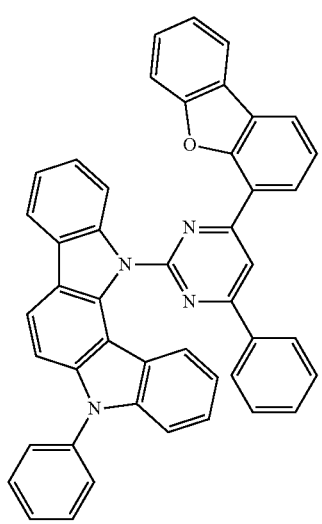
[E-ET 22]
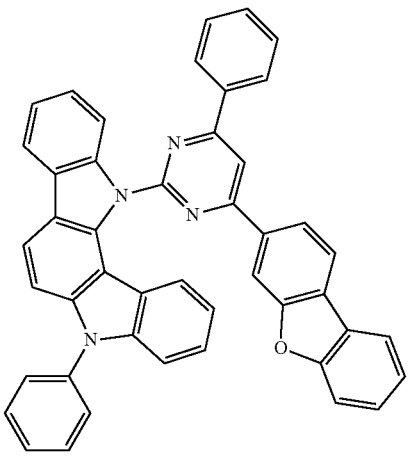
[E-ET 23]
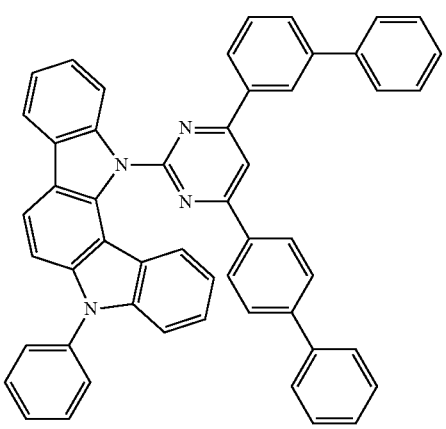
[E-ET 24]
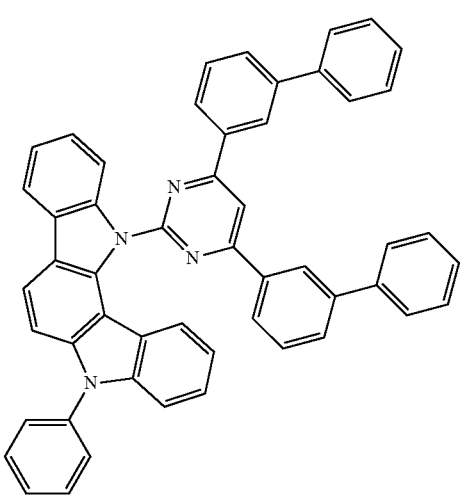

[E-ET 25]
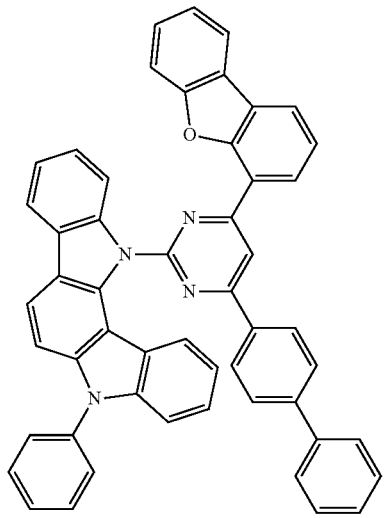
[E-ET 28]
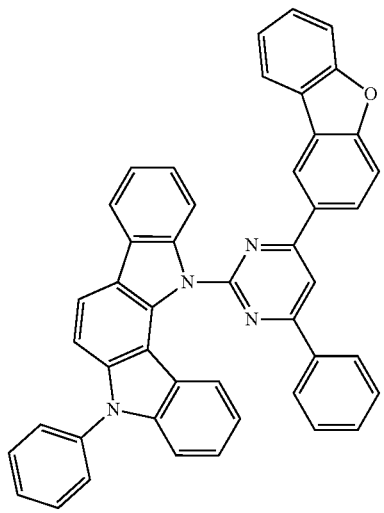
[E-ET 26]
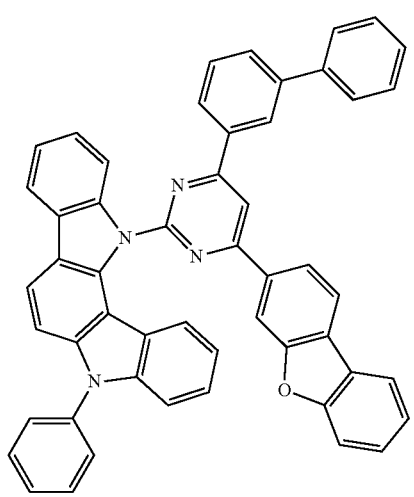
[E-ET 29]
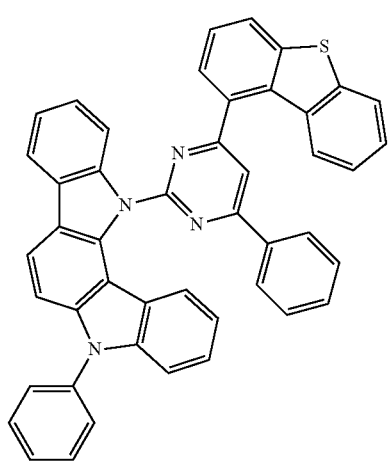
[E-ET 27]
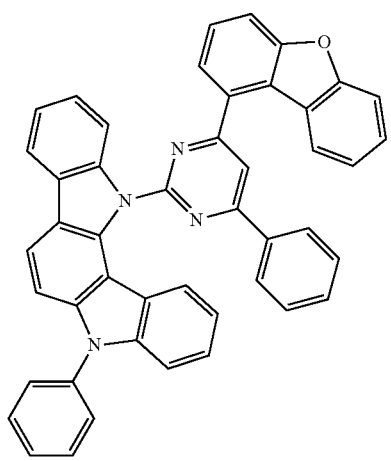
[E-ET 30]
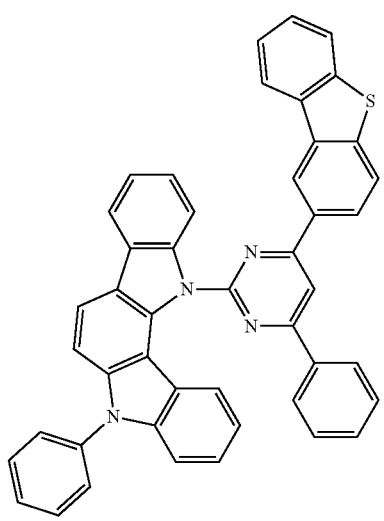

[E-ET 31]
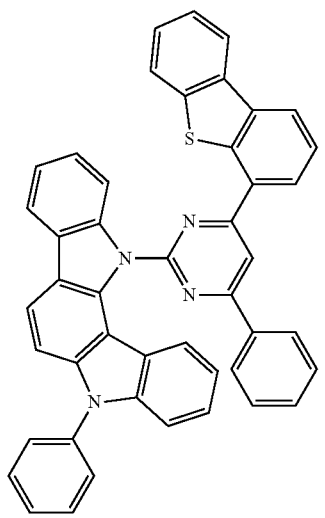
[E-ET 32]
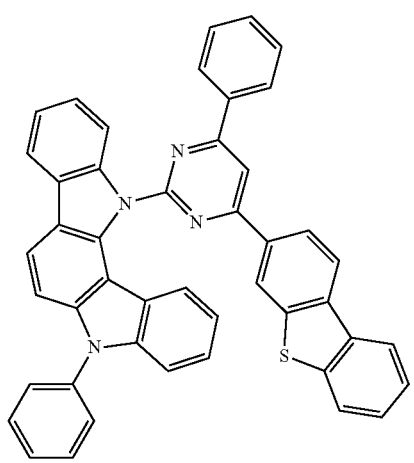
[E-ET 33]
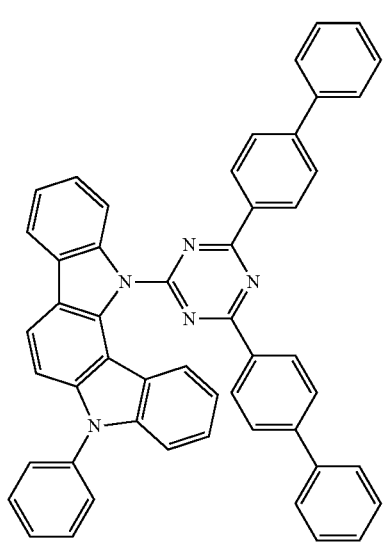
[E-ET 34]
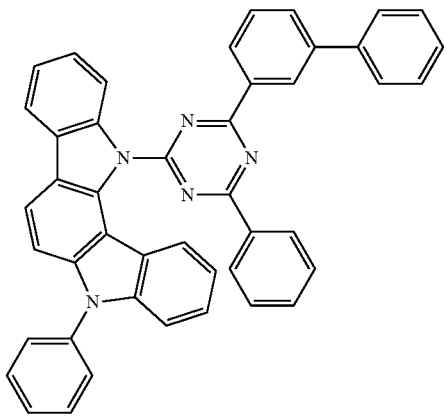
[E-ET 35]
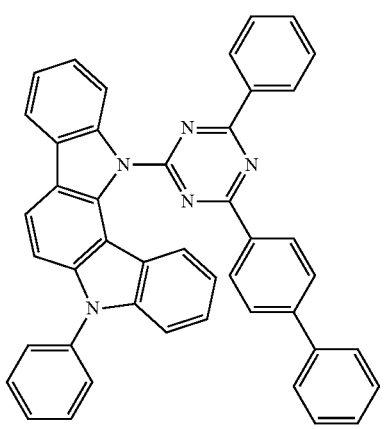
[E-ET 36]
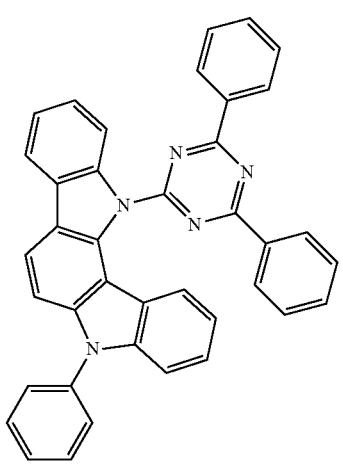

[E-ET 37]
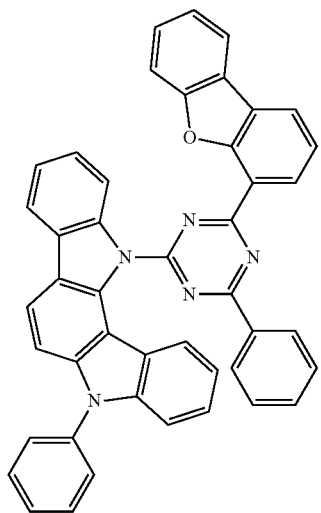
[E-ET 38]
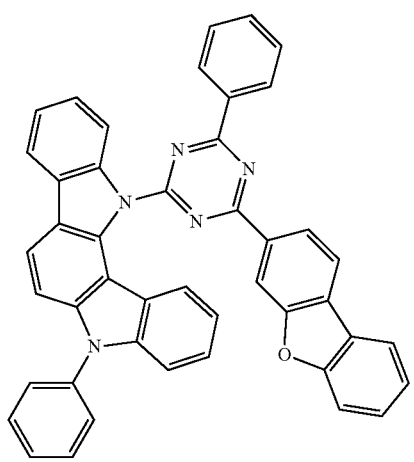
[E-ET 39]
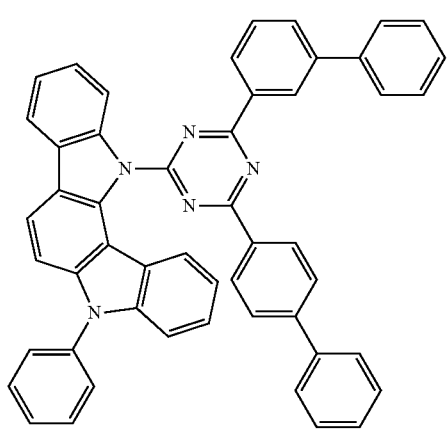
[E-ET 40]
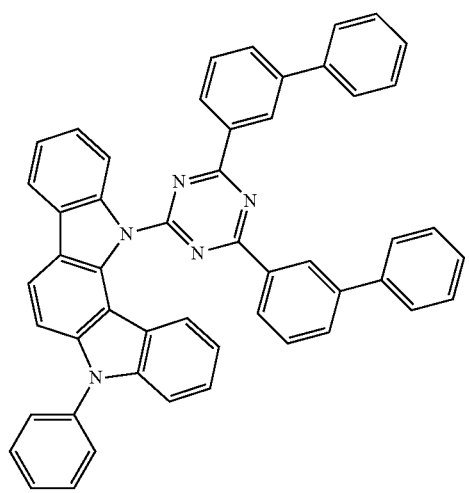
[E-ET 41]
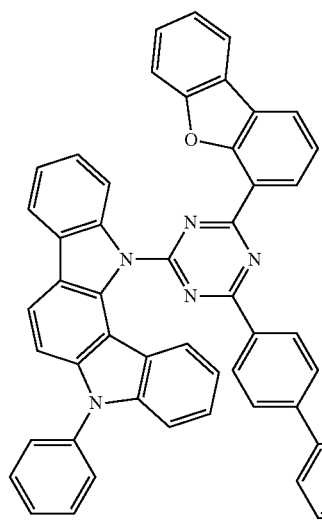
[E-ET 42]
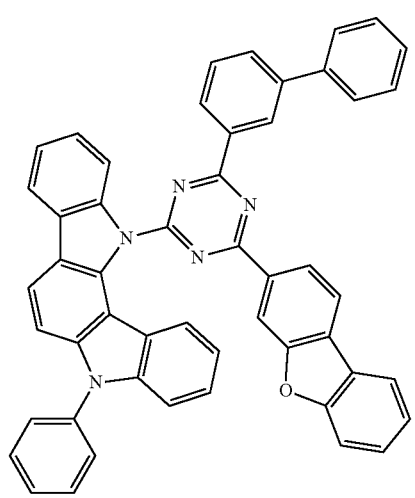

[E-ET 43]
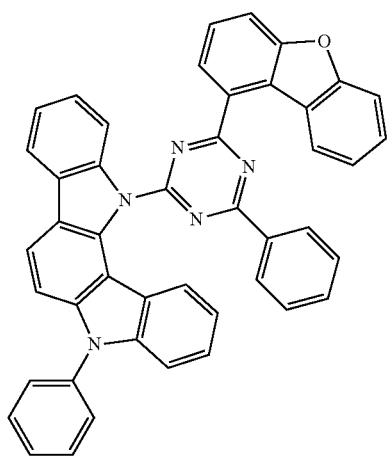
[E-ET 44]
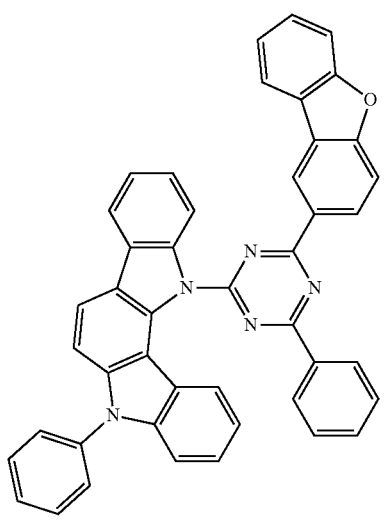
[E-ET 45]
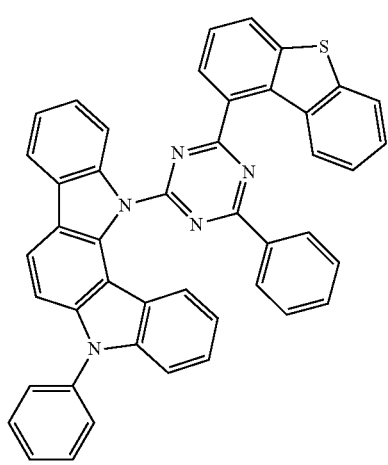
[E-ET 46]
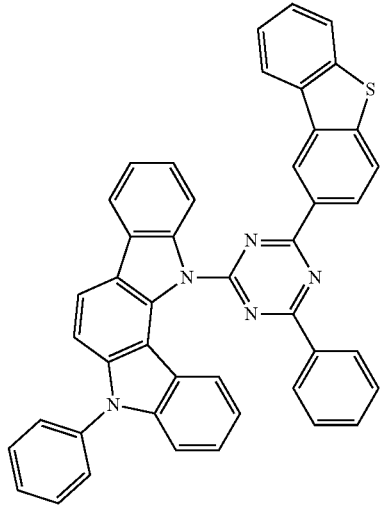
[E-ET 47]
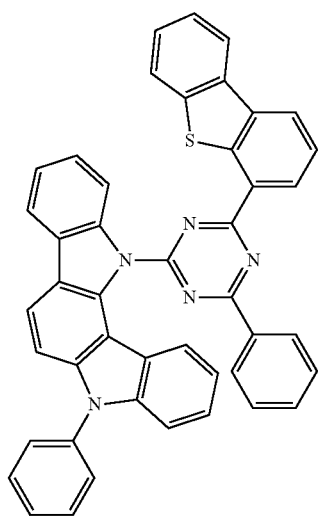
[E-ET 48]
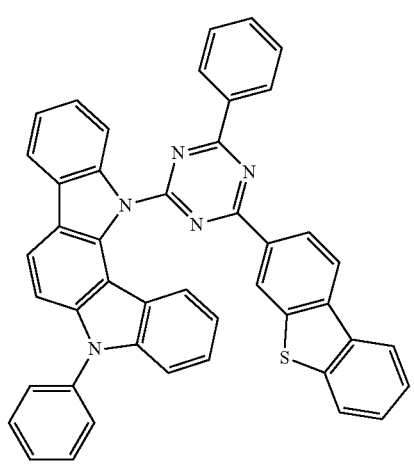

[E-ET 49]
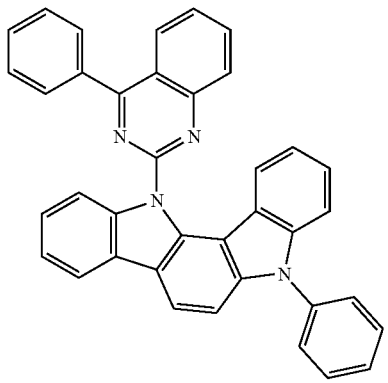
[E-ET 50]
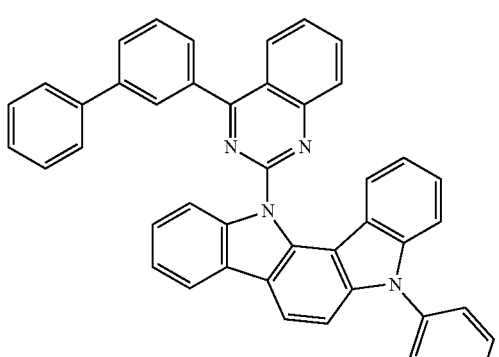
[E-ET 51]
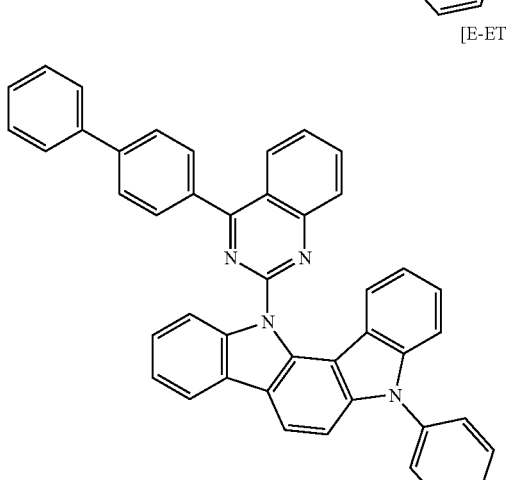
[E-ET 52]
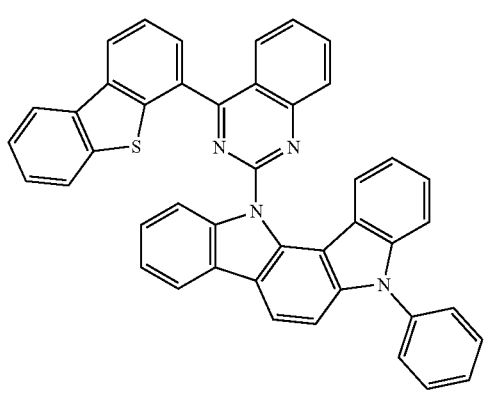
[E-ET 53]
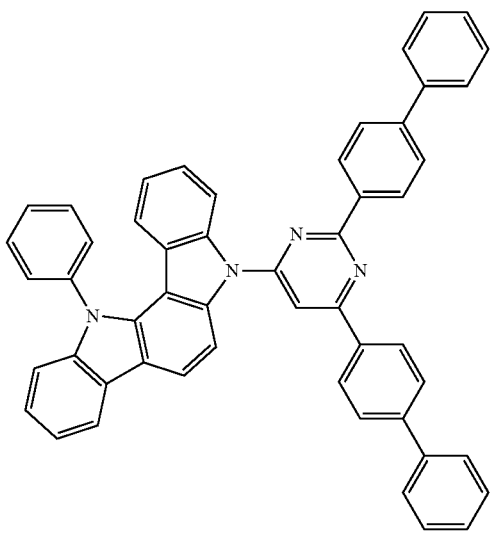
[E-ET 54]
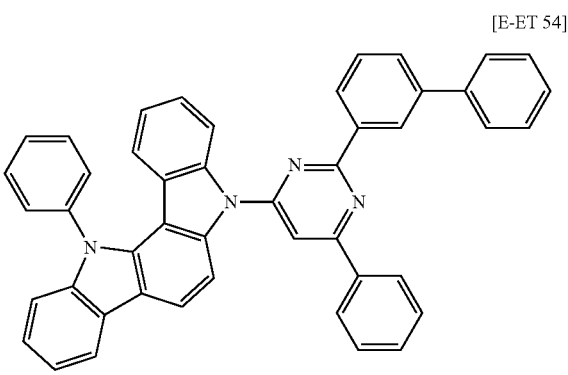
[E-ET 55]
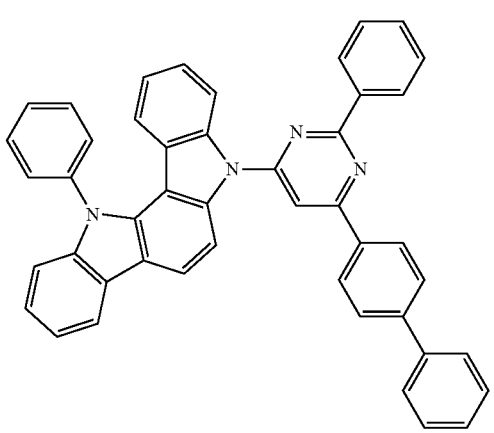

[E-ET 56]
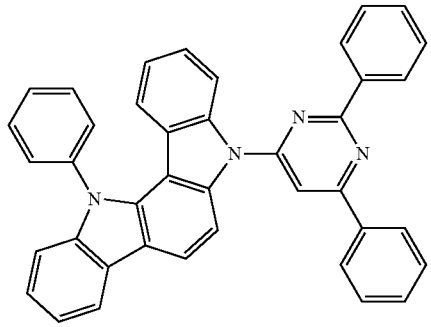
[E-ET 57]
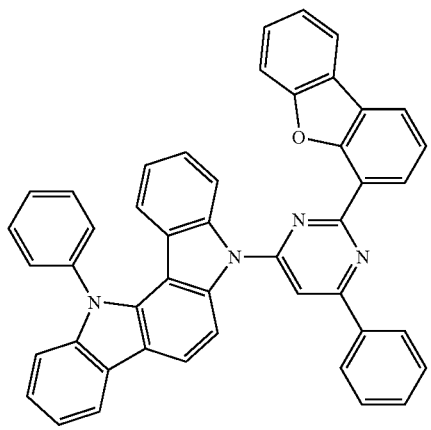
[E-ET 58]
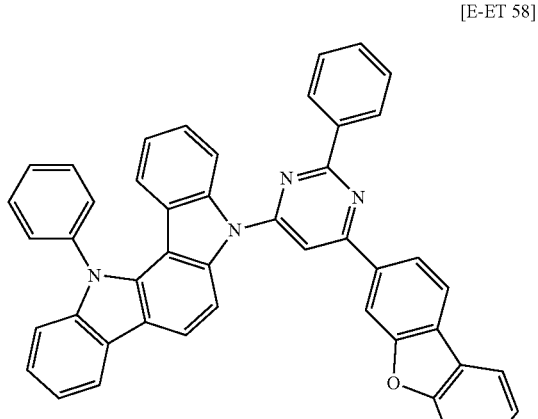
[E-ET 59]
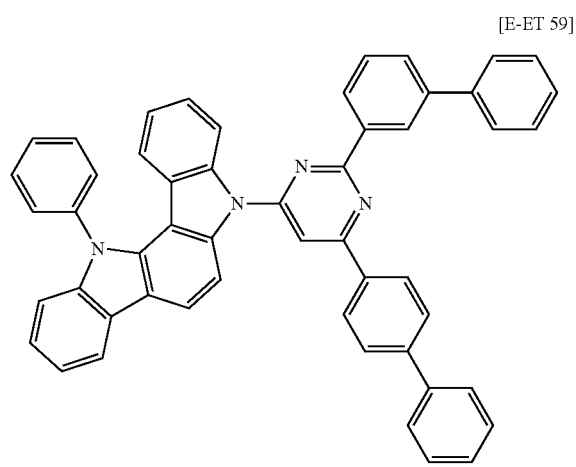
[E-ET 60]
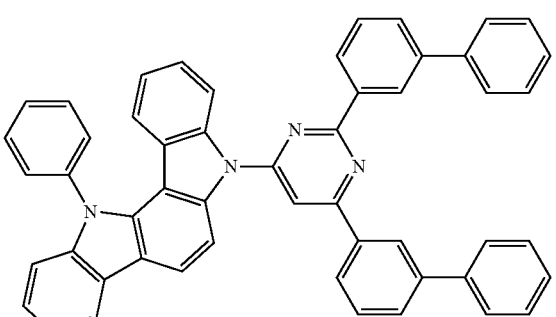
[E-ET 61]
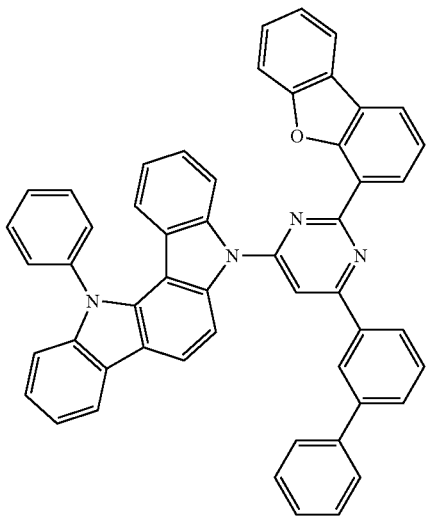
[E-ET 62]
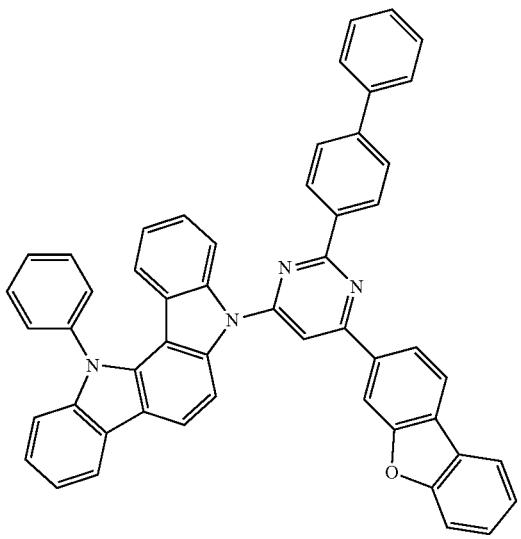

[E-ET 63]
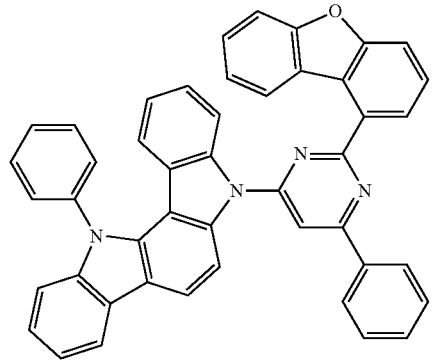
[E-ET 64]
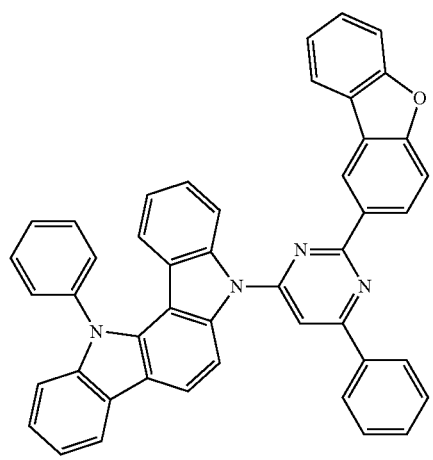
[E-ET 65]
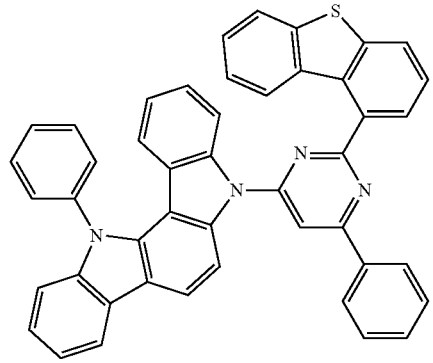
[E-ET 66]
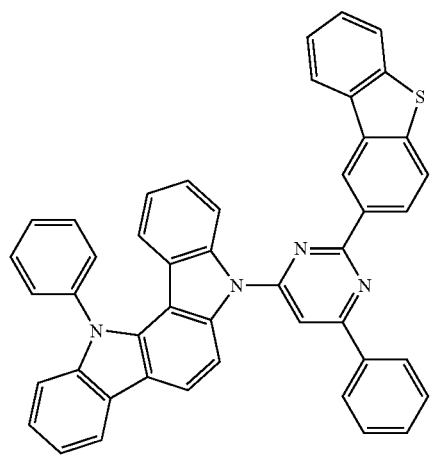
[E-ET 67]
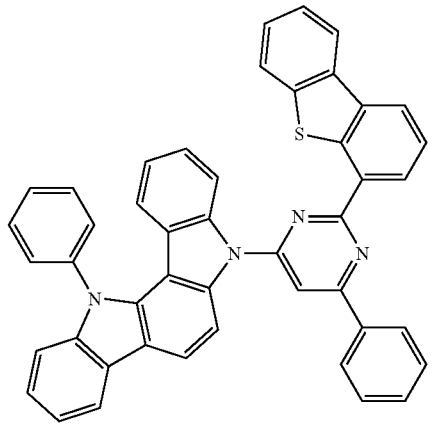
[E-ET 68]
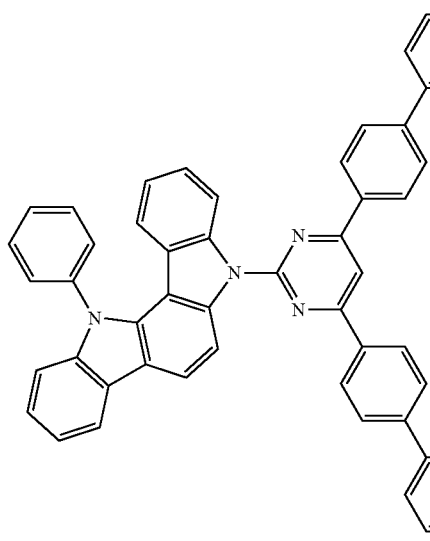
[E-ET 69]

-continued
[E-ET 70]
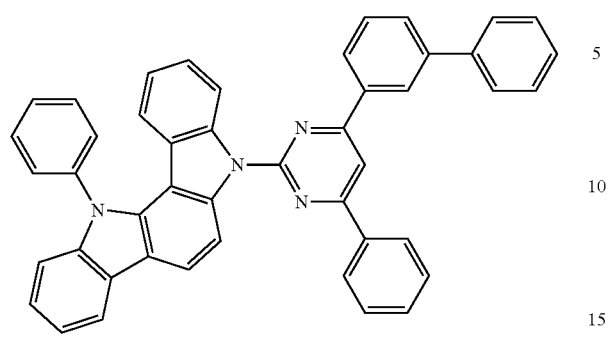
[E-ET 71]
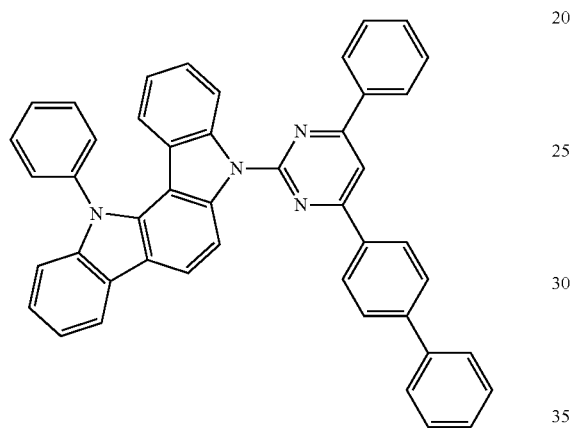
[E-ET 72]
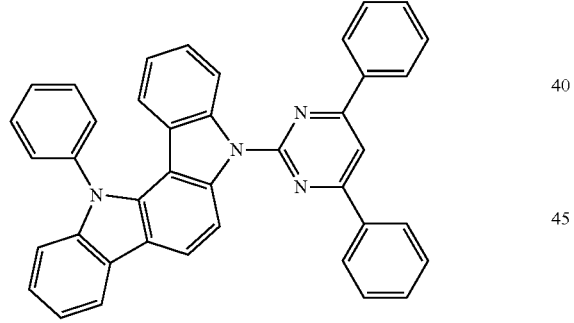
[E-ET 73]
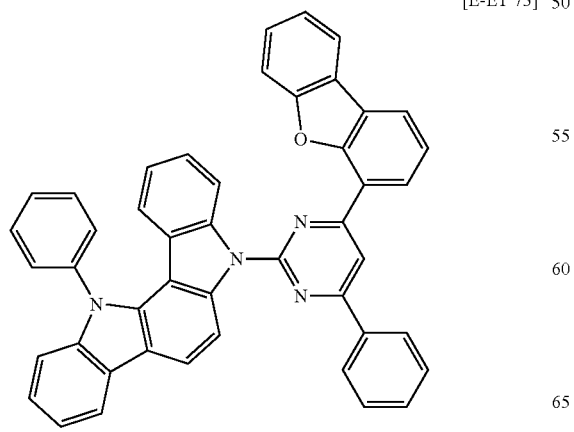
[E-ET 74]
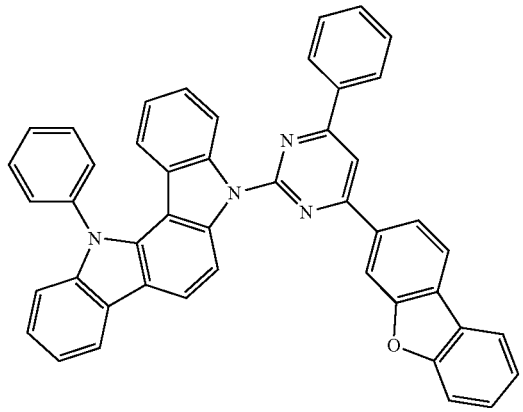
[E-ET 75]
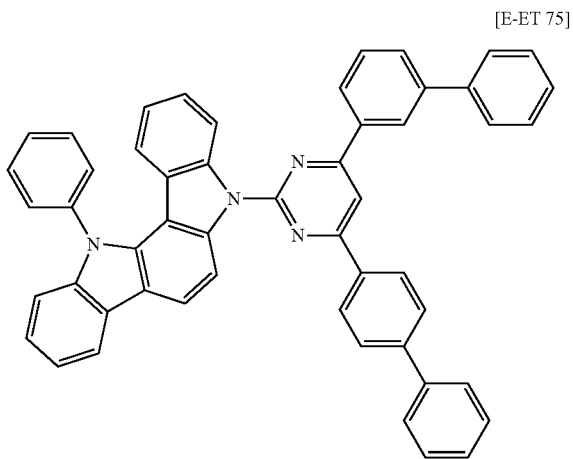
[E-ET 76]
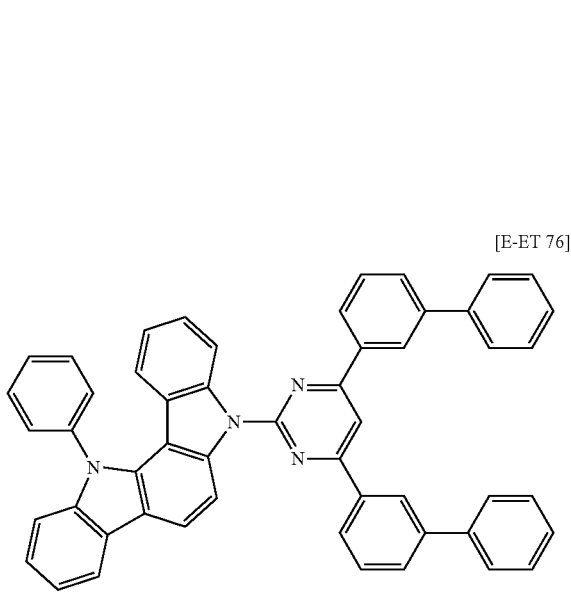

[E-ET 77]
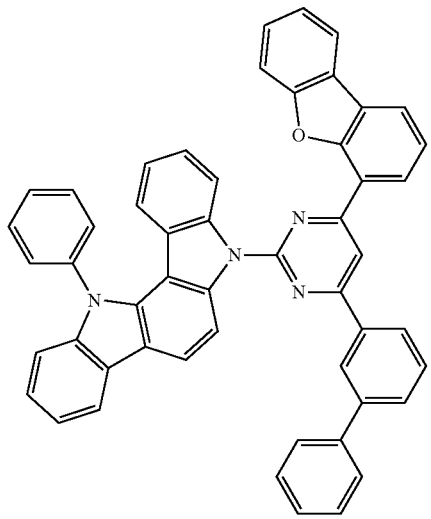
[E-ET 78]
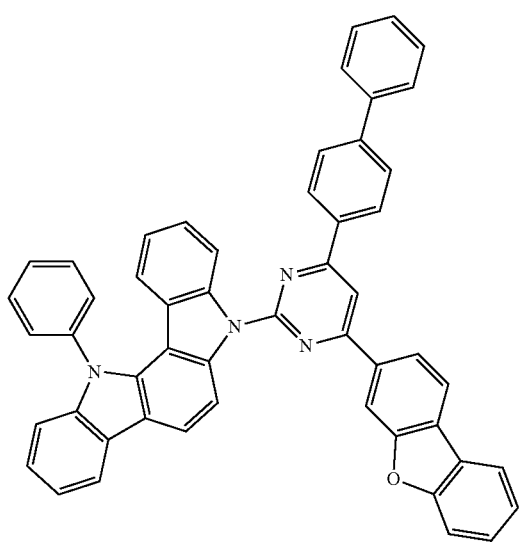
[E-ET 79]
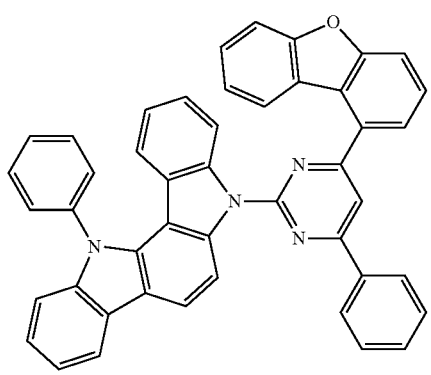
[E-ET 80]
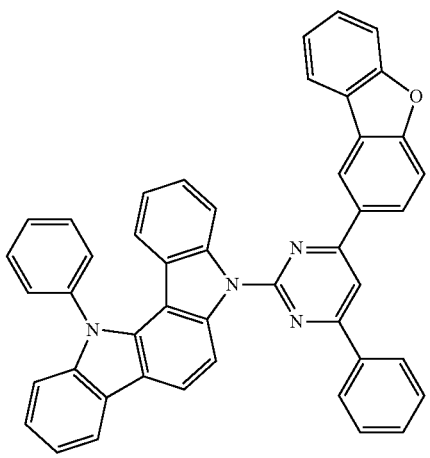
[E-ET 81]
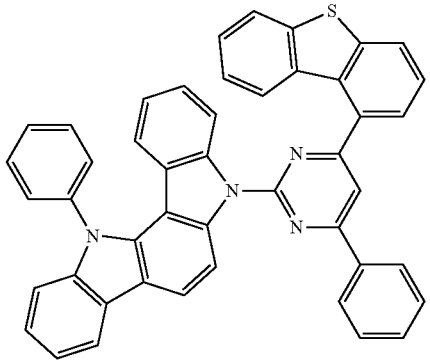
[E-ET 82]
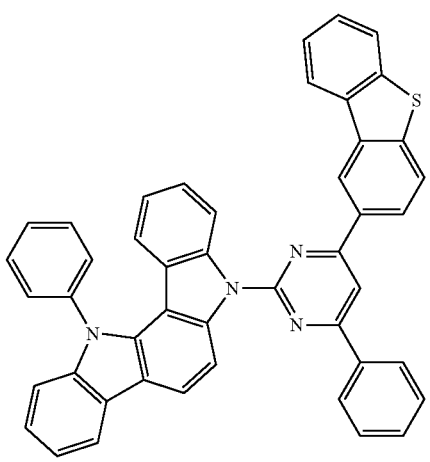

[E-ET 83]
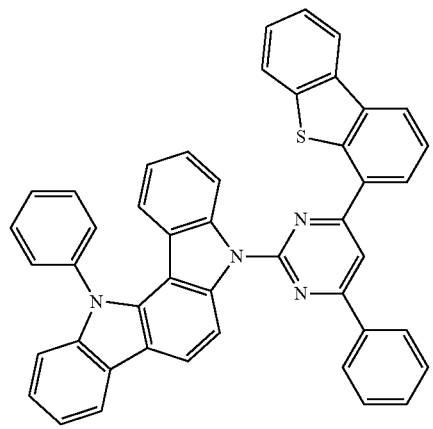
[E-ET 84]
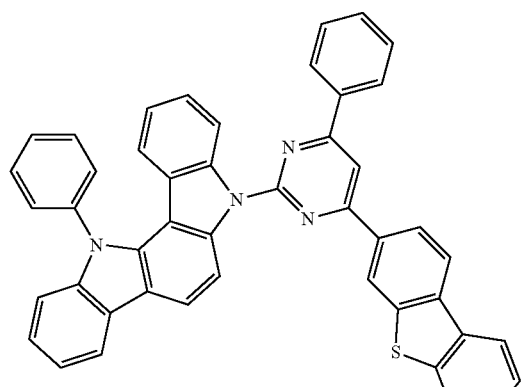
[E-ET 85]
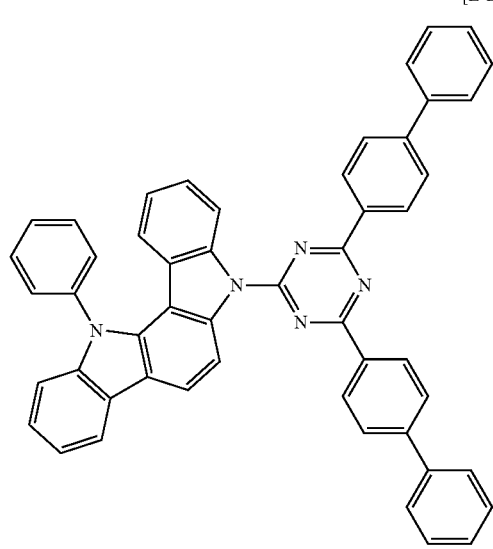
[E-ET 86]
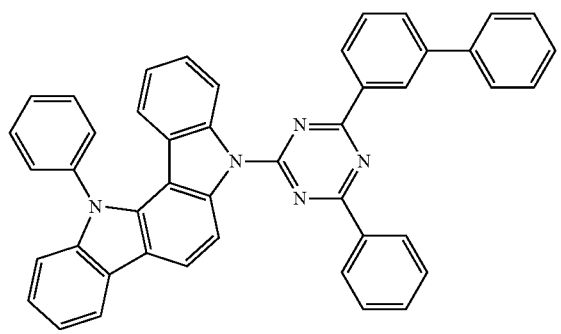
[E-ET 87]
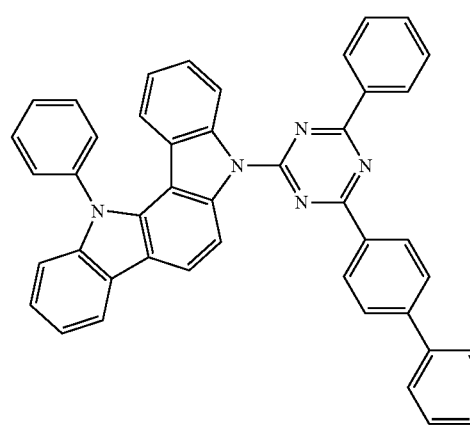
[E-ET 88]
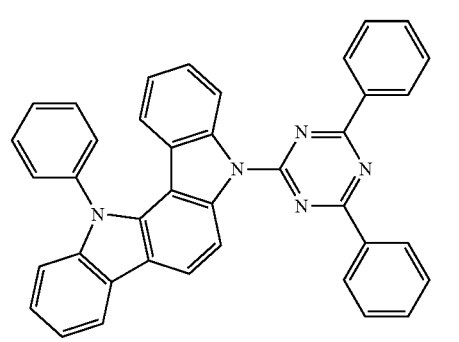
[E-ET 89]
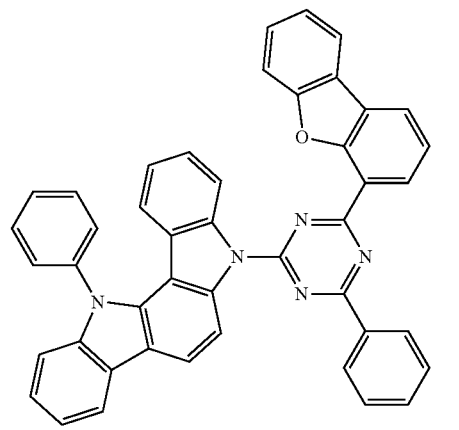

[E-ET 90]
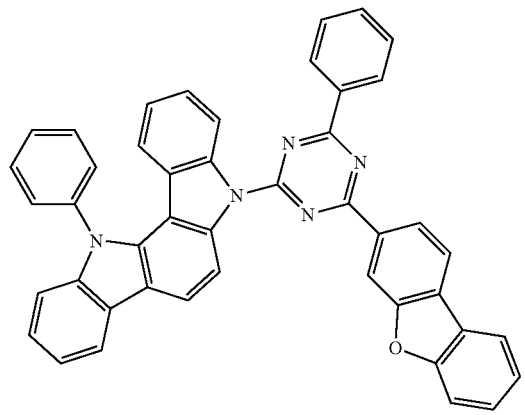
[E-ET 91]
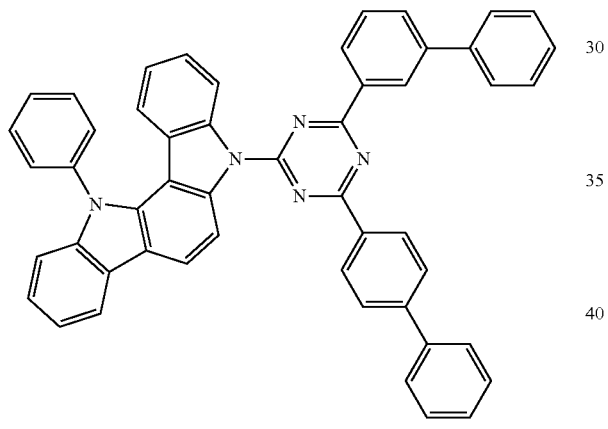
[E-ET 92]
[E-ET 93]
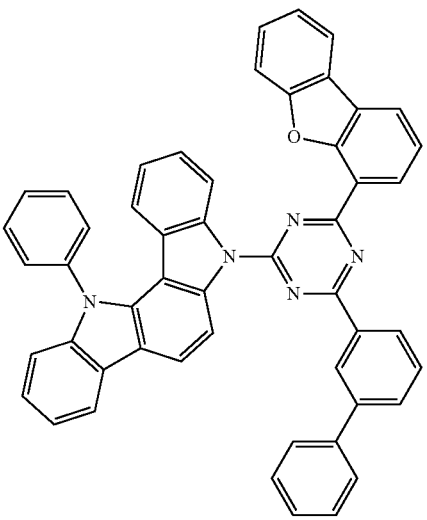
[E-ET 94]
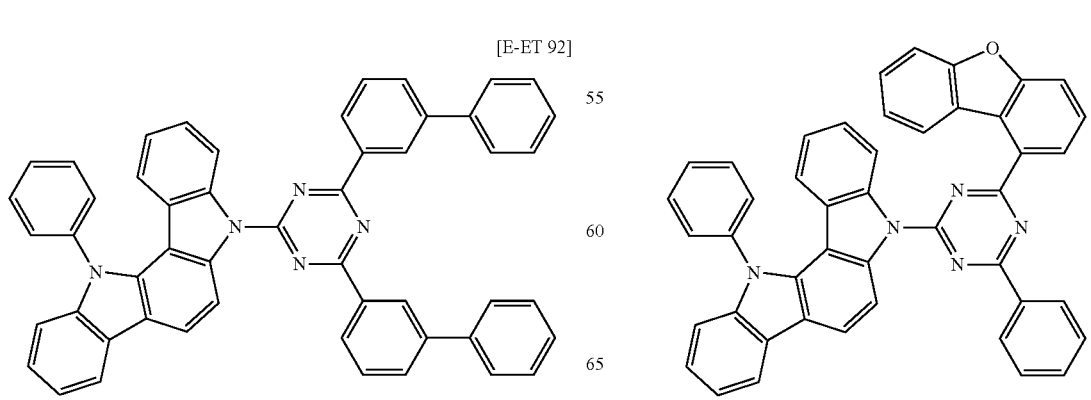
[E-ET 95]
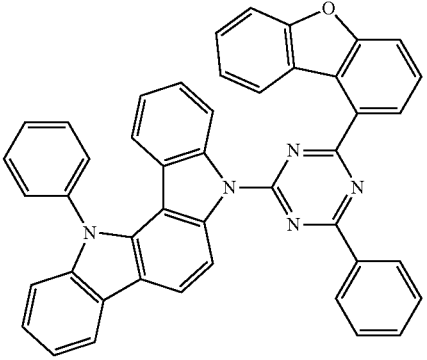

-continued
[E-ET 96]
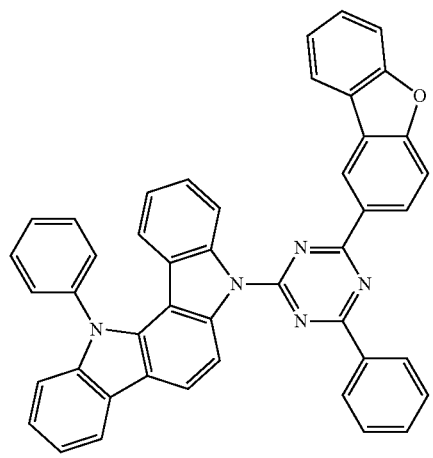
[E-ET 97]
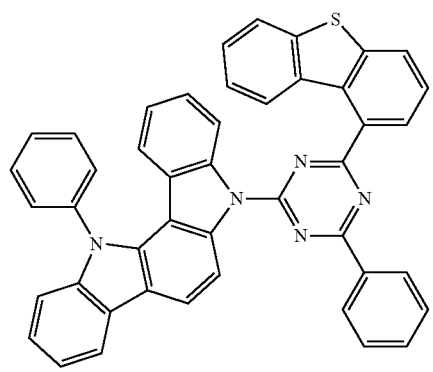
[E-ET 98]
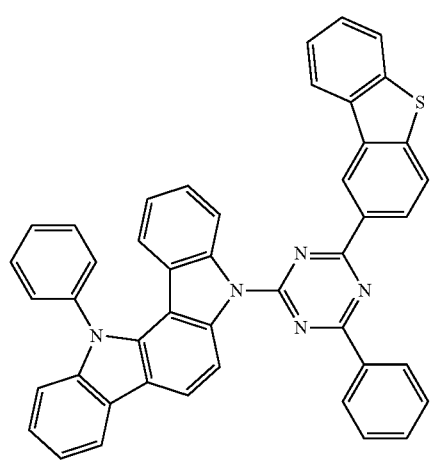
-continued
[E-ET 99]
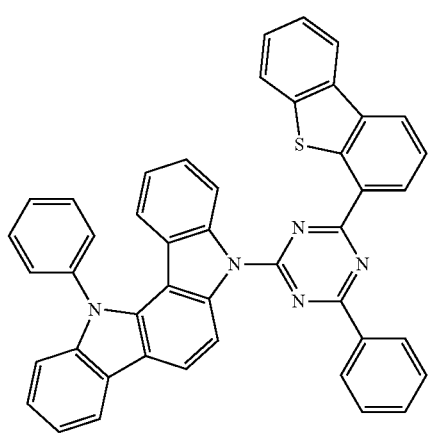
[E-ET 100]
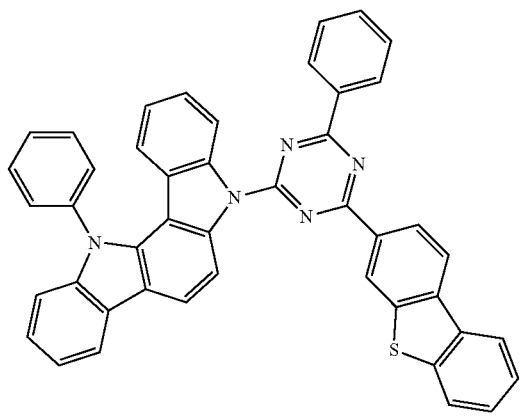
[E-ET 101]
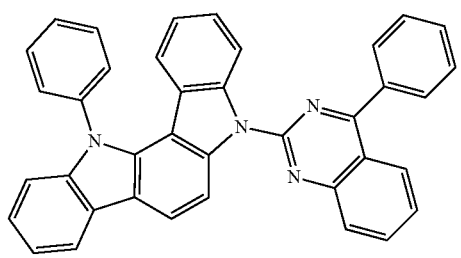
[E-ET 102]
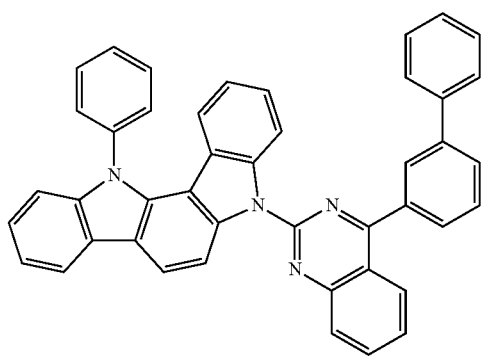

[E-ET 103]

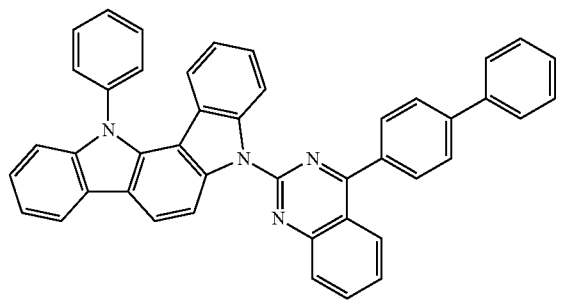

[E-ET 104]

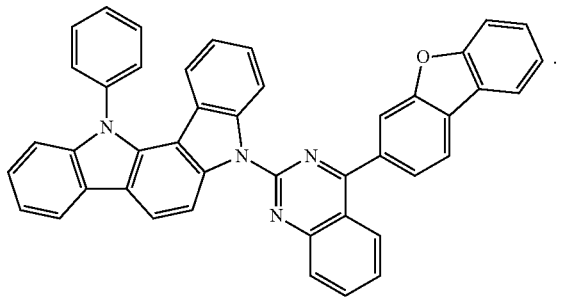

The first host compound and the second host compound may variously be combined to prepare various compositions.

For example, a composition according to an example embodiment may include a compound represented by Chemical Formula B1, Chemical Formula C1, Chemical Formula C2, Chemical Formula C3, Chemical Formula E1, Chemical Formula E2, or Chemical Formula E3 as a first host and a compound represented by Chemical Formula B-ET-a as a second host. Herein, $Ar^1$ and $Ar^2$ of Chemical Formula B1, Chemical Formula C1, Chemical Formula C2, Chemical Formula C3, Chemical Formula E1, Chemical Formula E2, and Chemical Formula E3 may independently be a substituted or unsubstituted phenyl group, a substituted or unsubstituted biphenyl group, a substituted or unsubstituted terphenyl group, a substituted or unsubstituted naphthyl group, a substituted or unsubstituted fluorenyl group, or a substituted or unsubstituted phenanthrenyl group, $L^1$ and $L^2$ may independently be a single bond, a substituted or unsubstituted phenylene group, or a substituted or unsubstituted biphenylene group, and $R^1$ to $R^{10}$ may independently be hydrogen, a substituted or unsubstituted C1 to C4 alkyl group, or a substituted or unsubstituted C6 to C12 aryl group; $Ar^3$ of Chemical Formula B-ET-a may be a substituted or unsubstituted phenyl group, or a substituted or unsubstituted biphenyl group, $L^3$ and $L^4$ may independently be a single bond, or a substituted or unsubstituted phenylene group, $R^{c2}$ and $R^{c4}$ may independently be a substituted or unsubstituted phenyl group, a substituted or unsubstituted para-biphenyl group, a substituted or unsubstituted meta-biphenyl group, a substituted or unsubstituted terphenyl group, a substituted or unsubstituted dibenzofuranyl group, or a substituted or unsubstituted dibenzothiophenyl group, and $R^{11}$ to $R^{14}$ may independently be hydrogen, a substituted or unsubstituted C1 to C4 alkyl group, or a substituted or unsubstituted C6 to C12 aryl group.

As described above, the first host compound is a compound having relatively strong hole transport characteristics and the second host compound is a compound having relatively strong electron transport characteristics, and thus improve luminous efficiency due to increased mobility of electrons and holes when they are used together compared with the compounds alone.

When a material having biased electron or hole characteristics is used to form a light emitting layer, excitons in a device including the light emitting layer are relatively more generated due to recombination of carriers on the interface between a light emitting layer and an electron transport layer or a hole transport layer. As a result, the molecular excitons in the light emitting layer interact with charges on the interface of the transport layers and thus, sharply deteriorate efficiency and light emitting life-span characteristics. In order to solve the problems, the first and second hosts are simultaneously included in the light emitting layer to make a light emitting region not be biased to either of the electron transport layer or the hole transport layer and a device capable of adjusting carrier balance in the light emitting layer may be provided and thereby efficiency and life-span characteristics may be remarkably improved.

The first host compound and the second host compound may be for example included in a weight ratio of about 1:10 to about 10:1. Specifically, they may be included in a weight ratio of about 2:8 to about 8:2, about 3:7 to about 7:3, about 4:6 to about 6:4, and about 5:5, for example about 7:3 or about 5:5. Within the ranges, bipolar characteristics may be effectively realized to improve efficiency and life-span simultaneously.

The composition may further include at least one compound in addition to the first host compound and the second host compound.

The composition may further include a dopant. The dopant may be a red, green, or blue dopant, for example a phosphorescent dopant.

The dopant is mixed with the first host compound and the second host compound in a small amount to cause light emission, and may be generally a material such as a metal complex that emits light by multiple excitation into a triplet or more. The dopant may be for example an inorganic, organic, or organic/inorganic compound, and one or more kinds thereof may be used.

Examples of the phosphorescent dopant may be an organometallic compound including Ir, Pt, Os, Ti, Zr, Hf, Eu, Tb, Tm, Fe, Co, Ni, Ru, Rh, Pd, or a combination thereof. The phosphorescent dopant may be for example a compound represented by Chemical Formula Z, but is not limited thereto.

$L_2MX$         [Chemical Formula Z]

In Chemical Formula Z, M is a metal, and L and X are the same or different, and are a ligand to form a complex compound with M.

The M may be for example Ir, Pt, Os, Ti, Zr, Hf, Eu, Tb, Tm, Fe, Co, Ni, Ru, Rh, Pd, or a combination thereof and the L and X may be for example a bidendate ligand.

The composition may be formed using a dry film formation method or a solution process.

Hereinafter, an organic optoelectronic device according to another embodiment is described.

An organic optoelectronic device according to another embodiment includes an anode and a cathode facing each other and at least one organic layer disposed between the anode and the cathode, wherein the organic layer includes the composition for an organic optoelectronic device.

Herein, an organic light emitting diode as one example of an organic optoelectronic device is described referring to drawings.

FIGS. 1 and 2 are cross-sectional views of organic light emitting diodes according to embodiments.

Referring to FIG. 1, an organic light emitting diode 100 according to an embodiment includes an anode 120 and a cathode 110 and an organic layer 105 disposed between the anode 120 and the cathode 110.

The anode 120 may be made of a conductor having a large work function to help hole injection and may be for example made of a metal, a metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example made of a metal, a metal oxide, and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al, and $BaF_2$/Ca, but is not limited thereto.

The organic layer 105 includes a light emitting layer 130 including the composition.

The light emitting layer 130 may for example include the composition.

Referring to FIG. 2, an organic light emitting diode 200 further include a hole auxiliary layer 140 in addition to the light emitting layer 130. The hole auxiliary layer 140 may further increase hole injection and/or hole mobility and block electrons between the anode 120 and the light emitting layer 130. The hole auxiliary layer 140 may be for example a hole transport layer, a hole injection layer, and/or an electron blocking layer, and may include at least one layer.

In an embodiment, in FIG. 1 or 2, an organic light emitting diode may further include an electron transport layer, an electron injection layer, or a hole injection layer as the organic layer 105.

The organic light emitting diodes 100 and 200 may be manufactured by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

Hereinafter, the embodiments are illustrated in more detail with reference to examples. These examples, however, are not in any sense to be interpreted as limiting the scope of the invention.

(Preparation of Composition for Organic Optoelectronic Device)

Hereinafter, starting materials and reactants used in Examples and Synthesis Examples were purchased from Sigma-Aldrich Co. Ltd. or TCI Inc. as far as there in no particular comment and may be easily synthesized as publicly known materials.

In the following Synthesis Examples, when "'B' is used instead of 'A'", the amounts of 'A' and 'B' are the same as based on a mole equivalent.

As specific examples of the compound for an organic optoelectronic device of the present disclosure, the compound was synthesized by the following reaction schemes.

Synthesis of First Host (HT Host) Compound

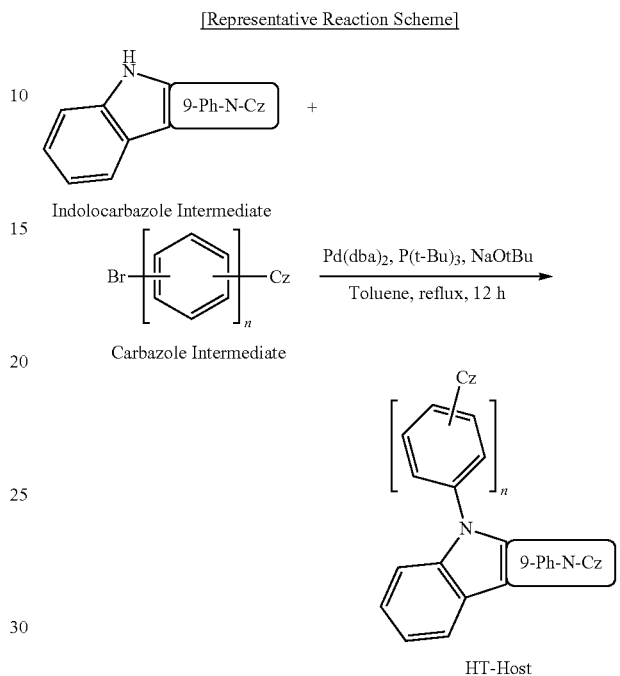

SYNTHESIS EXAMPLE 1: SYNTHESIS OF COMPOUND B-3

6.65 g (20 mmol) of Indolocarbazole Intermediate B and 7.97 g (20 mmol) of Carbazole Intermediate N-1, and 2.9 g (30 mmol) of sodium t-butoxide were put in a round-bottomed flask, and 200 ml of toluene was added thereto to dissolve them. 0.115 g (0.2 mmol) of $Pd(dba)_2$ and 0.101 g (0.5 mmol) of tri-tertiary-butylphosphine were sequentially added thereto and the mixture was refluxed and stirred under a nitrogen atmosphere for 12 hours. When a reaction was complete, the resultant was extracted with toluene and distilled water, an organic layer was dried with magnesium sulfate and filtered, and the filtrate was concentrated under a reduced pressure. A product was purified using silica gel column chromatography with n-hexane/dichloromethane (8:2 volume ratio) to obtain 10.5 g (yield: 81%) of a target compound, B-3.

LC-Mass (theoretical value: 649.25 g/mol, measured value: M+=649.13 g/mol)

SYNTHESIS EXAMPLES 2 TO 23: SYNTHESIS OF COMPOUNDS OF TABLE 1

Compound A-18; Compound B-18; Compound C-1; Compound C-3; Compound C-7; Compound C-8; Compound C-17 to Compound C-20; Compound E-3; Compound E-18; Compound E-20; Compound E-45; Compound E-46; Compound E-51; Compound E-52; Compound E-61 to Compound E-64; and Compound D-2 were synthesized according to the same method as the Representative Reaction Scheme by changing each of corresponding indolocarbazole intermediates and carbazole intermediates.

Chemical structures of synthesized compounds, used intermediates, yield amounts, yields, and LC/MS analysis results in Synthesis Examples 2 to 23 are shown in Table 1.

Used Intermediate Structures

[Indolocarbazole Intermediate]

Intermediate A

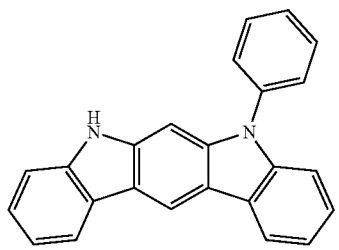

Intermediate B

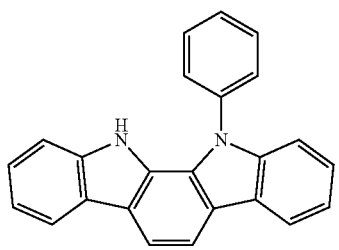

Intermediate C

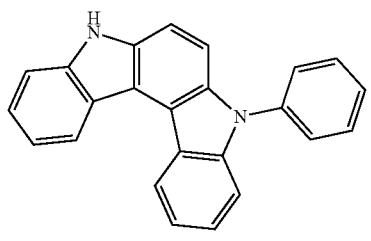

Intermediate D

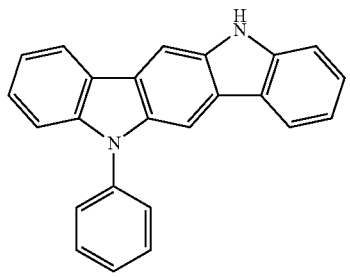

Intermediate Ea

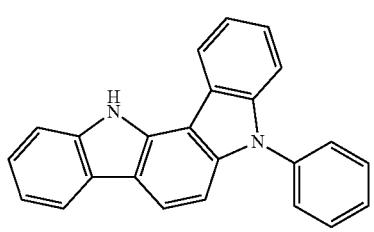

Intermediate Eb

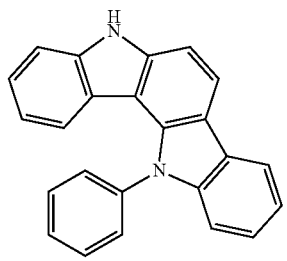

[Carbazole Intermediate]

Intermediate N-1

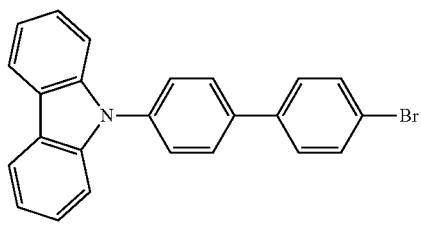

Intermediate N-2

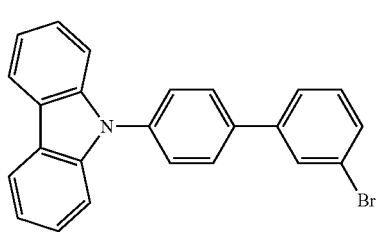

Intermediate N-3

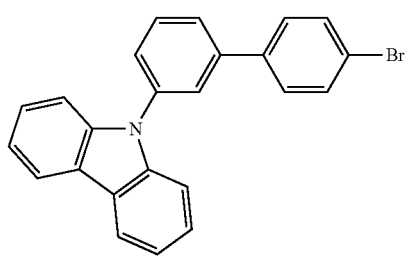

Intermediate N-4

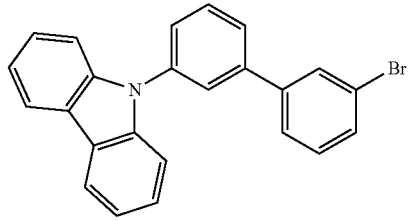

Intermediate M-1

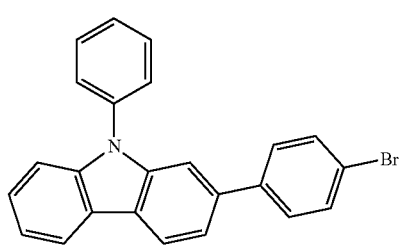

Intermediate M-2

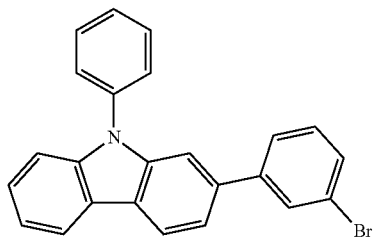

Intermediate M-3

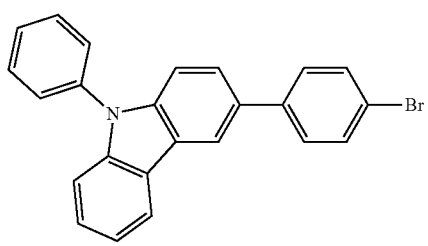

Intermediate M-4

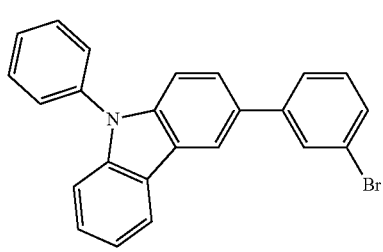

TABLE 1

| Synthesis Examples | Indolocarbazole Intermediate | Carbazole Intermediate | HT-Host | Amount (Yield) | LC/MS M+ = g/mol |
|---|---|---|---|---|---|
| Synthesis Example 1 | Intermediate B | Intermediate N-1 | B-3 | 10.5 g (81%) | 649.13 |
| Synthesis Example 2 | Intermediate B | Intermediate M-3 | B-18 | 10.4 g (80%) | 649.18 |
| Synthesis Example 3 | Intermediate C | Intermediate N-1 | C-3 | 12.1 g (93%) | 649.13 |
| Synthesis Example 4 | Intermediate C | Intermediate N-3 | C-8 | 12.0 g (92%) | 649.17 |
| Synthesis Example 5 | Intermediate C | Intermediate N-2 | C-1 | 11.7 g (90%) | 649.21 |
| Synthesis Example 6 | Intermediate C | Intermediate N-4 | C-7 | 11.7 g (90% | 649.23 |
| Synthesis Example 7 | Intermediate C | Intermediate M-3 | C-18 | 12.0 g (92%) | 649.22 |
| Synthesis Example 8 | Intermediate C | Intermediate M-1 | C-20 | 12.0 g (92%) | 649.13 |
| Synthesis Example 9 | Intermediate C | Intermediate M-4 | C-17 | 12.1 g (93%) | 649.11 |
| Synthesis Example 10 | Intermediate C | Intermediate M-2 | C-19 | 11.8 g (91%) | 649.17 |
| Synthesis Example 11 | Intermediate Eb | Intermediate N-1 | E-46 | 12.2 g (94%) | 649.18 |
| Synthesis Example 12 | Intermediate Eb | Intermediate N-3 | E-52 | 12.2 g (94%) | 649.20 |
| Synthesis Example 13 | Intermediate Eb | Intermediate N-4 | E-51 | 12.0 g (92%) | 649.20 |
| Synthesis Example 14 | Intermediate Eb | Intermediate N-2 | E-45 | 12.0 g (92%) | 649.22 |
| Synthesis Example 15 | Intermediate Eb | Intermediate M-3 | E-62 | 12.1 g (93%) | 649.23 |
| Synthesis Example 16 | Intermediate Eb | Intermediate M-1 | E-64 | 12.1 g (93%) | 649.21 |
| Synthesis Example 17 | Intermediate Eb | Intermediate M-4 | E-61 | 12.2 g (94%) | 650.12 |
| Synthesis Example 18 | Intermediate Eb | Intermediate M-2 | E-63 | 12.0 g (92%) | 649.55 |
| Synthesis Example 19 | Intermediate Ea | Intermediate N-1 | E-3 | 11.6 g (89%) | 649.23 |
| Synthesis Example 20 | Intermediate Ea | Intermediate M-3 | E-18 | 11.4 g 88%) | 649.56 |
| Synthesis Example 21 | Intermediate Ea | Intermediate M-1 | E-20 | 11.6 g (89%) | 649.78 |
| Synthesis Example 22 | Intermediate A | Intermediate M-3 | A-18 | 11.8 g (91%) | 649.45 |
| Synthesis Example 23 | Intermediate D | Intermediate N-1 | D-2 | 12.1 g (93%) | 649.23 |

Synthesis of Second Host (ET Host) Compound

SYNTHESIS EXAMPLE 24: SYNTHESIS OF COMPOUND B-ET 36

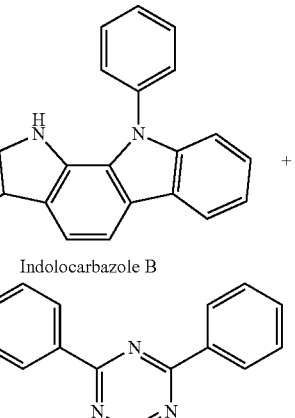

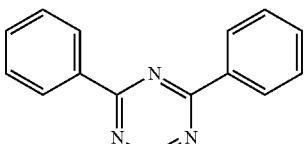

6.65 g (20 mmol) of Indolocarbazole Intermediate B and 200 ml of anhydrous dimethyl formamide were put in a round-bottomed flask to dissolve them. The resultant solution was cooled to 0° C. under a nitrogen atmosphere, 0.53 g (22 mmol) of sodium hydride [NaH] was slowly added thereto and the mixture was stirred at room temperature for 30 minutes. 5.35 g (20 mmol) of Trz-1 Intermediate was added to the reaction solution at room temperature and was stirred at 60° C. for 12 hours. When a reaction was complete, distilled water was added thereto and a solid produced therein was filtered and washed with distilled water. The solid was recrystallized in toluene and filtered to obtain a target compound, B-ET 36 (8.8 g, yield: 78%).

LC-Mass (theoretical value: 563.21 g/mol, measured value: M+=563.54 g/mol)

SYNTHESIS EXAMPLE 25: SYNTHESIS OF COMPOUND B-ET 33

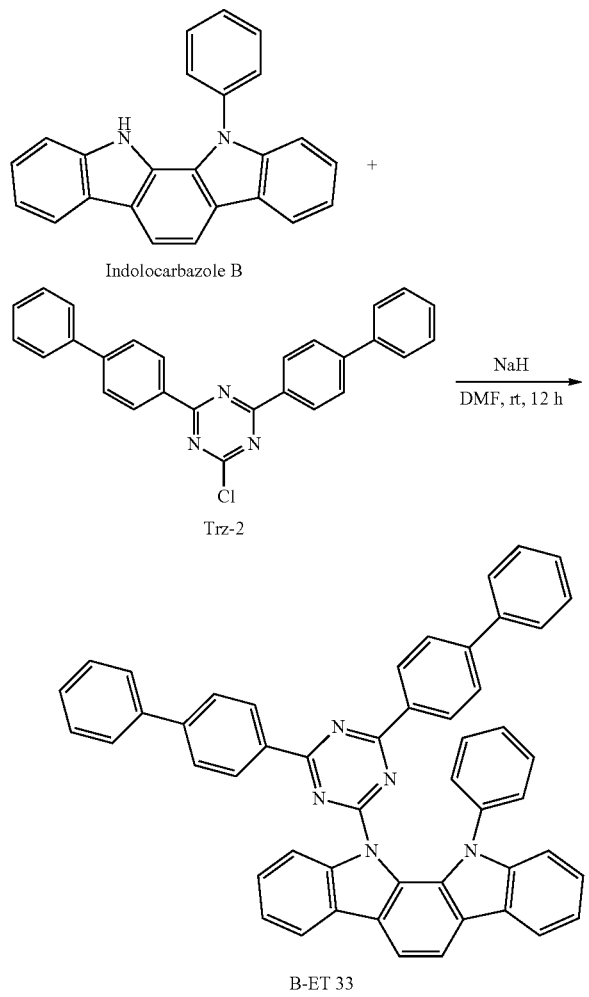

B-ET 33

A target compound, B-ET 33 (11.6 g, yield: 81%) was obtained according to the same method as in Synthesis Example 24 except using 8.4 g (20 mmol) of Trz-2 Intermediate instead of Trz-1 Intermediate.

LC-Mass (theoretical value: 715.27 g/mol, measured value: M+=715.33 g/mol)

Manufacture of Organic Light Emitting Diode

EXAMPLE 1

ITO (indium tin oxide) was coated to be 1500 Å thick on a glass substrate, and the coated glass was ultrasonic wave-washed with a distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, a 700 Å-thick hole injection layer was formed on the ITO substrate by vacuum depositing N4,N4'-diphenyl-N4,N4'-bis (9-phenyl-9H-carbazol-3-yl)biphenyl-4,4'-diamine (Compound A), and a hole transport layer was formed by depositing 1,4,5,8,9,11-hexaazatriphenylene-hexacarbonitrile (HAT-CN) (Compound B) in a thickness of 50 Å on the injection layer, and depositing N-(biphenyl-4-yl)-9,9-dimethyl-N-(4-(9-phenyl-9H-carbazol-3-yl)phenyl)-9H-fluoren-2-amine (Compound C) in a thickness of 1020 Å. On the hole transport layer, a 400 Å-thick light emitting layer was formed by vacuum-depositing Compound B-3 and Compound B-ET 33 as a host and tris(4-methyl-2,5-diphenylpyridine)iridium (III) (Compound D) as a dopant in a doping amount of 10 wt %. Herein, Compound B-3 and Compound B-ET 33 were used in a ratio of 7:3.

Subsequently, a 300 Å-thick electron transport layer was formed by vacuum-depositing 8-(4-(4-(naphthalen-2-yl)-6-(naphthalen-3-yl)-1,3,5-triazin-2-yl)phenyl)quinoline (Compound E) and Liq simultaneously in a 1:1 ratio on the light emitting layer, and Liq (15 Å) and Al (1200 Å) were sequentially vacuum-deposited on the electron transport layer to form a cathode, manufacturing an organic light emitting diode.

The organic light emitting diode has five organic thin layers, specifically a structure of ITO/A 700 Å/B 50 Å/C 1020 Å/EML[B-3: B-ET 33:D=X:X:10%] 400 Å/E:Liq 300 Å/Liq 15 Å/Al 1200 Å.

(X=weight ratio)

EXAMPLE 2 TO EXAMPLE 16

Organic light emitting diodes according to Examples 2 to 16 were manufactured according to the same method as Example 1 by changing the first host and the second host, and a mixing ratio of the first host and the second host as shown in Table 2.

COMPARATIVE EXAMPLES 1 TO 5

Organic light emitting diodes according to Comparative Examples 1 to 5 were manufactured according to the same method as Example 1 by respectively using CBP, B-ET 33, B-ET 36, C-18, and E-3 alone as a host of the light emitting layer as shown in Table 2.

Evaluation

Luminous efficiency and life-span characteristics of each of the organic light emitting diodes according to Examples 1 to 16 and Comparative Examples 1 to 5 were evaluated.

Specific measurement methods are as follows, and the results are shown in Table 2.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-span

Life-span was obtained by measuring time taken until current efficiency (cd/A) decreased down to 97% while luminance (cd/m$^2$) was maintained at 6000 cd/m$^2$.

TABLE 2

| Examples | First host | Second host | First host:Second host (wt/wt) | Driving voltage (V) | Luminous efficiency (cd/A) | Life-span T97 (h) |
|---|---|---|---|---|---|---|
| Example 1 | B-3 | B-ET 33 | 7:3 | 4.83 | 43.5 | 250 |
| Example 2 | C-8 | B-ET 33 | 7:3 | 4.71 | 49.6 | 310 |
| Example 3 | C-1 | B-ET 33 | 7:3 | 4.89 | 49.8 | 240 |
| Example 4 | E-52 | B-ET 33 | 7:3 | 4.90 | 51.9 | 320 |
| Example 5 | E-51 | B-ET 33 | 7:3 | 5.16 | 51.0 | 315 |
| Example 6 | C-3 | B-ET 33 | 7:3 | 4.53 | 48.7 | 400 |
| Example 7 | E-3 | B-ET 33 | 7:3 | 4.66 | 49.6 | 430 |
| Example 8 | E-62 | B-ET 33 | 7:3 | 4.67 | 48.5 | 591 |
| Example 9 | E-64 | B-ET 33 | 7:3 | 4.82 | 49.1 | 584 |
| Example 10 | E-61 | B-ET 33 | 7:3 | 4.50 | 50.3 | 484 |
| Example 11 | E-20 | B-ET 33 | 7:3 | 4.54 | 48.3 | 580 |
| Example 12 | E-18 | B-ET 33 | 7:3 | 4.50 | 51.8 | 620 |
| Example 13 | C-20 | B-ET 33 | 7:3 | 4.15 | 42.9 | 573 |
| Example 14 | C-18 | B-ET 33 | 7:3 | 4.17 | 42.5 | 420 |
| Example 15 | C-18 | B-ET 33 | 1:1 | 4.12 | 45.9 | 270 |
| Example 16 | C-18 | B-ET 36 | 1:1 | 4.15 | 47.1 | 350 |
| Comparative Example 1 | CBP | — | — | 7.20 | 19.5 | 1 |
| Comparative Example 2 | — | B-ET 33 | — | 5.21 | 25.4 | 85 |
| Comparative Example 3 | — | B-ET 36 | — | 5.17 | 29.5 | 74 |
| Comparative Example 4 | C-18 | — | — | 6.55 | 19.8 | 7 |
| Comparative Example 5 | E-3 | — | — | 6.95 | 20.7 | 4 |

* Life-spans of devices having luminance of 6000 cd/m$^2$ or less were not measurable Referring to Table 2, the organic light emitting diodes according to Examples 1 to 16 using the first host having excellent hole transport properties and the second host having excellent electron transport properties showed a lower driving voltage, high luminous efficiency and remarkably improved life-span characteristics compared with the organic light emitting diodes according to Comparative Examples 1 to 5 using a single host.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present disclosure in any way.

DESCRIPTION OF SYMBOLS 100, 200: organic light emitting diode
105: organic layer
110: cathode
120: anode
130: light emitting layer
140: hole auxiliary layer

What is claimed is:

1. A composition for an organic optoelectronic device, comprising:

at least one of a first host compound represented by one of Chemical Formula C, Chemical Formula E1, and Chemical Formula E2, and at least one of a second host compound represented by a combination of Chemical Formula 3 and Chemical Formula 4, wherein the first host compound and the second host compound are present in the composition in a weight ratio of first host compound:second host compound of about 6:4 to about 10:1,

[Chemical Formula C]

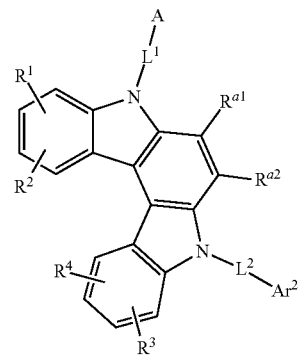

[Chemical Formula E1]

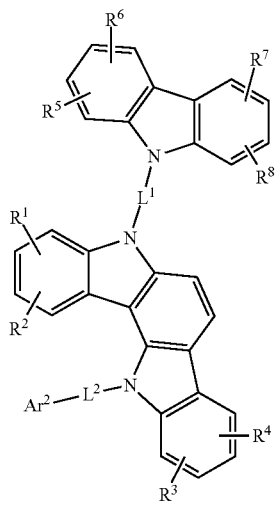

-continued

[Chemical Formula E2]

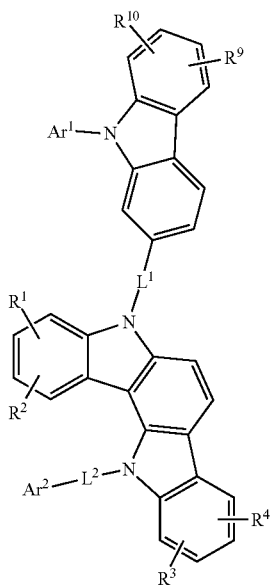

wherein, in Chemical Formula C,

A is a substituted or unsubstituted carbazolyl group, $Ar^2$ is a substituted or unsubstituted C6 to C20 aryl group, or a substituted or unsubstituted C2 to C20 heterocyclic group, $L^1$ and $L^2$ are independently a single bond or a substituted or unsubstituted C6 to C20 arylene group, and $R^{a1}$ to $R^{a2}$ and $R^1$ to $R^4$ are independently hydrogen, deuterium, a substituted or unsubstituted C1 to C10 alkyl group, a substituted or unsubstituted C6 to C20 aryl group, or a combination thereof;

wherein, in Chemical Formula E1 and Chemical Formula E2, $Ar^1$ and $Ar^2$ are independently a substituted or unsubstituted C6 to C20 aryl group, $L^1$ and $L^2$ are independently a single bond, or a substituted or unsubstituted C6 to C20 arylene group, and $R^1$ to $R^{10}$ are independently hydrogen, deuterium, a substituted or unsubstituted C1 to C10 alkyl group, a substituted or unsubstituted C6 to C20 aryl group, or a combination thereof;

[Chemical Formula 3]

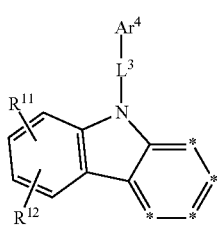

-continued

[Chemical Formula 4]

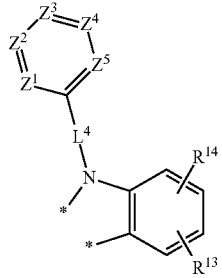

wherein, in Chemical Formulae 3 and 4, two adjacent *'s of Chemical Formula 3 are bound to two adjacent *'s of Chemical Formula 4 and the remainder *'s of Chemical Formula 3 not being bound to *'s of Chemical Formula 4 are $CR^b$, a substituted or unsubstituted C6 to C30 aryl group, or a substituted or unsubstituted C2 to C30 heterocyclic group, and $L^3$ and $L^4$ are independently a single bond or a substituted or unsubstituted C6 to C30 arylene group, $Z^1$ to $Z^5$ are independently N or $CR^c$, provided that at least two of $Z^1$ to $Z^5$ are N, $R^b$, $R^c$, and $R^{11}$ to $R^{14}$ are independently hydrogen, deuterium, a substituted or unsubstituted C1 to C10 alkyl group, a substituted or unsubstituted C6 to C20 aryl group, a substituted or unsubstituted C2 to C30 heterocyclic group, or a combination thereof, and $R^c$'s are independently present alone or adjacent groups thereof are linked with each other to form a substituted or unsubstituted aliphatic, aromatic, or heteroaromatic monocyclic or polycyclic ring; and the "substituted" refers to replacement of at least one hydrogen by deuterium, a C1 to C4 alkyl group, a C6 to C12 aryl group, or a C2 to C20 heterocyclic group.

2. The composition for an organic optoelectronic device as claimed in claim 1, wherein the first host compound is represented by one of Chemical Formula C1, Chemical Formula C2, Chemical Formula C3, Chemical Formula C4, Chemical Formula E1, and Chemical Formula E2:

[Chemical Formula C1]

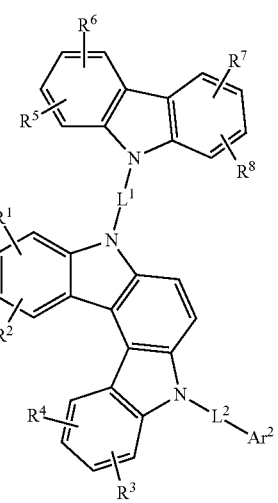

[Chemical Formula C2]

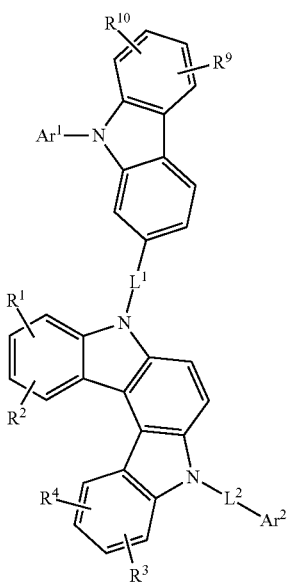

[Chemical Formula C3]

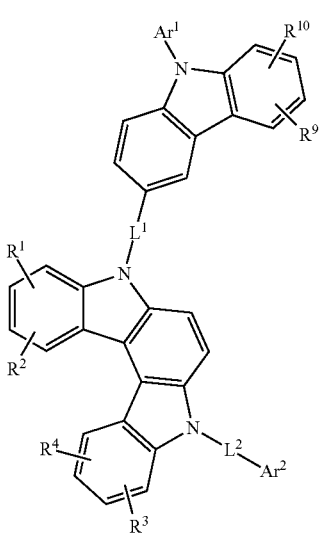

[Chemical Formula C4]

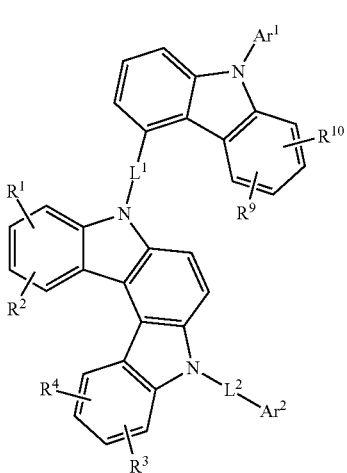

[Chemical Formula E1]

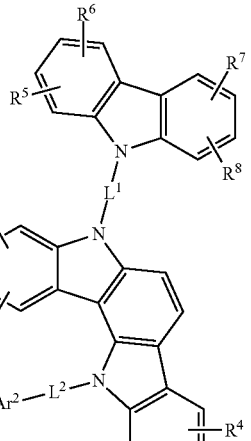

[Chemical Formula E2]

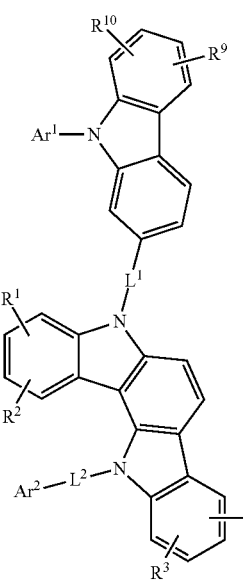

wherein, in Chemical Formula C1, Chemical Formula C2, Chemical Formula C3, and Chemical Formula C4, $Ar^1$ and $Ar^2$ are independently a substituted or unsubstituted C6 to C20 aryl group, $L^1$ and $L^2$ are independently a single bond or a substituted or unsubstituted C6 to C20 arylene group, and $R^1$ to $R^{10}$ are independently hydrogen, deuterium, a substituted or unsubstituted C1 to C10 alkyl group, a substituted or unsubstituted C6 to C20 aryl group, or a combination thereof, and in Chemical Formula E1 and Chemical Formula E2, $Ar^1$ and $Ar^2$ are independently a substituted or unsubstituted phenyl group, a substituted or unsubstituted biphenyl group, a substituted or unsubstituted terphenyl group, a substituted or unsubstituted naphthyl group, a substituted or unsubstituted fluorenyl group, or a substituted or unsubstituted phenanthrenyl group, $L^1$ and $L^2$ are independently a single bond, a substituted or unsubstituted phenylene group, or a substituted or unsubstituted biphenylene group, and $R^1$ to $R^{10}$ are independently hydrogen, a substituted or unsubstituted C1 to C4 alkyl group, or a substituted or unsubstituted C6 to C12 aryl group.

3. The composition for an organic optoelectronic device as claimed in claim 1, wherein, in Chemical Formula C, the L¹ is a single bond or is selected from selected from linking groups of Group I:

[Group I]

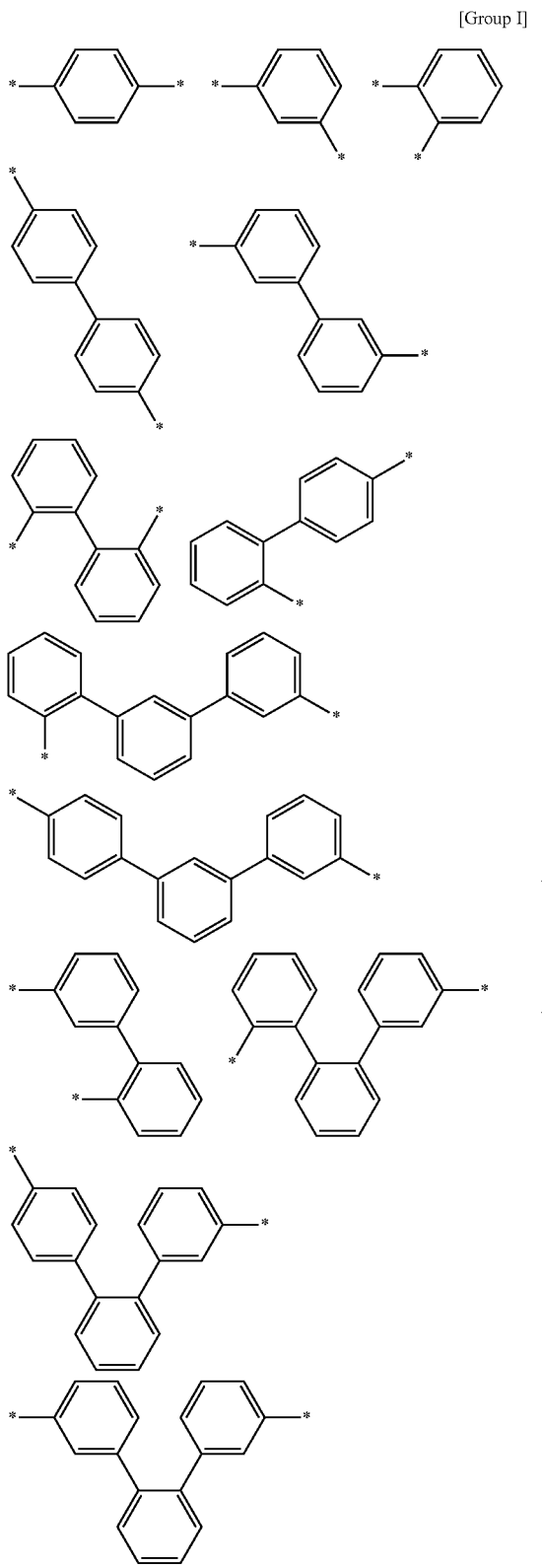
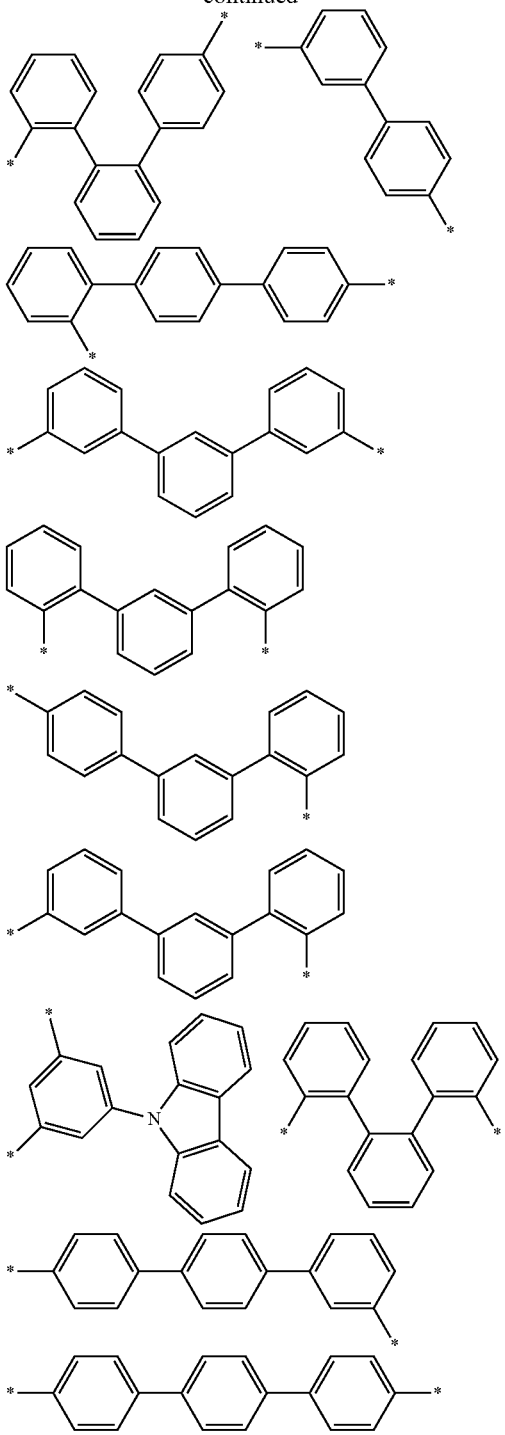

wherein, in Group I, * is a linking point with an adjacent atom.

4. The composition for an organic optoelectronic device as claimed in claim 1, wherein, in Chemical Formula C, the L² is a single bond or a substituted or unsubstituted phenylene group, and the Ar² is a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted fluorenyl group, a substituted or unsubstituted carbazolyl group, a substituted or unsubstituted dibenZofuranyl group, or a substituted or unsubstituted dibenzothiophenyl group.

5. The composition for an organic optoelectronic device of claim 1, wherein, in Chemical Formula C, the $L^1$ and $L^2$ are independently a single bond or a substituted or unsubstituted phenylene group, the $Ar^2$ is a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, or a substituted or unsubstituted fluorenyl group, and the "substituted" refers to replacement of at least one hydrogen by deuterium, C1 to C4 alkyl group, or C6 to C12 aryl group.

6. The composition for an organic optoelectronic device as claimed in claim 1, wherein the second host compound is represented by one of Chemical Formula A-ET, Chemical Formula B-ET, Chemical Formula C-ET, Chemical Formula D-ET, and Chemical Formula E-ET:

[Chemical Formula A-ET]

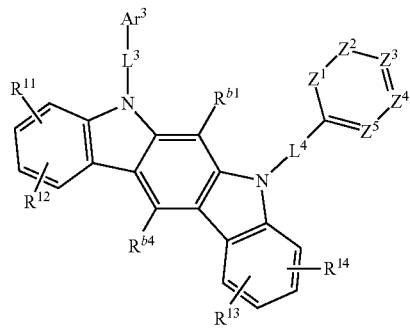

[Chemical Formula B-ET]

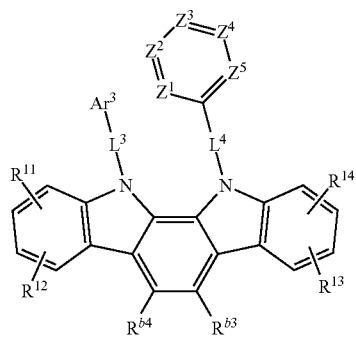

[Chemical Formula C-Et]

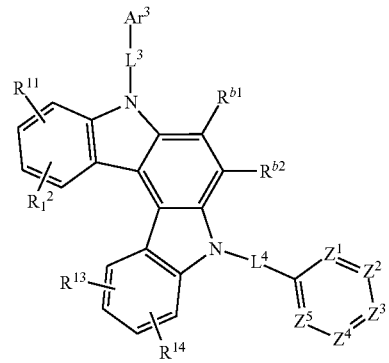

[Chemical Formula D-ET]

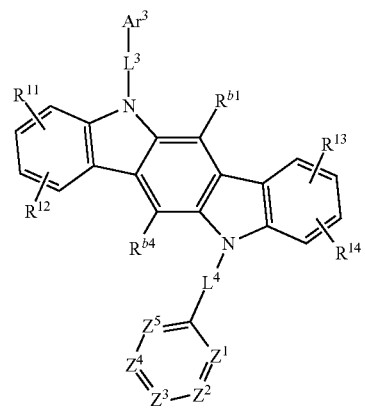

[Chemical Formula E-ET]

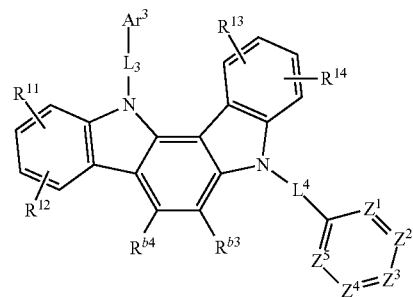

wherein, in Chemical Formula A-ET, Chemical Formula B-ET, Chemical Formula C-ET, Chemical Formula D-ET, and Chemical Formula E-ET, $Ar^3$ is a substituted or unsubstituted C6 to C30 aryl group, $L^3$ and $L^4$ are independently a single bond or a substituted or unsubstituted C6 to C30 arylene group, $Z^1$ to $Z^5$ are independently N or $CR^c$, at least two of $Z^1$ to $Z^5$ are N, $R^{b1}$ to $R^{b4}$, $R^c$, and $R^{11}$ to $R^{14}$ are independently hydrogen, deuterium, a substituted or unsubstituted C1 to C10 alkyl group, a substituted or unsubstituted C6 to C20 aryl group, a substituted or unsubstituted C2 to C30 heterocyclic group, or a combination thereof, and $R^c$'s are independently present alone or adjacent groups thereof are linked with each other to form a substituted or unsubstituted aliphatic, aromatic, or heteroaromatic monocyclic or polycyclic ring.

7. The composition for an organic optoelectronic device as claimed in claim 6, wherein the $Ar^3$ is a substituted or unsubstituted C6 to C30 aryl group, the L³ and L⁴ are independently a single bond, a substituted or unsubstituted phenylene group, or a substituted or unsubstituted biphenylene group, the $Z^1$ to $Z^5$ are independently N or $CR^c$, at least two of $Z^1$ to $Z^5$ are N, $R^c$ is hydrogen, deuterium, a substituted or unsubstituted C1 to C4 alkyl group, a substituted or unsubstituted phenyl group, a substituted or unsubstituted biphenyl group, a substituted or unsubstituted naphthyl group, a substituted or unsubstituted terphenyl group, a substituted or unsubstituted triphenyl group, a substituted or unsubstituted dibenzofuranyl group, a substituted or unsubstituted dibenzothiophenyl group, a substituted or unsubstituted fluorenyl group, or a combination thereof, $R^c$'s are independently present alone or adjacent groups thereof are linked with each other to form a substituted or unsubstituted quinazolinyl group, and $R^{b1}$ to $R^{b4}$ and $R^{11}$ to $R^{14}$ are independently hydrogen, deuterium, a substituted or unsubstituted C1 to C4 alkyl group, a substituted or unsubstituted C6 to C12 aryl group, or a combination thereof.

8. The composition for an organic optoelectronic device as claimed in claim 1, wherein the second host compound is represented by one of Chemical Formula B-ET-a, Chemical Formula B-ET-b, Chemical Formula B-ET-c, Chemical Formula B-ET-d, and Chemical Formula B-ET-e:

[Chemical Formula B-ET-a]

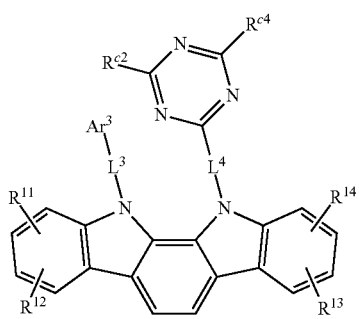

[Chemical Formula B-ET-b]

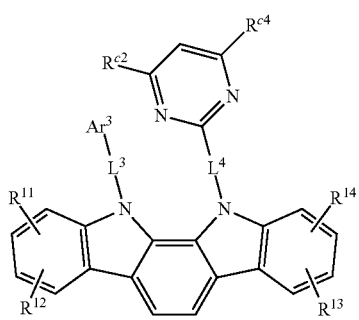

[Chemical Formula B-ET-c]

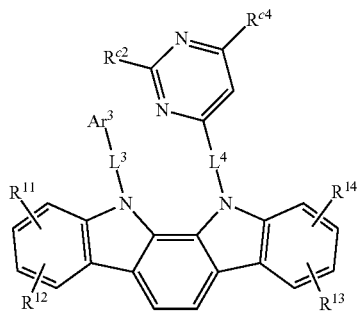

[Chemical Formula B-ET-d]

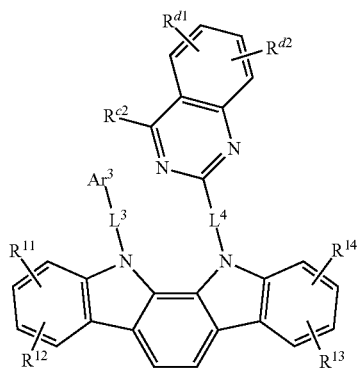

[Chemical Formula B-ET-e]

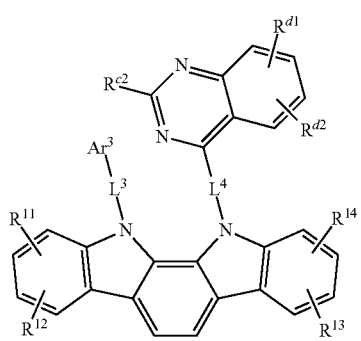

wherein, in Chemical Formula B-ET-a, Chemical Formula B-ET-b, Chemical Formula B-ET-c, Chemical Formula B-ET-d, and Chemical Formula B-ET-e, $Ar^3$ is a substituted or unsubstituted C6 to C30 aryl group, $L^3$ and $L^4$ are independently a single bond or a substituted or unsubstituted C6 to C30 arylene group, and $R^{c2}$ to $R^{c5}$, $R^{d1}$, $R^{d2}$, and $R^{11}$ to $R^{14}$ are independently hydrogen, deuterium, a substituted or unsubstituted C1 to C10 alkyl group, a substituted or unsubstituted C6 to C20 aryl group, a substituted or unsubstituted C2 to C30 heterocyclic group, or a combination thereof.

9. The composition for an organic optoelectronic device as claimed in claim 1, wherein the first host compound is represented by one of Chemical Formula C1, Chemical Formula C2, Chemical Formula C3, Chemical Formula E1, and Chemical Formula E2, and the second host compound is represented by Chemical Formula B-ET-a:

[Chemical Formula C1]
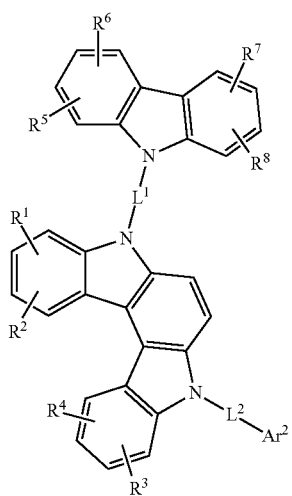
[Chemical Formula C2]
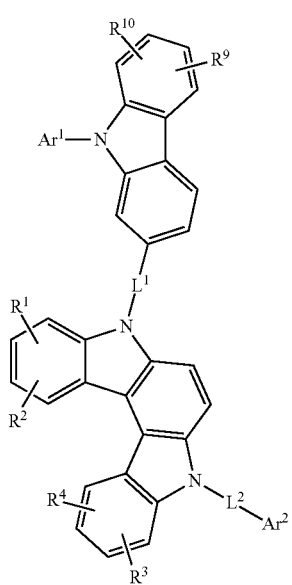
[Chemical Formula C3]
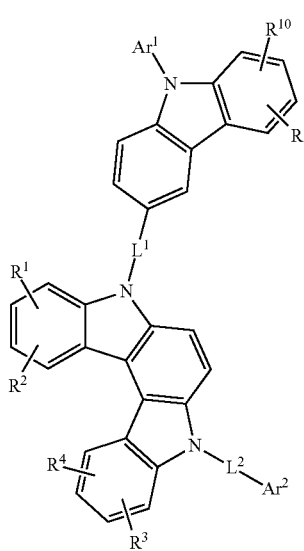
-continued
[Chemical Formula E1]
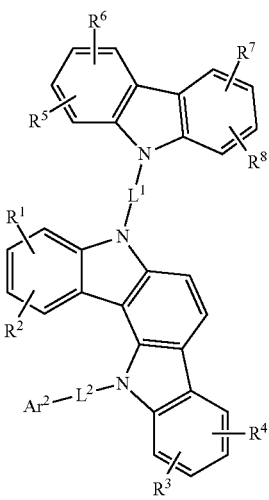
[Chemical Formula E2]
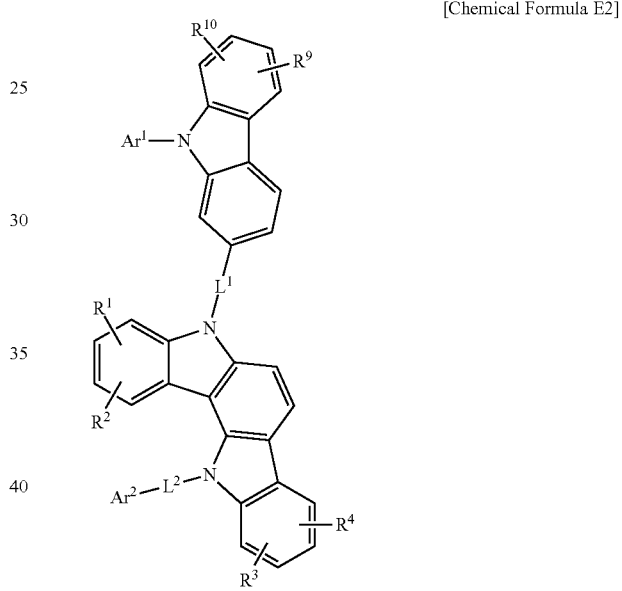
[Chemical Formula E3]
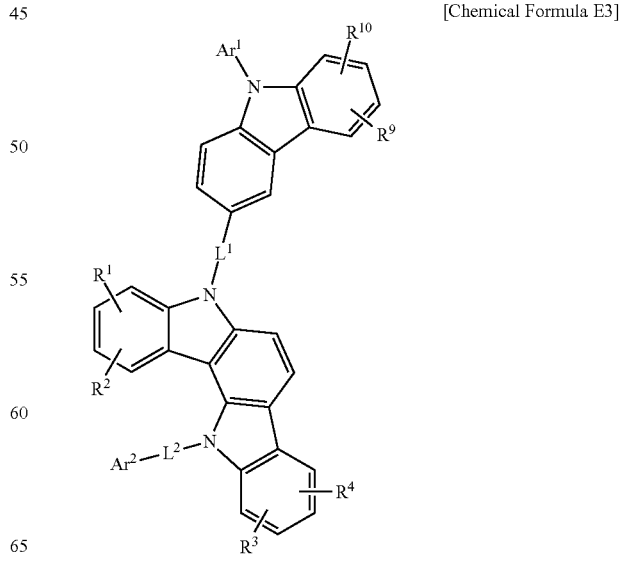

wherein, in Chemical Formula C1, Chemical Formula C2, Chemical Formula C3, Chemical Formula E1, and Chemical Formula E2, $Ar^1$ and $Ar^2$ are independently a substituted or unsubstituted phenyl group, a substituted or unsubstituted biphenyl group, a substituted or unsubstituted terphenyl group, a substituted or unsubstituted naphthyl group, a substituted or unsubstituted fluorenyl group, or a substituted or unsubstituted phenanthrenyl group, $L^1$ and $L^2$ are independently a single bond, a substituted or unsubstituted phenylene group, or a substituted or unsubstituted biphenylene group, and $R^1$ to $R^{10}$ are independently hydrogen, a substituted or unsubstituted C1 to C4 alkyl group, or a substituted or unsubstituted C6 to C12 aryl group;

[Chemical Formula B-ET-a]

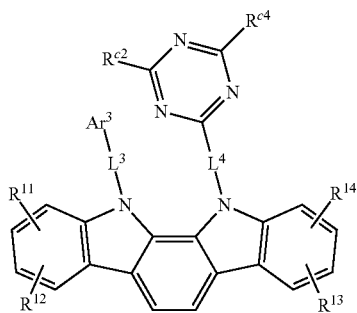

wherein, in Chemical Formula B-ET-a, $Ar^3$ is a substituted or unsubstituted phenyl group, a substituted or unsubstituted biphenyl group, $L^3$ and $L^4$ are independently a single bond or a substituted or unsubstituted phenylene group, $R^{c2}$ and $R^{c4}$ are independently a substituted or unsubstituted phenyl group, a substituted or unsubstituted para-biphenyl group, a substituted or unsubstituted meta-biphenyl group, a substituted or unsubstituted terphenyl group, a substituted or unsubstituted dibenzofuranyl group, or a substituted or unsubstituted dibenzothiophenyl group, and $R^{11}$ to $R^{14}$ are independently hydrogen, a substituted or unsubstituted C1 to C4 alkyl group, or a substituted or unsubstituted C6 to C12 aryl group.

10. An organic optoelectronic device, comprising:
an anode and a cathode facing each other, and
at least one organic layer disposed between the anode and the cathode,
wherein the organic layer includes the composition for an organic optoelectronic device as claimed in claim 1.

11. The organic optoelectronic device as claimed in claim 10, wherein the organic layer includes a light emitting layer, and
the composition for an organic optoelectronic device is included as a host of the light emitting layer.

12. A display device comprising the organic optoelectronic device as claimed in claim 10.

13. The composition for an organic optoelectronic device of claim 1, wherein the weight ratio of first host compound: second host compound is about 7:3 to about 10:1.

* * * * *